United States Patent [19]

Tsui et al.

[11] Patent Number: 5,981,178
[45] Date of Patent: Nov. 9, 1999

[54] METHODS FOR SCREENING FOR MUTATIONS AT VARIOUS POSITIONS IN THE INTRONS AND EXONS OF THE CYSTIC FIBROSIS GENE

[75] Inventors: Lap-Chee Tsui, Toronto; Johanna M. Rommens, Willowdale, both of Canada; Bat-sheva Kerem, Jerusalem, Israel

[73] Assignee: HSC Research Development Corporation, Toronto, Canada

[21] Appl. No.: 08/469,461

[22] Filed: Jun. 6, 1995

Related U.S. Application Data

[62] Division of application No. 07/890,609, filed as application No. PCT/CA91/00009, Jan. 11, 1991, Pat. No. 5,869,280.

[30] Foreign Application Priority Data

| Jan. 10, 1990 | [CA] | Canada | 2007699 |
| Mar. 1, 1990 | [CA] | Canada | 2011253 |
| Jul. 10, 1990 | [CA] | Canada | 2020817 |

[51] Int. Cl.$^6$ .............................. C12Q 1/68; G07H 17/00
[52] U.S. Cl. ........................... 435/6; 435/810; 536/24.31; 514/851
[58] Field of Search .............................. 435/6, 91.1, 91.2, 435/91.21, 810; 536/24.31, 24.33, 25.32; 514/851

[56] References Cited

U.S. PATENT DOCUMENTS

| 4,322,274 | 3/1982 | Wilson et al. . | |
| 4,844,893 | 7/1989 | Honsik et al. | 424/85.8 |
| 4,847,201 | 7/1989 | Kaswasaki et al. | 435/70 |
| 4,853,331 | 8/1989 | Herrnstadt et al. | 435/252.11 |
| 4,861,589 | 8/1989 | Ju | 424/93 |
| 4,861,719 | 8/1989 | Miller | 435/236 |
| 4,868,116 | 9/1989 | Morgan et al. | 435/240.2 |
| 4,980,286 | 12/1990 | Morgan et al. | 435/172.3 |
| 5,240,846 | 8/1993 | Collins et al. | 435/240.1 |

FOREIGN PATENT DOCUMENTS

| 0 226 288 | 6/1987 | European Pat. Off. | 1/68 |
| 0 288 299 | 10/1988 | European Pat. Off. | 1/68 |
| 0 446 017 | 9/1991 | European Pat. Off. | 5/12 |
| 2 203 742 | 10/1988 | United Kingdom | 12/4 |
| WO 91/02796 | 3/1991 | WIPO | 15/12 |
| WO 91/10734 | 7/1991 | WIPO | 15/12 |
| WO 92/05273 | 4/1992 | WIPO | 21/6 |
| WO 93/17040 | 9/1993 | WIPO . | |

OTHER PUBLICATIONS

Bear et al., Purification and Functional Reconstitution of the Cystic Fibrosis Transmembrane Conductance Regulator (CFTR), *Cell*, 68:809–818 (1992).

Rommens et al., cAMP–Inducible Chloride Conductance in Mouse Fibroblast Lines Stably Expressing the Human Cystic Fibrosis Transmembrane Conductance Regulator, *Proc. Natl. Acad. Sci. USA* 88:7500–7504 (1991).

Kartner et al., Expression of the Cystic Fibrosis Gene in Non–Epithelial Invertebrate Cells Produces a Regulated Anion Conductance, *Cell* 64:681–691 (1991).

Zielenski et al., Genomic DNA Sequence of the Cystic Fibrosis Transmembrane Conductance Rgulator (CFTR) Gene, *Genomics* 10:214–228 (1991).

Drumm et al., Correction of the Cystic Fibrosis Defect in Vitro by Retrovirus–Mediated Gene Transfer, *Cell* 62:1227–1223 (1990).

Quinton, P.M., Cystic Fibrosis: A Disease in Electrolyye Transport, *FASEB J.* 4:2709–2717 (1990).

The Cystic Fibrosis Genetic Analysis Consortium World-wide Survey of the ΔF508 Mutation–Report from the Cystic Fibrosis Genetic Analysis Consortium, *Am J. Hum. Genet.* 47:354–359 (1990).

Venglarik et al., A Simple Assay for Agonist–Regulated Cl and K Conductances in Salt–Secreting Epithelial Cells, *Am. J. Physiol.* 259:C358–C364 (1990).

Boat et al., Human Respiratory Tract Secretions, *Archives of Biochemistry and Biophyics* 177:95–104 (1976).

Green et al., Chromosomal Region of the Cystic Fibrosis Gene in Yeast Artificial Chromosomes: A Model for Human Genome Mapping, *Science* 250:94–98 (1990).

Cliff et al., Separate Cl$^+$ Conductances Activated by cAMP and Ca$^{2+}$ in Cl$^+$–Secreting Epithelial Cells, *Proc. Natl. Acad. Sci. USA* 87:4956–4960 (1990).

Welsh, M.J., Abnormal Regulation of Ion Channels in Cystic Fibrosis Epithelia, *FASEB J.* 4:2718–2725 (1990).

Hyde et al., Structural Model of ATP–Binding Proteins Associated with Cystic Fibrosis, Multidrug Resistance and Bacterial Transport, *Nature* 346:362–365 (1990).

Feinberg et al., A Technique for Radiolabeling DNA Restriction Endonuclease Fragments to High Specific Activity, *Analytical Biochemistry* 132:6–13 (1983).

Slot et al., No Evidence for Expression of the Insulin–Regulatable Glucose Transported in Endothelial Cells, *Nature* 346:369–371 (1990).

Sato et al., Defective Beta Adrenergic Response of Cystic Fibrosis Sweat Glands In Vivo and In Vitro, *J. Clin. Invest.* 73:1763–1771 (1984).

Wilson, et al., Correction of CD18–Deficient Lymphocytes by Retrovirus–Mediated Gene Transfer, *Science* 248:1413–1416 (1990).

Schoumacher et al., A Cystic Fibrosis Pancreatic Adenocarcinoma Cell Line, *Proc. Natl. Acad. Sci. USA* 87:4012–4016 (1990).

White et al., A Frame–Shift Mutation in the Cystic Fibrosis Gene, *Nature* 344:665–667 (1990).

(List continued on next page.)

*Primary Examiner*—Karen Cochrane Carlson
*Attorney, Agent, or Firm*—Bell Seltzer Intellectual Property Law Group of Alston & Bird LLP

[57] ABSTRACT

The cystic fibrosis gene and its gene product are described for mutant forms. The genetic and protein information is used in developing DNA diagnosis, protein diagnosis, carrier and patient screening, cloning of the gene and manufacture of the protein, and development of cystic fibrosis affected animals.

15 Claims, 46 Drawing Sheets

OTHER PUBLICATIONS

Wilson et al., Expression of Human Adenosine Deaminase in Mice Reconstituted with Retrovirus–Transduced Hematopoietic Stem Cells, *Proc. Natl. Acad. Sci. USA* 87:439–443 (1990).

Taussig, L.M., Cystic Fibrosis: An Overview, *Cystic Fibrosis* (Taussig, L.M., ed.) *Thieme–Stralto* N.Y., N.Y., pp. 1–9 (1984).

Sanbrook et al, Oligonucleotide–Mediated Mutagenesis in Molecular Cloning, *A Laboratory Manual* 2nd Ed., Cold Spring Harbor Press, Cold Spring Harbor, NY, pp. 15.51–15.80 (1989).

Fulton et al., A 12 Megabase Restriction Map at the Cystic Fibrosis Locus, *Nucleic Acids Research* 17(1):271–284 (1989).

Smith, M., In Vitro Mutagenesis, *Ann. Rev. Genet.* 19:423–462 (1985).

Boucher et al., $Na^+$ Transport in Cystic Fibrosis Respiratory Epithelia, *J. Clin. Invest.* 78:1245–1252 (1986).

Wahl et al., Cosmid Vectors for Rapid Genomic Walking, Restriction Mapping, and Gene Transfer, *Proc. Natl. Acad. Sci. USA* 84:2160–2164 (1987).

Korman et al., Expression of Human Class II Major Histocompatibility Complex Antigens Using Retrovirus Vectors, *Proc. Natl. Acad. Sci. USA* 84:2150–2154 (1987).

Meakin et al., γ–Crystallins of the Human Eye Lens: Expression Analysis of Five Members of the Gene Family, *Molecular and Cellular Biology* 7(8):2671–2679 (1987).

Schoumacher et al., Phosphorylation Fails to Activate Chloride Channels from Cystic Fibrosis Airway Cells, *Nature* 330:752–754 (1987).

Smith et al., Cystic Fibrosis: Diagnostic Testing and the Search for the Gene, *Clin. Chem.* 35/7(B):B17–B20 (1989).

Frizzell, R.A., Cystic Fibrosis: A Disease of Ion Channels?, *Tins* 10(5):190–193 (1987).

Buchwald et al., Current Status of the Genetics of Cystic Fibrosis, *Genetics and Epithelial Cell Dysfunction in Cystic Fibrosis* (Alan R. Liss, Inc.), pp. 19–29 (1987).

Willumsen et al., Activation of an Apical $Cl^+$ Conductance by $Ca^{2+}$ Ionophores in Cystic Fibrosis Airway Epithelia, *Am. J. Physiol.* 256:C226–C233 (1989).

Li et al., Cyclic AMP–Dependent Protein Kinase Opens Chloride Channels in Normal but not Cystic Fibrosis Airway Epithelium, *Nature* 331:358–360 (1988).

Wilson et al., Correction of the Genetic Defect of Hepatocytes from the Watanabe Heritable Hyperlipidemic Rabbit, *Proc. Natl. Acad. Sci. USA* 85:4421–4425 (1988).

Short et la., λ ZAP: A Bacteriophage λ Expression Vector with In Vivo Excision Properties, *Nucleic Acids Research* 16(15):7583–7600 (1988).

Koshland, D.E., Jr., The Cystic Fibrosis Gene Story, *Science* 256(4922):1029 (1989).

Farrall et al., Recombinations Between IRP and Cystic Fibrosis, *Am. J. Hum. Genet.* 43:471–475 (1988).

Marx, J.L., The Cystic Fibrosis Gene is Found, *Science* 245:923–925 (1989).

Rommens et al., Identification of the Cystic Fibrosis Gene: Chromosome Walking and Jumping, *Science* 245:1059–1065 (1989).

Landry, et al., Purification and Reconsititution of Chloride Channels from Kidney and Trachea, *Science* 244:1469–1472 (1989).

Rommens et al., Genetic and Physical Mapping of the Chromosomal Region Containing th Cystic Fibrosis Locus, *Am. J. Hum. Genetics* 43(3 Suppl.):A199 (1988).

Cheng, S. H. et al., Defective Intracellular Transport and Processing of CFTR is the Molecular Basis of Most Cystic Fibrosis, *Cell* 63:827–834 (Nov. 16, 1990).

Boat et al., Cystic Fibrosis, *The Metabolic Basis Of Inherited Disease II*, 6th ed., Chapter 108, (McGraw Hill, NY), pp. 2649–2680 (1989).

Tsui et al., Cystic Fibrosis Locus Defined by a Genetically Linked Polymorphic DNA Marker, *Science* 230:1054–57 (1985).

Zengerling et al., Mapping of DNA Markers Linked to the Cystic Fibrosis Locus on the Long Arm of Chromosome 7, *Am. J. Hum. Genet.* 40:228–236 (1987).

Rommens et al., Identification and Regional Localization of DNA Markers on Chromosome 7 for the Cloning of the Cystic Fibrosis Gene, *Am. J. Hum. Genet.* 43:654–663 (1988).

White et al., A Closely Linked Genetic Marker for Cystic Fibrosis, *Nature* 318:382–384 (1985).

Wainwright et al., Localization of Cystic Fibrosis Locus to Human Chromosome 7cen–q22, *Nature* 318:384–385, (1985).

Estivill et al., A Candidate for the Cystic Fibrosis Locus Isolated By Selection for Methylation–Free Islands, *Nature* 326:840–845 (1987).

Collins et al., Construction of a General Human Chromosome Jumping Library, with Application to Cystic Fibrosis, *Science* 235:1046–1049 (1987).

Ianuzzi et al., Isolation of Additional Polymorphic Clones from the Cystic Fibrosis Region, Using Chromosome Jumping from D7S8, *Am. J. Hum. Genet.* 44:695–703, 1989.

Estivill et al., Isolation of a New DNA Marker in Linkage Disequilibrium with Cystic Fibrosis, Situated Between J3.II (D7S8) and IRP, *Am. J. Hum. Genet.* 44:704–710, 1989.

Rommens et al., Physical Localization of Two DNA Markers Closely Linked to the Cystic Fibrosis Locus by Pulsed–Field Gel Electrophoresis, *Am. J. Hum. Genet.*, 45:932–941 (1989).

Drumm et al., Physical Mapping of the Cystic Fibrosis Region By Pulsed–Field Gel Electrophoresis, *Genomics* 2:346–354 (1988).

Kerem et al., DNA Marker Haplotype Assocation with Pancreatic Sufficiency in Cystic Fibrosis, *Am. J. Hum. Genet.* 44:827–834 (1989).

Poustka et al., A Long–Range Restriction Map Encompassing the Cystic Fibrosis Locus and Its Closely Linked Genetic Markers, *Genomics* 2:337–345 (1988).

Dean et al., Approaches to Localization Disease Genes As Applied to Cystic Fibrosis, *Nucleic Acids Research* 18:345–350 (1989).

Collie et al., Culture of Sweat Gland Epithelial Cells From Normal Individuals and Patients with Cystic Fibrosis, *In Vitro Cell. Develop. Biol.* 21:597–602 (1985).

Tabcharani et al., Bicarbonate Permeability Of The Outwardly Rectifying Anion Channel, *J. Memb Biol.* 112:109–122 (1989).

Spence et al., Linkage of DNA Markers to Cystic Fibrosis in 26 Families, *Am. J. Hum. Genet.* 39:729–734 (1986).

Estivill et al., Patterns of Polymorphism and Linkage Disequilibrium for Cystic Fibrosis, *Genomi* 1:257–263 (1987).

Tsui et al., Mapping of the Cystic Fibrosis Locus on Chromosome 7, *Cold Spring Harbor Symp Quant. Biol.* LI:325–335 (1986).

Corey et al., Familial Concordance of Pancreatic Function in Cystic Fibrosis, *J. Pediatrics* 115:274–277 (1989).

Beaudet et al., Linkage Disequilibrium, Cystic Fibrosis, and Genetic Counseling, *Am. J. Hum. Genet.* 44:319–326 (1989).

Brock, *Amniotic Fluid Alkaline Phosphatase Isoenzymes in Early Prenatal Diagnosis of Cystic Fibrosis, The Lancet* pp. 941–943, Oct. 22, 1983.

Jetten et al., *Persistence of Abnormal Chloride Conductance Regulation in Transformed Cystic Fibrosis Epithelia, Science* 244:1472–1475 (1989).

Yankaskas et al., *Culture of Human Nasal Epithelial Cells on Collagen Matrix Supports, Am. Rev. Respir. Dis.* 132:1281–1287 (1985).

Scholte et al., *Immortalization of Nasal Polyp Epithelial Cells from Cystic Fibrosis Patients, Exp. Cell. Res.* 182:559–571 (1989).

Harris et al., *Establishment of a Tissue Culture System for Epithelial Cells Dervied From Human Pancreas: A Model for the Study of Cystic Fibrosis, Journal of Cell Science* 87, 695–703 (1987).

Stutts et al., *Chloride Uptake into Cultured Airway Epithelial Cells From Cystic Fibrosis Patients and Normal Individuals, Proc. Natl. Acad. Sci. USA* 82:6677–6681 (1985).

Frizzell et al., *Altered Regulation of Airway Epithelial Cell Chloride Channels in Cystic Fibrosis, Science* 233:558–560 (1986).

Welsh et al., *Chloride and Potassium Channels In Cystic Fibrosis Airway Epithelia, Nature* 322:467–470 (1986).

Widdicombe et al., *Cystic Fibrosis Decreases the Apical Membrane Chloride Permeability of Monolayers Cultured from Cells of Trachael Epithelium, Proc. Natl. Acad. Sci. USA* 82:6167–6171 (1985).

Tsui et al., *Cystic Fibrosis: Progress in Mapping the Disease Locus Using Polymorphic DNA Markers. I., Cytogenet. Cell. Genet.* 39:299–301 (1985).

Knowlton et al., *Polymorphic DNA Marker Linked To Cystic Fibrosis Is Located on Chromosome 7, Nature* 318:380–382 (1985).

Tsui et al., *Genetic Analysis of Cystic Fibrosis Using Linked DNA Markers, Am. J. Hum. Genet.* 39:720–728 (1986).

Beaudet et al., *Linkage of Cystic Fibrosis to Two Tightly Linked DNA Markers: Joint Report From A Collaborative Study, Am. J. Hum. Genet.* 39:681–693 (1986).

Buchwald et al., *Linkage of Cystic Fibrosis to the Proα2(I) Collagen Gene, COL1A2, On Chromosome 7, Cytogenet. Cell. Genet.* 41:234–239 (1986).

Schmiegelow et al., *Linkage Between the Loci for Cystic Fibrosis and Paraoxonase, Clinical Genetics* 29:374–377 (1986).

Tsui et al., *Progress Towards Cloning of the Cystic Fibrosis Gene—Identification of New DNA Markers In The 7Q31 Region, Protides of the Biological Fluids* 35:51–54 (1987).

Tsui et al., *Progress Towards Cloning the Cystic Fibrosis Gene, Phil. Trans. R. Soc. Lond.* B319:263–273 (1988).

Scambler et al., *Chromosome Mediated Gene Transfer of Six DNA Markers Linked to the Cystic Fibrosis Locus on Human Chromosome Seven, Nucleic Acids Res.* 14:7159–7174 (1986).

Michiels et al., *Derivation of Clones Close to met by Preparative Field Inversion Gel Electrophoresis, Science* 236:1305–1308 (1987).

Lathrop et al., Refined Linkage Map of Chromosome 7 in the Region of the Cystic Fibrosis Gene, *Am. J. Hum. Genet.* 42:38–44 (1988).

Buchwald et al., The Genetics of Cystic Fibrosis—mid 1987, *Excerta Med. Asia Pacific Congress* 74:3–9 (1987).

Riordan et al., Utilization of Cultured Epithelial Cells From the Sweat Gland in Studies of the CF Defect, *Genetics and Epithelial Cell Dysfunction in Cystic Fibrosis*, Alan R. Liss, Inc., pp. 59–71 (1987).

Reddy et al., Electrical Properties of Cultured Reabsorptive Sweat Duct Cells From Normal and Cystic Fibrosis Subjects: Intracellular Microelectrode Analysis, *Cellular and Molecular Basis of Cystic Fibrosis* (Mastella et al., Eds) *San Francisco Press, Inc.*, San Francisco, Calif., pp. 383–393 (1988).

Riordan, Reaching Between the Functional and Genetic Defects in Cystic Fibrosis, *Pediatric Pulmonary Suppl.* 1:29 (1987).

Reddy et al., Retention of Basic Electrophysiologic Properties By Human Sweat Duct Cells In Primary Culture, *In Vitro Cell. Develop. Biol.* 24:905–910 (1988).

Riordan et al., Molecular Studies of Cultured Epithial Cells From the Sweat Gland, Cellular and Molecular Basis of Cystic Fibrosis (Mastella et al., Eds) *San Francisco Press, Inc.*, San Francisco, Calif., pp. 416–424 (1988).

Reddy et al., Lack of β–Adrenergic Responsiveness In Cells Cultured From Reabsorptive Sweat Ducts Of Cystic Fibrosis (CF) Subjects, *Pediatric Pulmonology Suppl.* 1:115 (1987).

Jensen et al., Chloride Channel Expression in Cultures of Sweat Gland Epithelial Cells in Cystic Fibrosis, *J. Cell. Biol.* 107:139a #788 (1989).

Orr et al., In vivo and In vitro Phosphorylation of Apical Membrane Proteins of the T–84 Colonic Epithelial Cell Line, *J. Cell. Biol.* 107:493a #2776 (1989).

Chen et al., A cAMP–Regulated Chloride Channel in Lymphocytes That Is Affected in Cystic Fibrosis *Science* 243:657–660 (1988).

Dodge, Implications of the New Genetics for Screening for Cystic Fibrosis, *The Lancet*, pp. 672–677 (Sep. 17, 1988).

Beaudet et al., Prenatal Diagnosis of Cystic Fibrosis, *J. Ped.* 111:630–633 (1987).

Dean, Molecular and Genetic Analysis of Cystic Fibrosis, *Genomics* 3:93–99 (1988).

Dean, et al., Multiple Mutations in Highly Conserved Residues Are Found in Mildly Affected Cystic Fibrosis Patients, *Cell*, vol. 61:863–870 (1990).

Cutting et al., A Cluster of Cystic Fibrosis Mutations in the First Nucleotide–Binding Fold of the Cystic Fibrosis Conductance Regulator Protein, *Nature*, vol. 346:366–369 (1990).

Kerem et al., Identification of Mutations in Regions Corresponding to the Two Putative Nucleotide (ATP)–binding Folds of the Cystic Fibrosis Gene, *Proc. Natl. Acad. Sci. USA*, vol. 87:8447–8451 (1990).

Kerem et al., Identification of the Cystic Fibrosis Gene: Genetic Analysis, *Science*, vol. 245:1073–1080 (1989).

Riordan et al., Identification of the Cystic Fibrosis Gene: Cloning and Characterization of Complementary DNA, *Science*, vol. 245:1066–1073 (1989).

Cheng et al., Increased Sulfation of Glycoconjugates by Cultured Nasal Epithelial Cells from Patients with Cystic Fibrosis, *J.Clin.Invest.*, vol. 84, pp. 68–72, (Jul. 1989).

FIG. 1A.

```
                    ↟↟
   1 AATTGGAAGCAAATGACATCACAGCAGGTCAGAGAAAAAGGGTTGAGCGGCAGGCACCCA

61 GAGTAGTAGGTCTTTGGCATTAGGAGCTTGAGCCCAGACGGCCCTAGCAGGGACCCCAGC

M  Q  R  S  P  L  E  K  A  S  V  V  S  K  L  F     16
 121 GCCCGAGAGACCATGCAGAGGTCGCCTCTGGAAAAGGCCAGCGTTGTCTCCAAACTTTTT

F  S  W  T  R  P  I  L  R  K  G  Y  R  Q  R  L  E  L  S  D     36
 181 TTCAGCTGGACCAGACCAATTTTGAGGAAAGGATACAGACAGCGCCTGGAATTGTCAGAC

I  Y  Q  I  P  S  V  D  S  A  D  N  L  S  E  K  L  E  H  E     56
 241 ATATACCAAATCCCTTCTGTTGATTCTGCTGACAATCTATCTGAAAAATTGGAAACAGAA

W  D  R  E  L  A  S  K  K  N  P  K  L  I  N  A  L  R  R  C     76
 301 TGGGATAGAGAGCTGGCTTCAAAGAAAAATCCTAAACTCATTAATGCCCTTCGGCGATGT

F  F  W  R  F  M  F  Y  G  I  F  L  Y  L  G  E  V  T  K  A     96
 361 TTTTTCTGGAGATTTATGTTCTATGGAATCTTTTTATATTTAGGGGAAGTCACCAAAGCA

V  Q  P  L  L  L  G  R  I  I  A  S  Y  D  P  D  N  K  E  E    116
 421 GTACAGCCTCTCTTACTGGGAAGAATCATAGCTTCCTATGACCCGGATAACAAGGAGGAA

R  S  I  A  I  Y  L  G  I  G  L  C  L  L  F  I  V  R  T  L    136
 481 CGCTCTATCGCGATTTATCTAGGCATAGGCTTATGCCTTCTCTTTATTGTGAGGACACTG

L  L  H  P  A  I  F  G  L  H  H  I  G  M  Q  M  R  I  A  M    156
 541 CTCCTACACCCAGCCATTTTTGGCCTTCATCACATTGGAATGCAGATGAGAATAGCTATG

F  S  L  I  Y  K  K  T  L  K  L  S  S  R  V  L  D  K  I  S    176
 601 TTTAGTTTGATTTATAAGAAGACTTTAAAGCTGTCAAGCCGTGTTCTAGATAAAATAAGT

I  G  Q  L  V  S  L  L  S  N  N  L  N  K  F  D  E  G  L  A    196
 661 ATTGGACAACTTGTTAGTCTCCTTTCCAACAACCTGAACAAATTTGATGAAGGACTTGCA

L  A  H  F  V  W  I  A  P  L  Q  V  A  L  L  M  G  L  I  W    216
 721 TTGGCACATTTCGTGTGGATCGCTCCTTTGCAAGTGGCACTCCTCATGGGGCTAATCTGG

E  L  L  Q  A  S  A  F  C  G  L  G  F  L  I  V  L  A  L  F    236
 781 GAGTTGTTACAGGCGTCTGCCTTCTGTGGACTTGGTTTCCTGATAGTCCTTGCCCTTTTT

Q  A  G  L  G  R  M  M  M  K  Y  R  D  Q  R  A  G  K  I  S    256
 841 CAGGCTGGGCTAGGGAGAATGATGATGAAGTACAGAGATCAGAGAGCTGGGAAGATCAGT

E  R  L  V  I  T  S  E  M  I  E  N  I  Q  S  V  K  A  Y  C    276
 901 GAAAGACTTGTGATTACCTCAGAAATGATTGAAAATATCCAATCTGTTAAGGCATACTGC

W  E  E  A  M  E  K  M  I  E  N  L  R  Q  T  E  L  K  L  T    296
 961 TGGGAAGAAGCAATGGAAAAAATGATTGAAAACTTAAGACAAACAGAACTGAAACTGACT

R  K  A  A  Y  V  R  Y  F  N  S  S  A  F  F  F  S  G  F  F    316
1021 CGGAAGGCAGCCTATGTGAGATACTTCAATAGCTCAGCCTTCTTCTTCTCAGGGTTCTTT

V  V  F  L  S  V  L  P  Y  A  L  I  K  G  I  I  L  R  K  I    336
1081 GTGGTGTTTTTATCTGTGCTTCCCTATGCACTAATCAAAGGAATCATCCTCCGGAAAATA

F  T  T  I  S  F  C  I  V  L  R  M  A  V  T  R  Q  F  P  W    356
1141 TTCACCACCATCTCATTCTGCATTGTTCTGCGCATGGCGGTCACTCGGCAATTTCCCTGG

A  V  Q  T  W  Y  D  S  L  G  A  I  N  K  I  Q  D  F  L  Q    376
1201 GCTGTACAAACATGGTATGACTCTCTTGGAGCAATAAACAAAATACAGGATTTCTTACAA

K  Q  E  Y  K  T  L  E  Y  N  L  T  T  T  E  V  V  M  E  N    396
1261 AAGCAAGAATATAAGACATTGGAATATAACTTAACGACTACAGAAGTAGTGATGGAGAAT

V  T  A  F  W  E  E  G  F  G  E  L  F  E  K  A  K  Q  N  N    416
1321 GTAACAGCCTTCTGGGAGGAGGGATTTGGGGAATTATTTGAGAAAGCAAAACAAAACAAT
```

FIG. 1B.

```
           N  N  R  K  T  S  N  G  D  D  S  L  F  F  S  N  F  S  L  L
1381     AACAATAGAAAAACTTCTAATGGTGATGACAGCCTCTTCTTCAGTAATTTCTCACTTCTT        436

G  T  P  V  L  K  D  I  N  F  K  I  E  R  G  Q  L  L  A  V
1441     GGTACTCCTGTCCTGAAAGATATTAATTTCAAGATAGAAAGAGGACAGTTGTTGGCGGTT        456

A  G  S  T  G  A  G  K  T  S  L  L  M  M  I  M  G  E  L  E
1501     GCTGGATCCACTGGAGCAGGCAAGACTTCACTTCTAATGATGATTATGGGAGAACTGGAG        476

P  S  G  K  I  K  H  S  G  R  I  S  F  C  S  Q  F  S  W
1561     CCTTCAGAGGGTAAAATTAAGCACAGTGGAAGAATTTCATTCTGTTCTCAGTTTTCCTGG        496

I  M  P  G  T  I  K  E  N  I  I  F  G  V  S  Y  D  E  Y  R
1621     ATTATGCCTGGCACCATTAAAGAAAATATCATCTTTGGTGTTTCCTATGATGAATATAGA        516

Y  R  S  V  I  K  A  C  Q  L  E  E  D  I  S  K  F  A  E  K
1681     TACAGAAGCGTCATCAAGCATGCCAACTAGAAGAGGACATCTCCAAGTTTGCAGAGAAA        536

D  N  I  V  L  G  E  G  G  I  T  L  S  G  G  Q  R  A  R  I
1741     GACAATATAGTTCTTGGAGAAGGTGGAATCACACTGAGTGGAGGTCAACGAGCAAGAATT        556

S  L  A  R  A  V  Y  K  D  A  D  L  Y  L  L  D  S  P  F  G
1801     TCTTTAGCAAGAGCAGTATACAAAGATGCTGATTTGTATTTATTAGACTCTCCTTTTGGA        576

Y  L  D  V  L  T  E  K  E  I  F  E  S  C  V  C  K  L  M  A
1861     TACCTAGATGTTTTAACAGAAAAAGAAATATTTGAAAGCTGTGTCTGTAAACTGATGGCT        596

N  K  T  R  I  L  V  T  S  K  M  E  H  L  K  K  A  D  K  I
1921     AACAAAACTAGGATTTTGGTCACTTCTAAAATGGAACATTTAAAGAAAGCTGACAAAATA        616

L  I  L  H  E  G  S  S  Y  F  Y  G  T  F  S  E  L  Q  N  L
1981     TTAATTTTGCATGAAGGTAGCAGCTATTTTTATGGGACATTTTCAGAACTCCAAAATCTA        636

Q  P  D  F  S  S  K  L  M  G  C  D  S  F  D  Q  F  S  A  E
2041     CAGCCAGACTTTAGCTCAAAACTCATGGGATGTGATTCTTTCGACCAATTTAGTGCAGAA        656

R  R  N  S  I  L  T  E  T  L  H  R  F  S  L  E  G  D  A  P
2101     AGAAGAAATTCAATCCTAACTGAGACCTTACACCGTTTCTCATTAGAAGGAGATGCTCCT        676

V  S  W  T  E  T  K  K  Q  S  F  K  Q  T  G  E  F  G  E  K
2161     GTCTCCTGGACAGAAACAAAAAAACAATCTTTTAAACAGACTGGAGAGTTTGGGGAAAAA        696

R  K  N  S  I  L  N  P  I  N  S  I  R  K  F  S  I  V  Q  K
2221     AGGAAGAATTCTATTCTCAATCCAATCAACTCTATACGAAAATTTTCCATTGTGCAAAAG        716

T  P  L  Q  M  N  G  I  E  E  D  S  D  E  P  L  E  R  R  L
2281     ACTCCCTTACAAATGAATGGCATCGAAGAGGATTCTGATGAGCCTTTAGAGAGAAGGCTG        736

S  L  V  P  D  S  E  Q  G  E  A  I  L  P  R  I  S  V  I  S
2341     TCCTTAGTACCAGATTCTGAGCAGGGAGAGGCGATACTGCCTCGCATCAGCGTGATCAGC        756

T  G  P  T  L  Q  A  R  R  R  Q  S  V  L  N  L  M  T  H  S
2401     ACTGGCCCCACGCTTCAGGCACGAAGGAGGCAGTCTGTCCTGAACCTGATGACACACTCA        776

V  N  Q  G  Q  N  I  H  R  K  T  T  A  S  T  R  K  V  S  L
2461     GTTAACCAAGGTCAGAACATTCACCGAAAGACAACAGCATCCACACGAAAAGTGTCACTG        796

A  P  Q  A  N  L  T  E  L  D  I  Y  S  R  R  L  S  Q  E  T
2521     GCCCCTCAGGCAAACTTGACTGAACTGGATATATATTCAAGAAGGTTATCTCAAGAAACT        816
```

FIG. IC.

```
            G  L  E  I  S  E  E  I  N  E  E  D  L  K  E  C  F  F  D  D    836
2581  GGCTTGGAAATAAGTGAAGAAATTAACGAAGAAGACTTAAAGGAGTGCTTTTTTGATGAT

M  E  S  I  P  A  V  T  T  W  N  T  Y  L  R  Y  I  T  V  H    856
2641  ATGGAGAGCATACCAGCAGTGACTACATGGAACACATACCTTCGATATATTACTGTCCAC

K  S  L  I  F  V  L  I  W  C  L  V  I  F  L  A  E  V  A  A    876
2701  AAGAGCTTAATTTTTGTGCTAATTTGGTGCTTAGTAATTTTTCTGGCAGAGGTGGCTGCT

S  L  V  V  L  W  L  L  G  N  T  P  L  Q  D  K  G  N  S  T    896
2761  TCTTTGGTTGTGCTGTGGCTCCTTGGAAACACTCCTCTTCAAGACAAAGGGAATAGTACT

H  S  R  N  N  S  Y  A  V  I  I  T  S  T  S  S  Y  Y  V  F    916
2821  CATAGTAGAAATAACAGCTATGCAGTGATTATCACCAGCACCAGTTCGTATTATGTGTTT

Y  I  Y  V  G  V  A  D  T  L  L  A  M  G  F  F  R  G  L  P    936
2881  TACATTTACGTGGGAGTAGCCGACACTTTGCTTGCTATGGGATTCTTCAGAGGTCTACCA

L  V  H  T  L  I  T  V  S  K  I  L  H  H  K  M  L  H  S  V    956
2941  CTGGTGCATACTCTAATCACAGTGTCGAAAATTTTACACCACAAAATGTTACATTCTGTT

L  Q  A  P  M  S  T  L  N  T  L  K  A  G  I  L  N  R  F    976
3001  CTTCAAGCACCTATGTCAACCCTCAACACGTTGAAAGCAGGTGGGATTCTTAATAGATTC

S  K  D  I  A  I  L  D  D  L  L  P  L  T  I  F  D  F  I  Q    996
3061  TCCAAAGATATAGCAATTTTGGATGACCTTCTGCCTCTTACCATATTTGACTTCATCCAG

L  L  L  I  V  I  G  A  I  A  V  V  A  V  L  Q  P  Y  I  F   1016
3121  TTGTTATTAATTGTGATTGGAGCTATAGCAGTTGTCGCAGTTTTACAACCCTACATCTTT

V  A  T  V  P  V  I  V  A  F  I  M  L  R  A  Y  F  L  Q  T   1036
3181  GTTGCAACAGTGCCAGTGATAGTGGCTTTTATTATGTTGAGAGCATATTTCCTCCAAACC

S  Q  Q  L  K  Q  L  E  S  E  G  R  S  P  I  F  T  H  L  V   1056
3241  TCACAGCAACTCAAACAACTGGAATCTGAAGGCAGGAGTCCAATTTTCACTCATCTTGTT

T  S  L  K  G  L  W  T  L  R  A  F  G  R  Q  P  Y  F  E  T   1076
3301  ACAAGCTTAAAAGGACTATGGACACTTCGTGCCTTCGGACGGCAGCCTTACTTTGAAACT

L  F  H  K  A  L  N  L  H  T  A  N  W  F  L  Y  L  S  T  L   1096
3361  CTGTTCCACAAAGCTCTGAATTTACATACTGCCAACTGGTTCTTGTACCTGTCAACACTG

R  W  F  Q  M  R  I  E  M  I  F  V  I  F  F  I  A  V  T  F   1116
3421  CGCTGGTTCCAAATGAGAATAGAAATGATTTTTGTCATCTTCTTCATTGCTGTTACCTTC

I  S  I  L  T  T  G  E  G  E  G  R  V  G  I  I  L  T  L  A   1136
3481  ATTTCCATTTTAACAACAGGAGAAGGAGAAGGAAGAGTTGGTATTATCCTGACTTTAGCC

M  N  I  M  S  T  L  Q  W  A  V  N  S  S  I  D  V  D  S  L   1156
3541  ATGAATATCATGAGTACATTGCAGTGGGCTGTAAACTCCAGCATAGATGTGGATAGCTTG

H  R  S  V  S  R  V  F  K  F  I  D  M  P  T  E  G  K  P  T   1176
3601  ATGCGATCTGTGAGCCGAGTCTTTAAGTTCATTGACATGCCAACAGAAGGTAAACCTACC

K  S  T  K  P  Y  K  N  G  Q  L  S  K  V  M  I  I  E  N  S   1196
3661  AAGTCAACCAAACCATACAAGAATGGCCAACTCTCGAAAGTTATGATTATTGAGAATTCA

H  V  K  K  D  D  I  W  P  S  G  G  Q  H  T  V  K  D  L  T   1216
3721  CACGTGAAGAAAGATGACATCTGGCCCTCAGGGGGCCAAATGACTGTCAAAGATCTCACA

A  K  Y  T  E  G  G  N  A  I  L  E  N  I  S  Y  S  I  S  P   1236
3781  GCAAAATACACAGAAGGTGGAAATGCCATATTAGAGAACATTTCCTTCTCAATAAGTCCT

G  Q  R  V  G  L  L  G  R  T  G  S  G  K  S  T  L  L  S  A   1256
3841  GGCCAGAGGGTGGGCCTCTTGGGAAGAACTGGATCAGGGAAGAGTACTTTGTTATCAGCT
```

FIG. ID.

```
          F  L  R  L  L  N  T  E  G  E  I  Q  I  D  G  V  S  W  D  S    1276
3901  TTTTTGAGACTACTGAACACTGAAGGAGAAATCCAGATCGATGGTGTGTCTTGGGATTCA

I  T  L  Q  Q  W  R  K  A  F  G  V  I  P  Q  K  V  F  I  F    1296
3961  ATAACTTTGCAACAGTGGAGGAAAGCCTTTGGAGTGATACCACAGAAAGTATTTATTTTT

S  G  T  F  R  K  N  L  D  P  Y  E  Q  W  S  D  Q  E  I  W    1316
4021  TCTGGAACATTTAGAAAAAACTTGGATCCCTATGAACAGTGGAGTGATCAAGAAATATGG

K  V  A  D  E  V  G  L  R  S  V  I  E  Q  F  P  G  K  L  D    1336
4081  AAAGTTGCAGATGAGGTTGGGCTCAGATCTGTGATAGAACAGTTTCCTGGGAAGCTTGAC

F  V  L  V  D  G  G  C  V  L  S  H  G  H  K  Q  L  H  C  L    1356
4141  TTTGTCCTTGTGGATGGGGGCTGTGTCCTAAGCCATGGCCACAAGCAGTTGATGTGCTTG

A  R  S  V  L  S  K  A  K  I  L  L  L  D  E  P  S  A  H  L    1376
4201  GCTAGATCGTTCTCAGTAAGGCGAAGATCTTGCTGCTTGATGAACCCAGTGCTCATTTG

D  P  V  T  Y  Q  I  I  R  R  T  L  K  Q  A  F  A  D  C  T    1396
4261  GATCCAGTAACATACCAAATAATTAGAAGAACTCTAAAACAAGCATTTGCTGATTGCACA

V  I  L  C  E  H  R  I  E  A  M  L  E  C  Q  Q  F  L  V  I    1416
4321  GTAATTCTCTGTGAACACAGGATAGAAGCAATGCTGGAATGCCAACAATTTTTGGTCATA

E  E  N  K  V  R  Q  Y  D  S  I  Q  K  L  L  N  E  R  S  L    1436
4381  GAAGAGAACAAAGTGCGGCAGTACGATTCCATCCAGAAACTGCTGAACGAGAGGAGCCTC

F  R  Q  A  I  S  P  S  D  R  V  K  L  F  P  H  R  N  S  S    1456
4441  TTCCGGCAAGCCATCAGCCCCTCCGACAGGGTGAAGCTCTTTCCCCACCGGAACTCAAGC

K  C  K  S  K  P  Q  I  A  A  L  K  E  E  T  E  E  E  V  Q    1476
4501  AAGTGCAAGTCTAAGCCCCAGATTGCTGCTCTGAAAGAGGAGACAGAAGAAGAGGTGCAA

D  T  R  L  -                                                  1480
4561  GATACAAGGCTTTAGAGAGCAGCATAAATGTTGACATGGGACATTTGCTCATGGAATTGG
4621  AGCTCGTGGGACAGTCACCTCATGGAATTGGAGCTCGTGGAACAGTTACCTCTGCCTCAG
4681  AAAACAAGGATGAATTAAGTTTTTTTTTAAAAAAGAAACATTTGGTAAGGGGAATTGAGG
4741  ACACTGATATGGGTCTTGATAAATGGCTTCCTGGCAATAGTCAAATTGTGTGAAAGGTAC
4801  TTCAAATCCTTGAAGATTTACCACTTGTGTTTTGCAAGCCAGATTTTCCTGAAAACCCTT
4861  GCCATGTGCTAGTAATTGGAAAGGCAGCTCTAAATGTCAATCAGCCTAGTTGATCAGCTT
4921  ATTGTCTAGTGAAACTCGTTAATTTGTAGTGTTGGAGAAGAACTGAAATCATACTTCTTA
4981  GGGTTATGATTAAGTAATGATAACTGGAAACTTCAGCGGTTTATATAAGCTTGTATTCCT
5041  TTTTCTCTCCTCTCCCATGATGTTTAGAAACACAACTATATTGTTTGCTAAGCATTCCA
5101  ACTATCTCATTTCCAAGCAAGTATTAGAATACCACAGGAACCACAAGACTGCACATCAAA
5161  ATATGCCCCATTCAACATCTAGTGAGCAGTCAGGAAAGAGAACTTCCAGATCCTGGAAAT
5221  CAGGGTTAGTATTGTCCAGGTCTACCAAAAATCTCAATATTTCAGATAATCACAATACAT
5281  CCCTTACCTGGGAAAGGGCTGTTATAATCTTTCACAGGGGACAGGATGGTTCCCTTGATG
5341  AAGAAGTTGATATGCCTTTTCCCAACTCCAGAAAGTGACAAGCTCACAGACCTTTGAACT
5401  AGAGTTTAGCTGGAAAAGTATGTTAGTGCAAATTGTCACAGGACAGCCCTTCTTTCCACA
5461  GAAGCTCCAGGTAGAGGGTGTGTAAGTAGATAGGCCATGGGCACTGTGGGTAGACACACA
5521  TGAAGTCCAAGCATTTAGATGTATAGGTTGATGGTGGTATGTTTCAGGCTAGATGTATG
5581  TACTTCATGCTGTCTACACTAAGAGAGAATGAGAGACACACTGAAGAAGCACCAATCATG
5641  AATTAGTTTTATATGCTTCTGTTTTATAATTTTGTGAAGCAAATTTTTTCTCTAGGAAA
5701  TATTTATTTTAATAATGTTTCAAACATATATTACAATGCTGTATTTTAAAAGAATGATTA
5761  TGAATTACATTTGTATAAAATAATTTTTATATTTGAAATATTGACTTTTTATGGCACTAG
5821  TATTTTTATGAAATATTATGTTAAAACTGGGACAGGGGAGAACCTAGGGTGATATTAACC
5881  AGGGGCCATGAATCACCTTTTGGTCTGGAGGGAAGCCTTGGGCTGATCGAGTTGTTGCC
5941  CACAGCTGTATGATTCCCAGCCAGACACAGCCTCTTAGATGCAGTTCTGAAGAAGATGGT
6001  ACCACCAGTCTGACTGTTTCCATCAAGGGTACACTGCCTTCTCAACTCCAAACTGACTCT
6061  TAAGAAGACTGCATTATATTTATTACTGTAAGAAAATATCACTTGTCAATAAAATCCATA
6121  CATTTGTGT(A)n
```

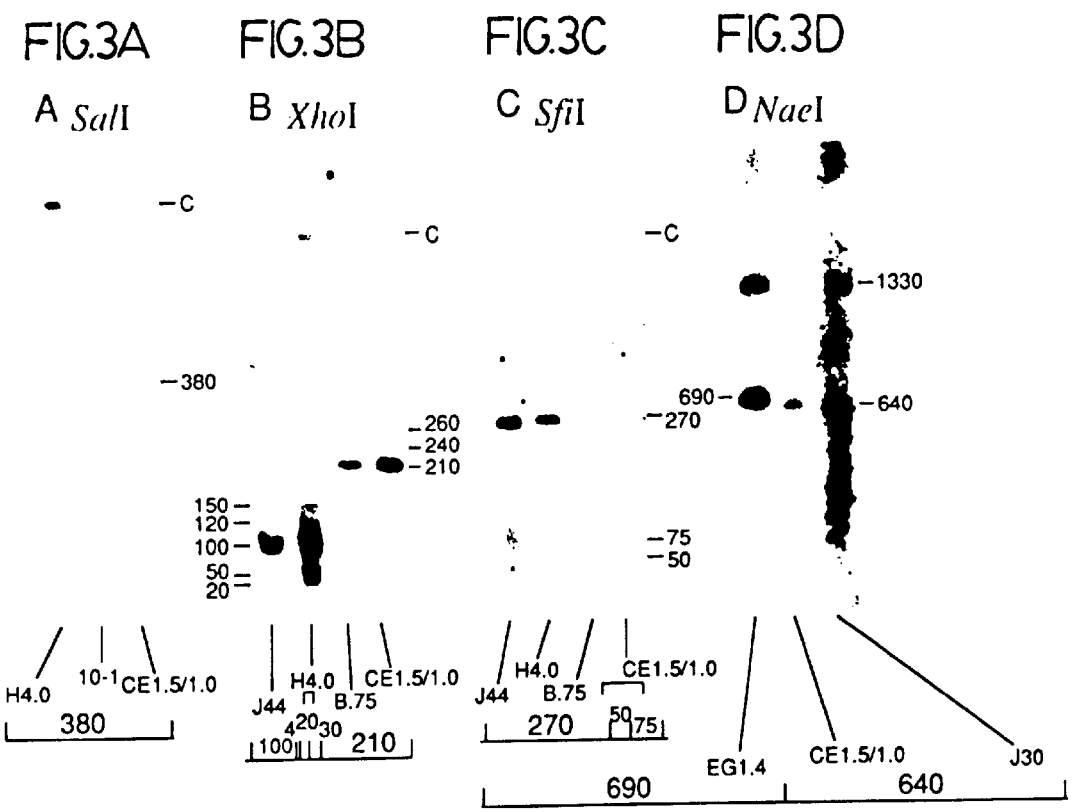

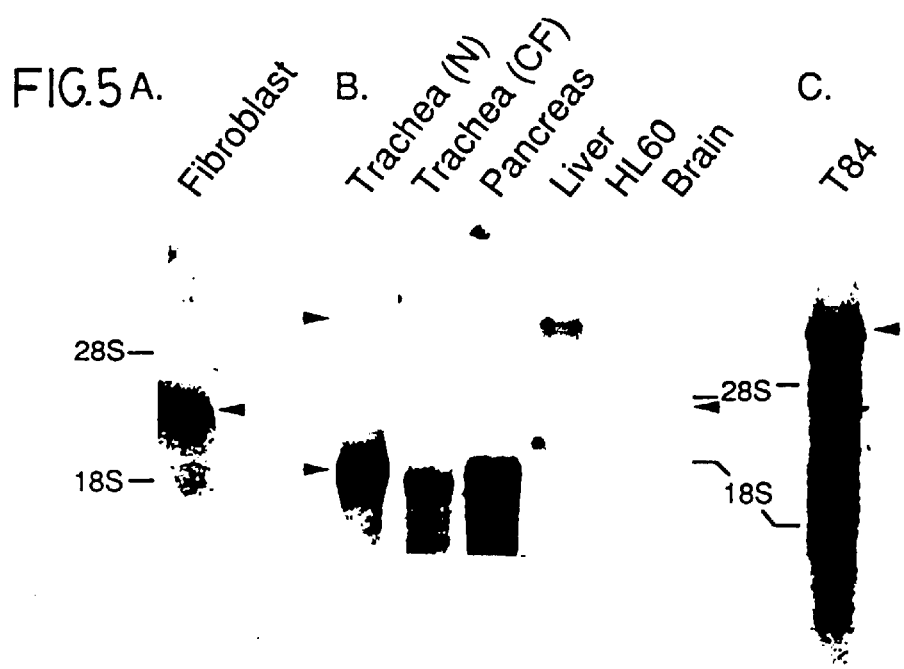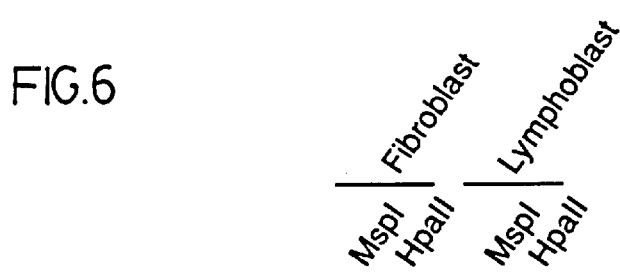

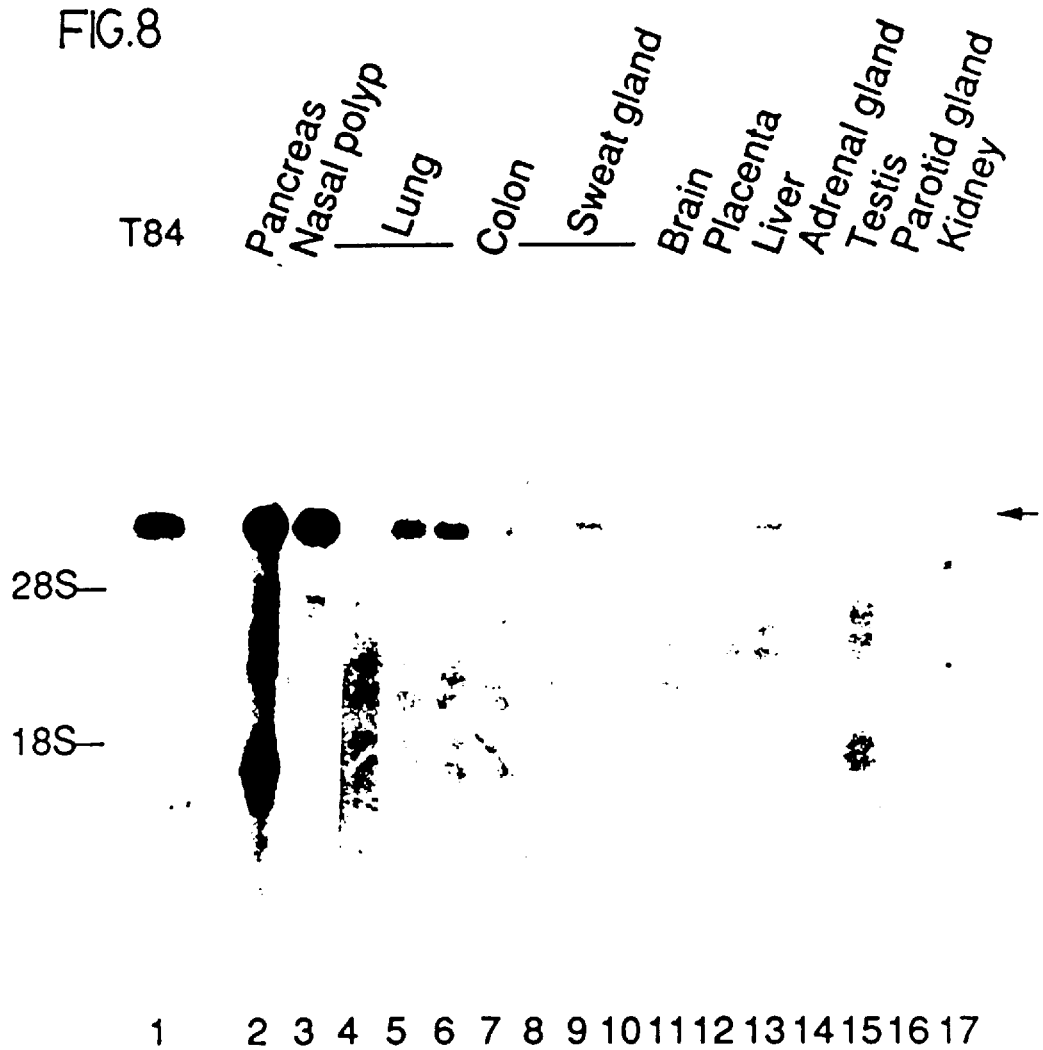

FIG.10A

Marker  Primer extension product

630

310
281
271
234
                — 216
194 —

118 — ≡
            — 100

75   —

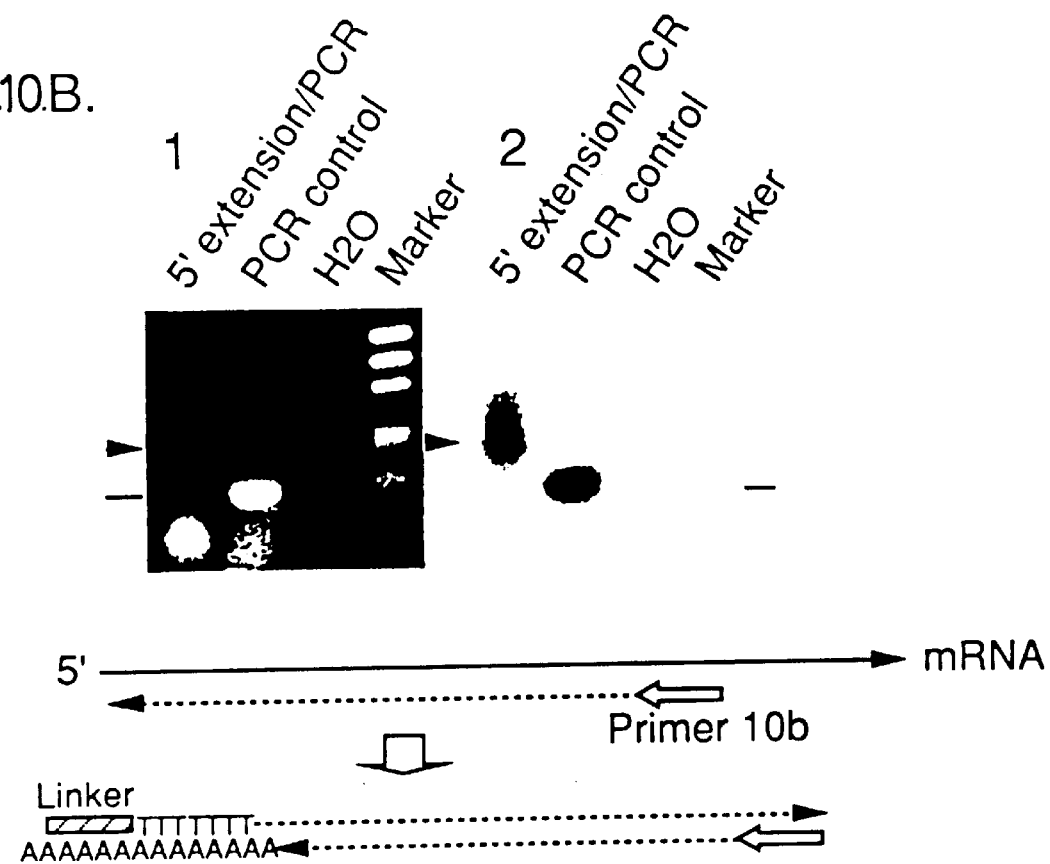
FIG.10.B.

FIG.10C.
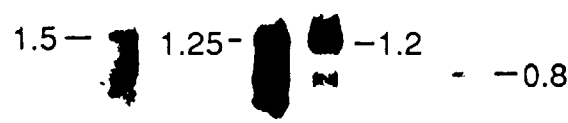
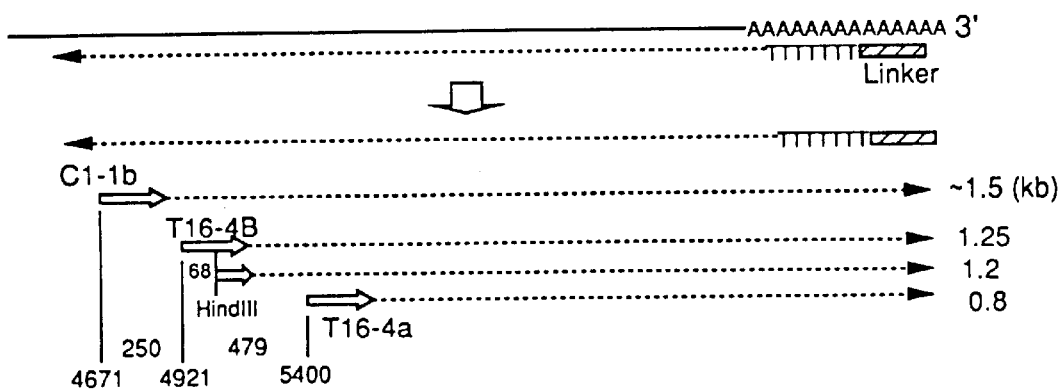

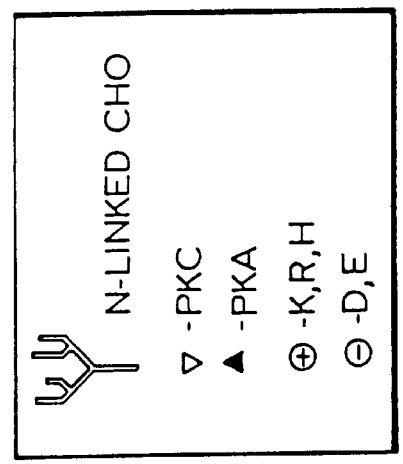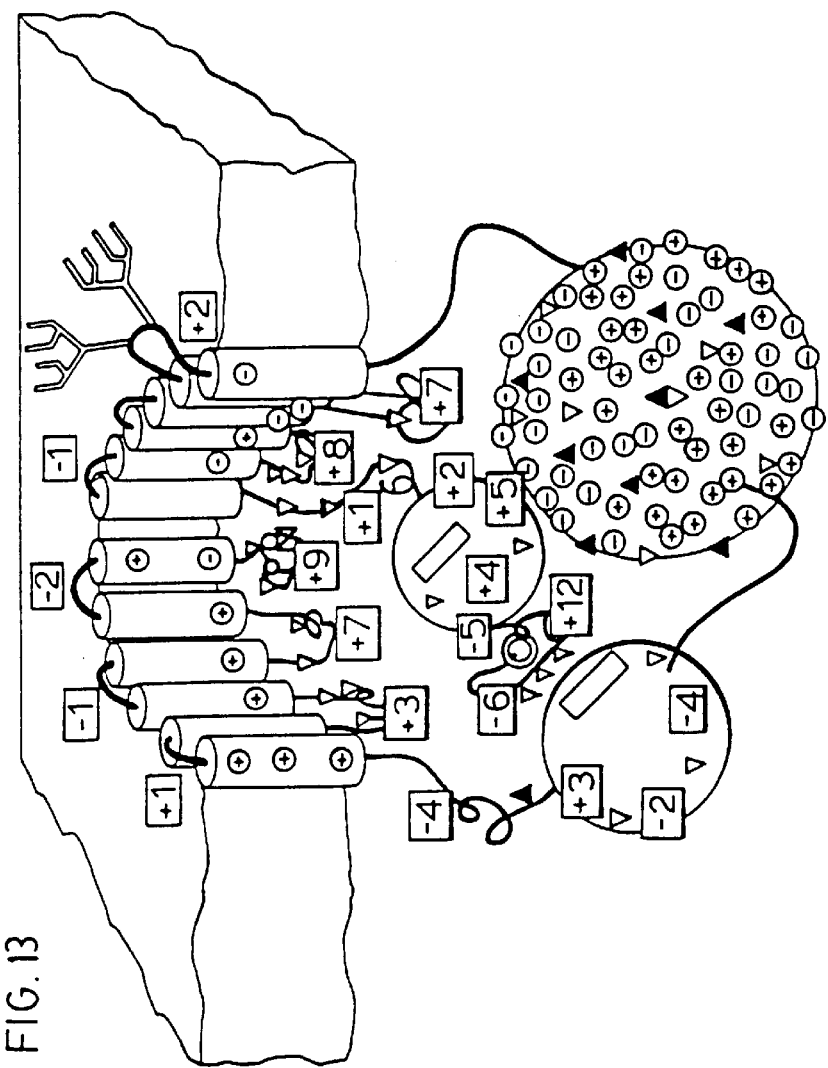
FIG. 13

FIG. 15A.

```
CFTR    (N)  FSLLGTPVLKDINFKIERGQLLAVAGSTGAGKTSLLMMIMG    ISFCSQFSWIMPGTIK-ENIIFGVSYD
CFTR    (C)  YTEGGNAILENISFSISPGQRVGLLGRTGSGKSTLLSAFLR    DSITLQQWRKAFGVIPQKVFIFSGTFR
hmdr1   (N)  PSRKEVKILKGLNLKVQSGQTVALVGNSGCGKSTTVQLMQR    IGVVSQEPVLFATTI-AENIRYGRENV
hmdr1   (C)  PTRPDIPVLQGLSLEVKKGQTLALVGSSGCGKSTVVQLLER    LGIVSQEPILFDCSI-AENIAYGDNSR
mmdr1   (N)  PSRSEVQILKGLNLKVKSGQTVALVGNSGCGKSTTVQLMQR    IGVVSQEPVLFATTI-AENIRYGREDV
mmdr1   (C)  PTRPNIPVLQGLSLEVKKGQTLALVGSSGCGKSTVVQLLER    LGEVSQEPILFDCSI-AENIAYGDNSR
mmdr2   (N)  PSRANIKILKGLNLKVKSGQTVALVGNSGCGKSTTVQLLQR    IGVVSQEPVLSFTTI-AENIRYGRGNV
mmdr2   (C)  PTRANVPVLQGLSLEVKKGQTLALVGSSGCGKSTVVQLLER    LGIVSQEPILFDCSI-AENIAYGDNSR
pfmdr   (N)  DTRKDVEIYKDLSFTLLKEGKTYAFVGESGCGKSTILKLIE    IGVVSQDPLLFSNSI-KNNIKYSLYSL
pfmdr   (C)  ISRPNVPIYKNLSFTCDSKKTTAIVGETGSGKSTFMNLLLR    FSIVSQEPMLFNMSI-YENIKFGREDA
STE6    (N)  PSRPSEAVLKNVSLNFSAGQFTFIVGKSGSGKSTLSNLLLR    ITVVEQRCTLFNDTL-RKNILLGSTDS
STE6    (C)  PSAPTAFVYKNMNFDMFCGQTLGIIGESGTGKSTLVLLLTK    ISVVEQKPLLFNGTI-RDNLTYGLQDE
hlyB         YKPDSPVILDNINISIKQGEVIGIVGRSGSGKSTLIKLIQR    VGVVLQDNVLLNRSI-IDNISLAPGMS
White        IPAPRKHLLKNVCGVAYPGELLAVMGSSGAGKTTLLNALAF    RCAYVQQDDLFIGLIAREHLIFQAMVR
MbpX         KSLGNLKILDRVSLYVPKFSLIALLGPSGSGKSSLLRILAG    MSFVFQHYALFKHMTVYENISFGLRLR
BtuD         QDVAESTRLGPLSGEVRAGRILHLVGPNGAGKSTLLARIAG    YLSQQTPPFATPVWHYLTLHQHDKTR
PstB         FYYGKFHALKNINLDTAKNQVTAFIGPSGCGKSTLLRTFNK    VGMVFQKPTPFPMSI-YDNIAFGVRLF
hisP         RRYGGHEVLKGVSLQARAGDVISIIGSSGSGKSTFLRCINF    GIMVFQHFNLWSHMTVLENVMEAPIQV
malK         KAWGEVVSKDINIDIHEGEFVVFVGPSGCGKSTLLRMIAG    VGMVFQSYALYPHLSVAENMSFGLKPA
oppD         TPDGDVTAVNDLNFTLRAGETLGIVGESGSGKSQTAFALMG    ISMIFQDPMTSLNPYMRVGEQLMEVLM
oppF         QPPKTLKAVDGVTLRLYEGETLGVVGESGCGKSTFARAIIG    IQMIFQDPLASLNPRMTIGEIIAEPLR
RbsA    (N)  KAVPGVKALSGAALNVYPGRVMALVGENGAGKSTMMKVLTG    AGIIHQELNLIPQLTIAENIFLGREFV
RbsA    (C)  VDNLCGPGVNDVSFTLRKGEILGVSGLMGAGRTELMKVLYG    ISEDRKRDGLVLGMSVKENMSLTALRY
UvrA         LTGARGNNLKDVTLTLPVGLFTCITGVSGSGKSTLINDTLF    TYTGVFTPVRELFAGVPESRARGYTPG
NodI         KSYGGKIVVNDLSFTIAAGECFGLLGPNGAGKSTIIRMILG    IGIVSQEDNLDLEFTVRENLLVYGRYF
FtsE         AYLGGRQALQGVTFHMQPGEMAFLTGHSGAGKSTLLKLICG    IGMIFQDHHLLMDRTVYDNVAIPLIIA
```

FIG. 15B.

```
CFTR   (N)  GEGGITLSGGQRARISLARAVYKDADLYLLLDSPFGYLDVLTEK
CFTR   (C)  VDGGCVLSHGHKQLMCLARSVLSKAKILLLDEPSAHLDPVTYQ
hmdr1  (N)  GERGAQLSGGQKQRIAIARALVRNPKILLLDEATSALDTESEA
hmdr1  (C)  GDKGTLLSGGQKQRIAIARALVRQPHILLLDEATSALDTESEK
mmdr1  (N)  GERGAQLSGGQKQRIAIARALVRNPKILLLDEATSALDTESEA
mmdr1  (C)  GDKGTQLSGGQKQRIAIARALVRQPHILLLDEATSALDTESEK
mmdr2  (N)  GDRGAQLSGGQKQRIAIARALVRNPKILLLDEATSALDTESEA
mmdr2  (C)  GDKGTQLSGGQKQRIAIARALIRQPRVLLLDEATSALDTESEK
pfmdr  (N)  GSNASKLSGGQKQRISIARAIMRNPKILILDEATSSLDNKSEY
pfmdr  (C)  PYGKS-LSGGQKQRIAIARALLREPKILLLDEATSSLDSNSEK
STE6   (N)  GTGGVTLSGGQQQRVAIARAFIRDTPILFLDEAVSALDIVHRN
STE6   (C)  RIDTTLLSGGQAQRLCIARALLRKSKILILDECTSALDSVSSS
hlyB        GEQGAGLSGGQRQRIAIARALVNNPKILIFDEATSALDYASEH
White       PGRVKGLSGGERKRLAFASEALTDPPLLICDEPTSGLDSFTAH
MbpX        FEYPAQLSGGQKQRVALARSLAIQPDLLL-DEPFGALDGELRR
BtuD        GRSTNQLSGGEWQRVRLAAVVLQITLLLLDEPMNSLDVAQQSA
PstB        HQSGYSLSGGQQQRLCIARGIAIRPEVLLLDEPCSALDPISTG
hisP        GKYPVHLSGGQQQRVSIARALAMEPDVLLFDEPTSALDPELVG
malK        DRKPKALSGGQRQRVAIGRTLVAEPSVFLLDEPLSNLDAALRV
oppD        KMYPHEFSGGMRQRVMIAMALLCRPKLLIADEPTTALDVTVQA
oppF        NRYPHEFSGGQCQRIGIARALILEPKLIICDDAVSALDVSIQA
RbsA   (N)  DKLVGDLSIGDQQMVEIAKVLSFESKVIIMDEPTCALIDTETE
RbsA   (C)  EQAIGLLSGGNQQKVAIARGLMTRPKVLILDEPTPGVDVGAKK
UvrA        GQSATTLSGGEAQRVKLARELSKRGLYILDEPTTGLHFADIQQ
NodI        NTRVADLSGGMKRRLTLAGALINDPQLLILDEPTTGLDPHARH
FtsE        KNFPIQLSGGEQQRVGIARAVVNKPAVLLADEPTGNLDDALSE
```

FIG. 18A.

```
CCACCCTTGGAGTTCACTCACTAACCTCAAACTAATAAGCTTGTTCTTTTCCGACACGAAGGCCTAAGTAAATGCATCAGACCCACA
CTGCCGCGGAACTTTTCGGCTCTCTAAGGCTGTATTTGATATACGAAAGGCACATTTCCTTCCTTCAAAATGCACCTTGCAAACGTAACAGGGAC
CCGACTAGGATCATCGGGAAAGGAGGAGGCCAGGCTCCGGGAAGCTGGTGCAGCGGTTCTCTGGCAGCGGCAAGCTCCTGGCTCTGCCGTCTGGTGCGACCTGTCGCC
GGCTCTAGGAAGCTCTCCGGGAGCCGTTCTCTGTCCTCCAGGTGCCAACTGACCTAAAGAGAGGCCCGACTGTCGCC
ACCTGGGGATGGGCCTGTGCTGGGCAGGACACGCGACCTGGGCGAGGTGCTGGGTGAGAAGCCGCTAGAGCAAATTTGGG
CGGGGCGGGCGAAGGAGGAGAGAAGGAGCCAGGTGCTCGGCGGGGAGGGGTGCTCGCAGTGAAGCCGTAGGGGTGGGTGGGGGATT
CCGGACCAGGCAGCACTCGGCTTTAACCTGGCAGTGAGGCGAAAGAGCAAAGGCACCCAGAGTAGTAGGTCTTTGGCATTAGGAGCTTGAGCCCAGACGGCCC
GAAGCAATGACATCACGCAGGTCAGAGAAAAAGGGTTGAGCGGTCAGAGAAAAAGGGTTGAGCG
    exon 1    Met Gln Arg Ser Pro Leu Glu Lys Ala Ser Val Val Ser Lys Leu Phe Phe Se
TAGCAGGCACCCCAGCGCCCAGACC ATG CAG AGG TCG CCT CTG GAA AAG GCC AGC GTT GTC TCC AAA CTT TTT TTC AG
GTGAGAAGGTGGCCAACCGAGCTTCGGAAAGACACGTGCCACGAAAGAGGAGGCCGTGTATGGGTTGGGGTAAAGGAATAAGCAGTTTTA
AAAAGATGCGCTATCATTGTTTGAAAGAAATGTGGGTATTGTAGAATAAACAGAATAAAACAGAATAAAGAGATGAAGAATGAACTGAAGCTGAT
TGAATAGAGAAGCCACACTGGTTAGAATCTGAAAAGTTAGAATCTCAAGTACGCTACTATGCACACTGTTGTCTTCTTGGCACATACAGGTGCCATCCTG
AAATACTGTTAATAAGTAGTCCAGAAAACATTTCTGACTAAGTTATGTTTATTGGTTTCCCCTCATCCGTAAAAATTTGAAAGCTTAAAGTATTTTATTGTTATGAG
CATATAGTAAGTGCTCAGAAAACATTTCTGACTAAGTATTTCACAGTAATGATTCTTCAAAATGAAGCACATTTAATAAATGATGAAAATGTTACTTCACAAGCTA
ACTGGATATATCTAGTATTGACAAGAATAGATACCGAAGTTATATCCAACTGACATTATATTCATAAGCAATTCATAGCCTAATGTGATGAGCCACAGAAGCTT...
AAACCATACTATTATCCCTCCCAATCCCTTGACAAGTGACAGTCACATTAGTTGACAAATATTGATGTTTATACAGGTGTAGCCTGTAAGAGATGA
AGCCTGGTATTTATAGAAATTGACTTATTTATTCTACATGTGCATATTTTCATAAAGTTGATAGTATCAGATTCCAAATCT
    exon 2                        r Trp Thr Arg Pro Ile Leu Arg Lys Gly Tyr Arg Gln
GTATGGAGACCAAATCAAGTGAATATCTGTTCCTCCCTCTCTTATTTAG C TGG ACC AGA CCA ATT TTG AGG AAA GGA TAC AGA CAG
Arg Leu Glu Leu Ser Asp Ile Tyr Gln Ile Pro Ser Val Asp Ser Ala Asp Asn Leu Ser Glu Lys Leu Glu Ar
CGC CTG GAA TTG TCA GAC ATA TAC CAA ATC CCT TCT GTT GAT TCT GCT GAC AAT CTA TCT GAA AAA TTG GAA AG G
TATGTTCATGTACATGTTTAGTTGAAGAGAAGAACCAAACATATTAGAAGACAAATATTTAATTAGAAGACAAACATATTATATAGTTAATTCTTATATTAA
AAATAGGAGCCAAGTATGTGGTCTAATGCCTGTAATCCAACTATTGGAGGCCAAGAGATGAGAGATGCTTGAGACCAGGAGTTGCTTGAGACCAGGAGTTGCTTGAGAGCTTGT...
GCAACATAGCAAGATGTTATCTCTACACAAAATAAAAAAGTTAGCTGGAATGGTAGTGCATGCTTGTA
```

FIG. 18B.

```
..........................................................................
AGGAATCGCCAGATATCGGCTGAGTCGTTGGTGTTGTATGGTCTCCATGAGATTTGTCTCTATAATACTTGGTTAATCTCCTTGGATATACTTGTG
                                                              exon 3     g Glu Trp Asp
                                                                           GAA TGG GAT
TGAATCAACTATGTTAAGGAATAGGACACTAAATATTGCACATGCAACTAAACTATTGGTCCCACTTTTATTCTTTTGCAG A GAA TGG GAT
Arg Glu Ala Leu Ser Lys Lys Asn Pro Lys Leu Ile Asn Ala Leu Arg Arg Cys Phe Phe Trp Arg Phe Met Phe
AGA GAG GCT CTG GCT TCA AAG AAA AAT CCT AAA CTC ATT AAT GCC CTT CGG CGA TGT TTT TTC TGG AGA TTT ATG TTC
Tyr Gly Ile Phe Leu Tyr Leu Gly
TAT GGA ATC TTT TTA TAT TTA GGG GTAAGGATCTCATTGTACATTCATTATGTATCACATAATCTAGTAAGGATAAGTAA.........
CTACGAAATCTGGTGAATAGTGTAAAAATATAAAGTGTCTCCCACTGTGCTATAACAAATCCCAGTCTTATTCAAAGTACCAAGATATTG
..........................................................................
CCACTATTCACTGTTAACTTAAATACCTCATATGTAACTGTCTCCCCACTGTGCTATAACAAATCCCAGTCTTATTCAAAGTACCAAGATATTG
AAATAGTGCTAAGAGTTCACATAGTGTAAGAGCTGAGCTGGATGACCCTCTATATAAACTCATTTAAGTCCCTCTAAGATGAAAGTCTTGTGTTGAAATTCTCAGGGT
                                      exon 4         Glu Val Thr Lys Ala Val Gln Pro Leu Leu Gly
                                                      GAA GTC ACC AAA GCA GTA CAG CCT CTC TTA CTG GGA
ATTTATGAGAATAAATGAAATTTAATTCTCTGTTTTCCCTTTGTAG GAA GTC ACC AAA GCA GTA CAG CCT CTC TTA CTG GGA
Arg Ile Ile Ala Ser Tyr Asp Pro Asp Asn Lys Glu Glu Arg Ser Ile Ala Ile Tyr Leu Gly Ile Gly Leu Cys
AGA ATC ATA GCT TCC TAT GAC CCG GAT AAC AAG GAG GAA CGC TCT ATC GCG ATT TAT CTA GGC ATA GGC TTA TGC
Leu Leu Phe Ile Val Arg Thr Leu Leu His Pro Ala Ile Phe Gly Leu His His Ile Gly Met Gln Met Arg
CTT CTC TTT ATT GTG AGG ACA CTG CTC CTA CAC CCA GCC ATT TTT GGC CTT CAT CAC ATT GGA ATG CAG ATG AGA
Ile Ala Met Phe Ser Leu Ile Tyr Lys Lys
ATA GCT ATG TTT AGT TTG ATT TAT AAG AAG GTAATACTTCCTGCACAGGCCCCATGGCACATATATTCTGTATCGTACATGTTTAATG
TCATAAATAGGTAGTGAGCTGGTACAAGTAAGGATAAATGCTGAAATTAATTAATGCCAGGAATAATTAATGCTCTTAAT
..........................................................................
TATCCTTGATAATTAATTGACTTAAACTGATAATTATTGAGTATC.........
TAATTATTCTGCTAGAATGCTGGAAATAAAACAACTAGAAGCATGCCAGTATATATATTGACTGTTGAAAGAAACATTATGACTGAGAAGATAGTA
AGCTAGAATGAATAGAATAATTTCATTACCTTACTTAATAAGATGAATAACTGAATTAGTCATATATAATTTACTTATAATATATTTGTA
                                          exon 5       Thr Leu Lys Leu Ser Ser Arg Val Leu Asp Lys Ile Ser Ile
                                                        ACT TTA AAG CTG TCA AGC CGT GTT CTA GAT AAA ATA AGT ATT
TTTTGTTGTTGAAATTATCTAACTTTCCATTTTCTTTTAG ACT TTA AAG CTG TCA AGC CGT GTT CTA GAT AAA ATA AGT ATT
Gly Gln Leu Val Ser Leu Leu Ser Asn Leu Asn Lys Phe Asp Glu
GGA CAA CTT GTT AGT CTC CTT TCC AAC AAC CTG AAC AAA TTT GAT GAA GTATGTACCTATTGATTAATCTTTTAGGCACTATT
GTTATAAATTATACAACTGGAAAGGGAGTTTTCCTGGTCAGATAATAATAGTAATTAGTGTTAAGTCTTGCTCAGCTCTAGCTTCCCTATTCTGAAAC
TAAGAAAGGTCAATTGTATAGCAGAGCATTCTGGGGTCTGGTAGAACCACCCAACTCAAAGCACCTTAGCCTGTGTTGTTAATAAGATTTTCAAAAC
TTAATTCTTATCAGACCTTGCTTCTTTTAAAC.........
```

FIG. 18C.

```
............
GACATGATACTTAAGATGTCCAATCTGATTCCACTGATTCACTGATGAATAAAATGCTTAAAATGCACTGACTTGAAATTGTTTTTGGAAAACCGATTCTATG
TGTAGAATGTTTAAGCACATTGCTATGTCTGATGTAATGATTACCTAGATTTAGTGTGCTCAGAACCAGAAGTGTTTGATCATATAAGCTCCTTT
                                                     exon 6a    Gly Leu Ala
ACTTGCTTCTTTCATATATGATTGTTAGTTTCTAGGGGTGAAGATACAATGACACCTGTTTTGCTGTCTTTTATTTCCAG GGA CTT GCA
Leu Ala His Phe Val Trp Ile Ala Pro Leu Gln Val Ala Leu Leu Met Gly Leu Ile Trp Glu Leu Leu Gln Ala
TTG GCA CAT TTC GTG TGG ATC GCT CCT TTG CAA GTG GCA CTC CTC ATG GGG CTA ATC TGG GAG TTG TTA CAG GCG
Ser Ala Phe Cys Gly Leu Gly Phe Leu Ile Val Leu Ala Leu Phe Gln Ala Gly Leu Gly Arg Met Met Met Lys
TCT GCC TTC TGT GGA CTT GGT TTC CTG ATA GTC CTT GCC CTT TTT CAG GCT GGG CTA GGG AGA ATG ATG ATG AAG
Tyr Ar
TAC AG GTAGCAACCTATTTCATAACTTGAAAGTTTTAAAAATTATGTTTCAAAAAGCCCACTTAGTAAAACCAGACTGCTCTATGCATAGAACA
GTGATCTTCAGTGTCATTAAATTTTTTTTTTTTGAGACAGAGTCTAGATCTGTCACCCAGGCTGGAGTGCAGTGGCACGATCTTGGCTCACT
GCACTGCAACTTCTGCCTCCCAGGTTCAAGCAATTCTCCTGCCTCGGCCTCGGTGTCCACCACCACCCAGCTAATTTTG
TATTTAGAGAGACAGGGTTTCACCAGGTTGCCGCCGCCTAAAATACTTTTTGTAGATTGATGGTGTAAATATTACTTCTGTATCAATGGTACATTTTTACTTGTCAGTCTA
GAATTCTTATAAATATGTCAGTTCATTTGTAGATTATAAACAGGTAAAACATTTATGTACAGGATAAAACATTATGTGAATTAAAGGAATACCTAATT
TTTGTGTAGAGTTTATTAGCTTTATGCTTAGGATAAAGGCTTGACCTTGAGTTTGTGTTACAGATATCTGCTTTTTCATCTCTAAAATAGAGATACCACC
ATGACTTACACAAGTCACTGCTTAAGACATGCAGCACTATGGAATATGCCCATGTCTGTTGAATAAAATAATCGTGTTGAATAAGAATATGACTTAAAACCTTGACCAGTTCTAAAACAGTAGTTATTATTTTGT
GAATCCCAGATTGCATGTCCTCTAAGCATGACATAGCATATGGAATAGCAGCATTACTCAAGCCACTTCACCAGCGTCTGCCACATAGGAGGCATTACCAAACCTGAGCAGTTCTAATAGATAATTGACTGTTTTA
TACCATCTATTGATAATAAATAATGCCCATCTGTTGAATAAATATGCTGTAACTTAAAACCTTGAGCAGTTCTAATAGATAATTTGACTGTTTTTA
CTATTAGATTGATTGATTGATTACAG A GAT CAG AGA GCT GGG AAG ATC AGT GAT GAA AGA CTT GTG ATT ACC
        exon 6b     g Asp Gln Arg Ala Gly Lys Ile Ser Glu Arg Leu Val Ile Thr
Ser Glu Met Ile Glu Asn Ile Gln Ser Val Lys Ala Tyr Cys Trp Glu Ala Met Glu Lys Met Ile Glu Asn
TCA GAA ATG ATT GAA AAT ATC CAA TCT GTT AAG GCA TAC TGC TGG GAA GCA ATG GAA AAA ATG ATT GAA AAC
Leu Arg Gl
TTA AGA CA GTAAGTGTTGCAACAATCAAATGATTGCATTAAGTTCTGTCAATATTCATGCATTAGTTGCACAATTTGCACAAATTCTCACTTTCATGGGCGTGTAGTTTATGTAGTT
TTTGATGTTTGTGACAATCAAATGATTGCATTAAGTTCTGTCAATATTCATGCATTAGTTGCACAATTTGCACAAATTCTCACTTTCATGGGCGTGTAGTTTATGTAGTT
GGTCCAGGGTGTTATTTATGCTGCAAGTATATTATACTGATACGTTATTAAGAATTCCTACATATGTCACTCACTGCTCAATACATTATTCGTTA
AAAACAATTATCAAGATACTGAAGGCTATTGTAACTCACATGGAACTGGGAGAGTAATACAATTCTGAACCAAATAGATGA............
```

FIG. 18D.

```
...TTACAAGTACTACAAGCAAAACACTGTACTTCATTGTTCATTTCATATAAGTACTGAGGCCCAGAGAGATTAATAACATGCCAAGTCACA...
...CAGGTCATATGATGTGGAGCCAGTTAAAAATAGGCAAAGACTCTAAAGACTTCAAGATCCCTGATATTGAAAATA
                         exon 7              n  Thr Glu Leu Lys Leu Thr Arg Lys Ala Ala Tyr Val Arg Tyr
AATAACATCCTGAATTTTATGTTATTGTTTTATAG A ACA GAA CTG AAA CTG ACT CGG AAG GCA GCC TAT GTG AGA TAC
Phe Asn Ser Ser Ala Phe Phe Phe Ser Gly Phe Phe Val Phe Leu Ser Val Leu Pro Tyr Ala Leu Ile Lys
TTC AAT AGC TCA GCC TTC TTC TTC TCA GGG TTC TTT GTG GTG TTA TCT CCC TAT GCA CTA ATC AAA
Gly Ile Ile Leu Arg Lys Ile Phe Thr Thr Ile Ser Phe Cys Ile Val Leu Arg Met Ala Val Thr Arg Gln Phe
GGA ATC ATC CTC CGG AAA ATA TTC ACC ACC ATC TCA TTC TGC ATT GTT CTG CGC ATG GCG GTC ACT CGG CAA TTT
Pro Trp Ala Val Gln Thr Trp Tyr Asp Ser Leu Gly Ala Ile Asn Lys Ile Gln
CCC TGG GCT GTA CAA ACA TGG TAT GAC TCT GGA GCA ATA AAC ATA CAG GTAATGTACCATAATGCTGCATTATATA
CTATGATTTAAATAATCAGTCAATAGTTCATAATAGATCAGTTGTCACCTTAAACTTCTTCCTAGCATTTCCTTCACTAGGAAGTTATAAAA
AGTTGCCAGCTAATACTGATGTAGCTAGCAGTTCACCTTAAACTTTCTCAGCATTCTCTGACACAGTATGATGGATGAGAGTGGCATTATGCAAATTACCTTAAA
ATCCCAATAATACTGATGTAGCTAGCAGCTTTGAGAAA...
...GCACATTAGTGGGTAATTCAGGGTTGCTTTGTAAATTCATCACTAAGGTTAGCATGTAATAGTACAAGGAAGAATCAGTGTATGTTAAATCTAATGTAT
AAAAGTTTATAAAATATCATATGTTAGAGAGTATATTTCAAATATGAATCCTAGTGCTTGGCAAATTAACTTAGAACACTAATAAAATTATTT
TATTAAGAAATAATTACTATTCATTATTAAAATTCATATAAGATGTAGCACAATGAGTATAAAGTAGTAGATAATGCATTAATGCTATTCTGA
            exon 8       Asp Phe Leu Gln Lys Gln Glu Tyr Lys Thr Leu Glu Tyr Asn Leu Thr
TTCTATAATGTTTTGCTCTCTTTTATAAATAG GAT TTC TTA CAA AAG CAA GAA TAT AAG ACA TTG GAA TAT AAC TTA ACG
Thr Thr Glu Val Val Met Glu Asn Val Thr Ala Phe Trp Glu Glu
ACT ACA GAA GTA GTG ATG GAG AAT GTA ACA GCC TTC TGG GAG GAG GTCAGAATTTTAAAAATTGTTGCTCTAAACACCTAAC
TGTTTCTTCTTGTGAATATGGATTCATCCTAATGGGAATAAAATTAGAATGATGATATAACTGGTAGAACTGGAAGGAGATCACTCACTTATTT
CTAGATTAAGAAGTAGAGGAATGCCAGGTGCTCATGTGTGTAATCCAGCACTTCGGAGAGACCACTTTCGGATCCTGAGTCAGGAGTTCAAG
ACCAGCCTGCCAACATGGTAAACCGGTTCTCTACTAATAAAATACAAAAATTAACTG...
```

FIG. 18E.

```
.........GGTAGTGACTTAAGCTGTGTGACTTTAGTCATTCATTTAACTGCTGAGTCAGTCACAGTCTACAGCTTTGAAAGAGGAGGATTATAAATCTATCTCATGTTAATG..........
CTGAAGATTAAATAATAGTGTTTATGTACCCCGCTTATAGGAGAGAGAGGGTGTGTGTGTGTGTGTGTGTGTGTGTGTGTGTATGTGTATGTGTATGTGTATACATG..........
TATGTATTCAGTCTCTTACTGAAATTAAAAAATCTTTAACTTGATCATGTCCTAGAAACCGTATGCTATATA..........
TTATGTACTATAAGTAATATGTATACAGTGTAATGGATCATGGGCCATGTGCTTTCAAACTAATTGTACATAAAACAAGCATCTATTGAAATATCT..........
                                                exon 9     Gly Phe Gly Glu Leu Phe Glu Lys Ala Lys
GACAAACTCATCTTTATTTTGATGTCTGTCTGTCTGTGTGTGTGTGTGTGTGTGTGTTTTTTAACAG GGA TTT GGG GAA TTA TTT GAG AAA GCA AAA
Gln Asn Asn Asn Arg Lys Thr Ser Asn Gly Asp Asp Phe Ser Leu Phe Ser Asn Phe Ser Leu Leu Gly Thr-
CAA AAC AAT AAC AGA AAA ACT AGT AAT GGT GAT GAC TTC TTC AGT AAT TTC TCA CTT CTT GGT ACT
Pro Val Leu Asp Lys Asn Phe Lys Ile Glu Arg Gly Gln Leu Ala Val Ala Gly Ser Thr Gly Ala Gly
CCT GTC CTG AAA GAT ATT AAT TTC AAG ATA AGA GAA CAG TTG GCG GTT GCT GGA TCC ACT GGA GCA GGC
Lys
AAG GTAGTTCTTTTGTCTCTTCACTATTAAGAACTTAATTGGTGTCTCATGTCTCTTTTTTTCTAGTTGTAGTGCTGAAGTATTTTGAGAAAT
TCTTACATGAGCATTAGGAGAATGTATGGGTGTAGTGTCTTGTATAATTGTTCCACTGATAATTACTCTAGTTTTTTATTCCTCATATATT
TTCAGTGGCTTTTCTCCTTTATATTTGCACCACATGCACTGCAGCATTCAATAACTTATTGAATAACAAATC
ATCCATTTATCCATTCTTAACCAGAACAGACATTTTTCAGAGCTGGTCCAGAAAATCATGACTTACATTTGCCTTAGTAACCACATAAACAAAAG
TCTCCATTTTGTTGAC..........
AAG GTAGTTCTTTGTCTCTTCACTATTAAGAACTTAATTGGTGTCTCATGTCTCTTTTTTTCTAGTTGTAGTGCTGAAGTATTTTGAGAAAT
CACTGTAGCTGTACTACCTTCCATCCTCCAACTATTCCAACTATCTGAATCATGTGCCCTTCTCTGTGAACCTCTATCATAATACTGTCACACTGTA
TTGTAATTGTCTCTTTTACTTTCCCTGTATCTTTTGTCATAGCAGGAAGTATTTAAATATTTGAATCAAATGAGTTAATGA
ACTTTACAAATAAGAATATACACTTCTGCTTAGGATGATAATGGAGGCAAGTGAATCCTGACCGTGATTGATAATGACCTAATAATGATGGGTTTA
exon 10 Thr Ser Leu Leu Met Met Ile Met Gly Glu Leu.Glu Pro Ser Glu Gly Lys Ile Lys His Ser Gly Arg
TTTCCAG ACT TCA CTT CTA ATG ATG ATT ATG GGA GAA CTG GAG CCT TCA GAG CCT AAA ATT AAG CAC AGT GGA AGA
Ile Ser Phe Cys Ser Gln Phe Ser Trp Ile Met Pro Gly Thr Ile Lys Glu Asn Ile Ile Phe Gly Val Ser Tyr
ATT TCA TTC TGT TCT CAG TTT TCC TGG ATT ATG CCT GGC ACC ATT AAA GAA AAT ATC ATC TTT GGT GTT TCC TAT
Asp Glu Tyr Arg Tyr Arg Ser Val Ile Lys Ala Cys Gln Leu Glu Glu
GAT GAA TAT AGA TAC AGA AGC GTC ATC AAA GCA TGC CAA CTA GAA GAG GTAAGAAACTATGCAAACTTTTTGATTATGCATA
TGAACCCTTCACTACACTACCCAAATTATATATTTGGCTCCATATTCAATCGGTTAGTCTACATATATTTATGTTCCTCTAGGTAAGCTACTGAATGG
ATCAATTAATAAAACACATGACCTATGCTTAAGAAGCTTGCAAACACATGAAATAAATGCAATTATTTTTAAATAATGGGTTCATTGATCACATA
AATGCATTTTATGAAATGTGAGAATTTGTTCACTCATTAGTGAGACAAACGTCAATGGTTATTTATATGGCATGCATATAGTGATATGTGGT..........
```

FIG. 18F.

```
.:..:..:..:..:..:..:..:..:..:..:..:..:..:..:..:..:..:..:..:..:..:..:..:..:..
ATATCCCATAAATATACACATATTTAATTTGTATTTATATTATTATTTATGATCATTCATGACATTTAAAATTACAGGAAAAATTACAT
CTAAAATTTCAGCAATGTGTGTTTTTGACCAACTAAATAAATTGCATTTGAAATAATGGAGATGCAATGTTCAAAATTTCAACTGTGTTAAGCAATAGT
                                                                              exon 11    Asp
GTGATATATGATTACATTAGAAGGAAGATGTGCCTTTCAAATTCAGATTGAGCATACTAAAAGTGACTCTCTAATTTCTATTTTGGTAATAG GAC
Ile Ser Lys Phe Ala Glu Asp Ile Val Leu Gly Asn Ile Thr Leu Ser Gly Ile Gly Gln Arg Ala
ATC TCC AAG TTT GCA GAG GAC ATT GTT CTT GGA ATC ACA CTG AGT GGA ATC GGA CAA CGA GCA
Arg Ile Ser Leu Ala Ar
AGA ATT TCT TTA GCA AG GTGAATAACTAATTATTGCTCTAGCAAGCATTTGCTGTAAATGTCATTCATGTAAAAAATTACAGACATTTCTCTA
TGCTTTATATCTGTTCTGGAATTGAAAAAATCCTCTGGGTTTTATGCGGTTAAGAATAACTATAAATAATGGTATAGTATCC
AGATTGGTAGAGATTATGTTACTCAGAATCTGTGCCCGTATCTTGG...
.:..:..:..:..:..:..:..:..:..:..:..:..:..:..:..:..:..:..:..:..:..:..:..:..:..
CTTACAGTTAGCAAAATCACTTCAGCAGTTCTTCTGGAATGTCTGTGAAAAGTGATAAAATCTTCTGCAACTTATTCTTTATTCCTCATTTAAATAATCT
ACCATAGTAAAAACATGTATAAAAGTGCTACTTCTGCACCACTTTCAGTGAATGCGATGGTGTGACCATATTGTAATGCATGTA
                                                 exon12    g Ala Val Tyr
GTGAACTGTTTAAGGCAAATCATCTACACTAGATGACCAGGAATAGAGAGGAAATGTAATTAATTCCATTTTCTTTTAG A GCA GTA TAC
Lys Asp Ala Asp Leu Tyr Leu Leu Asp Leu Leu Tyr Leu Asp Val Leu Thr Glu Lys Glu Ile Phe Glu
AAA GAT GCT GAT TTG TAT TTA TTA GAC TCT CCT TTT GGA TAC CTA GAT GTT TTA ACA GAA AAA GAA ATA TTT GAA
Se
AG GTATGTTCTTTGAATACCTTACTTCTATAATGCTCATGCTAAAATAAAAGAAAAGACAGACTGTCCATCATAGATTGCATTTTACCTCTTGAGAAATAT
GTTCACCATTGTGTATGCAGAATGTAGCATGTATTAACTCAAATCTCAAGATTCAAGATTACTTCCATTAAAACCTTTT
CTCACCGCCTCATGCTAAACCAGTTTCTCATTGTTATAGCAATTGCTATACTGTTATAGCAATTGCTATCTAGTTTTGCAGTATCATTGCCTTGTGATATATATT
ACTTTAATT...
```

FIG. 18G.

```
.........................................................
GAATTCACAAGTACCAATTAATTACTACAGAGTACTATTAGAATCATTAAAATAAAATGTATGATAGAGATTATGCAATAAACATTAA
                                                         exon 13     r Cys Val Cys Lys Leu
..........................................................................................
CAAAATGCTAAAATACGAGACATATTGAATAAGTATTTATAAAATGATATTTATATCTTAAAG C TGT GTC TGT AAA CTG
Met Ala Asn Lys Ile Leu Val Thr Arg Ile Leu His Leu Lys Ala Asp Lys Ile Leu Ile Leu
ATG GCT AAC AAA ACT AGG ATT TTG GTC ACT TCT AAA ATG GAA CAT TTA AAG GCT GAC AAA ATA TTA ATT TTG
His Glu Gly Ser Ser Tyr Phe Phe Gly Thr Phe Asn Leu Gln Asn Leu Gln Pro Asp Phe Ser Ser Lys Leu
CAT GAA GGT AGC AGC TAT TTT TTT GGG ACA TTT TCA GAA CTC CAA AAT CTA CAG CCA GAC TTT AGC TCA AAA CTC
Met Gly Cys Asp Ser Phe Gln Phe Ser Ala Glu Arg Arg Asn Ser Ile Leu Thr Glu Thr Leu His Arg Phe
ATG GGA TGT GAT TCT TTC CAA TTT AGT GCA GAA AGA AAT TCA ATC CTA ACT GAG ACC TTA CAC CGT TTC
Ser Leu Glu Gly Asp Ala Pro Val Ser Trp Glu Thr Lys Gln Ser Phe Lys Gln Thr Gly Gln Phe Gly
TCA TTA GAA GGA GAT GCT CCT GTC TCC TGG GAA ACA AAA CAA TCT TTT AAA CAG ACT GGA GAG TTT GGG
Glu Lys Arg Lys Asn Ser Ile Leu Asn Pro Ile Arg Ser Ile Arg Lys Phe Ser Ile Val Gln Lys Thr Pro Leu
GAA AAA AGG AAG AAT TCT ATT CTC AAT CCA ATC CGA AAC TCT ATA CGA AAA TTT TCC ATT GTG CAA AAG ACT CCC TTA
Gln Met Asn Gly Ile Glu Glu Asp Ser Arg Leu Glu Arg Arg Leu Ser Leu Val Pro Asp Ser Glu Gln
CAA ATG AAT GGC ATC GAA GAG GAT TCT CGA CCT TTA GAG AGA AGG CTG TCC TTA GTA CCA GAT TCT GAG CAG
Gly Glu Ala Ile Leu Pro Arg Ile Ser Val Ile Ser Thr Gly Pro Thr Leu Gln Ala Arg Arg Gln Ser Val
GGA GAG GCG ATA CTG CCT CGC ATC AGC GTG ATC AGC ACT GGC CCC ACG CTT CAG GCA CGA AGG CAG TCT GTC
Leu Asn Leu Met Thr His Ser Val Asn Gln Ile Asn His Arg Lys Thr Thr Ala Ser Thr Arg Lys Val
CTG AAC CTG ATG ACG CAC TCA GTT AAC CAA ATT CAC CGA AAG ACA ACA GCA TCC ACA CGA AAA GTG
Ser Leu Ala Pro Gln Ala Asn Leu Thr Glu Leu Asp Leu Tyr Ser Arg Arg Leu Ser Gln Glu Thr Gly Leu Glu
TCA CTG GCC CCT CAG GCA AAC TTG ACT GAA CTG GAT TTA TAT TCA AGA AGG TTA TCT CAA GAA ACT GGC TTG GAA
Ile Ser Glu Gly Ile Glu Asn Glu Asp Leu Lys
ATA AGT GAA GGA ATT GAA AAC GAA GAC TTA AAG GTAGGTATACATCGCTTGGGGTATTCACCCCACAGAATGCAATGAGTAGAATG
CAATATGTAGCATGTAACAAATTACTAAATCATAGGATAAGGTATCTTAAACTCAGAAGTATGAAGTTCATTAATTATACAAGCAAC
GTTAAATGTAAATAACAAATGATTCTTTTGCAATGGACATATCTCTTCCCATAAAATGGGAAAGATTTAGTTTTTGGTCCTCTACTAAGCCAGTG
ATAACTGTGACTATAGTTAGAAAGCATTTGCTTTATTACCATCTTGAACCCCTCTGTG....................
```

FIG. 18H.

```
.........................................................................
GGAAACTTCATTTAGATGATGTATCATTCATTCATTTGATAAAGGTATGCCACTGTTAAGCCTTTAATGTAAAATGTCCAATAATAATACAGTTATAATCA
GTGATACATTTTAGAATTTGAAAATTACGATGTTTCTCATTTTAATAAAGCTGTGTGCTCCAGTAGACATTATTCTGGCTATAGAATGACATCAT
ACATGGCATTATAATGATTATATTGTTAAATACACTTAGATTCAAGTAATACTATTCTTTTATTTCATTATTAAAATAAAACCACAATGGTGG
                exon 14a   Glu Cys Phe Phe Asp Asp Met Glu Ser Ile Pro Ala Val
CATGAAACTGTACTGTCTTATTGTAATAGCCATAATTCTTTATTCAG GAG TGC TTT TTT GAT GAT ATG GAG AGC ATA CCA GCA GTG
Thr Thr Trp Asn Thr Tyr Leu Arg Tyr Ile Thr Val His Lys Ser Leu Ile Phe Val Leu Ile Trp Cys Leu Val
ACT ACA TGG AAC ACA TAC CTT CGA TAT ATT ACT GTC CAC AAG AGC TTA ATT TTT GTG CTA ATT TGG TGC TTA GTA
Ile Phe Leu Ala Glu
ATT TTT CTG GCA GAG GTAAGAATGTCTATTGTAAAGTATTACTGGATTTAAAGTTAAATTAGATAGTTGGGGATGTACATATATATGCAC
ACACATAAATATGTATATATACACATGTATATACATGTACATATAAGTATGCATATATCACACATATAGTTTATATGTATATATTACATATATTG
TGATTTTACAGTATATAATGGTATAGATTCATATAGTTCTTAGCTTCTGAAAATCAACAAGTAGAACCACTACTGA........................
.........................................................................
GAATTCCATTAACTTAATGTGGTCTCTCATCACAATAATAGTACTTAGAACACCTAGCAGCTGCTGACCCAGGAACACAAAGCAAGCAAGAAGATGAAAT
TGTGTGTACCTTGATATTGTGTACACATCAAATGGTGTGATGTGAATTTAGAGATGTGGGCATGGGAGGAATAGGTGAAGATGTTAGAAAAAATCAACT
  exon 14b     Val Ala Ala Ser Leu Val Val Leu Trp Leu Leu Gly As
GTCTCTGTTCCATTCCAG GTG GCT GCT TCT TTG GTT GTG CTC TGG CTC CTT GGA AA GTGAGTATTCCATGTCCTATTGTGTAGAT
TGTGTTTTATTCTGTGTTGATTAAATATTGTAATCCACTATGTTTGTATGTATTGTAATCCACTTGTTCATTTCTCCCAAGCATTATGGTAGTGGAAAG
ATAAGGTTTTGTTAAATGATGACCATTAGTGGGTGAGGTGACACATTCCTAGTCCTAGCTCCTCCACAGGCTGACCTGAGGATCACTTGAGC
CCAGGAGTTCAGGGCTGTAGTGTTGTATCATTGTGAGTAGCCACCACCCTGACAATAGTGAGATCCTATATCTAAATAAATAA..A
TAAATGAATAAATTGTGAGCATGTGCAGCTCCTG.............................
```

FIG. 18I.

```
..:TCCTATATCTAATAATAATAATAAATAAATGAATAATTGTGAGCATGTGAGCTCCTGCAGTTCTAAAGATAATAGTTCTGTTCTGTTCTCAGTTCTGTGAACACAA
TAAAATATTGAAATAACATTACATTATTAGGGTTTCTTCAAATTTTTAATAAAGAACAACTCATCTATCAATAGTGAGAAAACATATC
TATTTCTTGCAATAATAGTATGATTTGAGGTTAAGGTGCATGCTCTCTTGTTACAGCAAAATATTGTATTATTAGACTCAAGTTTAGTTCCATTTACA
                                exon 15        n Thr Pro Leu Gln Asp Lys Gly Asn Ser
TGTATTGGAAATTCAGTAAGTAACTTGGCTGCCAAATAACGATTTCCTATTGCTTTACAG C ACT CCT CTT CAA GAC AAA GGG AAT AGT
Thr His Ser Arg Asn Ser Tyr Ala Val Ile Thr Ser Tyr Tyr Val Phe Tyr Ile Tyr Val
ACT CAT AGT AGT AGA AAT AAC AGC TAT GCA GTG ATT ATC ACC AGT TCG TAT TAT GTG TTT TAC ATT TAC GTG
Gly Val Ala Asp Thr Leu Leu Ala Met Gly Phe Phe Arg Gly Leu Pro Leu Val His Thr Leu Ile Thr Val Ser
GGA GTA GCC GAC ACT TTG CTT GCT ATG GGT TTC TTC AGA GGT CTA CCA CTG CAT ACT CTA ATC ACA GTG TCG
Lys Ile Leu His His Lys Met Ser Val Leu Gln Ala Pro Met Ser Thr Leu Asn Thr Leu Lys Ala G
AAA ATT TTA CAC CAC AAA ATG TTA CAT TCT GTT CTT CAA GCA CCT ATG TCA ACC CTC AAC ACG TTG AAA GCA G GT
ACTTTACTAGGTCTAAGAAATGAAACTGCTGATCCTGTGGTTTTCTAATGCCAGTGCTGCCTTTGCACAGAGGCA
TGTGCCTTTGTT.......................................
..:GTAAGATGTAAGCAGGATGACTACCCACCTATTCCTGACATATTTATAGTAAAGCTATTTCAGAGAATTGGTCGTTACTGAATCTTACAAGAATC
TGAAACTTTAAAGGTTAAAGTTTAAAAGACATAACTTGAACACATAATTATTTGAACATGTTGGAAAGAAACAAAATTCTAAGTCTATCTGATT
CTATTGCTAATTCTTATTGGGTTCTGAATGCGTCACTGTGATCCAAACTTAGTATTGAATATATGTCGATATATCTTAAAAATTAGTGTTTTTGAG
          exon 16        ly Gly Ile Leu Asn Arg Phe Ser Lys Asp Ile Ala Ile Leu Asp Asp Leu Leu Pro
GAATTGTCATCTGTATATTATAG GT GGG ATT CTT AAT AGA TTC TCC AAA GAT ATA GCA ATT TTG GAT GAC CTT CTG CCT
Leu Thr Ile Phe Asp Phe Ile Gln
CTT ACC GAT TTC ATC CAG GTATGTAAAAATAAGTACCGTTAAGTATGTCTGTATTATTAAAAAACAATAACAAAGCAAATGTGA
TTTGTTTCATTTTTATTGATTGAGGGTGAAGTCCTGTCTATTGCATTAATTTGTAATTATCCAAGCCTTCAAATAGACATAAGTTAGTAA
TCAATAATAAGTCAGAACTGCTTACCTGGCCCAAACCTGAGGCAATCCACATTTAGATGTAATAGCTGTCTGTCTACTGGGAGTGATTGAGAGGCACAA
GGACCATCTTTCCAAATCACTGGCAC.......
```

FIG. 18J.

```
..............................AGTGCACCAGCATGGCACATGTATACATATGTAACTAACCTGACAATGTGACATGTACCCTAAACTTAAAGTATATAAATAAAAAAAGTT
TGAGGTGTTAAAGTATGCAAAAAAAAAAAGAAATAATCACTGACACACTTGTCCACTTGCAATGTGAAATGTTACTCACCACATGTTTCT
exon 17a    Leu Leu Leu Ile Val Ile Gly Ala Ile Ala Val Val Ala Val Leu Gln Pro Tyr Ile Phe Val Ala
TTGATCTTACAG TTG TTA TTA ATT GTG ATT GGA GCT ATA GCA GTT GTC GCA GTT TTA CAA CCC TAC ATC TTT GTT GCA
Thr Val Pro Val Ile Val Ala Phe Ile Met Leu Arg Ala Tyr Phe Leu Gln Thr Ser Gln Leu Lys Gln Leu
ACA GTG CCA GTG ATA GTG GCT TTT ATT ATG GCT TTA AGA GCA TAT TTC CTC CAA ACC TCA CAG CAA CTC AAA CAA CTG
Glu Ser Glu G
GAA TCT GAA G GTATGACAGTGAATGTCCGATACTCATCTGTAAAAAAGCTATAAGAGCTATTTGAGATTCTTTATTGTTAATCTACTTAAAAAA
ATTCTGCTTTAAACTTTTACATCATATAACAATATATTTTTCTACATGCATGTGTATATAAAGAAACTATATTACAAGTACACATGGATTTTTT
TCTTAATTAATGACCATGTGACTTCATTTGTTTAAATAGTATATAGAATCTTACCACAGTTGGTGTACGGACATTCATTTAT..............
..............................TTCAAGAATGGCACCAGTGTGAAAAAAGCTTTTACCAATGACATTTGTGATATTCTAATTAGTCTTTTCAGTACAGATATATGAA
                               exon 17b   ly Arg Ser Pro Ile Phe Thr His Lys Leu Val Thr
AATTACATTTGTGTTATGTTATTGCAATGTTTCTATGGAAATATTCACAG GC AGG AGT CCA ATT TTC ACT CAT CTT GTT ACA
Ser Leu Lys Gly Leu Phe Thr Leu Arg Ala Phe Gly Arg Gln Pro Tyr Phe Glu Thr Leu Phe His Lys Ala Leu
AGC TTA AAA GGA CTA TGG ACA CTT CGT GCC TTC GGA CGG CAG CCT TAC TTT GAA ACT CTG TTC CAC AAA GCT CTG
Asn Leu His Thr Ala Asn Trp Phe Leu Ser Thr Leu Arg Trp Phe Gln Met Arg Ile Glu Met Ile Phe
AAT TTA CAT ACT GCC AAC TGG TTC TTG TAC CTG TCA ACA CTG CGC TGG TTC CAA ATG AGA ATA GAA ATG ATT TTT
Val Ile Phe Phe Ile Ala Val Thr Phe Ile Ser Ile Leu Thr Thr G
GTC ATC TTC TTC ATT GCT GTT ACC TTC ATT TCA ATT TTA ACA ACA G GTACTATGAACTCATTAACTTTAGCTAAGCATTAAGT
AAAAAATTTCAATGAATAAAATGCTGCATTCATAGGTATCATCTTTAGAGTTTACAATTTGTTGGTTTATTATTGAAC
AAGTGATTCTTTGAAATTCCATTGTTTCATTGTTAAACAAATAATTCCTTGAAATCGGTATATATATCGGTATATATATATATATATATATA
TATATACATATATATAGTATTATATCCCGTTTCACAGTTCTTAAAAACCGATGCACACAGATTGTCGAGTAGCAATTCTGTGATTGAAGGGAAATA
TGTCACCCTCTTCATCTCATATTGGTGAAGGGTCCTAGCTTCAAAATTAATAGATTCCTAAAGAGGGGAAATGAAACACCGCCATTTACACACACAC
ACACACACAGAGTTCCTCTCTGTGCGGTAAGTTTG.........
```

FIG. 18K.

```
..............................................................................
TTATTACTTATAGAATAATAGTAGAAGAGACAAATATGTACCTACCCATTACAACACCTCCAATACCAGTAACATTTTTAAAAAGGCAACACT
TTCCTAATATTCAATCGCTCTTGATTTAAAAATCCTGGTTGAATACTATTACTATATGCAGAGCATTATTAGTAGATGCTGATGAACTGAGATTT
AAAAATGTTAAATTACCATAAAATTGAATTAATGTGATATGCCCTAGGAGAAGTGTGAATAAAGTCGTTCACAGAAGAGAAATAAC
                 exon 18        ly Glu Gly Glu Gly Arg Val Gly Ile Ile Leu Thr Leu Ala Met Asn
ATGAGGTTCATTTACGTCTTTGTGCATCTATAG GA GAA GGA GAA AGA GTT GGT ATT ATC CTG ACT TTA GCC ATG AAT
Ile Met Ser Thr Leu Gln Trp Ala Val Asn Ser Ser Ile Asp Val Asp Ser Leu
ATC ATG AGT ACA TTG CAG TGG GCT GTA AAC TCC AGC ATA GAT GTG GAT AGC TTG
TGAAAAATTCAGACAAGTAACAAGTATATGAGTAATAGCATGAGGAAGAACTATATACCGTATATTGAGCTTAAGAAATAAACATTACAGATAAATG
AGGGTCACTGTATCTGTCATTAAATCCTTATCTCTTCTTCTTCTTCATAGATAGCCACTACTGAAGATCTAATACTGCCAGTGAGCATTCTTTCACCTG
TTTCCTTATTCAGGATTTCTAGGAGAAATACCTAGGGGTGTATTGCTGGGTCATAGGATTCACCCATGCTTAAC.........
                                   exon 19     Met Arg Ser
TTCTCTTCAGTTAAACTTTTAATTTTAATTATATCCAATTATTCCTGTAGTTCATTGAAATGCTCTGCCATTCTTAAAAACAAAAATGTGTTATTTTATTCAG ATG CGA TCT
ACAAGTATTTTTTAGGAAGCATCAAACTAATTGTGAATTGCTCTGCCATTCTTAAAAACAAAAATGTGTTATTTTATTCAG Val Ser Thr Lys Pro Tyr Lys Asn
Val Ser Arg Val Phe Lys Phe Ile Asp Met Pro Thr Glu Gly Lys Pro Thr Lys Ser Thr Lys Pro Tyr Lys Asn
GTG AGC CGA GTC TTT AAG TTC ATT GAC ATG CCA ACA GAA GGT AAA CCT ACC AAG TCA ACC AAA CCA TAC AAG AAT
Gly Gln Leu Ser Lys Val Met Ile Ile Glu Asn Ser His Val Lys Asp Asp Ile Trp Pro Ser Gly Gly Gln
GGC CAA CTC TCG AAA GTT ATG ATT ATT GAG AAT TCA CAC GTG AAG GAT GAC ATC TGG CCC TCA GGG GGC CAA
Met Thr Val Lys Asp Leu Thr Ala Lys Tyr Thr Glu Gly Gly Asn Ala Ile Leu Glu Ser Phe Ser Ile
ATG ACT GTC AAA GAT CTC ACA GCA AAA TAC ACA GAA GGT GGA AAT GCC ATA TTA GAG AAC ATT TCC TTC TCA ATA
Ser Pro Gly Gln Arg
AGT CCT GGC CAG AGG GTGAGATTGAACACTGCTTGTTGTTAGACTGTGTTCAGTAAGTCCCAGTGAATCCCAGTAAGCCTGAAGCCAAGTGTGTAGCAGA
ATCTATTGTAACATATTGTAACAGTAGAATCAATATTAAACACACATGTTTATTATATGGAGTCATTATTTTTAATATGAATTTAATTGCAGA
GTCTGAACTATATAT..........................................................
```

FIG. 18L.

```
..:...........
AAGGTCACTGAGTGATAAGGAAGTCTGCATCAGGGTCCAATTCCTTATGGCCAGTTCTCTATTCTGTTCGTTCCAAGTTGTGTTTGTCTCCATATATCAACATTG
GTCAGGATTGAAAGTGTGCAACAAGTTGAATGAATAAGTGACAGATAAAATATTCCAATGTTTTATTGAAGTACAATA
                                                          exon 20  Val Gly Leu Leu Gly Arg Thr Gly
CTGAATTATGTTATGGCATGGTACCTATATGTCACAGAAGTGATCCCATCACTTTACCTTATAG GTG GGC CTC TTG GGA AGA ACT GGA
Ser Gly Lys Ser Thr Leu Ser Ala Phe Leu Arg Leu Asn Thr Glu Gly Glu Ile Gln Ile Asp Gly Val
TCA GGG AAG AGT ACT TTG TTA TCA GCT TTT TTG AGA CTA CTG AAC ACT GAA GGA GAA ATC CAG ATC GAT GGT GTG
Ser Trp Asp Ser Ile Thr Leu Gln Gln Trp Arg Lys Ala Phe Gly Val Ile Pro Gln
TCT TGG GAT TCA ATA ACT TTG CAA CAG TGG AGG AAA GCC TTT GGA GTG ATA CCA CAG GTGAGCAAAAGGACTTAGCCAGAA
AAAGGCAACTAAATTATATTTTTACTGTACTTGTACTCTGTGATACTTGATACTCATATTCATAACTGTTCAAAATCATATTGTTATGCATTGCTGTCTTT
TTTCTCCAGTGCAGTTTTCTCATAGCCAGAAAAAGATGTCTCTAAAAGTTTGGAATTC.............
..:...........
TTTTAATATTCTACAATTAACAATTATCTCAATTCTTTATTCTAAAGACATTGGATTAGAAAAATGTTCACAAGGACTCCAAATATGCTGTAGTAT
TGTTTCTTAAAAGAATGATACAAGCAGACATGATAAATATTAAAAATTGAGAGAACTTGATGGTAAGTACATGGGTGTTCTTATTTTAAAATAATT
                                                                             exon 21   Lys
TTTCTACTTGAAATATTTTACAATACAATAAGGGAAAAATAAAAGTTATTAAGTTATTCATACTTTCTTCTTCTTTTTTTGCTATAG AAA
Val Phe Ile Phe Ser Gly Thr Phe Arg Lys Asn Leu Asp Pro Tyr Glu Gln Trp Ser Asp Ile Trp Lys
GTA TTT ATT TTT TCT GGA ACA TTT AGA AAC TTG GAT CCC TAT GAA CAG TGG AGT GAT ATA TGG AAA
Val Ala Asp Glu
GTT GCA GAT GAG GTAAGGCTGCTAACTGAAATGATTTGAAAGGGTAACTCATCAACACAAATGGCTGATATAGCTGACATCATTCTACACAC
TTTGTGTGCATGTATGTGTGTGCACACTTTAAAATGGAGTACCTAACATACCTGGAGCAACAGTACTTTGACTGGACCTACCCTACCTAACTGAAATGA
TTTGAAAGAGGTAACTCATACCAACACAAATGGTTGATATGGCTAAGATCATTCTACACACTTGTGTGCATGTATTCTGTGCACACTTCAAAATGG
AGTACCCTAAAATACCTGGCGCGACAAGTACTTTGACTGAGCCTACTT...........
```

FIG. 18M.

```
.........CACAGTTGACTACTATTTATGCTGTCCTCAGTCAGTTGTCCTCAGTCATGATGAAGATGGAGGTAGCACCAAGGATGATGTCATACCTCCATCCTTATGCT....
ACATTCTATCTCTGTCTACATAAGATGTCATACTAGAGGCATATCTGCAATGTATACATTATCTTTCCAGCATGCATTCAGTTGTTGTGAATAA.................
TTATGTACACCTTTATAAACCTGAGCCTCACAGAGCCATGTGCCACGTATGTTCTTACTACTTTGATACCTGGCACGTAATAGACACTCATTG..................
AAGTTCCTAATGAATGAAGTACAAAGATAAACAAGTTATAGACTGATTCTTTGAGCTGTCAAGGTGTAATAGACTTTGCTCAATCAATTCAA...................
TGGTGGCAGGTAGTGGGGTAGAGGGATTGGTATGAAAACATAAGCTTTCAGAACTCCTGTGTTTATTTTAGAATGTCAACTGCTTGAGTGTTTTAA................
         exon 22    Val Gly Leu Arg Ser Val Ile Glu Gln Phe Pro Gly Lys Leu Asp Phe
CTCTGTGGTATCTGAACTATCTCTCTAACTGCAG GTT GGG CTC AGA TCT GTG ATA GAA CAG TTT CCT GGG AAG CTT GAC TTT
Val Leu Val Asp Gly Gly Cys Val Leu Ser His Gly His Lys Gln Leu Met Cys Leu Ala Arg Ser Val Leu Ser
GTC CTT GTG GAT GGG GGC TGT GTC CTA AGC CAT GGC CAC AAG CAG TTG ATG TGC TTG GCT AGA TCT GTC AGT
Lys Ala Lys Ile Leu Leu Asp Leu Pro Ser Ala His Leu Asp Pro Va
AAG GCG AAG ATC TTG CTG CTT GAT GAA CCC AGT GCT CAT TTG GAT GTA GT GTGAGTTTAGATGTCTCTTACTTAATAGCAC
AGTGGGAACAGAATCATTAAGCTGCTTCATGACACATATTTCTATTAGGCTGTCATGTCTCGCTGTGGGGGTCTCCCAAGATATGAATAATTGCC
CAGTGGAAATGAGCATAAATGACATATTCCTGCTAAGACTCATATTTCTGTGTTTCTTCCGAAGATAGTTTT......................
.........GCATGTTTATAGCCCCAAATAAAGAAGTACTGGATCTCTACATAATGAAAATGTACTCATTATTAAGTTCTTGAAATATTTGTCCTGTTATTT
ATGGATACTTAGAGTCTACCCCATGGTTGAAAGCTGTGGCTACCTATATCAACATTATGTGAAAGAACTTAAGAACTAATAAGTAATTAAAGA
                                                       exon 23   1 Thr Tyr
GATAATAGAACAATAGACATATTATCAAGTAAATACAGATCATTACTGTCTGTGATATTATGTGTATTTCTTTCTTTCTAG A ACA TAC
Gln Ile Ile Arg Arg Thr Leu Lys Gln Ala Phe Ala Asp Cys Thr Val Ile Leu Cys Glu His Arg Ile Glu Ala
CAA ATA ATT AGA AGA ACT CTA AAA CAA GCA TTT GCT GAT TGC ACA GTA ATT CTC TGT GAA CAC AGG ATA GAA GCA
Met Leu Glu Cys Gln Gln Phe Leu
ATG CTG GAA TGC CAA CAA TTT TTG GTGAGTCTTTATAACTTACTTACTTAAGATCTCATTGCCCTGTAATTCTTGATAACAATCTCACATGTGA
TAGTTCCTGCAAATTGCAACAATGTCAACAAGTTCTTTCAAAAATATGTATCATACAGGCCATTCAAAATAGCTGCACAAGTTTTCACTTT
GATCTGAGCCATGTGTGAGTTGTAATATAGTAAATCTAAAATGCAGCATATTACTAAGTTATGTTTATAAATAGGATATATATACTTTGAGCCCTT
TATTTGGGACCAAGTCATACAAAATACTCTACTGTTTAAGATTTAAAAAGGTCCCTGATCTTCAATAACTAAAGTCCCATGATGTGGTCTGG
ACAGGCCTAGTTGTCTGATTTATGTATTATGACAAAGTTGAGAGGCACATTCATTTCTAGCCATGATTGGTTCAGTAGTACCTT
TCTCAACCACTTCTCACTGTTCTTAAAAAACTGTCACATGCCAGGCACAGTGGCTTACATCGTAATCCAATACTTGGAGGCTGAGGTGGGGG
ATTACTTGAGGCCAGGAATTC..........................................................
```

FIG. 18N.

```
...AGATGGTAGAACCTCCTTAGCCAAAAGGACAGCAGTTAAATGACATACCTGATTGTTCAAATGCAAGCCTCGACATTCTTTGACTTT...
                                                                      Val Ile
                                                                      exon 24
TATTTCCTTGAGCCTGTCCTGCCCACTTCTGTCCCTGCTCTGACCTCTGCCTTCTGCCCAGATCTCACTAACAGCCATTCCCTAG GTC ATA
                                                         Glu Glu Asn Lys Val Arg Gln Tyr Asp Ser Ile Glu Gln Lys Leu Leu Asn Glu Arg Ser Leu Phe Arg Gln Ala Ile
GAA GAG AAC AAA GTG CGG CAG TAC GAT TCC ATC CAG AAA CTG CTG AAC GAG AGG AGC CTC TTC CGG CAA GCC ATC
Ser Pro Ser Asp Arg Val Lys Leu Phe Pro His Arg Asn Ser Lys Ser Cys Lys Ser Lys Pro Gln Ile Ala Ala
AGC CCC TCC GAC AGG GTG AAG CTC TTT CCC CAC CGG AAC TCA AGC AAG TGC AAG TCT AAG CCC CAG ATT GCT GCT
Leu Lys Glu Glu Thr Glu Glu Val Gln Asp Thr Arg Leu AM
CTG AAA GAG GAG ACA GAA GAG GTG CAA GAT ACA AGG CTT TAG AGAGCAGCATAAATGTTGACATGGACATTGCTCATGGA
ATGGAGCTCGTGGGACTCACCTCATGGAATTGGAGCTCGTTACCTCTGCCTCAGAAACAAGGATGAATTAAGTTTTTTAAAAAG
AACATTGGTAAGGGAATTGAGGACACTGATATGGCTTCTTGATAATGCTTCCTGGAATAGTCAATTGTGAAAGTACTTCAAATCCTGAAG
ATTACCACTGTGTTTGCAAGCCAGATTTCCTGAAACCCTGCTAGTGTGCCATGTGCTAAAATGTCTAAATGTCAATCAGCCTAGTTGATC
AGCTTATTGTCTAGTGAAACTCGTTAATTGTAGTGTTGGAGAAGAACTGAAATCATCTCTTAGGTTATGATTAGTAATGATAACTGGAACTCAGC
GGTTTATATAAGCTGTATTCCTTTTCTCCTCCCCATGATGTTAGAAACACCATTCAACACTATATGTTGCTAAGCATTCCAGGAGCAGTTCAGGAAAGAACTTCCAGATCCTGA
CAAGTATTAGAATACCACAGGAACCACAAGACTGCACAAAAATCTCAATATATTCAGATAATCACAGGGACAGGATGGTTCCTTGATGAAGAAGTTGATATGCCTTTCCAAC
AATCAGGGTTAGTATGTCCAGTCTACCTGGGAAAGGCTGTTATAAGTAGTTAGCTGAACTGTTAGCTAGCATAGAGTTTAGCTGGACAGGATGTAGTAGTCACAGGACAGCCCCTCTTCCACAGAAGCT
TCCAGAAAGTGACAAGTCACAGACTCTGAACTTGAACAGCCTTTGAACTGAATGGGCACATGGGCTAGAACACACAGAAGCCAGCATTAGATGTATAGTTGATCGGTGATGTTTC
CCAGGTAGAGGGTGTAAGTAGATAGGCCATGGGCACTGTGTAGACACACTAAGAGAATGAGAAGCACCAATCATGAATTAGTTTTATATGCTTCTGTTTA
AGGCTAGAATGTATGTACTTCATGCTGTCTACAGAAGAATATTTCTCTAGGAAATATTTCTCAAACATATTAAATGCTGTATTTTAAAGAATGATTATGAATT
TAATTTGTGAAGCAAAATTTTCTCTAGGAAATATTTTTATATTGAAATATTGACTTTTTATGCCACTAGTATTTTATGAAATATTGTTAAAACTGGACAGGGAGAACCTA
ACATTGTATAAAAATAATTTTATATTGAAATATTGACTTTTTATGCCACTAGTATTTTATGAAATATTGTTAAAACTGGACAGGGAGAACCTA
GGGTGATATTAACCAGGGCCATGAATCACCTTTGTCTGGAGGAAGCCTTGCTGATCAAGGTGTTGCCCACAGCCTGTCCACAGCCTGTATGATTCCAGCCAGA
CACAGCCTCTTAGATGCAGTTCTGAAGAAGATGGTACCACTGTTCCATCAAGGTACACACTTGTGAACTTTGTGTTTGAACTTTGTGTTTCAGATGCGGTTCACTTGTCAT
AGACTGCATTATTATTACTGTAAGAAAATATCACTTGTCAATAAAATCCATACATTGTGTGAAACACACGAATTCGTCTCTTTAGATATAGCCTC...
GTTTCATCAGTCCTCTCACTCAGTTCCAATTTCTAAGCTTCATGAACATGAAACACGAATTCGTCTCTTTAGATATAGCCTC...
```

FIG. 19
A. 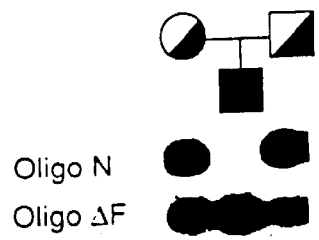
Oligo N
Oligo ΔF
B. 
Clone 5-3-15    CF son    Carrier father
C.
```
              501                              510
              ThrIleLysGluArgIleIlePheGlyValSer
Normal        ACCATTAAAGAAAATATCATCTTTGGTGTTTCC
              ThrIleLysGluArgIle    PheGlyValSer
ΔI507         ACCATTAAAGAAAATATC    TTTGGTGTTTCC
              ThrIleLysGluArgIleIle    GlyValSer
ΔF508         ACCATTAAAGAAAATATCAT     TGGTGTTTCC
```
FIG. 20
Heteroduplexes
Homoduplexes

SEQUENCE LISTING

<160> NUMBER OF SEQ ID NOS: 33

<210> SEQ ID NO 1
<211> LENGTH: 6130
<212> TYPE: DNA
<213> ORGANISM: Homo sapiens
<220> FEATURE:
<221> NAME/KEY: CDS

<222> LOCATION: (133)..(4572)

<400> SEQUENCE: 1

```
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga cc atg cag agg tcg cct ctg gaa aag gcc agc gtt gtc tcc     171
             Met Gln Arg Ser Pro Leu Glu Lys Ala Ser Val Val Ser
               1               5                  10 aaa ctt ttt ttc agc tgg acc aga cca att ttg agg aaa gga tac aga       219
Lys Leu Phe Phe Ser Trp Thr Arg Pro Ile Leu Arg Lys Gly Tyr Arg
     15                  20                  25 cag cgc ctg gaa ttg tca gac ata tac caa atc cct tct gtt gat tct       267
Gln Arg Leu Glu Leu Ser Asp Ile Tyr Gln Ile Pro Ser Val Asp Ser
 30                  35                  40                  45 gct gac aat cta tct gaa aaa ttg gaa aga gaa tgg gat aga gag ctg       315
Ala Asp Asn Leu Ser Glu Lys Leu Glu Arg Glu Trp Asp Arg Glu Leu
                 50                  55                  60 gct tca aag aaa aat cct aaa ctc att aat gcc ctt cgg cga tgt ttt       363
Ala Ser Lys Lys Asn Pro Lys Leu Ile Asn Ala Leu Arg Arg Cys Phe
         65                  70                  75 ttc tgg aga ttt atg ttc tat gga atc ttt tta tat tta ggg gaa gtc       411
Phe Trp Arg Phe Met Phe Tyr Gly Ile Phe Leu Tyr Leu Gly Glu Val
     80                  85                  90 acc aaa gca gta cag cct ctc tta ctg gga aga atc ata gct tcc tat       459
Thr Lys Ala Val Gln Pro Leu Leu Leu Gly Arg Ile Ile Ala Ser Tyr
 95                 100                 105 gac ccg gat aac aag gag gaa cgc tct atc gcg att tat cta ggc ata       507
Asp Pro Asp Asn Lys Glu Glu Arg Ser Ile Ala Ile Tyr Leu Gly Ile
110                 115                 120                 125 ggc tta tgc ctt ctc ttt att gtg agg aca ctg ctc cta cac cca gcc       555
Gly Leu Cys Leu Leu Phe Ile Val Arg Thr Leu Leu Leu His Pro Ala
                130                 135                 140 att ttt ggc ctt cat cac att gga atg cag atg aga ata gct atg ttt       603
Ile Phe Gly Leu His His Ile Gly Met Gln Met Arg Ile Ala Met Phe
        145                 150                 155 agt ttg att tat aag aag act tta aag ctg tca agc cgt gtt cta gat       651
Ser Leu Ile Tyr Lys Lys Thr Leu Lys Leu Ser Ser Arg Val Leu Asp
    160                 165                 170 aaa ata agt att gga caa ctt gtt agt ctc ctt tcc aac aac ctg aac       699
Lys Ile Ser Ile Gly Gln Leu Val Ser Leu Leu Ser Asn Asn Leu Asn
175                 180                 185 aaa ttt gat gaa gga ctt gca ttg gca cat ttc gtg tgg atc gct cct       747
Lys Phe Asp Glu Gly Leu Ala Leu Ala His Phe Val Trp Ile Ala Pro
190                 195                 200                 205 ttg caa gtg gca ctc ctc atg ggg cta atc tgg gag ttg tta cag gcg       795
Leu Gln Val Ala Leu Leu Met Gly Leu Ile Trp Glu Leu Leu Gln Ala
                210                 215                 220 tct gcc ttc tgt gga ctt ggt ttc ctg ata gtc ctt gcc ctt ttt cag       843
Ser Ala Phe Cys Gly Leu Gly Phe Leu Ile Val Leu Ala Leu Phe Gln
                225                 230                 235 gct ggg cta ggg aga atg atg atg aag tac aga gat cag aga gct ggg       891
Ala Gly Leu Gly Arg Met Met Met Lys Tyr Arg Asp Gln Arg Ala Gly
        240                 245                 250 aag atc agt gaa aga ctt gtg att acc tca gaa atg att gaa aat atc       939
Lys Ile Ser Glu Arg Leu Val Ile Thr Ser Glu Met Ile Glu Asn Ile
    255                 260                 265 caa tct gtt aag gca tac tgc tgg gaa gaa gca atg gaa aaa atg att      987
Gln Ser Val Lys Ala Tyr Cys Trp Glu Glu Ala Met Glu Lys Met Ile
270                 275                 280                 285
```

```
gaa aac tta aga caa aca gaa ctg aaa ctg act cgg aag gca gcc tat    1035
Glu Asn Leu Arg Gln Thr Glu Leu Lys Leu Thr Arg Lys Ala Ala Tyr
            290                 295                 300 gtg aga tac ttc aat agc tca gcc ttc ttc ttc tca ggg ttc ttt gtg    1083
Val Arg Tyr Phe Asn Ser Ser Ala Phe Phe Phe Ser Gly Phe Phe Val
        305                 310                 315 gtg ttt tta tct gtg ctt ccc tat gca cta atc aaa gga atc atc ctc    1131
Val Phe Leu Ser Val Leu Pro Tyr Ala Leu Ile Lys Gly Ile Ile Leu
    320                 325                 330 cgg aaa ata ttc acc acc atc tca ttc tgc att gtt ctg cgc atg gcg    1179
Arg Lys Ile Phe Thr Thr Ile Ser Phe Cys Ile Val Leu Arg Met Ala
335                 340                 345 gtc act cgg caa ttt ccc tgg gct gta caa aca tgg tat gac tct ctt    1227
Val Thr Arg Gln Phe Pro Trp Ala Val Gln Thr Trp Tyr Asp Ser Leu
350                 355                 360                 365 gga gca ata aac aaa ata cag gat ttc tta caa aag caa gaa tat aag    1275
Gly Ala Ile Asn Lys Ile Gln Asp Phe Leu Gln Lys Gln Glu Tyr Lys
                370                 375                 380 aca ttg gaa tat aac tta acg act aca gaa gta gtg atg gag aat gta    1323
Thr Leu Glu Tyr Asn Leu Thr Thr Thr Glu Val Val Met Glu Asn Val
            385                 390                 395 aca gcc ttc tgg gag gag gga ttt ggg gaa tta ttt gag aaa gca aaa    1371
Thr Ala Phe Trp Glu Glu Gly Phe Gly Glu Leu Phe Glu Lys Ala Lys
        400                 405                 410 caa aac aat aac aat aga aaa act tct aat ggt gat gac agc ctc ttc    1419
Gln Asn Asn Asn Asn Arg Lys Thr Ser Asn Gly Asp Asp Ser Leu Phe
    415                 420                 425 ttc agt aat ttc tca ctt ctt ggt act cct gtc ctg aaa gat att aat    1467
Phe Ser Asn Phe Ser Leu Leu Gly Thr Pro Val Leu Lys Asp Ile Asn
430                 435                 440                 445 ttc aag ata gaa aga gga cag ttg ttg gcg gtt gct gga tcc act gga    1515
Phe Lys Ile Glu Arg Gly Gln Leu Leu Ala Val Ala Gly Ser Thr Gly
                450                 455                 460 gca ggc aag act tca ctt cta atg atg att atg gga gaa ctg gag cct    1563
Ala Gly Lys Thr Ser Leu Leu Met Met Ile Met Gly Glu Leu Glu Pro
            465                 470                 475 tca gag ggt aaa att aag cac agt gga aga att tca ttc tgt tct cag    1611
Ser Glu Gly Lys Ile Lys His Ser Gly Arg Ile Ser Phe Cys Ser Gln
        480                 485                 490 ttt tcc tgg att atg cct ggc acc att aaa gaa aat atc atc ttt ggt    1659
Phe Ser Trp Ile Met Pro Gly Thr Ile Lys Glu Asn Ile Ile Phe Gly
    495                 500                 505 gtt tcc tat gat gaa tat aga tac aga agc gtc atc aaa gca tgc caa    1707
Val Ser Tyr Asp Glu Tyr Arg Tyr Arg Ser Val Ile Lys Ala Cys Gln
510                 515                 520                 525 cta gaa gag gac atc tcc aag ttt gca gag aaa gac aat ata gtt ctt    1755
Leu Glu Glu Asp Ile Ser Lys Phe Ala Glu Lys Asp Asn Ile Val Leu
                530                 535                 540 gga gaa ggt gga atc aca ctg agt gga ggt caa cga gca aga att tct    1803
Gly Glu Gly Gly Ile Thr Leu Ser Gly Gly Gln Arg Ala Arg Ile Ser
            545                 550                 555 tta gca aga gca gta tac aaa gat gct gat ttg tat tta tta gac tct    1851
Leu Ala Arg Ala Val Tyr Lys Asp Ala Asp Leu Tyr Leu Leu Asp Ser
        560                 565                 570 cct ttt gga tac cta gat gtt tta aca gaa aaa gaa ata ttt gaa agc    1899
Pro Phe Gly Tyr Leu Asp Val Leu Thr Glu Lys Glu Ile Phe Glu Ser
    575                 580                 585 tgt gtc tgt aaa ctg atg gct aac aaa act agg att ttg gtc act tct    1947
Cys Val Cys Lys Leu Met Ala Asn Lys Thr Arg Ile Leu Val Thr Ser
590                 595                 600                 605
```

| | | | | | | | | | | | | | | | |
|---|---|---|---|---|---|---|---|---|---|---|---|---|---|---|---|
| aaa | atg | gaa | cat | tta | aag | aaa | gct | gac | aaa | ata | tta | att | ttg | cat | gaa | 1995 |
| Lys | Met | Glu | His | Leu | Lys | Lys | Ala | Asp | Lys | Ile | Leu | Ile | Leu | His | Glu | |
| | | | | 610 | | | | | 615 | | | | | 620 | | |

| ggt | agc | agc | tat | ttt | tat | ggg | aca | ttt | tca | gaa | ctc | caa | aat | cta | cag | 2043 |
| Gly | Ser | Ser | Tyr | Phe | Tyr | Gly | Thr | Phe | Ser | Glu | Leu | Gln | Asn | Leu | Gln | |
| | | 625 | | | | | 630 | | | | | 635 | | | | |

| cca | gac | ttt | agc | tca | aaa | ctc | atg | gga | tgt | gat | tct | ttc | gac | caa | ttt | 2091 |
| Pro | Asp | Phe | Ser | Ser | Lys | Leu | Met | Gly | Cys | Asp | Ser | Phe | Asp | Gln | Phe | |
| | 640 | | | | | 645 | | | | | 650 | | | | | |

| agt | gca | gaa | aga | aga | aat | tca | atc | cta | act | gag | acc | tta | cac | cgt | ttc | 2139 |
| Ser | Ala | Glu | Arg | Arg | Asn | Ser | Ile | Leu | Thr | Glu | Thr | Leu | His | Arg | Phe | |
| 655 | | | | | 660 | | | | | 665 | | | | | | |

| tca | tta | gaa | gga | gat | gct | cct | gtc | tcc | tgg | aca | gaa | aca | aaa | aaa | caa | 2187 |
| Ser | Leu | Glu | Gly | Asp | Ala | Pro | Val | Ser | Trp | Thr | Glu | Thr | Lys | Lys | Gln | |
| 670 | | | | 675 | | | | | 680 | | | | | 685 | | |

| tct | ttt | aaa | cag | act | gga | gag | ttt | ggg | gaa | aaa | agg | aag | aat | tct | att | 2235 |
| Ser | Phe | Lys | Gln | Thr | Gly | Glu | Phe | Gly | Glu | Lys | Arg | Lys | Asn | Ser | Ile | |
| | | | | 690 | | | | | 695 | | | | | 700 | | |

| ctc | aat | cca | atc | aac | tct | ata | cga | aaa | ttt | tcc | att | gtg | caa | aag | act | 2283 |
| Leu | Asn | Pro | Ile | Asn | Ser | Ile | Arg | Lys | Phe | Ser | Ile | Val | Gln | Lys | Thr | |
| | | | 705 | | | | | 710 | | | | | 715 | | | |

| ccc | tta | caa | atg | aat | ggc | atc | gaa | gag | gat | tct | gat | gag | cct | tta | gag | 2331 |
| Pro | Leu | Gln | Met | Asn | Gly | Ile | Glu | Glu | Asp | Ser | Asp | Glu | Pro | Leu | Glu | |
| | | | 720 | | | | | 725 | | | | | 730 | | | |

| aga | agg | ctg | tcc | tta | gta | cca | gat | tct | gag | cag | gga | gag | gcg | ata | ctg | 2379 |
| Arg | Arg | Leu | Ser | Leu | Val | Pro | Asp | Ser | Glu | Gln | Gly | Glu | Ala | Ile | Leu | |
| | 735 | | | | | 740 | | | | | 745 | | | | | |

| cct | cgc | atc | agc | gtg | atc | agc | act | ggc | ccc | acg | cct | cag | gca | cga | agg | 2427 |
| Pro | Arg | Ile | Ser | Val | Ile | Ser | Thr | Gly | Pro | Thr | Pro | Gln | Ala | Arg | Arg | |
| 750 | | | | | 755 | | | | | 760 | | | | | 765 | |

| agg | cag | tct | gtc | ctg | aac | ctg | atg | aca | cac | tca | gtt | aac | caa | ggt | cag | 2475 |
| Arg | Gln | Ser | Val | Leu | Asn | Leu | Met | Thr | His | Ser | Val | Asn | Gln | Gly | Gln | |
| | | | | 770 | | | | | 775 | | | | | 780 | | |

| aac | att | cac | cga | aag | aca | aca | gca | tcc | aca | cga | aaa | gtg | tca | ctg | gcc | 2523 |
| Asn | Ile | His | Arg | Lys | Thr | Thr | Ala | Ser | Thr | Arg | Lys | Val | Ser | Leu | Ala | |
| | | | 785 | | | | | 790 | | | | | 795 | | | |

| cct | cag | gca | aac | ttg | act | gaa | ctg | gat | ata | tat | tca | aga | agg | tta | tct | 2571 |
| Pro | Gln | Ala | Asn | Leu | Thr | Glu | Leu | Asp | Ile | Tyr | Ser | Arg | Arg | Leu | Ser | |
| | | 800 | | | | | 805 | | | | | 810 | | | | |

| caa | gaa | act | ggc | ttg | gaa | ata | agt | gaa | gaa | att | aac | gaa | gaa | gac | tta | 2619 |
| Gln | Glu | Thr | Gly | Leu | Glu | Ile | Ser | Glu | Glu | Ile | Asn | Glu | Glu | Asp | Leu | |
| | 815 | | | | | 820 | | | | | 825 | | | | | |

| aag | gag | tgc | ttt | ttt | gat | gat | atg | gag | agc | ata | cca | gca | gtg | act | aca | 2667 |
| Lys | Glu | Cys | Phe | Phe | Asp | Asp | Met | Glu | Ser | Ile | Pro | Ala | Val | Thr | Thr | |
| 830 | | | | | 835 | | | | | 840 | | | | | 845 | |

| tgg | aac | aca | tac | ctt | cga | tat | att | act | gtc | cac | aag | agc | tta | att | ttt | 2715 |
| Trp | Asn | Thr | Tyr | Leu | Arg | Tyr | Ile | Thr | Val | His | Lys | Ser | Leu | Ile | Phe | |
| | | | 850 | | | | | 855 | | | | | 860 | | | |

| gtg | cta | att | tgg | tgc | tta | gta | att | ttt | ctg | gca | gag | gtg | gct | gct | tct | 2763 |
| Val | Leu | Ile | Trp | Cys | Leu | Val | Ile | Phe | Leu | Ala | Glu | Val | Ala | Ala | Ser | |
| | | | | 865 | | | | | 870 | | | | | 875 | | |

| ttg | gtt | gtg | ctg | tgg | ctc | ctt | gga | aac | act | cct | ctt | caa | gac | aaa | ggg | 2811 |
| Leu | Val | Val | Leu | Trp | Leu | Leu | Gly | Asn | Thr | Pro | Leu | Gln | Asp | Lys | Gly | |
| | | | 880 | | | | | 885 | | | | | 890 | | | |

| aat | agt | act | cat | agt | aga | aat | aac | agc | tat | gca | gtg | att | atc | acc | agc | 2859 |
| Asn | Ser | Thr | His | Ser | Arg | Asn | Asn | Ser | Tyr | Ala | Val | Ile | Ile | Thr | Ser | |
| | | 895 | | | | | 900 | | | | | 905 | | | | |

| acc | agt | tcg | tat | tat | gtg | ttt | tac | att | tac | gtg | gga | gta | gcc | gac | act | 2907 |
| Thr | Ser | Ser | Tyr | Tyr | Val | Phe | Tyr | Ile | Tyr | Val | Gly | Val | Ala | Asp | Thr | |
| 910 | | | | | 915 | | | | | 920 | | | | | 925 | |

| | | |
|---|---|---|
| ttg ctt gct atg gga ttc ttc aga ggt cta cca ctg gtg cat act cta<br>Leu Leu Ala Met Gly Phe Phe Arg Gly Leu Pro Leu Val His Thr Leu<br>930                935                940 | | 2955 |
| atc aca gtg tcg aaa att tta cac cac aaa atg tta cat tct gtt ctt<br>Ile Thr Val Ser Lys Ile Leu His His Lys Met Leu His Ser Val Leu<br>945                950                955 | | 3003 |
| caa gca cct atg tca acc ctc aac acg ttg aaa gca ggt ggg att ctt<br>Gln Ala Pro Met Ser Thr Leu Asn Thr Leu Lys Ala Gly Gly Ile Leu<br>960                965                970 | | 3051 |
| aat aga ttc tcc aaa gat ata gca att ttg gat gac ctt ctg cct cct<br>Asn Arg Phe Ser Lys Asp Ile Ala Ile Leu Asp Asp Leu Leu Pro Pro<br>975                980                985 | | 3099 |
| acc ata ttt gac ttc atc cag ttg tta tta att gtg att gga gct ata<br>Thr Ile Phe Asp Phe Ile Gln Leu Leu Leu Ile Val Ile Gly Ala Ile<br>990                995                1000                1005 | | 3147 |
| gca gtt gtc gca gtt tta caa ccc tac atc ttt gtt gca aca gtg cca<br>Ala Val Val Ala Val Leu Gln Pro Tyr Ile Phe Val Ala Thr Val Pro<br>1010                1015                1020 | | 3195 |
| gtg ata gtg gct ttt att atg ttg aga gca tat ttc ctc caa acc tca<br>Val Ile Val Ala Phe Ile Met Leu Arg Ala Tyr Phe Leu Gln Thr Ser<br>1025                1030                1035 | | 3243 |
| cag caa ctc aaa caa ctg gaa tct gaa ggc agg agt cca att ttc act<br>Gln Gln Leu Lys Gln Leu Glu Ser Glu Gly Arg Ser Pro Ile Phe Thr<br>1040                1045                1050 | | 3291 |
| cat ctt gtt aca agc tta aaa gga cta tgg aca ctt cgt gcc ttc gga<br>His Leu Val Thr Ser Leu Lys Gly Leu Trp Thr Leu Arg Ala Phe Gly<br>1055                1060                1065 | | 3339 |
| cgg cag cct tac ttt gaa act ctg ttc cac aaa gct ctg aat tta cat<br>Arg Gln Pro Tyr Phe Glu Thr Leu Phe His Lys Ala Leu Asn Leu His<br>1070                1075                1080                1085 | | 3387 |
| act gcc aac tgg ttc ttg tac ctg tca aca ctg cgc tgg ttc caa atg<br>Thr Ala Asn Trp Phe Leu Tyr Leu Ser Thr Leu Arg Trp Phe Gln Met<br>1090                1095                1100 | | 3435 |
| aga ata gaa atg att ttt gtc atc ttc ttc att gct gtt acc ttc att<br>Arg Ile Glu Met Ile Phe Val Ile Phe Phe Ile Ala Val Thr Phe Ile<br>1105                1110                1115 | | 3483 |
| tcc att tta aca aca gga gaa gga gaa gga aga gtt ggt att atc ctg<br>Ser Ile Leu Thr Thr Gly Glu Gly Glu Gly Arg Val Gly Ile Ile Leu<br>1120                1125                1130 | | 3531 |
| act tta gcc atg aat atc atg agt aca ttg cag tgg gct gta aac tcc<br>Thr Leu Ala Met Asn Ile Met Ser Thr Leu Gln Trp Ala Val Asn Ser<br>1135                1140                1145 | | 3579 |
| agc ata gat gtg gat agc ttg atg cga tct gtg agc cga gtc ttt aag<br>Ser Ile Asp Val Asp Ser Leu Met Arg Ser Val Ser Arg Val Phe Lys<br>1150                1155                1160                1165 | | 3627 |
| ttc att gac atg cca aca gaa ggt aaa cct acc aag tca acc aaa cca<br>Phe Ile Asp Met Pro Thr Glu Gly Lys Pro Thr Lys Ser Thr Lys Pro<br>1170                1175                1180 | | 3675 |
| tac aag aat ggc caa ctc tcg aaa gtt atg att att gag aat tca cac<br>Tyr Lys Asn Gly Gln Leu Ser Lys Val Met Ile Ile Glu Asn Ser His<br>1185                1190                1195 | | 3723 |
| gtg aag aaa gat gac atc tgg ccc tca ggg ggc caa atg act gtc aaa<br>Val Lys Lys Asp Asp Ile Trp Pro Ser Gly Gly Gln Met Thr Val Lys<br>1200                1205                1210 | | 3771 |
| gat ctc aca gca aaa tac aca gaa ggt gga aat gcc ata tta gag aac<br>Asp Leu Thr Ala Lys Tyr Thr Glu Gly Gly Asn Ala Ile Leu Glu Asn<br>1215                1220                1225 | | 3819 |
| att tcc ttc tca ata agt cct ggc cag agg gtg ggc ctc ttg gga aga<br>Ile Ser Phe Ser Ile Ser Pro Gly Gln Arg Val Gly Leu Leu Gly Arg<br>1230                1235                1240                1245 | | 3867 |

```
act gga tca ggg aag agt act ttg tta tca gct ttt ttg aga cta ctg        3915
Thr Gly Ser Gly Lys Ser Thr Leu Leu Ser Ala Phe Leu Arg Leu Leu
            1250                1255                1260 aac act gaa gga gaa atc cag atc gat ggt gtg tct tgg gat tca ata        3963
Asn Thr Glu Gly Glu Ile Gln Ile Asp Gly Val Ser Trp Asp Ser Ile
        1265                1270                1275 act ttg caa cag tgg agg aaa gcc ttt gga gtg ata cca cag aaa gta        4011
Thr Leu Gln Gln Trp Arg Lys Ala Phe Gly Val Ile Pro Gln Lys Val
    1280                1285                1290 ttt att ttt tct gga aca ttt aga aaa aac ttg gat ccc tat gaa cag        4059
Phe Ile Phe Ser Gly Thr Phe Arg Lys Asn Leu Asp Pro Tyr Glu Gln
1295                1300                1305 tgg agt gat caa gaa ata tgg aaa gtt gca gat gag gtt ggg ctc aga        4107
Trp Ser Asp Gln Glu Ile Trp Lys Val Ala Asp Glu Val Gly Leu Arg
1310                1315                1320                1325 tct gtg ata gaa cag ttt cct ggg aag ctt gac ttt gtc ctt gtg gat        4155
Ser Val Ile Glu Gln Phe Pro Gly Lys Leu Asp Phe Val Leu Val Asp
            1330                1335                1340 ggg ggc tgt gtc cta agc cat ggc cac aag cag ttg atg tgc ttg gct        4203
Gly Gly Cys Val Leu Ser His Gly His Lys Gln Leu Met Cys Leu Ala
        1345                1350                1355 aga tct gtt ctc agt aag gcg aag atc ttg ctg ctt gat gaa ccc agt        4251
Arg Ser Val Leu Ser Lys Ala Lys Ile Leu Leu Leu Asp Glu Pro Ser
    1360                1365                1370 gct cat ttg gat cca gta aca tac caa ata att aga aga act cta aaa        4299
Ala His Leu Asp Pro Val Thr Tyr Gln Ile Ile Arg Arg Thr Leu Lys
1375                1380                1385 caa gca ttt gct gat tgc aca gta att ctc tgt gaa cac agg ata gaa        4347
Gln Ala Phe Ala Asp Cys Thr Val Ile Leu Cys Glu His Arg Ile Glu
1390                1395                1400                1405 gca atg ctg gaa tgc caa caa ttt ttg gtc ata gaa gag aac aaa gtg        4395
Ala Met Leu Glu Cys Gln Gln Phe Leu Val Ile Glu Glu Asn Lys Val
            1410                1415                1420 cgg cag tac gat tcc atc cag aaa ctg ctg aac gag agg agc ctc ttc        4443
Arg Gln Tyr Asp Ser Ile Gln Lys Leu Leu Asn Glu Arg Ser Leu Phe
        1425                1430                1435 cgg caa gcc atc agc ccc tcc gac agg gtg aag ctc ttt ccc cac cgg        4491
Arg Gln Ala Ile Ser Pro Ser Asp Arg Val Lys Leu Phe Pro His Arg
    1440                1445                1450 aac tca agc aag tgc aag tct aag ccc cag att gct gct ctg aaa gag        4539
Asn Ser Ser Lys Cys Lys Ser Lys Pro Gln Ile Ala Ala Leu Lys Glu
1455                1460                1465 gag aca gaa gaa gag gtg caa gat aca agg ctt tagagagcag cataaatgtt     4592
Glu Thr Glu Glu Glu Val Gln Asp Thr Arg Leu
1470                1475                1480 gacatgggac atttgctcat ggaattggag ctcgtgggac agtcacctca tggaattgga     4652
gctcgtggaa cagttacctc tgcctcagaa acaaggatg aattaagttt ttttttaaaa     4712
aagaaacatt tggtaagggg aattgaggac actgatatgg gtcttgataa atggcttcct     4772
ggcaatagtc aaattgtgtg aaaggtactt caaatccttg aagatttacc acttgtgttt     4832
tgcaagccag attttcctga aaacccttgc catgtgctag taattggaaa ggcagctcta     4892
aatgtcaatc agcctagttg atcagcttat tgtctagtga aactcgttaa tttgtagtgt     4952
tggagaagaa ctgaaatcat acttcttagg gttatgatta agtaatgata actggaaact     5012
tcagcggttt atataagctt gtattccttt ttctctcctc tccccatgat gtttagaaac     5072
acaactatat tgtttgctaa gcattccaac tatctcattt ccaagcaagt attagaatac     5132
cacaggaacc acaagactgc acatcaaaat atgccccatt caacatctag tgagcagtca     5192
```

-continued

```
ggaaagagaa cttccagatc ctggaaatca gggttagtat tgtccaggtc taccaaaaat        5252
ctcaatattt cagataatca caatacatcc cttacctggg aaagggctgt tataatcttt        5312
cacaggggac aggatggttc ccttgatgaa gaagttgata tgccttttcc caactccaga        5372
aagtgacaag ctcacagacc tttgaactag agtttagctg gaaaagtatg ttagtgcaaa        5432
ttgtcacagg acagcccttc ttccacaga agctccaggt agagggtgtg taagtagata         5492
ggccatgggc actgtgggta gacacacatg aagtccaagc atttagatgt ataggttgat        5552
ggtggtatgt tttcaggcta gatgtatgta cttcatgctg tctacactaa gagagaatga       5612
gagacacact gaagaagcac caatcatgaa ttagttttat atgcttctgt tttataattt        5672
tgtgaagcaa aatttttct ctaggaaata tttattttaa taatgtttca aacatatatt         5732
acaatgctgt attttaaaag aatgattatg aattacattt gtataaaata atttttatat        5792
ttgaaatatt gacttttat ggcactagta tttttatgaa atattatgtt aaaactggga         5852
caggggagaa cctagggtga tattaaccag gggccatgaa tcaccttttg gtctggaggg        5912
aagccttggg gctgatcgag ttgttgccca cagctgtatg attcccagcc agacacagcc        5972
tcttagatgc agttctgaag aagatggtac caccagtctg actgtttcca tcaagggtac        6032
actgccttct caactccaaa ctgactctta agaagactgc attatattta ttactgtaag       6092
aaaatatcac ttgtcaataa aatccataca tttgtgta                                6130
```

<210> SEQ ID NO 2
<211> LENGTH: 1480
<212> TYPE: PRT
<213> ORGANISM: Homo sapiens

<400> SEQUENCE: 2

```
    Met Gln Arg Ser Pro Leu Glu Lys Ala Ser Val Val Ser Lys Leu Phe
    1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
    65                  70                  75                  80

Phe Met Phe Tyr Gly Ile Phe Leu Tyr Leu Gly Glu Val Thr Lys Ala
                    85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
        130                 135                 140

Leu His His Ile Gly Met Gln Met Arg Ile Ala Met Phe Ser Leu Ile
    145                 150                 155                 160

Tyr Lys Lys Thr Leu Lys Leu Ser Ser Arg Val Leu Asp Lys Ile Ser
                    165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
```

```
            210                 215                 220
Cys Gly Leu Gly Phe Leu Ile Val Leu Ala Leu Phe Gln Ala Gly Leu
225                 230                 235                 240

Gly Arg Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
        290                 295                 300

Phe Asn Ser Ser Ala Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640
```

-continued

```
Ser Ser Lys Leu Met Gly Cys Asp Ser Phe Asp Gln Phe Ser Ala Glu
            645                 650                 655
Arg Arg Asn Ser Ile Leu Thr Glu Thr Leu His Arg Phe Ser Leu Glu
            660                 665                 670
Gly Asp Ala Pro Val Ser Trp Thr Glu Thr Lys Lys Gln Ser Phe Lys
            675                 680                 685
Gln Thr Gly Glu Phe Gly Glu Lys Arg Lys Asn Ser Ile Leu Asn Pro
        690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
            725                 730                 735
Ser Leu Val Pro Asp Ser Glu Gln Gly Glu Ala Ile Leu Pro Arg Ile
            740                 745                 750
Ser Val Ile Ser Thr Gly Pro Thr Pro Gln Ala Arg Arg Arg Gln Ser
            755                 760                 765
Val Leu Asn Leu Met Thr His Ser Val Asn Gln Gly Gln Asn Ile His
            770                 775                 780
Arg Lys Thr Thr Ala Ser Thr Arg Lys Val Ser Leu Ala Pro Gln Ala
785                 790                 795                 800
Asn Leu Thr Glu Leu Asp Ile Tyr Ser Arg Arg Leu Ser Gln Glu Thr
            805                 810                 815
Gly Leu Glu Ile Ser Glu Glu Ile Asn Glu Glu Asp Leu Lys Glu Cys
            820                 825                 830
Phe Phe Asp Asp Met Glu Ser Ile Pro Ala Val Thr Thr Trp Asn Thr
            835                 840                 845
Tyr Leu Arg Tyr Ile Thr Val His Lys Ser Leu Ile Phe Val Leu Ile
        850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
            885                 890                 895
His Ser Arg Asn Asn Ser Tyr Ala Val Ile Ile Thr Ser Thr Ser Ser
            900                 905                 910
Tyr Tyr Val Phe Tyr Ile Tyr Val Gly Val Ala Asp Thr Leu Leu Ala
            915                 920                 925
Met Gly Phe Phe Arg Gly Leu Pro Leu Val His Thr Leu Ile Thr Val
            930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
            965                 970                 975
Ser Lys Asp Ile Ala Ile Leu Asp Asp Leu Leu Pro Pro Thr Ile Phe
            980                 985                 990
Asp Phe Ile Gln Leu Leu Leu Ile Val Ile Gly Ala Ile Ala Val Val
            995                 1000                1005
Ala Val Leu Gln Pro Tyr Ile Phe Val Ala Thr Val Pro Val Ile Val
        1010                1015                1020
Ala Phe Ile Met Leu Arg Ala Tyr Phe Leu Gln Thr Ser Gln Gln Leu
025                 1030                1035                1040
Lys Gln Leu Glu Ser Glu Gly Arg Ser Pro Ile Phe Thr His Leu Val
                1045                1050                1055
Thr Ser Leu Lys Gly Leu Trp Thr Leu Arg Ala Phe Gly Arg Gln Pro
            1060                1065                1070
```

```
Tyr Phe Glu Thr Leu Phe His Lys Ala Leu Asn Leu His Thr Ala Asn
    1075                1080                1085

Trp Phe Leu Tyr Leu Ser Thr Leu Arg Trp Phe Gln Met Arg Ile Glu
    1090                1095                1100

Met Ile Phe Val Ile Phe Phe Ile Ala Val Thr Phe Ile Ser Ile Leu
    105                 1110                1115                1120

Thr Thr Gly Glu Gly Glu Gly Arg Val Gly Ile Ile Leu Thr Leu Ala
                1125                1130                1135

Met Asn Ile Met Ser Thr Leu Gln Trp Ala Val Asn Ser Ser Ile Asp
                1140                1145                1150

Val Asp Ser Leu Met Arg Ser Val Ser Arg Val Phe Lys Phe Ile Asp
                1155                1160                1165

Met Pro Thr Glu Gly Lys Pro Thr Lys Ser Thr Lys Pro Tyr Lys Asn
    1170                1175                1180

Gly Gln Leu Ser Lys Val Met Ile Ile Glu Asn Ser His Val Lys Lys
    185                 1190                1195                1200

Asp Asp Ile Trp Pro Ser Gly Gly Gln Met Thr Val Lys Asp Leu Thr
                1205                1210                1215

Ala Lys Tyr Thr Glu Gly Gly Asn Ala Ile Leu Glu Asn Ile Ser Phe
                1220                1225                1230

Ser Ile Ser Pro Gly Gln Arg Val Gly Leu Leu Gly Arg Thr Gly Ser
        1235                1240                1245

Gly Lys Ser Thr Leu Leu Ser Ala Phe Leu Arg Leu Leu Asn Thr Glu
        1250                1255                1260

Gly Glu Ile Gln Ile Asp Gly Val Ser Trp Asp Ser Ile Thr Leu Gln
265                 1270                1275                1280

Gln Trp Arg Lys Ala Phe Gly Val Ile Pro Gln Lys Val Phe Ile Phe
                1285                1290                1295

Ser Gly Thr Phe Arg Lys Asn Leu Asp Pro Tyr Glu Gln Trp Ser Asp
        1300                1305                1310

Gln Glu Ile Trp Lys Val Ala Asp Glu Val Gly Leu Arg Ser Val Ile
        1315                1320                1325

Glu Gln Phe Pro Gly Lys Leu Asp Phe Val Leu Val Asp Gly Gly Cys
    1330                1335                1340

Val Leu Ser His Gly His Lys Gln Leu Met Cys Leu Ala Arg Ser Val
345                 1350                1355                1360

Leu Ser Lys Ala Lys Ile Leu Leu Leu Asp Glu Pro Ser Ala His Leu
                1365                1370                1375

Asp Pro Val Thr Tyr Gln Ile Ile Arg Arg Thr Leu Lys Gln Ala Phe
        1380                1385                1390

Ala Asp Cys Thr Val Ile Leu Cys Glu His Arg Ile Glu Ala Met Leu
        1395                1400                1405

Glu Cys Gln Gln Phe Leu Val Ile Glu Glu Asn Lys Val Arg Gln Tyr
    1410                1415                1420

Asp Ser Ile Gln Lys Leu Leu Asn Glu Arg Ser Leu Phe Arg Gln Ala
425                 1430                1435                1440

Ile Ser Pro Ser Asp Arg Val Lys Leu Phe Pro His Arg Asn Ser Ser
                1445                1450                1455

Lys Cys Lys Ser Lys Pro Gln Ile Ala Ala Leu Lys Glu Glu Thr Glu
                1460                1465                1470

Glu Glu Val Gln Asp Thr Arg Leu
        1475                1480
```

-continued

<210> SEQ ID NO 3
<211> LENGTH: 22846
<212> TYPE: DNA
<213> ORGANISM: Homo sapiens

<400> SEQUENCE: 3

| | | | | | |
|---|---|---|---|---|---|
| ccacccttgg | agttcactca | cctaaacctc | aaactaataa | agcttggttc | ttttctccga | 60 |
| cacgcaaagg | aagcgctaag | gtaaatgcat | cagacccaca | ctgccgcgga | acttttcggc | 120 |
| cttgcaaacg | taacagggac | ccgactagga | tcatcgggaa | aggaggagg | aggaggaagg | 240 |
| caggctccgg | ggaagctggt | ggcagcgggt | cctgggtctg | gcggaccctg | acgcgaagga | 300 |
| gggtctagga | agctctccgg | ggagccgttc | tcccgccggt | ggcttcttct | gtcctccagc | 360 |
| gttgccaact | ggacctaaag | agaggccgcg | actgtcgccc | acctgcggga | tgggcctggt | 420 |
| gctgggcggt | aaggacacgg | acctggaagg | agcgcgcgcg | agggagggag | gctgggagtc | 480 |
| agaatcggga | aagggaggtg | cggggcggcg | agggagcgaa | ggaggagagg | aggaaggagc | 540 |
| gggagggtg | ctggcggggg | tgcgtagtgg | gtggagaaag | ccgctagagc | aaatttgggg | 600 |
| ccggaccagg | cagcactcgg | cttttaacct | gggcagtgaa | ggcgggggaa | agagcaaaag | 660 |
| gaagggtgg | tgtgcggagt | aggggtgggt | gggggaatt | ggaagcaaat | gacatcacag | 720 |
| caggtcagag | aaaagggtt | gagcggcagg | cacccagagt | agtaggtctt | tggcattagg | 780 |
| agcttgagcc | cagacggccc | tagcagggac | cccagcgccc | agagaccatg | cagaggtcgc | 840 |
| ctctggaaaa | ggccagcgtt | gtctccaaac | ttttttcag | gtgagaaggt | ggccaaccga | 900 |
| gcttcggaaa | gacacgtgcc | cacgaaagag | gagggcgtgt | gtatgggttg | ggtttggggt | 960 |
| aaaggaataa | gcagttttta | aaaagatgcg | ctatcattca | ttgttttgaa | agaaaatgtg | 1020 |
| ggtattgtag | aataaaacag | aaagcattaa | gaagagatga | agaatgaac | tgaagctgat | 1080 |
| tgaatagaga | gccacatcta | cttgcaactg | aaaagttaga | atctcaagac | tcaagtacgc | 1140 |
| tactatgcac | ttgttttatt | tcatttttct | aagaaactaa | aaatacttgt | taataagtac | 1200 |
| ctangtatgg | tttattggtt | ttcccccttc | atgccttgga | cacttgattg | tcttcttggc | 1260 |
| acatacaggt | gccatgcctg | catatagtaa | gtgctcagaa | acatttcttt | gactgaattc | 1320 |
| agccaacaaa | aattttgggg | taggtagaaa | atatatgctt | aaagtattta | ttgttatgag | 1380 |
| actggatata | tctagtattt | gtcacaggta | aatgattctt | caaaaattga | agcaaattt | 1440 |
| gttgaaatat | ttattttgaa | aaaagttact | tcacaagcta | taaattttaa | aagccatagg | 1500 |
| aatagatacc | gaagttatat | ccaactgaca | tttaataaat | tgtattcata | gcctaatgtg | 1560 |
| atgagccaca | gaagcttaaa | ccatactatt | attccctccc | aatccctttg | acaaagtgac | 1620 |
| agtcacatta | gttcagagat | attgatgttt | tatacaggtg | tagcctgtaa | gagatgaagc | 1680 |
| ctggtattta | tagaaattga | cttatttat | tctcatattt | acatgtgcat | aattttccat | 1740 |
| atgccagaaa | agttgaatag | tatcagattc | caaatctgta | tggagaccaa | atcaagtgaa | 1800 |
| tatctgttcc | tcctctcttt | attttagctg | gaccagacca | attttgagga | aaggatacag | 1860 |
| acagcgcctg | gaattgtcag | acatatacca | aatcccttct | gttgattctg | ctgacaatct | 1920 |
| atctgaaaaa | ttgaaaggt | atgttcatgt | acattgttta | gttgaagaga | gaaattcata | 1980 |
| ttattaatta | tttagagaag | agaaagcaaa | catattataa | gtttaattct | tatatttaaa | 2040 |
| aataggagcc | aagtatggtg | gctaatgcct | gtaatcccaa | ctatttggga | ggccaagatg | 2100 |
| agaggattgc | ttgagaccag | gagtttgata | ccagcctggg | caacatagca | agatgttatc | 2160 |
| tctacacaaa | ataaaaagtt | agctgggaat | ggtagtgcat | gcttgtaagg | aatctgccag | 2220 |
| atatctggct | gagtgtttgg | tgttgtatgg | tctccatgag | attttgtctc | tataatactt | 2280 |

```
gggttaatct ccttggatat acttgtgtga atcaaactat gttaagggaa ataggacaac    2340
taaaatattt gcacatgcaa cttattggtc ccactttttta ttcttttgca gagaatggga    2400
tagagagctg gcttcaaaga aaatcctaa actcattaat gcccttcggc gatgtttttt     2460
ctggagattt atgttctatg gaatctttttt atatttaggg gtaaggatct catttgtaca   2520
ttcattatgt atcacataac tatatgcatt tttgtgatta tgaaaagact acgaaatctg    2580
gtgaataggt gtaaaaatat aaaggatgaa tccaactcca aacactaaga aaccacctaa    2640
aactctagta aggataagta accactattc actgtttaac ttaaaatacc tcatatgtaa    2700
acttgtctcc cactgttgct ataacaaatc ccaagtctta tttcaaagta ccaagatatt    2760
gaaaatagtg ctaagagttt cacatatggt atgaccctct atataaactc attttaagtc    2820
tcctctaaag atgaaaagtc ttgtgttgaa attctcaggg tattttatga gaaataaatg    2880
aaatttaatt tctctgtttt tccccttttg taggaagtca ccaaagcagt acagcctctc    2940
ttactgggaa gaatcatagc ttcctatgac ccggataaca aggaggaacg ctctatcgcg    3000
atttatctag gcataggctt atgccttctc tttattgtga ggacactgct cctacaccca    3060 gccattttttg gccttcatca cattggaatg cagatgagaa tagctatgtt tagtttgatt    3120
tataagaagg taatacttcc ttgcacaggc cccatggcac atatattctg tatcgtacat    3180
gttttaatgt cataaattag gtagtgagct ggtacaagta agggataaat gctgaaatta    3240
atttaatatg cctattaaat aaatggcagg ataattaat gctcttaatt atccttgata    3300
atttaattga cttaaactga taattattga gtatctaatt atttctgcct agatgctggg    3360
aaataaaaca actagaagca tgccagtata atattgactg ttgaaagaaa catttatgaa    3420
cctgagaaga tagtaagcta gatgaataga atataatttt cattaccttt acttaataat    3480
gaatgcataa taactgaatt agtcatatta taatttttact tataatatat ttgtattttg    3540
tttgttgaaa ttatctaact ttccattttt cttttagact ttaaagctgt caagccgtgt    3600
tctagataaa ataagtattg acaacttgt tagtctcctt tccaacaacc tgaacaaatt      3660
tgatgaagta tgtacctatt gatttaatct tttaggcact attgttataa attatacaac    3720
tggaaaggcg gagttttcct gggtcagata atagtaatta gtggttaagt cttgctcagc    3780
tctagcttcc ctattctgga aactaagaaa ggtcaattgt atagcagagc accattctgg    3840
ggtctggtag aaccacccaa ctcaaaggca ccttagcctg ttgttaataa gatttttcaa    3900
aacttaattc ttatcagacc ttgcttcttt taaacgacat gatacttaag atgtccaatc    3960
ttgattccac tgaataaaaa tatgcttaaa aatgcactga cttgaaattt gttttttggg    4020
aaaaccgatt ctatgtgtag aatgtttaag cacattgcta tgtgctccat gtaatgatta    4080
cctagatttt agtgtgctca gaaccacgaa gtgtttgatc atataagctc cttttacttg    4140 ctttcttttca tatatgattg ttagtttcta ggggtggaag atacaatgac acctgttttt   4200
gctgtgcttt tattttccag ggacttgcat tggcacattt cgtgtggatc gctcctttgc    4260
aagtggcact cctcatgggg ctaatctggg agttgttaca ggcgtctgcc ttctgtggac    4320
ttggtttcct gatagtcctt gcccttttc aggctgggct agggagaatg atgatgaagt     4380
acaggtagca acctatttttc ataacttgaa agttttaaaa attatgtttt caaaaagccc    4440
actttagtaa aaccaggact gctctatgca tagaacagtg atcttcagtg tcattaaatt    4500
tttttttttt tttttttga gacagagtct agatctgtca cccaggctgg agtgcagtgg    4560
cacgatcttg gctcactgca ctgcaacttc tgcctcccag gctcaagcaa ttctcctgcc    4620
tcagcctccg gagtagctgg gattagaggc gcatgcacca cacccagcta atttttgtat   4680
```

```
tttagtagag acagggtttc accaggttgc ccaggctggt ctcgaatgcc tgacctcagg    4740
tgatccgccc acctcggcct cccaaagtac tgatattaca ggcatgagct accgcgcccg    4800
gcctaaaaaa tactttttaa gatggtgtaa atattacttt ctgtatcaat ggtacatttt    4860
ttacttgtca gtctctagaa tttctttata aatatgttga ttcagttcat ttttgtagat    4920
tataaaacag gtaaaaaagg ataaaacatt tatgtgaatt aaagggaata cctaattttt    4980
gtgtagagtt tattagcttt tactactctg gtttatggat catcacacca gagccttagt    5040
tactttgtgt tacagaataa ctaatatgag tgaatgaatg acttacacaa gtcactgctt    5100
aggataaagg gcttgagttt gtcagctaga gtatgacaga aagtatctaa gttttggagt    5160
caaatagcac tttgtttgaa tcccagattg catgcttact agttatgtga ccttagtcaa    5220
gccacttcac ctcactgagt ctttgctttt ttcatctcta aaatagagat acccaccgct    5280
cataggctgt cataaggata gagatagcat atggaatgag tctgtacagc gtctggcaca    5340
taggaggcat ttaccaaaca gtagttatta ttttgttac catctatttg ataataaaat    5400
aatgcccatc tgttgaataa aagaaatatg acttaaaacc ttgagcagtt cttaatagat    5460
aatttgactt gttttactag ttagattgat tgattgattg attgattgat ttacagagat    5520
cagagagctg ggaagatcag tgaaagactt gtgattacct cagaaatgat tgaaaatatc    5580
caatctgtta aggcatactg ctgggaagaa gcaatggaaa aaatgattga aaacttaaga    5640
cagtaagttt tccaataat ttcaatattg ttagtaattc tgtccttaat ttttttaaaaa    5700
tatgtttatc atggtagact tccacctcat atttgatgtt tgtgacaatc aaatgattgc    5760
atttaagttc tgtcaatatt catgcattag ttgcacaaat tcactttcat gggctgtagt    5820
tttatgtagt tggtccaggg tgttatttta tgctgcaagt atattatact gatacgttat    5880
taaagaattt cctacatatg ttcactgctg ctcaatacat ttatttcgtt aaaaacaatt    5940
atcaagatac tgaaggctga ttggtaactc acatggaact gggagagtat acaattctga    6000
accaaataga tgatttacaa gtactacaag caaaacactg gtactttcat tgttatcttt    6060
tcatataagg taactgaggc ccagagagat taaataacat gcccaaggtc acacaggtca    6120
tatgatgtgg agccaggtta aaaatatagg cagaaagact ctagagacca tgctcagatc    6180
ttccattcca agatccctga tatttgaaaa ataaaataac atcctgaatt ttattgttat    6240
tgttttttat agaacagaac tgaaactgac tcggaaggca gcctatgtga gatacttcaa    6300
tagctcagcc ttcttcttct cagggttctt tgtggtgttt ttatctgtgc ttccctatgc    6360
actaatcaaa ggaatcatcc tccggaaaat attcaccacc atctcattct gcattgttct    6420
gcgcatggcg gtcactcggc aatttccctg ggctgtacaa acatggtatg actctcttgg    6480
agcaataaac aaaatacagg taatgtacca taatgctgca ttatatacta tgatttaaat    6540
aatcagtcaa tagatcagtt ctaatgaact ttgcaaaaat gtgcgaaaag atagaaaaag    6600
aaatttcctt cactaggaag ttataaaagt tgccagctaa tactaggaat gttcaccttla    6660
aactttcct agcatttctc tggacagtat gatggatgag agtggcattt atgcaaatta    6720
ccttaaaatc ccaataatac tgatgtagct agcagctttg agaaagcaca ttagtgggta    6780
attcagggtt gctttgtaaa ttcatcacta aggttagcat gtaatagtac aaggaagaat    6840
cagttgtatg ttaaatctaa tgtataaaaa gttttataaa atatcatatg tttagagagt    6900
atatttcaaa tatgatgaat cctagtgctt ggcaaattaa ctttagaaca ctaataaaat    6960
tatttttatta agaaataatt actatttcat tattaaaatt catatataag atgtagcaca    7020
atgagagtat aaagtagatg taataatgca ttaatgctat tctgattcta taatatgttt    7080
```

```
ttgctctctt ttataaatag gatttcttac aaaagcaaga atataagaca ttggaatata    7140
acttaacgac tacagaagta gtgatggaga atgtaacagc cttctgggag gaggtcagaa    7200
tttttaaaaa attgtttgct ctaaacacct aactgttttc ttctttgtga atatggattt    7260
catcctaatg gcgaataaaa ttagaatgat gatataactg gtagaactgg aaggaggatc    7320
actcacttat tttctagatt aagaagtaga ggaatggcca ggtgctcatg gttgtaatcc    7380
cagcactttc gggagaccaa ggcgggtgga tcacctgagg tcaggagttc aagaccagcc    7440
tgccaacatg gtaaaacccg gtctctacta aaaatacaaa aaattaactg ggtagtgact    7500
ttaaagctgt gtgactttag tcatttaact gctgagtcac agtctacagc tttgaaagag    7560
gaggattata aaatctatct catgttaatg ctgaagatta ataatagtg tttatgtacc    7620 ccgcttatag gagaagaggg tgtgtgtgtg tgtgtgtgtg tgtgtgtgtg tgtatgtgta    7680
tgtatacatg tatgtattca gtctttactg aaattaaaaa atctttaact tgataatggg    7740
caaatatctt agttttagat catgtcctct agaaaccgta tgctatataa ttatgtacta    7800
taaagtaata atgtatacag tgtaatggat catgggccat gtgcttttca aactaattgt    7860
acataaaaca agcatctatt gaaatatct gacaaactca tcttttattt ttgatgtgtg    7920
tgtgtgtgtg tgtgtgtgtt ttttaacag ggatttgggg aattatttga gaaagcaaaa    7980
caaaacaata acaatagaaa aacttctaat ggtgatgaca gcctcttctt cagtaatttc    8040
tcacttcttg gtactcctgt cctgaaagat attaatttca agatagaaag aggacagttg    8100
ttggcggttg ctggatccac tggagcaggc aaggtagttc ttttgttctt cactattaag    8160
aacttaattt ggtgtccatg tctctttttt tttctagttt gtagtgctgg aaggtatttt    8220
tggagaaatt cttacatgag cattaggaga atgtatgggt gtagtgtctt gtataataga    8280
aattgttcca ctgataattt actctagttt tttatttcct catattattt tcagtggctt    8340
tttcttccac atctttatat tttgcaccac attcaacact gtatcttgca catggcgagc    8400
attcaataac tttattgaat aaacaaatca tccatttat ccattcttaa ccagaacaga    8460
cattttttca gagctggtcc aggaaaatca tgacttacat tttgccttag taaccacata    8520 aacaaaagt ctccattttt gttgaccact gtagctgtac taccttccat ctcctcaacc    8580
tattccaact atctgaatca tgtgcccttc tctgtgaacc tctatcataa tacttgtcac    8640
actgtattgt aattgtctct tttacttttcc cttgtatctt ttgtgcatag cagagtacct    8700
gaaacaggaa gtattttaaa tattttgaat caaatgagtt aatagaatct ttacaaataa    8760
gaatatacac ttctgcttag gatgataatt ggaggcaagt gaatcctgag cgtgatttga    8820
taatgaccta ataatgatgg gtttttattc cagacttcac ttctaatgat gattatggga    8880
gaactggagc cttcagaggg taaaattaag cacagtggaa gaatttcatt ctgttctcag    8940
ttttcctgga ttatgcctgg caccattaaa gaaaatatca tctttggtgt ttcctatgat    9000
gaatatagat acagaagcgt catcaaagca tgccaactag aagaggtaag aaactatgtg    9060
aaaacttttt gattatgcat atgaacccctt cacactaccc aaattatata tttggctcca    9120
tattcaatcg gttagtctac atatatttat gtttcctcta tgggtaagct actgtgaatg    9180
gatcaattaa taaacacat gacctatgct ttaagaagct tgcaaacaca tgaaataaat    9240
gcaatttatt ttttaaataa tgggttcatt tgatcacaat aaatgcattt tatgaaatgg    9300
tgagaatttc gttcactcat tagtgagaca aacgtctcaa tggttatttta tatggcatgc    9360 atatagtgat atgtggtata tacccataaa tatacacata ttttaatttt tggtatttta    9420
taattattat ttaatgatca ttcatgacat tttaaaaatt acaggaaaaa tttacatcta    9480
```

```
aaatttcagc aatgttgttt ttgaccaact aaataaattg catttgaaat aatggagatg    9540
caatgttcaa aatttcaact gtggttaaag caatagtgtg atatatgatt acattagaag    9600
gaagatgtgc ctttcaaatt cagattgagc atactaaaag tgactctcta attttctatt    9660
tttggtaata ggacatctcc aagtttgcag agaaagacaa tatagttctt ggagaaggtg    9720
gaatcacact gagtggaggt caacgagcaa gaatttcttt agcaaggtga ataactaatt    9780
attggtctag caagcatttg ctgtaaatgt cattcatgta aaaaaattac agacatttct    9840
ctattgcttt atattctgtt tctggaattg aaaaaatcct ggggtttat ggctagtggg     9900 ttaagaatca catttaagaa ctataaataa tggtatagta tccagatttg gtagagatta    9960
tggttactca gaatctgtgc ccgtatcttg gcttacagtt agcaaaatca cttcagcagt   10020
tcttggaatg ttgtgaaaag tgataaaaat cttctgcaac ttattccttt attcctcatt   10080
taaaataatc taccatagta aaacatgta taaaagtgct acttctgcac cacttttgag    10140
aatagtgtta tttcagtgaa tcgatgtggt gaccatattg taatgcatgt agtgaactgt   10200
ttaaggcaaa tcatctacac tagatgacca ggaaatagag aggaaatgta atttaatttc   10260
cattttcttt ttagagcagt atacaaagat gctgatttgt atttattaga ctctccttt    10320 ggatacctag atgttttaac agaaaaagaa atatttgaaa ggtatgttct ttgaatacct   10380
tacttataat gctcatgcta aaataaaaga aagacagact gtcccatcat agattgcatt   10440
ttacctcttg agaaatatgt tcaccattgt tggtatggca gaatgtagca tggtattaac   10500
tcaaatctga tctgccctac tgggccagga ttcaagatta cttccattaa aacctttct    10560 caccgcctca tgctaaacca gtttctctca ttgctatact gttatagcaa ttgctatcta   10620
tgtagttttt gcagtatcat tgccttgtga tatatattac tttaattgaa ttcacaaggt   10680
accaatttaa ttactacaga gtacttatag aatcatttaa aatataataa aattgtatga   10740
tagagattat atgcaataaa acattaacaa aatgctaaaa tacgagacat attgcaataa   10800
agtatttata aaattgatat ttatatgttt ttatatctta aagctgtgtc tgtaaactga   10860
tggctaacaa aactaggatt ttggtcactt ctaaaatgga acatttaaag aaagctgaca   10920
aaatattaat tttgcatgaa ggtagcagct attttttatgg gacattttca gaactccaaa   10980
atctacagcc agactttagc tcaaaactca tgggatgtga ttctttcgac caatttagtg   11040
cagaaagaag aaattcaatc ctaactgaga ccttacaccg tttctcatta gaaggagatg   11100
ctcctgtctc ctggacagaa acaaaaaaac aatcttttaa acagactgga gagtttgggg   11160
aaaaaaggaa gaattctatt ctcaatccaa tcaactctat acgaaaattt tccattgtgc   11220
aaaagactcc cttacaaatg aatggcatcg aagaggattc tgatgagcct ttagagaaa    11280 ggctgtcctt agtaccagat tctgagcagg gagaggcgat actgcctcgc atcagcgtga   11340
tcagcactgg ccccacgctt caggcacgaa ggaggcagtc tgtcctgaac ctgatgacac   11400
actcagttaa ccaaggtcag aacattcacc gaaagacaac agcatccaca cgaaaagtgt   11460
cactggcccc tcaggcaaac ttgactgaac tggatatata ttcaagaagg ttatctcaag   11520
aaactggctt ggaaataagt gaagaaatta acgaagaaga cttaaaggta ggtatacatc   11580
gcttgggggt atttcacccc acagaatgca attgagtaga atgcaatatg tagcatgtaa   11640
caaaatttac taaaatcata ggattaggat aaggtgtatc ttaaaactca gaaagtatga   11700
agttcattaa ttatacaagc aacgttaaaa tgtaaaataa caaatgatttt cttttttgcaa  11760 tggacatatc tcttcccata aaatgggaaa ggatttagtt tttggtcctc tactaagcca   11820
gtgataactg tgactatagt tagaaagcat ttgctttatt accatcttga accctctgtg   11880
```

```
ggaaacttca tttagatggt atcattcatt tgataaaagg tatgccactg ttaagccttt    11940
aatggtaaaa ttgtccaata ataatacagt tatataatca gtgatacatt tttagaattt    12000
tgaaaaatta cgatgtttct cattttaat aaagctgtgt tgctccagta gacattattc      12060
tggctataga atgacatcat acatggcatt tataatgatt tatatttgtt aaaatacact     12120
tagattcaag taatactatt cttttatttt catatattaa aaataaaacc acaatggtgg    12180
catgaaactg tactgtctta ttgtaatagc cataattctt ttattcagga gtgcttttt      12240 gatgatatgg agagcatacc agcagtgact acatggaaca catacctccg atatattact    12300
gtccacaaga gcttaatttt tgtgctaatt tggtgcttag taattttct ggcagaggta      12360 agaatgttct attgtaaagt attactggat ttaaagttaa attaagatag tttggggatg    12420
tatacatata tatgcacaca cataaatatg tatatataca catgtataca tgtataagta    12480
tgcatatata cacacatata tcactatatg tatatatgta tatattacat atatttgtga    12540
ttttacagta tataatggta tagattcata tagttcttag cttctgaaaa atcaacaagt   12600
agaaccacta ctgagaattc cattaactta atgtggtctc atcacaaata atagtactta    12660
gaacacctag tacagctgct ggacccagga acacaaagca aggaagatg aaattgtgtg    12720 taccttgata ttggtacaca catcaaatgg tgtgatgtga atttagatgt gggcatggga    12780
ggaataggtg aagatgttag aaaaaaaatc aactgtgtct tgttccattc caggtggctg    12840
cttctttggt tgtgctgtgg ctccttggaa agtgagtatt ccatgtccta ttgtgtagat     12900
tgtgttttat ttctgttgat taaatattgt aatccactat gtttgtatgt attgtaatcc      12960
actttgtttc atttctccca agcattatgg tagtggaaag ataaggtttt ttgttaat      13020 gatgaccatt agttgggtga ggtgacacat tcctgtagtc ctagctcctc cacaggctga    13080
cgcaggagga tcacttgagc ccaggagttc agggctgtag tgttgtatca ttgtgagtag    13140
ccaccaccgc actccagcct ggacaatata gtgagatcct atatctaaaa taaaataaaa    13200
taaaatgaat aaattgtgag catgtgcagc tcctgtccta tatctaaata aataaataaa     13260
tgaataaatt gtgagcatgt gcagctcctg cagtttctaa agaatatagt tctgttcagt     13320
ttctgtgaaa cacaataaaa atatttgaaa taacattaca tatttagggt tttcttcaaa     13380 tttttaatt taataaagaa caactcaatc tctatcaata gtgagaaaac atatctattt     13440
tcttgcaata atagtatgat tttgaggtta agggtgcatg ctcttctaat gcaaatatt    13500 gtatttattt agactcaagt ttagttccat ttacatgtat tggaaattca gtaagtaact    13560
ttggctgcca aataacgatt tcctatttgc tttacagcac tcctcttcaa gacaaaggga   13620
atagtactca tagtagaaat aacagctatg cagtgattat caccagcacc agttcgtatt    13680
atgtgtttta catttacgtg ggagtagccg acactttgct tgctatggga ttcttcagag    13740
gtctaccact ggtgcatact ctaatcacag tgtcgaaaat tttacaccac aaaatgttac    13800
attctgttct tcaagcacct atgtcaaccc tcaacacgtt gaaagcaggt actttactag    13860
gtctaagaaa tgaaactgct gatccaccat caatagggcc tgtggttttg ttggttttct     13920
aatggcagtg ctggcttttg cacagaggca tgtgcctttg ttgtaagatt gtaagcagga    13980
tgagtaccca cctattcctg acataattta tagtaaaagc tatttcagag aaattggtcg    14040
ttacttgaat cttacaagaa tctgaaactt ttaaaaaggt ttaaaagtaa aagacaataa    14100
cttgaacaca taattattta gaatgtttgg aaagaaacaa aaatttctaa gtctatctga    14160
ttctatttgc taattcttat ttgggttctg aatgcgtcta ctgtgatcca aacttagtat    14220
tgaatatatt gatatatctt taaaaaatta gtgttttttg aggaatttgt catcttgtat    14280
```

-continued

```
attataggtg ggattcttaa tagattctcc aaagatatag caattttgga tgaccttctg    14340
cctcttacca tatttgactt catccaggta tgtaaaaata agtaccgtta agtatgtctg    14400
tattattaaa aaaacaataa caaaagcaaa tgtgattttg ttttcatttt ttatttgatt    14460
gagggttgaa gtcctgtcta ttgcattaat tttgtaatta ccaaagcct tcaaaataga    14520 cataagttta gtaaattcaa taataagtca gaactgctta cctggcccaa acctgaggca    14580
atcccacatt tagatgtaat agctgtctac ttgggagtga tttgagaggc acaaaggacc    14640
atctttccca aaatcactgg cacagtgcac cagcatggca catgtataca tatgtaacta    14700
acctcgacaa tgtgcacatg taccctaaaa cttaaagtat aataaaaaaa ataaaaaaaa    14760
gtttgaggtg tttaaagtat gcaaaaaaaa aaaagaaat aaatcactga cacactttgt    14820
ccactttgca atgtgaaaat gtttactcac caacatgttt tctttgatct tacagttgtt    14880
attaattgtg attggagcta tagcagttgt cgcagtttta caaccctaca tctttgttgc    14940
aacagtgcca gtgatagtgg cttttattat gttgagagca tatttcctcc aaacctcaca    15000
gcaactcaaa caactggaat ctgaaggtat gacagtgaat gtgcgatact catcttgtaa    15060
aaaagctata agagctattt gagattcttt attgttaatc tacttaaaaa aaattctgct    15120
tttaaacttt tacatcatat aacaataatt tttttctaca tgcatgtgta tataaaagga    15180
aactatatta caaagtacac atggattttt tttcttaatt aatgaccatg tgacttcatt    15240
ttggttttaa aataggtata tagaatctta ccacagttgg tgtacaggac attcatttat    15300
ttcaaagaat ggcaccagtg tgaaaaaaag cttttaacc aatgacattt gtgatatgat    15360
tattctaatt tagtcttttt caggtacaag atattatgaa aattacattt tgtgtttatg    15420
ttatttgcaa tgttttctat ggaaatattt cacaggcagg agtccaattt tcactcatct    15480
tgttacaagc ttaaaaggac tatggacact tcgtgccttc ggacggcagc cttactttga    15540
aactctgttc cacaaagctc tgaatttaca tactgccaac tggttcttgt acctgtcaac    15600
actgcgctgg ttccaaatga gaatagaaat gattttttgtc atcttcttca ttgctgttac    15660
cttcatttcc attttaacaa caggtactat gaactcatta actttagcta agcatttaag    15720
taaaaaattt tcaatgaata aaatgctgca ttctataggt tatcaatttt tgatatcttt    15780
agagtttagt aattaacaaa tttgttggtt tattattgaa caagtgatt ctttgaaatt    15840 tccattgttt tattgttaaa caaataattt ccttgaaatc ggtatatata tatatatagt    15900
atatatatat atatatatat atatatacat atatatatat agtattatcc ctgttttcac    15960
agttttaaaa accgatgcac acagattgtc gagtagcaat tctgtgattg aagggggaaat    16020 atgtcacctc ttcatactca tattggtgaa gggtcctagc ttcaaaatta atagattcct    16080
aaagagggga aatgaaacac cgcatttaca cacacacaca cacacacaca cacagagttc    16140
ctcttgtcgg taagtttgtt attacttata gaataatagt agaagagaca aatatggtac    16200
ctacccatta ccaacaacac ctccaatacc agtaacattt tttaaaaagg gcaacacttt    16260
cctaatattc aatcgctctt tgatttaaaa tcctggttga atacttacta tatgcagagc    16320
attattctat tagtagatgc tgtgatgaac tgagatttaa aaattgttaa aattagcata    16380
aaattgaaat gtaaatttaa tgtgatatgt gccctaggag aagtgtgaat aaagtcgttc    16440
acagaagaga gaaataacat gaggttcatt tacgtctttt gtgcatctat aggagaagga    16500
gaaggaagag ttggtattat cctgacttta gccatgaata tcatgagtac attgcagtgg    16560
gctgtaaact ccagcataga tgtggatagc ttggtaagtc ttatcatctt tttaactttt    16620
atgaaaaaaa ttcagacaag taacaaagta tgagtaatag catgaggaag aactatatac    16680
```

```
cgtatattga gcttaagaaa taaaacatta cagataaatt gagggtcact gtgtatctgt    16740
cattaaatcc ttatctcttc tttccttctc atagatagcc actatgaaga tctaatactg    16800
cagtgagcat tctttcacct gtttccttat tcaggatttt ctaggagaaa tacctagggg    16860
ttgtattgct gggtcatagg attcacccat gcttaacttc tcttcagtta aactttaat    16920 tatatccaat tatttcctgt tagttcattg aaaagcccga caaataacca agtgacaaat    16980
agcaagtgtt gcattttaca agttattttt taggaagcat caaactaatt gtgaaattgt    17040
ctgccattct taaaaacaaa aatgttgtta ttttatttc agatgcgatc tgtgagccga    17100
gtctttaagt tcattgacat gccaacagaa ggtaaaccta ccaagtcaac caaaccatac    17160
aagaatggcc aactctcgaa agttatgatt attgagaatt cacacgtgaa gaaagatgac    17220
atctggccct cagggggcca aatgactgtc aaagatctca cagcaaaata cacagaaggt    17280
ggaaatgcca tattagagaa catttccttc tcaataagtc ctggccagag ggtgagattt    17340
gaacactgct tgctttgtta gactgtgttc agtaagtgaa tcccagtagc ctgaagcaat    17400
gtgttagcag aatctatttg taacattatt attgtacagt agaatcaata ttaaacacac    17460
atgttttatt atatggagtc attattttta atatgaaatt taatttgcag agtctgaact    17520
atatataaag gtcagtgata aaggaagtct gcatcagggg tccaattcct tatggccagt    17580
ttctctattc tgttccaagg ttgtttgtct ccatatatca acattggtca ggattgaaag    17640
tgtgcaacaa ggtttgaatg aataagtgaa aatcttccac tggtgacagg ataaaatatt    17700
ccaatggttt ttattgaagt acaatactga attatgttta tggcatggta cctatatgtc    17760
acagaagtga tcccatcact tttaccttat aggtgggcct cttgggaaga actggatcag    17820
ggaagagtac tttgttatca gcttttttga gactactgaa cactgaagga gaaatccaga    17880
tcgatggtgt gtcttgggat tcaataactt tgcaacagtg gaggaaagcc tttggagtga    17940
taccacaggt gagcaaaagg acttagccag aaaaaaggca actaaattat attttttact    18000
gctatttgat acttgtactc aagaaattca tattactctg caaatatat ttgttatgca    18060 ttgctgtctt ttttttctcc agtgcagttt tctcataggc agaaaagatg tctctaaaag    18120
tttgggaatt ctttttaata ttctacaatt aacaattatc tcaatttctt tattctaaag    18180
acattggatt agaaaaatgt tcacaaggga ctccaaatat tgctgtagta tttgtttctt    18240 aaagaatga tacaaagcag acatgataaa atattaaaat ttgagagaac ttgatggtaa    18300
gtacatgggt gtttcttatt ttaaataat ttttctactt gaaatatttt acaatacaat    18360
aagggaaaaa taaaagtta tttaagttat tcatactttc ttcttctttt cttttttgct    18420
atagaaagta tttatttttt ctggaacatt tagaaaaaac ttggatccct atgaacagtg    18480
gagtgatcaa gaaatatgga aagttgcaga tgaggtaagg ctgctaactg aaatgatttt    18540 gaaagggta actcatacca acacaaatgg ctgatatagc tgacatcatt ctacacactt    18600
tgtgtgcatg tatgtgtgtg cacaacttta aaatggagta ccctaacata cctggagcaa    18660
caggtacttt tgactggacc taccctaac tgaaatgatt tgaaagagg taactctac    18720 caacacaaat ggttgatatg gctaagatca ttctacacac tttgtgtgca tgtatttctg    18780
tgcacaactt caaaatggag taccctaaaa tacctggcgc gacaagtact tttgactgag    18840
cctacttcac agttgactat tttatgctat cttttgtcct cagtcatgac agagtagaag    18900
atgggaggta gcaccaagga tgatgtcata cctccatcct ttatgctaca ttctatcttc    18960
tgtctacata agatgtcata ctagagggca tatctgcaat gtatacatat tatctttcc    19020 agcatgcatt cagttgtgtt ggaataattt atgtacacct ttataaacgc tgagcctcac    19080
```

```
aagagccatg tgccacgtat tgtttcttac tacttttgga tacctggcac gtaatagaca    19140
ctcattgaaa gtttcctaat gaatgaagta caaagataaa acaagttata gactgattct    19200
tttgagctgt caaggttgta aatagacttt tgctcaatca attcaaatgg tggcaggtag    19260
tgggggtaga gggattggta tgaaaaacat aagctttcag aactcctgtg tttattttta    19320
gaatgtcaac tgcttgagtg ttttttaactc tgtggtatct gaactatctt ctctaactgc    19380
aggttgggct cagatctgtg atagaacagt ttcctgggaa gcttgacttt gtccttgtgg    19440
atggggctg tgtcctaagc catggccaca agcagttgat gtgcttggct agatctgttc      19500
tcagtaaggc gaagatcttg ctgcttgatg aacccagtgc tcatttggat ccagtgtgag    19560
tttcagatgt tctgttactt aatagcacag tgggaacaga atcattatgc ctgcttcatg    19620
gtgacacata tttctattag gctgtcatgt ctgcgtgtgg gggtctccca agatatgaaa    19680
taattgccca gtggaaatga gcataaatgc atatttcctt gctaagagtt cttgtgtttt    19740
cttccgaaga tagttttgca tgtttatagc cccaaataaa agaagtactg gtgattctac    19800
ataatgaaaa tgtactcatt tattaaagtt tctttgaaat atttgtcctg tttatttatg    19860
gatacttaga gtctacccca tggttgaaaa gctgattgtg cgtaacgcta tatcaacatt    19920
atgtgaaaag aacttaaaga aataagtaat ttaaagagat aatagaacaa tagacatatt    19980
atcaaggtaa atacagatca ttactgttct gtgatattat gtgtggtatt ttctttcttt    20040
tctagaacat accaaataat tagaagaact ctaaaacaag catttgctga ttgcacagta    20100
attctctgtg aacacaggat agaagcaatg ctggaatgcc aacaattttt ggtgagtctt    20160
tataacttta cttaagatct cattgcccctt gtaattcttg ataacaatct cacatgtgat    20220
agttcctgca aattgcaaca atgtacaagt tcttttcaaa aatatgtatc atacagccat    20280
ccagctttac tcaaaatagc tgcacaagtt tttcactttg atctgagcca tgtggtgagg    20340
ttgaaatata gtaaatctaa aatggcagca tattactaag ttatgtttat aaataggata    20400
tatatacttt tgagcccttt atttgggacc aagtcataca aaatactcta ctgtttaaga    20460
ttttaaaaaa ggtccctgtg attctttcaa taactaaatg tcccatggat gtggtctgga    20520
caggcctagt tgtcttacag tctgatttat ggtattaatg acaaagttga gaggcacatt    20580
tcattttct agccatgatt tgggttcagg tagtacctttc tcaaccacc ttctcactgt       20640
tcttaaaaaa actgtcacat ggccaggcac agtggcttac atctgtaatc ccaatacttt    20700
gggaggctga ggtgggggga ttacttgagg ccaggaattc agatggtaga acctccttag    20760
agcaaaagga cacagcagtt aaatgtgaca tacctgattg ttcaaaatgc aaggctctgg    20820
acattgcatt ctttgacttt tattttcctt tgagcctgtg ccagtttctg tccctgctct    20880
ggtctgacct gccttctgtc ccagatctca ctaacagcca tttccctagg tcatagaaga    20940
gaacaaagtg cggcagtacg attccatcca gaaactgctg aacgagagga gcctcttccg    21000
gcaagccatc agcccctccg acagggtgaa gctctttccc caccggaact caagcaagtg    21060
caagtctaag ccccagattg ctgctctgaa agaggagaca gaagaagagg tgcaagatac    21120
aaggctttag agagcagcat aaatgttgac atgggacatt tgctcatgga attggagctc    21180
gtgggacagt cacctcatgg aattggagct cgtggaacag ttacctctgc ctcagaaaac    21240
aaggatgaat taagttttt tttaaaaaag aaacatttgg taagggaat tgaggacact      21300
gatatgggtc ttgataaatg gcttcctggc aatagtcaaa ttgtgtgaaa ggtacttcaa    21360
atccttgaag atttaccact tgtgttttgc aagccagatt ttcctgaaaa ccccttgccat    21420
gtgctagtaa ttggaaaggc agctctaaat gtcaatcagc ctagttgatc agcttattgt    21480
```

```
ctagtgaaac tcgttaattt gtagtgttgg agaagaactg aaatcatact tcttagggtt    21540
atgattaagt aatgataact ggaactcagc ggtttatata agcttgtatt ccttttctc    21600 tcctctcccc atgatgttta gaaacacaac tatattgttt gctaagcatt ccaactatct    21660
catttccaag caagtattag aataccacag gaaccacaag actgcacatc aaaatatgcc    21720
ccattcaaca tctagtgagc agtcaggaaa gagaacttcc agatcctgga aatcagggtt    21780
agtattgtcc aggtctacca aaaatctcaa tatttcagat aatcacaata catcccttac    21840
ctgggaaagg gctgttataa tctttcacag gggacaggag ggttccctta cctgggaaag    21900
ggctgttata atctttcaca ggggacagga tggttccctt gatgaagaag ttgatatgcc    21960
ttttcccaac tccagaaagt gacaagctca cagaccttg aactagagtt tagctggaaa    22020
agtatgttag tgcaaattgt cacaggacag cccttctttc cacagaagct ccaggtagag    22080
ggtgtgtaag tagataggcc atgggcactg tgggtagaca cacatgaagt ccaagcattt    22140
agatgtatag gttgatggtg gtatgttttc aggctagatg tatgtacttc atgctgtcta    22200
cactaagaga gaatgagaga cacactgaag aagcaccaat catgaattag ttttatatgc    22260
ttctgtttta taattttgtg aagcaaaatt ttttctctag gaaatattta ttttaataat    22320
gtttcaaaca tatattacaa tgctgtattt taaaagaatg attatgaatt acatttgtat    22380
aaaataattt ttatatttga aatattgact ttttatggca ctagtatttt tatgaaatat    22440
tatgttaaaa ctgggacagg ggagaaccta gggtgatatt aaccaggggc catgaatcac    22500
cttttggtct ggagggaagc cttggggctg atcgaggttg ttgcccacag ctgtatgatt    22560
cccagccaga cacagcctct tagatgcagt tctgaagaag atggtaccac cagtctgact    22620
gtttccatca agggtacact gccttctcaa ctccaaactg actcttaaga agactgcatt    22680
atatttatta ctgtaagaaa atatcacttg tcaataaaat ccatacattt gtgtgaaact    22740
ttgttgtttt cagatgcgtt cacttgtcat gtttcatcag tctctcactc caatttctaa    22800
gcttcatgga acatgaaaca cgaatctgtc ttttagatat agcctc                  22846
```

<210> SEQ ID NO 4
<211> LENGTH: 1480
<212> TYPE: PRT
<213> ORGANISM: Homo sapiens

<400> SEQUENCE: 4

```
        Met Gln Arg Ser Pro Leu Glu Lys Ala Ser Val Val Ser Lys Leu Phe
         1               5                  10                  15

Phe Ser Trp Thr Arg Pro Ile Leu Arg Lys Gly Tyr Arg Gln Arg Leu
                        20                  25                  30

Glu Leu Ser Asp Ile Tyr Gln Ile Pro Ser Val Asp Ser Ala Asp Asn
                    35                  40                  45

Leu Ser Glu Lys Leu Glu Arg Glu Trp Asp Arg Glu Leu Ala Ser Lys
                50                  55                  60

Lys Asn Pro Lys Leu Ile Asn Ala Leu Arg Arg Cys Phe Phe Trp Arg
         65                  70                  75                  80

Phe Met Phe Tyr Gly Ile Phe Leu Tyr Leu Gly Glu Val Thr Lys Ala
                        85                  90                  95

Val Gln Pro Leu Leu Leu Gly Arg Ile Ile Ala Ser Tyr Asp Pro Asp
                    100                 105                 110

Asn Lys Glu Glu Arg Ser Ile Ala Ile Tyr Leu Gly Ile Gly Leu Cys
                115                 120                 125

Leu Leu Phe Ile Val Arg Thr Leu Leu Leu His Pro Ala Ile Phe Gly
```

-continued

```
                130                 135                 140
Leu His His Ile Gly Met Gln Met Arg Ile Ala Met Phe Ser Leu Ile
145                 150                 155                 160
Tyr Lys Lys Thr Leu Lys Leu Ser Ser Arg Val Leu Asp Lys Ile Ser
                165                 170                 175
Ile Gly Gln Leu Val Ser Leu Leu Ser Asn Asn Leu Asn Lys Phe Asp
                180                 185                 190
Glu Gly Leu Ala Leu Ala His Phe Val Trp Ile Ala Pro Leu Gln Val
                195                 200                 205
Ala Leu Leu Met Gly Leu Ile Trp Glu Leu Gln Ala Ser Ala Phe
210                 215                 220
Cys Gly Leu Gly Phe Leu Ile Val Leu Ala Leu Phe Gln Ala Gly Leu
225                 230                 235                 240
Gly Arg Met Met Met Lys Tyr Arg Asp Gln Arg Ala Gly Lys Ile Ser
                245                 250                 255
Glu Arg Leu Val Ile Thr Ser Glu Met Ile Glu Asn Ile Gln Ser Val
                260                 265                 270
Lys Ala Tyr Cys Trp Glu Glu Ala Met Glu Lys Met Ile Glu Asn Leu
                275                 280                 285
Arg Gln Thr Glu Leu Lys Leu Thr Arg Lys Ala Ala Tyr Val Arg Tyr
                290                 295                 300
Phe Asn Ser Ser Ala Phe Phe Phe Ser Gly Phe Phe Val Val Phe Leu
305                 310                 315                 320
Ser Val Leu Pro Tyr Ala Leu Ile Lys Gly Ile Ile Leu Arg Lys Ile
                325                 330                 335
Phe Thr Thr Ile Ser Phe Cys Ile Val Leu Arg Met Ala Val Thr Arg
                340                 345                 350
Gln Phe Pro Trp Ala Val Gln Thr Trp Tyr Asp Ser Leu Gly Ala Ile
                355                 360                 365
Asn Lys Ile Gln Asp Phe Leu Gln Lys Gln Glu Tyr Lys Thr Leu Glu
                370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
Asn Asn Arg Lys Thr Ser Asn Gly Asp Asp Ser Leu Phe Phe Ser Asn
                420                 425                 430
Phe Ser Leu Leu Gly Thr Pro Val Leu Lys Asp Ile Asn Phe Lys Ile
                435                 440                 445
Glu Arg Gly Gln Leu Leu Ala Val Ala Gly Ser Thr Gly Ala Gly Lys
                450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
                500                 505                 510
Asp Glu Tyr Arg Tyr Arg Ser Val Ile Lys Ala Cys Gln Leu Glu Glu
                515                 520                 525
Asp Ile Ser Lys Phe Ala Glu Lys Asp Asn Ile Val Leu Gly Glu Gly
                530                 535                 540
Gly Ile Thr Leu Ser Gly Gly Gln Arg Ala Arg Ile Ser Leu Ala Arg
545                 550                 555                 560
```

-continued

Ala Val Tyr Lys Asp Ala Asp Leu Tyr Leu Leu Asp Ser Pro Phe Gly
            565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu His Glu Gly Ser Ser
            610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
                660                 665                 670

Gly Asp Ala Pro Val Ser Trp Thr Glu Thr Lys Lys Gln Ser Phe Lys
                675                 680                 685

Gln Thr Gly Glu Phe Gly Glu Lys Arg Lys Asn Ser Ile Leu Asn Pro
690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
            770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
                820                 825                 830

Phe Phe Asp Asp Met Glu Ser Ile Pro Ala Val Thr Thr Trp Asn Thr
                835                 840                 845

Tyr Leu Arg Tyr Ile Thr Val His Lys Ser Leu Ile Phe Val Leu Ile
850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
                900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

```
Asp Phe Ile Gln Leu Leu Leu Ile Val Ile Gly Ala Ile Ala Val Val
        995                1000                1005

Ala Val Leu Gln Pro Tyr Ile Phe Val Ala Thr Val Pro Val Ile Val
   1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
               1045                1050                1055

Thr Ser Leu Lys Gly Leu Trp Thr Leu Arg Ala Phe Gly Arg Gln Pro
           1060                1065                1070

Tyr Phe Glu Thr Leu Phe His Lys Ala Leu Asn Leu His Thr Ala Asn
       1075                1080                1085

Trp Phe Leu Tyr Leu Ser Thr Leu Arg Trp Phe Gln Met Arg Ile Glu
   1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
               1125                1130                1135

Met Asn Ile Met Ser Thr Leu Gln Trp Ala Val Asn Ser Ser Ile Asp
           1140                1145                1150

Val Asp Ser Leu Met Arg Ser Val Ser Arg Val Phe Lys Phe Ile Asp
       1155                1160                1165

Met Pro Thr Glu Gly Lys Pro Thr Lys Ser Thr Lys Pro Tyr Lys Asn
   1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
               1205                1210                1215

Ala Lys Tyr Thr Glu Gly Gly Asn Ala Ile Leu Glu Asn Ile Ser Phe
           1220                1225                1230

Ser Ile Ser Pro Gly Gln Arg Val Gly Leu Leu Gly Arg Thr Gly Ser
       1235                1240                1245

Gly Lys Ser Thr Leu Leu Ser Ala Phe Leu Arg Leu Leu Asn Thr Glu
1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
               1285                1290                1295

Ser Gly Thr Phe Arg Lys Asn Leu Asp Pro Tyr Glu Gln Trp Ser Asp
           1300                1305                1310

Gln Glu Ile Trp Lys Val Ala Asp Glu Val Gly Leu Arg Ser Val Ile
       1315                1320                1325

Glu Gln Phe Pro Gly Lys Leu Asp Phe Val Leu Val Asp Gly Gly Cys
   1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
               1365                1370                1375

Asp Pro Val Thr Tyr Gln Ile Ile Arg Arg Thr Leu Lys Gln Ala Phe
           1380                1385                1390

Ala Asp Cys Thr Val Ile Leu Cys Glu His Arg Ile Glu Ala Met Leu
       1395                1400                1405

Glu Cys Gln Gln Phe Leu Val Ile Glu Glu Asn Lys Val Arg Gln Tyr
```

```
                1410              1415              1420

Asp Ser Ile Gln Lys Leu Asn Glu Arg Ser Leu Phe Arg Gln Ala
                1425              1430              1435              1440

Ile Ser Pro Ser Asp Arg Val Lys Leu Phe Pro His Arg Asn Ser Ser
                    1445              1450              1455

Lys Cys Lys Ser Lys Pro Gln Ile Ala Ala Leu Lys Glu Glu Thr Glu
                    1460              1465              1470

Glu Glu Val Gln Asp Thr Arg Leu
                1475              1480

<210> SEQ ID NO 5
<211> LENGTH: 28
<212> TYPE: DNA
<213> ORGANISM: Homo sapiens

<400> SEQUENCE: 5
cggaattctc gagatctttt tttttttt                                      28

<210> SEQ ID NO 6
<211> LENGTH: 19
<212> TYPE: DNA
<213> ORGANISM: Homo sapiens

<400> SEQUENCE: 6
atgaagtcca aggatttag                                                19

<210> SEQ ID NO 7
<211> LENGTH: 10
<212> TYPE: RNA
<213> ORGANISM: Homo sapiens

<400> SEQUENCE: 7
agaccaugca                                                          10

<210> SEQ ID NO 8
<211> LENGTH: 24
<212> TYPE: DNA
<213> ORGANISM: Homo sapiens

<400> SEQUENCE: 8
gttggcatgc tttgatgacg cttc                                          24

<210> SEQ ID NO 9
<211> LENGTH: 24
<212> TYPE: DNA
<213> ORGANISM: Homo sapiens

<400> SEQUENCE: 9
gttttcctgg attatgcctg gcac                                          24

<210> SEQ ID NO 10
<211> LENGTH: 20
<212> TYPE: DNA
<213> ORGANISM: Homo sapiens

<400> SEQUENCE: 10
gcagagtacc tgaaacagga                                               20

<210> SEQ ID NO 11
<211> LENGTH: 20
<212> TYPE: DNA
<213> ORGANISM: Homo sapiens
```

```
<400> SEQUENCE: 11
cattcacagt agcttaccca                                           20

<210> SEQ ID NO 12
<211> LENGTH: 20
<212> TYPE: DNA
<213> ORGANISM: Homo sapiens

<400> SEQUENCE: 12
taatggatca tgggccatgt                                           20

<210> SEQ ID NO 13
<211> LENGTH: 20
<212> TYPE: DNA
<213> ORGANISM: Homo sapiens

<400> SEQUENCE: 13
acagtgttga atgtggtgca                                           20

<210> SEQ ID NO 14
<211> LENGTH: 16
<212> TYPE: DNA
<213> ORGANISM: Homo sapiens

<400> SEQUENCE: 14
gttgttggcg gttgct                                               16

<210> SEQ ID NO 15
<211> LENGTH: 16
<212> TYPE: DNA
<213> ORGANISM: Homo sapiens

<400> SEQUENCE: 15
gttgttggag gttgct                                               16

<210> SEQ ID NO 16
<211> LENGTH: 20
<212> TYPE: DNA
<213> ORGANISM: Homo sapiens

<400> SEQUENCE: 16
ggcataatcc aggaaaactg                                           20

<210> SEQ ID NO 17
<211> LENGTH: 20
<212> TYPE: DNA
<213> ORGANISM: Homo sapiens

<400> SEQUENCE: 17
ggcataatcc aggaaaacta                                           20

<210> SEQ ID NO 18
<211> LENGTH: 16
<212> TYPE: DNA
<213> ORGANISM: Homo sapiens

<400> SEQUENCE: 18
accttctcca agaact                                               16

<210> SEQ ID NO 19
<211> LENGTH: 16
<212> TYPE: DNA
<213> ORGANISM: Homo sapiens
```

-continued

```
<400> SEQUENCE: 19
accttctcaa agaact                                                 16

<210> SEQ ID NO 20
<211> LENGTH: 16
<212> TYPE: DNA
<213> ORGANISM: Homo sapiens

<400> SEQUENCE: 20
acactgagtg gaggtc                                                 16

<210> SEQ ID NO 21
<211> LENGTH: 16
<212> TYPE: DNA
<213> ORGANISM: Homo sapiens

<400> SEQUENCE: 21
acactgaggg gaggtc                                                 16

<210> SEQ ID NO 22
<211> LENGTH: 16
<212> TYPE: DNA
<213> ORGANISM: Homo sapiens

<400> SEQUENCE: 22
tgctcgttga cctcca                                                 16

<210> SEQ ID NO 23
<211> LENGTH: 16
<212> TYPE: DNA
<213> ORGANISM: Homo sapiens

<400> SEQUENCE: 23
tgctcgttga cctccc                                                 16

<210> SEQ ID NO 24
<211> LENGTH: 24
<212> TYPE: DNA
<213> ORGANISM: Homo sapiens

<400> SEQUENCE: 24
caactgtggt taaagcaata gtgt                                        24

<210> SEQ ID NO 25
<211> LENGTH: 24
<212> TYPE: DNA
<213> ORGANISM: Homo sapiens

<400> SEQUENCE: 25
gcacagattc tgagtaacca taat                                        24

<210> SEQ ID NO 26
<211> LENGTH: 15
<212> TYPE: DNA
<213> ORGANISM: Homo sapiens

<400> SEQUENCE: 26
gactctcctt ttgga                                                  15

<210> SEQ ID NO 27
<211> LENGTH: 15
<212> TYPE: DNA
<213> ORGANISM: Homo sapiens
```

-continued

```
<400> SEQUENCE: 27
gactctcatt ttgga                                                 15

<210> SEQ ID NO 28
<211> LENGTH: 20
<212> TYPE: DNA
<213> ORGANISM: Homo sapiens

<400> SEQUENCE: 28
gtatggtttg gttgacttgg                                            20

<210> SEQ ID NO 29
<211> LENGTH: 20
<212> TYPE: DNA
<213> ORGANISM: Homo sapiens

<400> SEQUENCE: 29
gtatggtttg gttgacttgt                                            20

<210> SEQ ID NO 30
<211> LENGTH: 20
<212> TYPE: DNA
<213> ORGANISM: Homo sapiens

<400> SEQUENCE: 30
tttggtaata ggacatctcc                                            20

<210> SEQ ID NO 31
<211> LENGTH: 20
<212> TYPE: DNA
<213> ORGANISM: Homo sapiens

<400> SEQUENCE: 31
tttggtaata agacatctcc                                            20

<210> SEQ ID NO 32
<211> LENGTH: 13
<212> TYPE: PRT
<213> ORGANISM: Homo sapiens

<400> SEQUENCE: 32

Gly Thr Ile Lys Glu Asn Ile Ile Phe Gly Val Ser Tyr
      1               5                  10

<210> SEQ ID NO 33
<211> LENGTH: 12
<212> TYPE: PRT
<213> ORGANISM: Homo sapiens

<400> SEQUENCE: 33

Gly Thr Ile Lys Glu Asn Ile Phe Gly Val Ser Tyr
      1               5                  10
```

METHODS FOR SCREENING FOR MUTATIONS AT VARIOUS POSITIONS IN THE INTRONS AND EXONS OF THE CYSTIC FIBROSIS GENE

This application is a divisional application of copending application Ser. No. 07/890,609 filed Jul. 13, 1992, which is a national phase filed of PCT/CA91/00009; filed Jan. 11, 1991; the disclosure of which is incorporated herein by reference in its entirety.

FIELD OF THE INVENTION

The present invention relates generally to the cystic fibrosis (CF) gene, and, more particularly to the identification, isolation and cloning of the DNA sequence corresponding to mutants of the CF gene, as well as their transcripts, gene products and genetic information at exon/intron boundaries. The present invention also relates to methods of screening for and detection of CF carriers, CF diagnosis, prenatal CF screening and diagnosis, and gene therapy utilizing recombinant technologies and drug therapy using the information derived from the DNA, protein, and the metabolic function of the protein.

BACKGROUND OF THE INVENTION

Cystic fibrosis (CF) is the most common severe autosomal recessive genetic disorder in the Caucasian population. It affects approximately 1 in 2000 live births in North America [Boat et al, *The Metabolic Basis of Inherited Disease,* 6th ed, pp 2649–2680, McGraw Hill, NY (1989)]. Approximately 1 in 20 persons are carriers of the disease.

Although the disease was first described in the late 1930's, the basic defect remains unknown. The major symptoms of cystic fibrosis include chronic pulmonary disease, pancreatic exocrine insufficiency, and elevated sweat electrolyte levels. The symptoms are consistent with cystic fibrosis being an exocrine disorder. Although recent advances have been made in the analysis of ion transport across the apical membrane of the epithelium of CF patient cells, it is not clear that the abnormal regulation of chloride channels represents the primary defect in the disease. Given the lack of understanding of the molecular mechanism of the disease, an alternative approach has therefore been taken in an attempt to understand the nature of the molecular defect through direct cloning of the responsible gene on the basis of its chromosomal location.

However, there is no clear phenotype that directs an approach to the exact nature of the genetic basis of the disease, or that allows for an identification of the cystic fibrosis gene. The nature of the CF defect in relation to the population genetics data has not been readily apparent. Both the prevalence of the disease and the clinical heterogeneity have been explained by several different mechanisms: high mutation rate, heterozygote advantage, genetic drift, multiple loci, and reproductive compensation.

Many of the hypotheses can not be tested due to the lack of knowledge of the basic defect. Therefore, alternative approaches to the determination and characterization of the CF gene have focused on an attempt to identify the location of the gene by genetic analysis.

Linkage analysis of the CF gene to antigenic and protein markers was attempted in the 1950's, but no positive results were obtained (Steinberg et al *Am. J. Hum. Genet.* 8: 162–176, (1956); Steinberg and Morton *Am. J. Hum. Genet* 8: 177–189, (1956); Goodchild et al *J. Med. Genet.* 7: 417–419, 1976.

More recently, it has become possible to use RFLP's to facilitate linkage analysis. The first linkage of an RFLP marker to the CF gene was disclosed in 1985 [Tsui et al. *Science* 230: 1054–1057, 1985] in which linkage was found between the CF gene and an uncharacterized marker DOCRI-917. The association was found in an analysis of 39 families with affected CF children. This showed that although the chromosomal location had not been established, the location of the disease gene had been narrowed to about 1% of the human genome, or about 30 million nucleotide base pairs.

The chromosomal location of the DOCRI-917 probe was established using rodent-human hybrid cell lines containing different human chromosome complements. It was shown that DOCR1-917 (and therefore the CF gene) maps to human chromosome 7.

Further physical and genetic linkage studies were pursued in an attempt to pinpoint the location of the CF gene. Zengerling et al [*Am. J. Hum. Genet.* 40: 228–236 (1987)] describe the use of human-mouse somatic cell hybrids to obtain a more detailed physical relationship between the CF gene and the markers known to be linked with it. This publication shows that the CF gene can be assigned to either the distal region of band q22 or the proximal region of band q31 on chromosome 7.

Rommens et al [*Am. J. Hum. Genet.* 43: 645–663, (1988)] give a detailed discussion of the isolation of many new 7q31 probes. The approach outlined led to the isolation of two new probes, D7S122 and D7S340, which are close to each other. Pulsed field gel electrophoresis mapping indicates that these two RFLP markers are between two markers known to flank the CF gene, MET [White, R., Woodward S., Leppert M., et al. *Nature* 318: 382–384, (1985)] and D7S8 [Wainwright, B. J., Scambler, P. J., and J. Schmidtke, *Nature* 318: 384–385 (1985)], therefore in the CF gene region. The discovery of these markers provides a starting point for chromosome walking and jumping.

Estivill et al, [*Nature* 326: 840–845 (1987)] disclose that a candidate cDNA gene was located and partially characterized. This however, does not teach the correct location of the CF gene. The reference discloses a candidate cDNA gene downstream of a CpG island, which are undermethylated GC nucleotide-rich regions upstream of many vertebrate genes. The chromosomal localization of the candidate locus is identified as the XV2C region. This region is described in European Patent Application 88303645.1. However, that actual region does not include the CF gene.

A major difficulty in identifying the CF gene has been the lack of cytologically detectable chromosome rearrangements or deletions, which greatly facilitated all previous successes in the cloning of human disease genes by knowledge of map position.

Such rearrangements and deletions could be observed cytologically and as a result, a physical location on a particular chromosome could be correlated with the particular disease. Further, this cytological location could be correlated with a molecular location based on known relationship between publicly available DNA probes and cytologically visible alterations in the chromosomes. Knowledge of the molecular location of the gene for a particular disease would allow cloning and sequencing of that gene by routine procedures, particularly when the gene product is known and cloning success can be confirmed by immunoassay of expression products of the cloned genes.

In contrast, neither the cytological location nor the gene product of the gene for cystic fibrosis was known in the prior art. With the recent identification of MET and D7S8, markers which flanked the CF gene but did not pinpoint its molecular location, the present inventors devised various novel gene cloning strategies to approach the CF gene in accordance with the present invention. The methods employed in these strategies include chromosome jumping from the flanking markers, cloning of DNA fragments from a defined physical region with the use of pulsed field gel electrophoresis, a combination of somatic cell hybrid and molecular cloning techniques designed to isolate DNA fragments from undermethylated CpG islands near CF, chromosome microdissection and cloning, and saturation cloning of a large number of DNA markers from the 7q31 region. By means of these novel strategies, the present inventors were able to identify the gene responsible for cystic fibrosis where the prior art was uncertain or, even in one case, wrong.

The application of these genetic and molecular cloning strategies has allowed the isolation and cDNA cloning of the cystic fibrosis gene on the basis of its chromosomal location, without the benefit of genomic rearrangements to point the way. The identification of the normal and mutant forms of the CF gene and gene products has allowed for the development of screening and diagnostic tests for CF utilizing nucleic acid probes and antibodies to the bene product. Through interaction with the defective gene product and the pathway in which this gene product is involved, therapy through normal gene product supplementation and gene manipulation and delivery are now made possible.

The gene involved in the cystic fibrosis disease process, hereinafter the "CF gene" and its functional equivalents, has been identified, isolated and cDNA cloned, and its transcripts and gene products identified and sequenced. A three base pair deletion leading to the omission of a phenylalanine residue in the gene product has been determined to correspond to the mutations of the CF gene in approximately 70% of the patients affected with CF, with different mutations involved in most if not all the remaining cases. This subject matter is disclosed in co-pending U.S. patent application Ser. No. 396,894 filed Aug. 22, 1989 and its related continuation-in-part applications Ser. No. 399,945 filed Aug. 24, 1989 and Ser. No. 401,609 filed Aug. 31, 1989.

SUMMARY OF THE INVENTION

According to this invention, other base pair deletions or alterations leading to the omission of amino acid residues in the gene product have been determined. According to this invention other nucleotide deletions or alterations leading to mutations in the DNA sequence resulting in frameshift or splice mutations have been determined.

With the identification and sequencing of the mutant gene and its gene product, nucleic acid probes and antibodies raised to the mutant gene product can be used in a variety of hybridization and immunological assays to screen for and detect the presence of either the defective CF gene or gene product. Assay kits for such screening and diagnosis can also be provided. The genetic information derived from the intron/exon boundaries is also very useful in various screening and diagnosis procedures.

Patient therapy through supplementation with the normal gene product, whose production can be amplified using genetic and recombinant techniques, or its functional equivalent, is now also possible. Correction or modification of the defective gene product through drug treatment means is now possible. In addition, cystic fibrosis can be cured or controlled through gene therapy by correcting the gene defect in situ or using recombinant or other vehicles to deliver a DNA sequence capable of expression of the normal gene product to the cells of the patient.

According to another aspect of the invention, a purified mutant CF gene comprises a DNA sequence encoding an amino acid sequence for a protein where the protein, when expressed in cells of the human body, is associated with altered cell function which correlates with the genetic disease cystic fibrosis.

According to another aspect of the invention, a purified RNA molecule comprises an RNA sequence corresponding to the above DNA sequence.

According to another aspect of the invention, a DNA molecule comprises a cDNA molecule corresponding to the above DNA sequence.

According to another aspect of the invention, a DNA molecule comprises a DNA sequence (SEQ ID NO: 1) encoding mutant CFTR polypeptide as further characterized by a nucleotide sequence variants resulting in deletion or alteration of amino acids or residue positions 85, 148, 178, 455, 493, 507, 542, 549, 551, 560, 563, 574, 1077 and 1092.

According to another aspect of the invention, a DNA molecule comprises an intronless DNA sequence encoding a mutant CFTR polypeptide having the sequence according to FIG. 1 for DNA sequence positions 1 to 4574 and, further characterized by nucleotide sequence variants resulting in deletion or alteration of DNA at DNA sequence positions 129, 556, 621+1, 711+1, 1717−1 and 3659.

According to another aspect of the invention, a DNA molecule comprises a cDNA molecule corresponding to the above DNA sequence.

According to another aspect of the invention, the cDNA molecule comprises a DNA sequence selected from the group consisting of:

(a) DNA sequences which correspond to the mutant DNA sequence selected from the group of mutant amino acid positions of 85, 148, 178, 455, 493, 507, 542, 549, 551, 560, 563, 574, 1077 and 1092 and mutant DNA sequence positions 129, 556, 621+1, 711+1, 1717−1 and 3659 and which encode, on expression, for mutant CFTR polypeptide;

(b) DNA sequences which correspond to a fragment of the selected mutant DNA sequence, including at least twenty nucleotides;

(c) DNA sequences which comprise at least twenty nucleotides and encode a fragment of the selected mutant CFTR protein amino acid sequence;

(d) DNA sequences encoding an epitope encoded by at least eighteen sequential nucleotides in the selected mutant DNA sequence.

According to another aspect of the invention, a DNA sequence selected from the group consisting of:

(a) DNA sequences which correspond to portions of DNA sequences of boundaries of exons/introns of the genomic CF gene;

(b) DNA sequences of at lest eighteen sequential nucleotides at boundaries of exons/introns of the genomic CF gene depicted in FIG. 18; and (c) DNA sequences of at least eighteen sequential nucleotides of intron portions of the genomic CF gene of FIG. 18.

According to another aspect of the invention, a purified nucleic acid probe comprises a DNA or RNA nucleotide sequence corresponding to the above noted selected DNA sequences of groups (a) to (c).

According to another aspect of the invention, purified RNA molecule comprising RNA sequence corresponds to the mutant DNA sequence selected from the group of mutant protein positions consisting of 85, 148, 178, 455, 493, 507, 542, 549, 551, 560, 563, 574, 1077 and 1092 and of mutant DNA sequence positions consisting of 129, 556, 621+1, 711+1, 1717−1 and 3659.

A purified nucleic acid probe comprising a DNA or RNA nucleotide sequence corresponding to the mutant sequences of the above recited group.

According to another aspect of the invention, a recombinant cloning vector comprising the DNA sequences of the mutant DNA and fragments thereof selected from the group of mutant protein positions consisting of 85, 148, 178, 455, 493, 507, 542, 549, 551, 560, 563, 574, 1077 and 1092 and selected from the group of mutant DNA sequence positions consisting of 129, 556, 621+1, 711+1, 1717−1 and 3659 is provided. The vector, according to an aspect of this invention, is operatively linked to an expression control sequence in the recombinant DNA molecule so that the selected mutant DNA sequences for the mutant CFTR polypeptide can be expressed. The expression control sequence is selected from the group consisting of sequences that control the expression of genes of prokaryotic or eukaryotic cells and their viruses and combinations thereof.

According to another aspect of the invention, a method for producing a mutant CFTR polypeptide comprises the steps of:

(a) culturing a host cell transfected with the recombinant vector for the mutant DNA sequence in a medium and under conditions favorable for expression of the mutant CFTR polypeptide selected from the group of mutant CFTR polypeptides at mutant protein positions 85, 148, 178, 455, 493, 507, 542, 549, 551, 560, 563, 574, 1077 and 1092 and mutant DNA sequence positions 129, 556, 621+1, 711+1, 1717−1 and 3659; and (b) isolating the expressed mutant CFTR polypeptide.

According to another aspect of the invention, a purified protein of human cell membrane origin comprises an amino acid sequence encoded by the mutant DNA sequences selected from the group of mutant protein positions at 85, 148, 178, 455, 493, 507, 542, 549, 551, 560, 563, 574, 1077 and 1092 and from the group of mutant DNA sequence positions 129, 556, 621+1, 711+1, 1717−1 and 3659 where the protein, when present in human cell membrane, is associated with cell function which causes the genetic disease cystic fibrosis.

According to another aspect of the invention, a method is provided for screening a subject to determine if the subject is a CF carrier or a CF patient comprising the steps of providing a biological sample of the subject to be screened and providing an assay for detecting in the biological sample, the presence of at least a member from the group consisting of:

(a) mutant CF gene selected from the group of mutant protein positions 85, 148, 178, 455, 493, 507, 542, 549, 551, 560, 563, 574, 1077 and 1092 and from the group of mutant DNA sequence positions 129, 556, 621+1, 711+1, 1717−1 and 3659;

(b) mutant CF gene products and mixtures thereof;

(c) DNA sequences which correspond to portions of DNA sequences of boundaries of exons/introns of the genomic CF gene;

(d) DNA sequences of at least eighteen sequential nucleotides at boundaries of exons/introns of the genomic CF gene depicted in FIG. 18; and (e) DNA sequences of at lest eighteen sequential nucleotides of intron portions of the genomic CF gene of FIG. 18.

According to another aspect of the invention, a kit for assaying for the presence of a CF gene by immunoassay techniques comprises:

(a) an antibody which specifically binds to a gene product of the mutant DNA sequence selected from the group of mutant protein positions 85, 148, 178, 455, 493, 507, 542, 549, 551, 560, 563, 574, 1077 and 1092 and from the group of mutant DNA sequence positions 129, 556, 621+1, 711+1, 1717−1 and 3659;

(b) reagent means for detecting the binding of the antibody to the gene product; and (c) the antibody and reagent means each being present in amounts effective to perform the immunoassay.

According to another aspect of the invention, a kit for assaying for the presence of a mutant CF gene by hybridization technique comprises:

(a) an oligonucleotide probe which specifically binds to the mutant CF gene having a mutation at a protein position selected from the group consisting of 85, 148, 178, 455, 493, 507, 542, 549, 551, 560, 563, 574, 1077 and 1092 or having a mutation at a DNA sequence position selected from the group consisting of 129, 556, 621+1, 711+1, 1717−1 and 3659;

(b) reagent means for detecting the hybridization of the oligonucleotide probe to the mutant CF gene; and (c) the probe and reagent means each being present in amounts effective to perform the hybridization assay.

According to another aspect of the invention, an animal comprises an heterologous cell system. The cell system includes a recombinant cloning vector which includes the recombinant DNA sequence corresponding to the mutant DNA sequence which induces cystic fibrosis symptoms in the animal.

According to another aspect of the invention, in a polymerase chain reaction to amplify a selected exon of a cDNA sequence of FIG. 1, the use of oligonucleotide primers from intron portions near the 5' and 3' boundaries of the selected exon of FIG. 18.

BRIEF DESCRIPTION OF THE DRAWINGS

FIG. 1 is the nucleotide sequence of the CF gene and the amino acid sequence of the CFTR protein amino acid sequence with Δ indicating mutations at the 507 and 508 protein positions.

FIGS. 3A through 3E depict the physical map of the region including and surrounding the CF gene generated by pulsed field gel electrophoresis. FIGS. 3A, 3B, 3C, and 3D show hybridization data for the restriction enzymes Sal I, Xho I, Sfi I, and Nae I, respectively generated by representative genomic and cDNA probes which span the region. The deduced physical maps for each restriction enzyme is shown below each panel. FIG. 3E shows a composite map of the entire MET-D7S8 interval (J. M. Rommens et al., Am. J. Hum. Genet. 45:932–941, 1990). The open boxed segment indicates the portion cloned by chromosome walking and jumping, and the filled arrow indicates the portion covered by the CF transcript.

FIG. 5 is an RNA blot hydridization analysis using genomic and cDNA probes. Hybridization to RNA of: A-fibroblast with cDNA probe G-2; B-trachea (from unafflicted and CF patient individuals), pancreas, liver, HL60 cell line and brain with genomic probe CF16; C-T84 cell line with cDNA probe 10-1.

FIG. 6 is the methylation status of the E4.3 cloned region at the 5' end of the CF gene.

FIG. 8 is an RNA gel blot analysis depicting hybridization by a portion of the CFTR cDNA (clone 10-1) to a 6.5 kb mRNA transcript in various human tissues.

FIGS. 9A, 9B, 9C and 9D are DNA blot hybridization analyses depicting hybridization by the CFTR cDNA clones to genomic DNA digested with EcoRI and Hind III.

FIGS. 10A, 10B and 10C are primer extension experiments which characterize the 5' and 3' ends of the CFTR cDNA.

FIG. 13 is a schematic model of the predicted CFTR protein.

FIG. 15 represents alignment of the most conserved segments of the extended NBFs of CFTR with comparable regions of other proteins.

FIG. 18 is the nucleotide sequence of the portions of introns and complete exons of the genomic CF gene for 27 exons identified and numbered sequentially as 1 through 24 with addition exons 6a, 6b, 14a, 14b and 17a, 17b of cDNA sequence of FIG. 1;

FIGS. 19A, 19B and 19C show the results of amplification of genomic DNA using intron oligonucleotides bounding exon 10 to note differences in the nucleotide sequence;

FIG. 20 shows the separation by gel electrophoresis of the amplified genomic DNA products of a CF family.

DETAILED DESCRIPTION OF THE PREFERRED EMBODIMENTS

1. Definitions

Figure 2A:
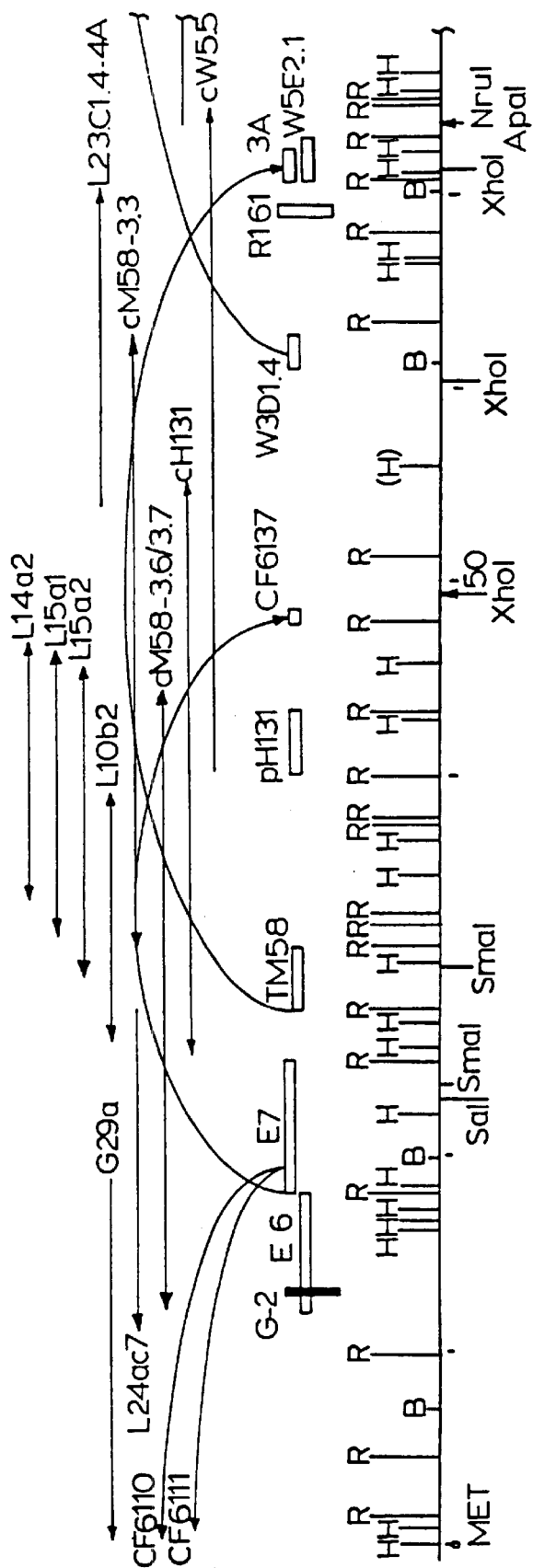
FIG. 2 is a restriction map of the CF gene and the schematic strategy used to chomosome walk and jump to the gene.
Figure 2B:
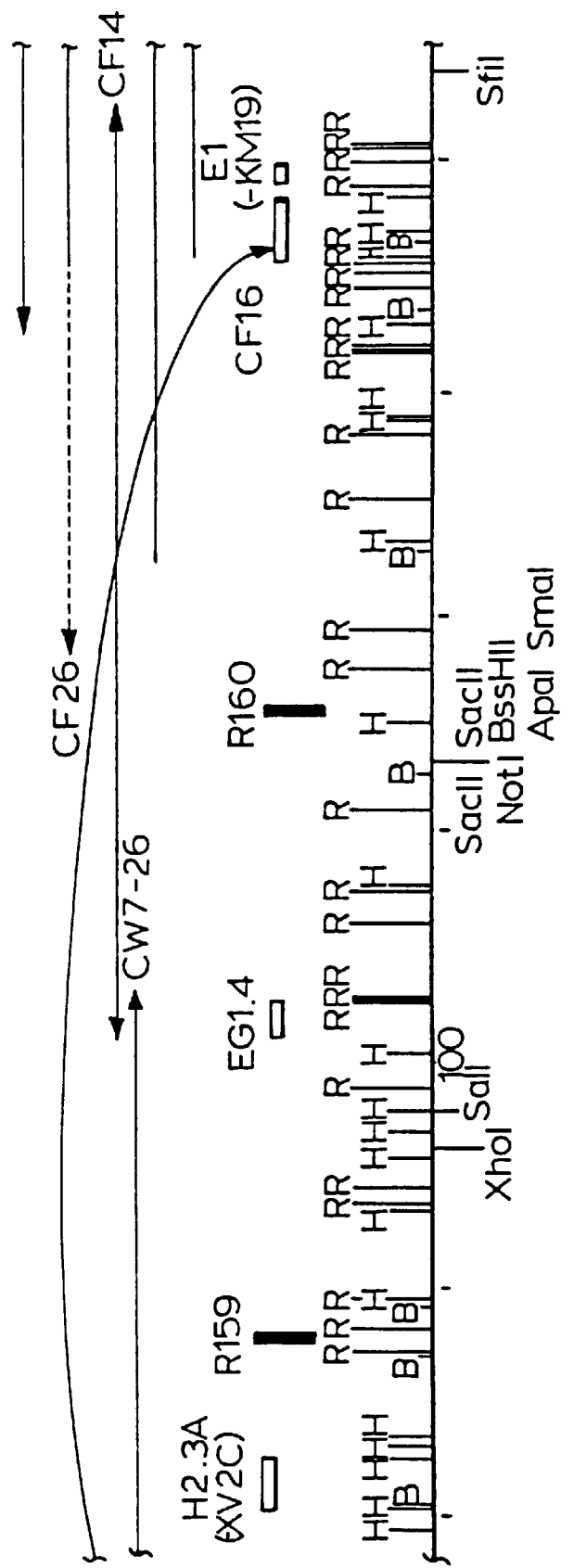
Figure 2C:
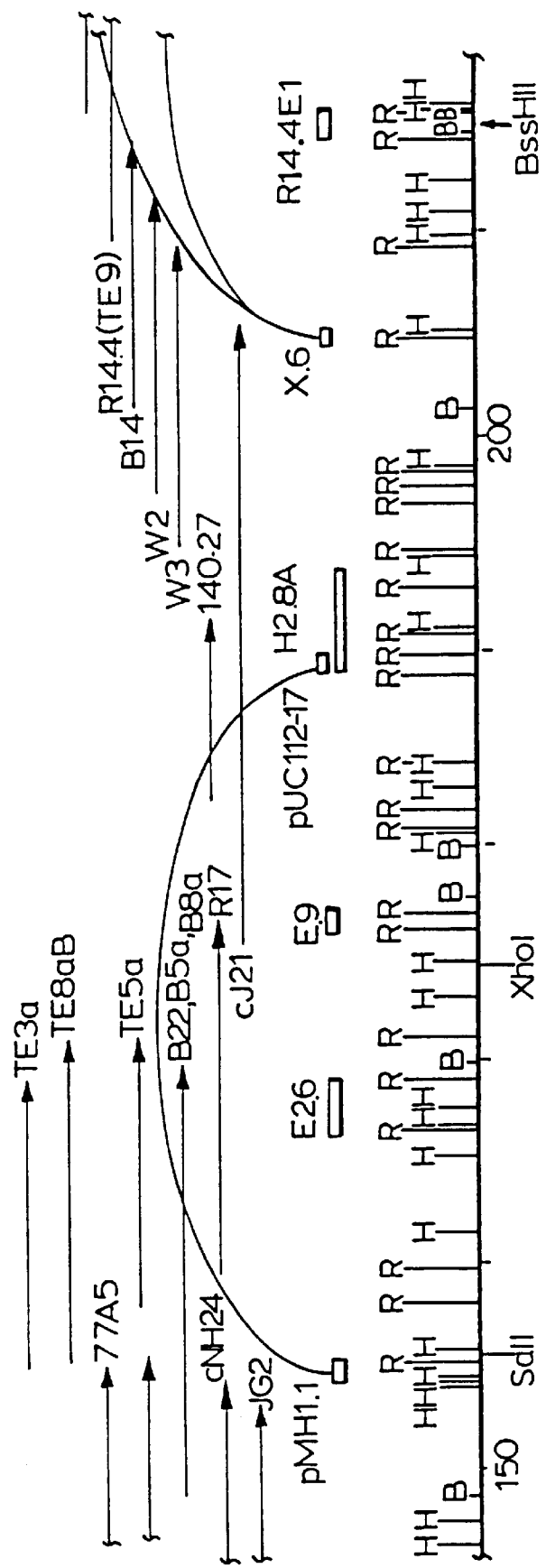
Figure 2D:
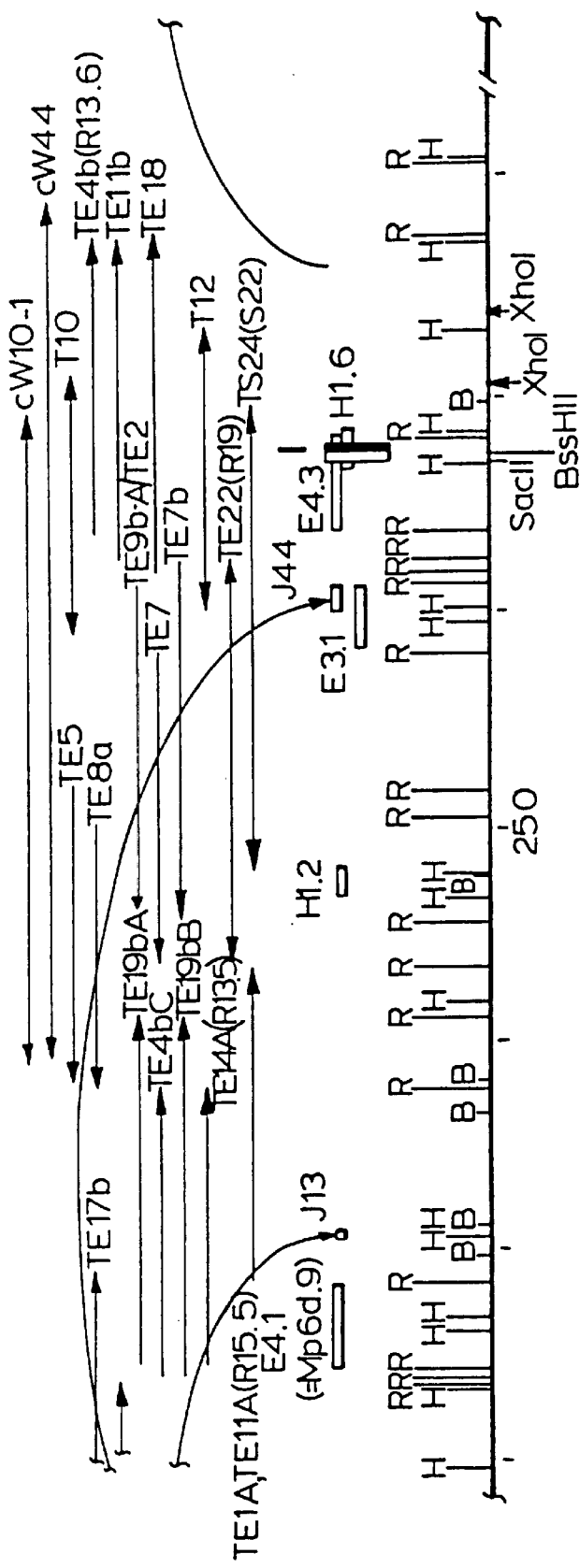
Figure 2E:
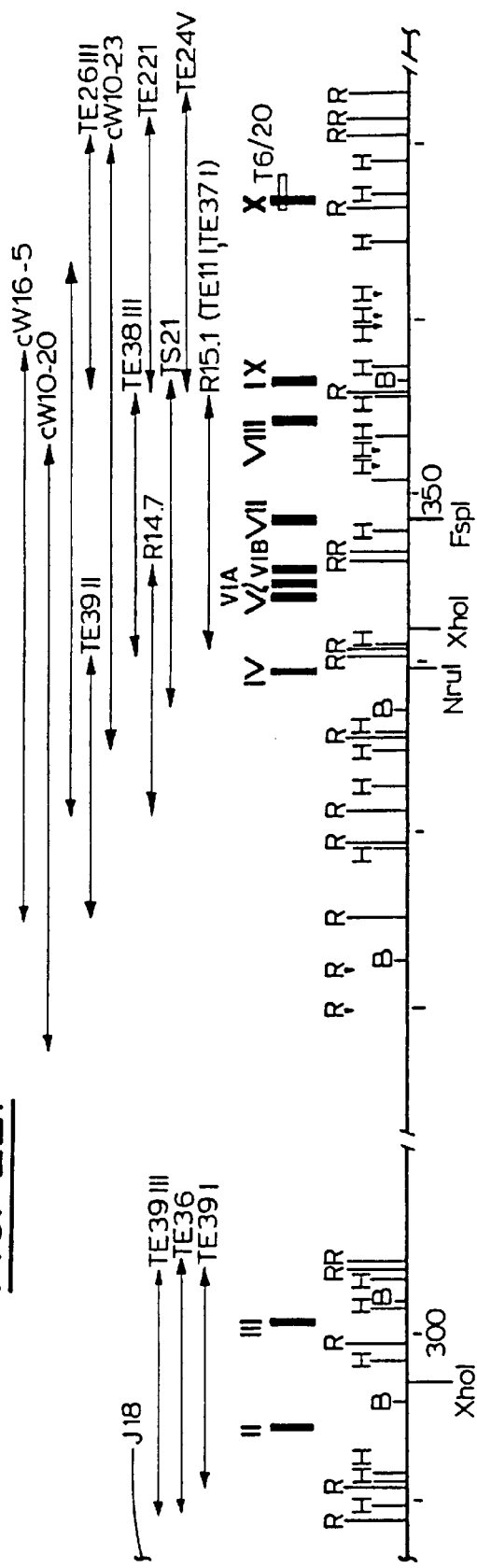
Figure 2F:
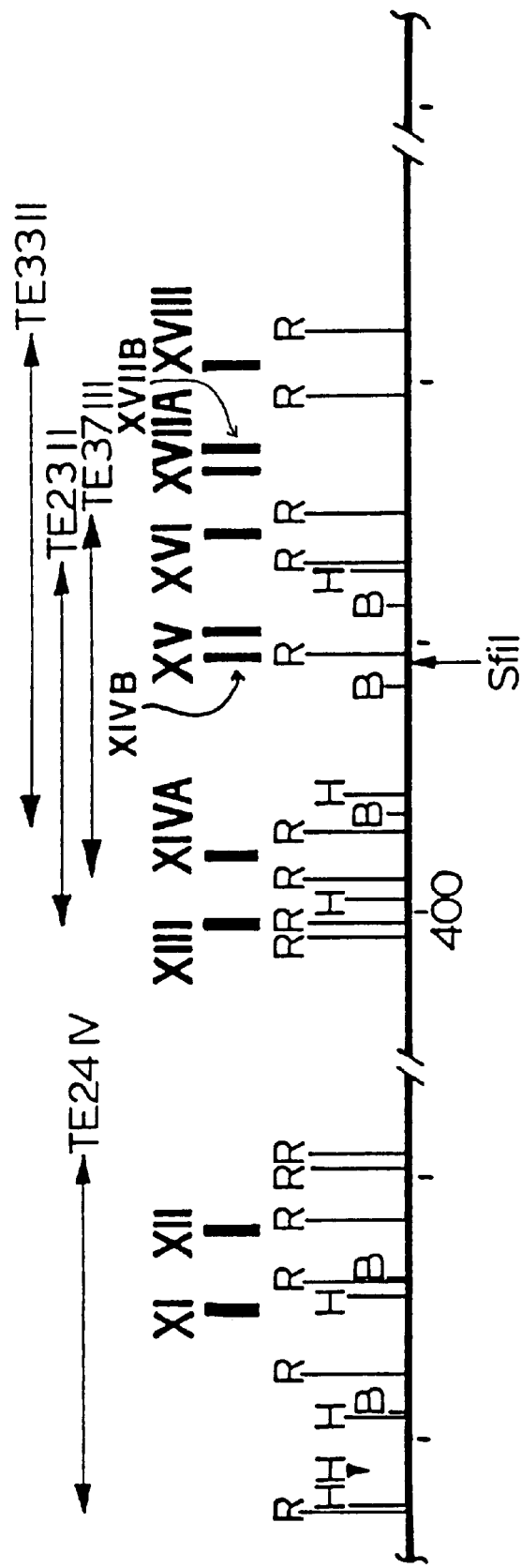
Figure 2G:
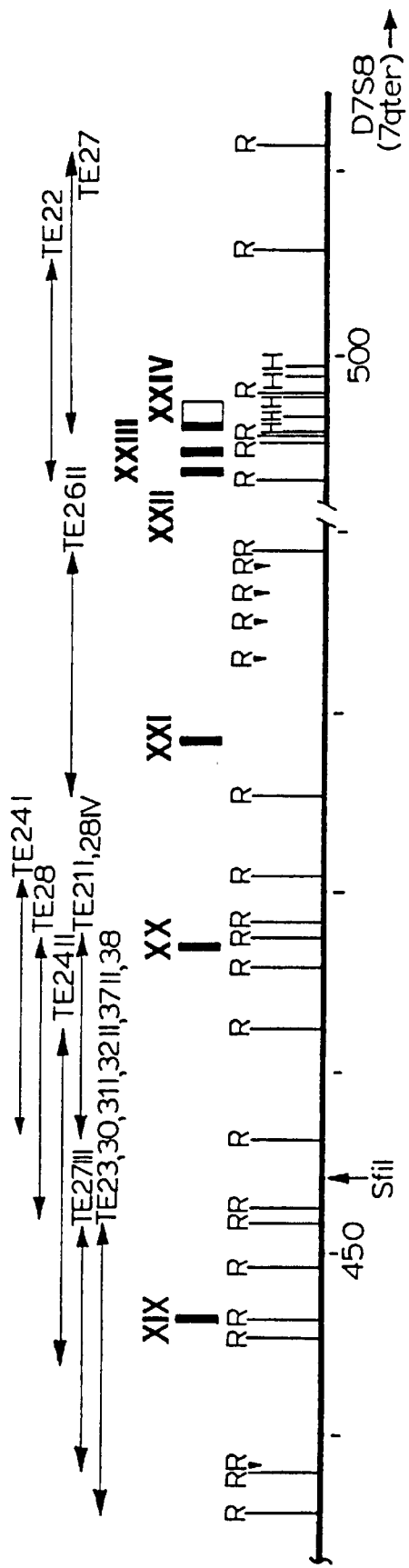

In order to facilitate review of the various embodiments of the invention and an understanding of various elements and constituents used in making the invention and using same, the following definition of terms used in the invention description is as follows:

CF—cystic fibrosis

CF carrier—a person in apparent health whose chromosomes contain a mutant CF gene that may be transmitted to that person's offspring.

CF patient—a person who carrier a mutant CF gene on each chromosome, such that they exhibit the clinical symptoms of cystic fibrosis.

CF gene—the gene whose mutant forms as associated with the disease cystic fibrosis. This definition is understood to include the various sequent polymorphisms that exist, wherein nucleotide substitutions in the gene sequence do not affect the essential function of the gene product. This term primarily relates to an isolated coding sequence, but can also include some or all of the flanking regulatory elements and/or introns.

Genomic CF gene—the CF gene which includes flanking regulatory elements and/or introns at boundaries of exons of the CF gene.

CF-PI—cystic fibrosis pancreatic insufficient, the major clinical subgroup of cystic fibrosis patients, characterized by insufficient pancreatic exocrine function.

CF-PS—cystic fibrosis pancreatic sufficient, a clinical subgroup of cystic fibrosis patients with sufficient pancreatic exocrine function for normal digestion of food.

CFTR—cystic fibrosis transmembrane conductance regulator protein, encoded by the CF gene. This definition includes the protein as isolated from human or animal sources, as produced by recombinant organisms, and as chemically or enzymatically synthesized. This definition is understood to include the various polymorphic forms of the protein wherein amino acid substitutions in the variable regions of the sequence does not affect the essential functioning of the protein, or its hydropathic profile or secondary or tertiary structure.

DNA—standard nomenclature is used to identify the bases.

Intronless DNA—a piece of DNA lacking internal non-coding segments, for example, cDNA.

IRP locus sequence—(protooncogene int-1 related), a gene located near the CF gene.

Mutant CFTR—a protein that is highly analagous to CFTR in terms of primary, secondary, and tertiary structure, but wherein a small number of amino acid substitutions and/or deletions and/or insertions result in impairment of its essential function, so that organisms whose epithelial cells express mutant CFTR rather than CFTR demonstrate the symptoms of cystic fibrosis.

mCF—a mouse gene orthologous to the human CF gene

NBFs—nucleotide (ATP) binding folds

ORF—open reading frame

PCR—polymerase chain reaction

Protein—standard single letter nomenclature is used to identify the amino acids

R-domain—a highly charged cytoplasmic domain of the CFTR protein

RSV—Rous Sarcoma Virus

SAP—surfactant protein

RFLP—restriction fragment length polymorphism 507 mutant CF gene—the CF gene which includes a DNA base pair mutation at the 506 or 507 protein position of the cDNA of the CF gene 507 mutant DNA sequence—equivalent meaning to the 507 mutant CF gene 507 mutant CFTR protein or mutant CFTR protein amino acid sequence, or mutant CFTR polypeptide—the mutant CFTR protein wherein an amino acid deletion occurs at the isoleucine 506 or 507 protein position of the CFTR.

Protein position means amino acid residue position.

2. Isolating the CF Gene

Using chromosome walking, jumping, and cDNA hybridization, DNA sequences encompassing >500 kilobase pairs (kb) have been isolated from a region on the long arm of human chromosome 7 containing the cystic fibrosis (CF) gene. This technique is disclosed in detail in the aforemention co-pending United States patent applications. For purposes of convenience in understanding and isolating the CF gene and identifying other mutations, such as at the 85, 148, 178, 455, 493, 507, 542, 549, 551, 560, 563, 574, 1077 and 1092 amino acid residue positions, the technique is reiterated here. Several transcribed sequences and conserved segments have been identified in this region. One of these corresponds to the CF gene and spans approximately 250 kb of genomic DNA. Overlapping complementary DNA (cDNA) clones have been isolated from epithelial cell libraries with a genomic DNA segment containing a portion of the cystic fibrosis gene. The nucleotide sequence of the isolated cDNA is shown in FIGS. 1 through 18. In each row of the respective sequences the lower row is a list by standard nomenclature of the nucleotide sequence. The upper row in each respective row of sequences is standard single letter nomenclature for the amino acid corresponding to the respective codon.

Accordingly, the isolation of the CF gene provided a cDNA molecule comprising a DNA sequence selected from the group consisting of:

(a) DNA sequences of SEQ ID NO: 1;

(b) DNA sequences having SEQ ID NO: 1 and encoding normal CFTR polypeptide (SEQ ID NO: 2);

(c) DNA sequences which correspond to a fragment of the sequence of FIG. 1 SEQ ID NO: 1 including at least 16 sequential nucleotides of SEQ ID NO: 1;

(d) DNA sequences which comprise at lest 16 nucleotides and encode a fragment of the amino acid sequence of FIG. 1 (SEQ ID NO: 2); and (e) DNA sequences encoding an epitope encoded by at least 18 sequential nucleotides of SEQ ID NO: 1.

According to this invention, the isolation of other mutations in the CF gene also provides a cDNA molecule comprising a DNA sequence selected from the group consisting of:

a) DNA sequences which correspond to the DNA sequence encoding mutant CFTR polypeptide characterized by cystic fibrosis-associated activity in human epithelial cells, or the DNA sequence of yet further characterized by a base pair mutation which results in the deletion of or a change for an amino acid at residue positions 85, 148, 178, 455, 493, 507, 542, 549, 551, 560, 563, 574, 1077 and 1092 of SEQ ID NO: 2;

b) DNA sequences which correspond to fragments of the mutant portion of the sequence of paragraph a) and which include at lest sixteen nucleotides;

c) DNA sequences which comprise at least sixteen nucleotides and encode a fragment of the amino acid sequence encoded for by the mutant portion of the DNA sequence of paragraph a); and d) DNA sequences encoding an epitope encoded by at least 18 sequential nucleotides in the mutant portion of the sequence of the DNA of paragraph a).

Transcripts of approximately 6,500 nucleotides in size are detectable in tissues affected in patients with CF. Based upon the isolated nucleotide sequence, the predicted protein consists of two similar regions, each containing a first domain having properties consistent with membrane association and a second domain believed to be involved in ATP binding.

A 3 bp deletion which results in the omission of a phenylalanine residue at the center of the first predicted nucleotide binding domain (amino acid position 508 of the CF gene product) was detected in CF patients. This mutation in the normal DNA sequence of FIG. 1 corresponds to approximately 70% of the mutations in cystic fibrosis patients. Extended haplotype data based on DNA markers closely linked to the putative disease gene suggest that the remainder of the CF mutant gene pool consists of multiple, different mutations. This is now exemplified by this invention at, for example, the 506 or 507 protein position. A small set of these latter mutant alleles (approximately 8%) may confer residual pancreatic exocrine function in a subgroup of patients who are pancreatic sufficient.

2.1 Chromosome Walking and Jumping

Large amounts of the DNA surrounding the D7S122 and D75340 linkage regions of Rommens et al supra were searched for candidate gene sequences. In addition to conventional chromosome walking methods, chromosome jumping techniques were employed to accelerate the search process. From each jump endpoint a new bidirectional walk could be initiated. Sequential walks halted by "unclonable" regions often encountered in the mammalian genome could be circumvented by chromosome jumping.

The chromosome jumping library used has been described previously [Collins et al, *Science* 235, 1046 (1987); Ianuzzi et al, *Am. J. Hum. Genet.* 44, 695 (1989)]. The original library was prepared from a preparative pulsed field gel, and was intended to contain partial EcoR1 fragments of 70–130 kb; subsequent experience with this library indicates that smaller fragments were also represented, and jumpsizes of 25–110 kb have been found. The library was plated on sup host MC1061 and screened by standard techniques, [Maniatis et al]. Positive clones were subcloned into pBRΔ23Ava and the beginning and end of the jump identified by EcoR1 and Ava 1 digestion, as described in Collins, *Genome analysis: A practical approach* (IRL, London, 1988), pp. 73–94). For each clone, a fragment from the end of the jump was checked to confirm its location on chromosome 7. The contiguous chromosome region covered by chromosome walking and jumping was about 250 kb. Direction of the jumps was biased by careful choice of probes, as described by Collins et al and Ianuzzi et al, supra. The entire region cloned, including the sequences isolated with the use of the CF gene cDNA, is approximately 500 kb.

The schematic representation of the chromosome walking and jumping strategy is illustrated in FIG. 2. CF gene exons are indicated by Roman numerals in this Figure. Horizontal lines above the map indicate walk steps whereas the arcs above the map indicate jump steps. The Figure proceeds from left to right in each of six tiers with the direction of ends toward 7cen and 7qter as indicated. The restriction map for the enzymes EcoRI, HindIII, and BamHI is shown above the solid line, spanning the entire cloned region. Restriction sites indicated with arrows rather than vertical lines indicate sites which have not been unequivocally position. Additional restriction sites for other enzymes are shown below the line. Gaps in the cloned region are indicated by ||. These occur only in the portion detected by cDNA clones of the CF transcript. These gaps are unlikely to be large based on pulsed field mapping of the region. The walking clones, as indicated by horizontal arrows above the map, have the direction of the arrow indicating the walking progress obtained with each clone. Cosmid clones begin with the letter c; all other clones are phage. Cosmid CF26 provided to be a chimera; the dashed portion is derived from a different genomic fragment on another chromosome. Roman numerals I through XXIV indicate the location of exons of the CF gene. The horizontal boxes shown above the line are probes used during the experiments. Three of the probes represent independent subcloning of fragments previously identified to detect polymorphisms in this region: H2.3A corresponds to probe XV2C (X. Estivill et al, *Nature,* 326: 840 (1987)), probe E1 corresponds to KM19 (Estivill, supra), and probe E4.1 corresponds to Mp6d.9 (X. Estivill et al. *Am. J. Hum. Genet.* 44, 704 (1989)). G-2 is a subfragment of E6 which detects a transcribed sequence. R161, R159, and R160 are synthetic oligonucleotides constructed from parts of the IRP locus sequence [B. J. Wainwright et al, *EMBO J.,* 7: 1743 (1988)], indicating the location of this transcript on the genomic map.

As the two independently isolated DNA markers, D7S122 (pH131) and D7S340 (TM58), were only approximately 10 kb apart (FIG. 2), the walks and jumps were essentially initiated from a single point. The direction of walking and jumping with respect to MET and D7S8 was then established with the crossing of several rare-cutting restriction endonuclease recognition sites (such as those for Xho I, Nru I and Not I, see FIG. 2) and with reference to the long range physical map of J. M. Rommens et al. *Am. J. Hum. Genet.,* in press; A. M. Poustka, et al, *Genomics* 2, 337 (1988); M. L. Drumm et al. *Genomics* 2, 346 (1988). The pulsed field mapping data also revealed that the Not I site identified by the inventors of the present invention (see FIG. 2, position 113 kb) corresponded to the one previously found associated with the IRP locus (Estivill et al 1987, supra). Since subsequent genetic studies showed that CF was most likely located between IRP and D7S8 [M. Farrall et al, *Am. J. Hum. Genet.* 43, 471 (1988), B. S. Kerem et al. *Am. J. Hum. Genet.* 44, 827 (1989)], the walking and jumping effort was continued exclusively towards cloning of this interval. It is appreciated, however, that other coding regions, as identified in FIG. 2, for example, G-2, CF14 and CF16, were located and extensively investigated. Such extensive investigations of these other regions revealed that they were not the CF gene based on genetic data and sequence analysis. Given the lack of knowledge of the location of the CF gene and its characteristics, the extensive and time consuming examination of the nearby presumptive coding regions did not advance the direction of search for the CF gene. However, these investigations were necessary in order to rule out the possibility of the CF gene being in those regions.

Three regions in the 280 kb segment were found out to be readily recoverable in the amplified genomic libraries initially used. These less colonable regions were located near the DNA segments H2.3A and X.6, and just beyond cosmid cW44, at positions 75–100 kb, 205–225 kb, and 275–285 kb in FIG. 2, respectively. The recombinant clones near H2.3A were found to be very unstable with dramatic rearrangements after only a few passages of bacterial culture. To fill in the resulting gaps, primary walking libraries were constructed using special host-vector systems which have been reported to allow propagation of unstable sequences [A. R. Wyman, L. B. Wolfe, D. Botstein, *Proc. Nat. Acad. Sci. U.S.A.* 82, 2880 (1985); K. F. Wertman, A. R. Wyman, D. Botstein, *Gene* 49, 253 (1986); A. R. Wyman, K. F. Wertman, D. Barker, C. Helms, W. H. Petri, *Gene,* 49, 263 (1986)]. Although the region near cosmid cW44 remains to be recovered, the region near X.6 was successfully rescued with these libraries.

2.2 Construction of Genomic Libraries

Genomic libraries were constructed after procedures described in Manatis, et al, *Molecular Cloning: A Laboratory Manual* (Cold Spring Harbor Laboratory, Cold Spring Harbor, N.Y. 1982) and are listed in Table 1. This includes eight phage libraries, one of which was provided by T. Maniatis [Fritsch et al, *Cell,* 19:959 (1980)]; the rest were constructed as part of this work according to procedures described in Maniatis et al, supra. Four phage libraries were cloned in λDASH (commercially available from Stratagene) and three in λFIX (commercially available from Stratagene), with vector arms provided by the manufacturer. One λDASH library was constructed from Sau 3A-partially digested DNA from a human-hamster hybrid containing human chromosome 7 (4AF/102K015) [Rommens et al *Am. J. Hum. Genet* 43, 4 (1988)], and other libraries from partial Sau3A, total BamHI, or total EcoRI digestion of human peripheral blood or lymphoblastoid DNA. To avoid loss of unstable sequences, five of the phage libraries were propagated on the recombination-deficient hosts DB1316 (recD$^{-}$), CES 200 (recBC$^{-}$) [Wyman et al, supra, Wertman et al supra, Wyman et al supra]; or TAP90 [Patterson et al *Nucleic Acids Res.* 15:6298 (1987)]. Three cosmid libraries were then constructed. In one the vector pCV108 [Lau et al *Proc. Natl. Acad. Sci USA* 80:5225 (1983)] was used to clone partially digested (Sau 3A) DNA from 4AF/102/K015 [Rommens et al *Am. J. Hum. Genet.* 43:4 (1988)]. A second cosmid library was prepared by cloning partially digested (Mbo I) human lumphoblastoid DNA into the vector pWE-IL2R, prepared by inserting the RSV (Rous Sarcoma Virus) promoter-driven cDNA for the interleukin-2 receptor α-chain (supplied by M. Fordis and B. Howard) in place of the neo-resistance gene of pWE15 [Wahl et al *Proc. Natl. Acad. Sci. USA* 84:2160 (1987)]. an additional partial Mbo I cosmid library was prepared in the vector pWE-IL2-Sal, created by inserting a Sal I linker into the Bam HI cloning site of pWE-EL2R (M. Drumm, unpublished data); this allows the use of the partial fill-in technique to ligate Sal I and Mbo I ends, preventing tandem insertions [Zabarovsky et al *Gene* 42:19 (1986)]. Cosmid libraries were propagated in *E. coli* host strains DH1 or 490A [M. Steinmetz, A. Winoto, K. Minard, L. Hood, *Cell* 28, 489 (1982)].

TABLE I

GENOMIC LIBRARIES

| Vector | Source of human DNA | Host | Complexity | Ref |
|---|---|---|---|---|
| λ Charon 4A | HaeII/AluI-partially digested total human liver DNA | LE392 | 1 × 10$^6$ (amplified) | Lawn et al 1980 |
| pCV108 | Sau3a-partially digested DNA from 4AF/KO15 | DK1 | 3 × 10$^6$ (amplified) | |

TABLE I-continued

GENOMIC LIBRARIES

| Vector | Source of human DNA | Host | Complexity | Ref |
|---|---|---|---|---|
| λdash | Sau3A-partially digested DNA from 4AF/KO15 | LE392 | $1 \times 10^6$ (amplified) | |
| λdash | Sau3A-partially digested total human peripheral blood DNA | DB1316 | $1.5 \times 10^6$ | |
| λdash | BamHI-digested total human peripheral blood DNA | DB1316 | $1.5 \times 10^6$ | |
| λdash | EcoRI-partially digested total human peripheral blood DNA | DB1316 | $8 \times 10^6$ | |
| λFIX | MboI-partially digested human lymphoblastoid DNA | LE392 | $1.5 \times 10^6$ | |
| λFIX | MboI-partially digested human lymphoblastoid DNA | CE200 | $1.2 \times 10^6$ | |
| λFIX | MboI-partially digested human lymphoblastoid DNA | TAP90 | $1.3 \times 10^6$ | |
| pWE-IL2R | MboI-partially digested human lymphoblastoid DNA | 490A | $5 \times 10^6$ | |
| pWE-IL2R Sal | MboI-partially digested human lymphoblastoid DNA | 490A | $1.2 \times 10^6$ | |
| 1Ch 3A Δ lac (jumping) | EcoRI-partially digested (24–110 kb) human lymphoblastoid DNA | Mc1061 | $3 \times 10^6$ | Collins et al., supra and Ianuzzi et al., supra. |

Three of the phage libraries were propagated and amplified in *E. coli* bacterial strain LE392. Four subsequent libraries were plated on the recombination-deficient hosts DB1316 (recD$^-$) or CES200 (rec BC$^-$) [Wyman 1985, supra; Wertman 1986, supra; and Wyman 1986, supra] or in one case TAP90 [T. A. Patterson and M. Dean, *Nucleic Acids Research* 15, 6298 (1987)].

Single copy DNA segments (free of repetitive elements) near the ends of each phage or cosmid insert were purified and used as probes for library screening to isolate overlapping DNA fragments by standard procedures. (Maniatis, et al, supra).

$1–2 \times 10^6$ phage clones were plated on 25–30 150 mm petri dishes with the appropriate indicator bacterial host and incubated at 37° C. for 10–16 hr. Duplicate "lifts" were prepared for each plate with nitrocellulose or nylon membranes, prehybridized and hybridized under conditions described [Rommens et al, 1988, supra]. Probes were labelled with $^{32}$P to a specific activity of $>5 \times 10^8$ cpm/μg using the random priming procedure [A. P. Feinberg and B. Vogelstein, *Anal. Biochem.* 132, 6 (1983)]. The cosmid library was spread on ampicillin-containing plates and screened in a similar manner.

DNA probes which gave high background signals could often be used more successfully by preannealing the boiled probe with 250 μg/ml sheared denatured placental DNA for 60 minutes prior to adding the probe to the hybridization bag.

For each walk step, the identity of the cloned DNA fragment was determined by hybridization with a somatic cell hybrid panel to confirm its chromosomal location, and by restriction mapping and Southern blot analysis to confirm its colinearity with the genome.

The total combined cloned region of the genomic DNA sequences isolated and the overlapping cDNA clones, extended >500 kb. To ensure that the DNA segments isolated by the chromosome walking and jumping procedures were colinear with the genomic sequence, each segment was examined by:

(a) hybridization analysis with human-rodent somatic hybrid cell lines to confirm chromosome 7 localization, (b) pulsed field gel electrophoresis, and (c) comparison of the restriction map of the cloned DNA to that of the genomic DNA.

Accordingly, single copy human DNA sequences were isolated from each recombinant phage and cosmid clone and used as probes in each of these hybridization analyses as performed by the procedure of Maniatis, et al supra.

While the majority of phage and cosmid isolates represented correct walk and jump clones, a few resulted from cloning artifacts or cross-hybridizing sequences from other regions in the human genome, or from the hamster genome in cases where the libraries were derived from a human-hamster hybrid cell line. Confirmation of correct localization was particularly important for clones isolated by chromosome jumping. Many jump clones were considered and resulted in non-conclusive information leading the direction of investigation away from the gene.

2.3 Confirmation of the Restriction Map

Further confirmation of the overall physical map of the overlapping clones was obtained by long range restriction mapping analysis with the use of pulsed field gel electrophoresis (J. J. Rommens, et al. *Am. J. Hum. Genet.* in press, A. M. Poustka et al, 1988, supra M. L. Drumm et al, 1988 supra).

Figure 3E:
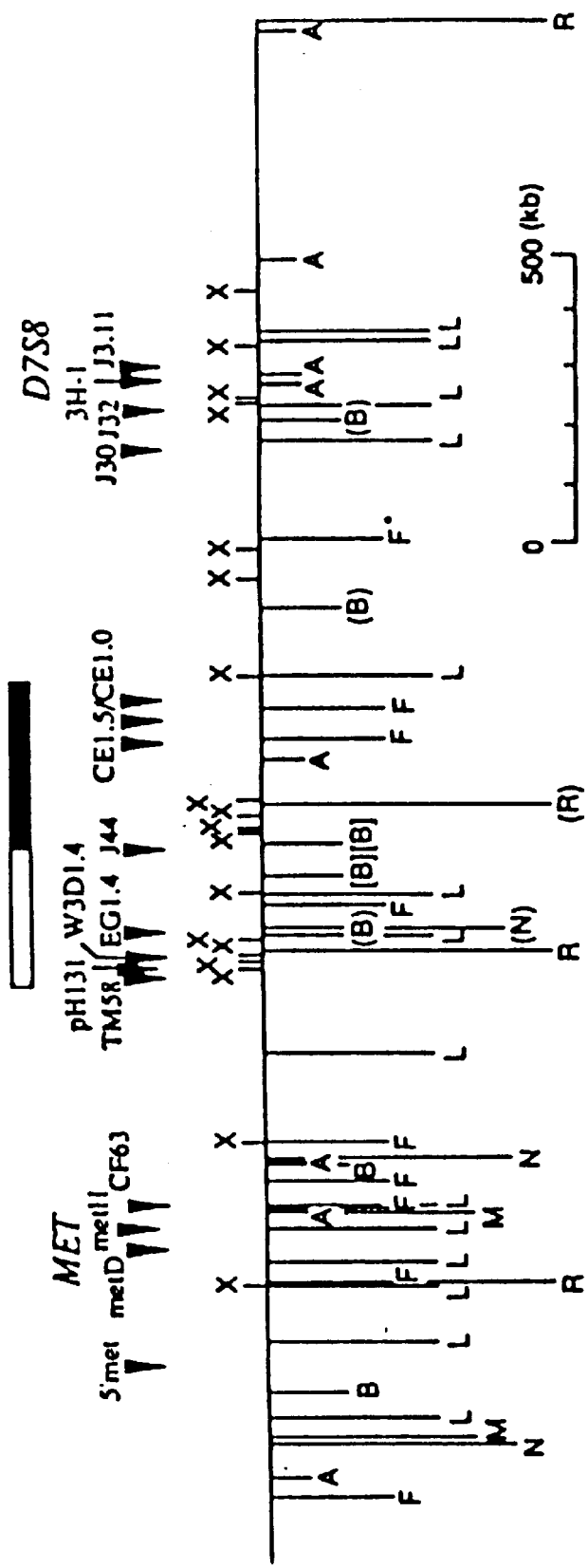

FIGS. 3A to 3E illustrates the findings of the long range restriction mapping study, where a schematic representation of the region is given in Panel E. DNA from the human-hamster cell line 4AF/102/K015 was digested with the enzymes (A) Sal I, (B) Xho I, (C) Sfi I and (D) Nae I, separated by pulsed field gel electrophoresis, and transferred to Zetaprobe™ (BioRad). For each enzyme a single blot was sequentially hybridized with the probes indicated below each of the panels of FIGS. A to D, with stripping of the blot between hybridizations. The symbols for each enzyme of FIG. 3E are: A, Nae I; B, Bss HII; F. Sfi I; L, Sal I; M, Mlu I; N, Not I; R, Nru I; and X, Xho 1. C corresponds to the compression zone region of the gel. DNA preparations, restriction digestion, and crossed field gel electrophoresis methods have been described (Rommens et al, in press, supra). The gels in FIG. 3 were run in 0.5X TBE at 7 volts/cm for 20 hours with switching linearly ramped from 10–40 second for (A), (B), and (C), and at 8 volts/cm for 20 hours with switching ramped linearly from 50–150 seconds for (D). Schematic interpretations of the hybridization pattern are given below each panel. Fragment lengths are in kilobases and were sized by comparison to oligomerized bacteriophage λDNA and *Saccharomyces cerevisiae* chromosomes.

H4.0, J44, EG1.4 are genomic probes generated from the walking and jumping experiments (see FIG. 2). J30 has been isolated by four consecutive jumps from D7S8 (Collins et al, 1987, supra; Ianuzzi et al, 1989, supra; M. Dean, et al, submitted for publication). 10-1, B.75, and CE1.5/1.0 are cDNA probes which cover different regions of the CF transcript: 10-1 contains exons I–VI, B.75 contains exons V–XII, and CE1.5/1.0 contains exons XII–XXIV. Shown in FIG. 3E is a composite map of the entire MET–D7S8 interval. The open boxed region indicates the segment cloned by walking and jumping, and the closed arrow portion indicates the region covered by the CF transcript. The CpG-rich region associated with the D7S23 locus (Estivill et al, 1987, supra) is at the Not I site shown in parentheses. This and other sites shown in parentheses or square brackets do not cut in 4AF/102/K015, but have been observed in human lymphoblast cell lines.

2.4 Identification of CF Gene

Based on the findings of long range restriction mapping detailed above it was determined that the entire CF gene is contained on a 380 kb Sal I fragment. Alignment of the restriction sites derived from pulsed field gel analysis to those identified in the partially overlapping genomic DNA clones revealed that the size of the CF gene was approximately 250 kb.

The most informative restriction enzyme that served to align the map of the cloned DNA fragments and the long range restriction map was Xho I; all of the 9 Xho 1 sites identified with the recombinant DNA clones appeared to be susceptible to at least partial cleavage in genomic DNA (compare maps in FIGS. 1 and 2). Furthermore, hybridization analysis with probes derived from the 3' end of the CF gene identified 2 SfiI sites and confirmed the position of the anticipated Nae I site.

These findings further supported the conclusion that the DNA segments isolated by the chromosome walking and jumping procedures were colinear with the genuine sequence.

2.5 Criteria for Identification

A positive result based on one or more of the following criteria suggested that a cloned DNA segment may contain candidate gene sequences:

(a) detection of cross-hybridizing sequences in other species (as many genes show evolutionary conservation), (b) identification of CpG islands, which often mark the 5' end of vertebrate genes [A. P. Bird, *Nature*, 321, 209 (1986); M. Gardiner-Garden and M. Frommer, *J. Mol. Biol.* 196, 261 (1987)], (c) examination of possible mRNA transcripts in tissues affected in CF patients, (d) isolation of corresponding cDNA sequences, (e) identification of open reading frames by direct sequencing of cloned DNA segments.

Figure 4A:
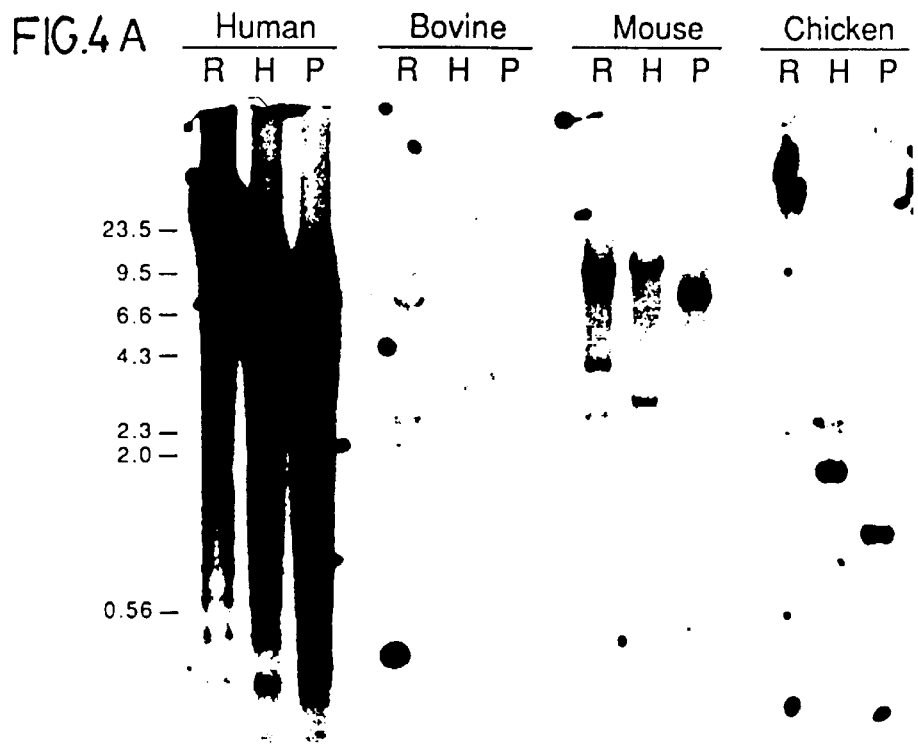
FIGS. 4A, 4B and 4C show the detection of conserved nucleotide sequences by cross-species hybridization.
Figure 4B:
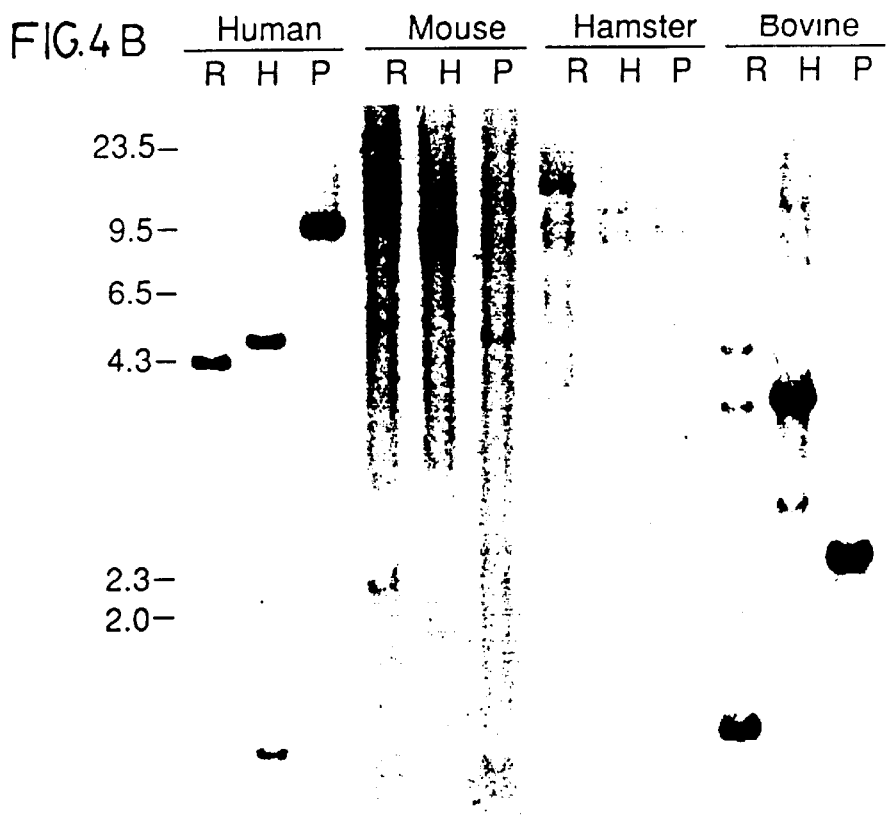
Figure 4C:
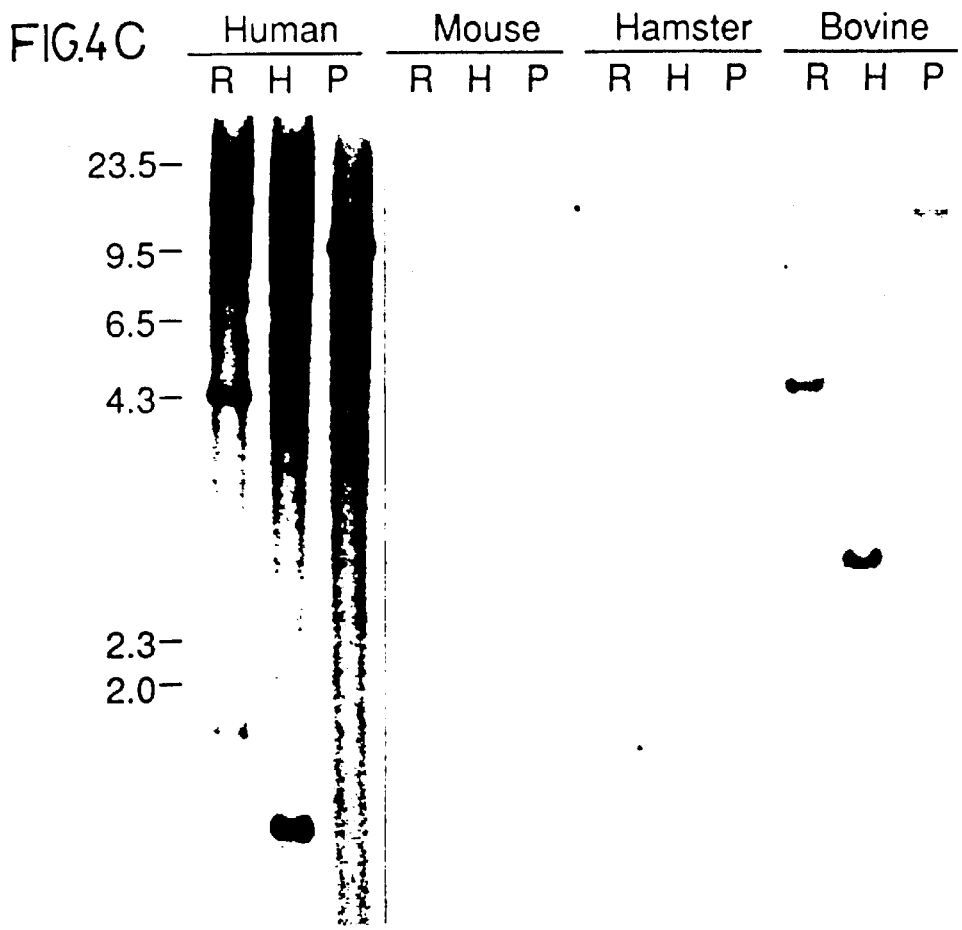

Cross-species hybridization showed strong sequence conservation between human and bovine DNA when CF14, E4.3 and H1.6 were used as probes, the results of which are shown in FIGS. 4A, 4B and 4C.

Human, bovine, mouse, hamster, and chicken genomic DNAs were digested with Eco RI (R), Hind III (H), and Pst I (P), electrophoresed, and blotted to Zetabind™ (BioRad). The hybridization procedures of Rommens et al, 1988, supra, were used with the most stringent wash at 55° C., 0.2 X SSC, and 0.1% SDS. The probes used for hybridization, in FIG. 4, included: (A) entire cosmid CF14, (B) E4.3, (C) H1.6. In the schematic of FIG. (D), the shaded region indicates the area of cross-species conservation.

Figure 4D:
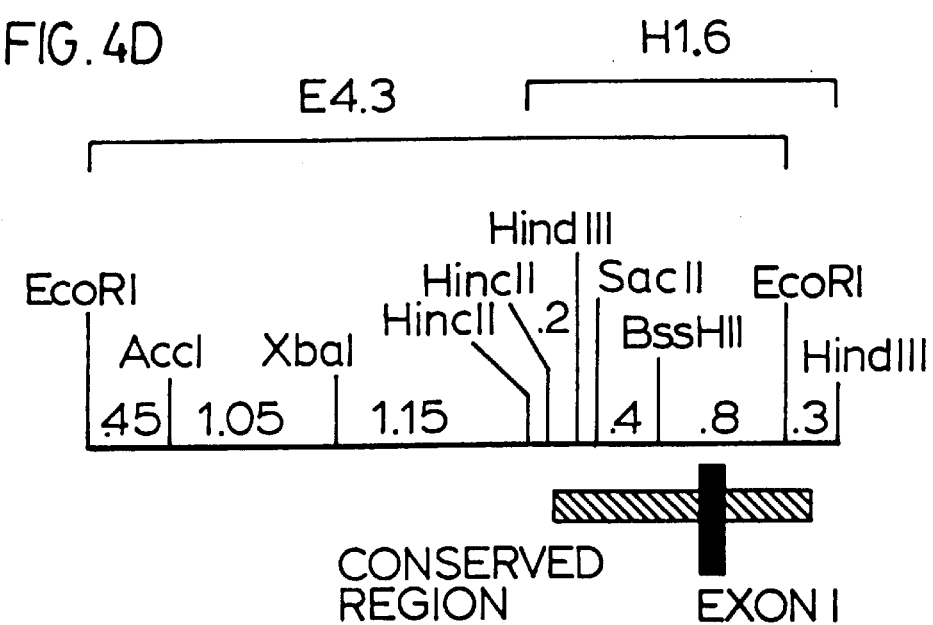
FIG. 4D is a restriction map of overlapping segments of probes E4.3 and H1.6.

The fact that different subsets of bands were detected in bovine DNA with these two overlapping DNA segments (H1.6 and E4.3) suggested that the conserved sequences were located a the boundaries of the overlapped region (FIG. 4(D)). When these DNA segments were used to detect RNA transcripts from a variety of tissues, no hybridization signal was detected. In an attempt to understand the cross-hybriding region and to identify possible open reading frames, the DNA sequences of the entire H1.6 and part of the E4.3 fragment were determined. The results showed that, except for a long stretch of CG-rich sequence containing the recognition sites for two restriction enzymes (Bss HII and Sac II), often found associated with undermethylated CpG islands, there were only short open reading frames which could not easily explain the strong cross-species hybridization signals.

To examine the methylation status of this highly CpG-rich region revealed by sequencing, genomic DNA samples prepared from fibroblasts and lymphoblasts were digested with the restriction enzymes Hpa II and Msp I and analyzed by gel blot hybridization. The enzyme Hpa II cuts the DNA sequence 5'-CCGG-3' only when the second cytosine is unmethylaced, whereas Msp I cuts this sequence regardless of the state of methylation. Small DNA fragments were generated by both enzymes, indicating that this CpG-rich region is indeed undermethylated in genomic DNA. The gel-blot hybridization with the E4.3 segment (FIG. 6) reveals very small hybridizing fragments with both enzymes, indicating the presence of a hypomethylated CpG island.

The above results strongly suggest the presence of a coding region at this locus. Two DNA segments (E4.3 and H1.6) which detected cross-species hybridization signals from this area were used as probes to screen cDNA libraries made from several tissues and cell types.

cDNA libraries from cultured epithelial cells were prepared as follows. Sweat gland cells derived from a non-CF individual and from a CF patient were grown to first passage as described [G. Collie et al, *In Vitro Cell. Dev. Biol.* 21, 592, 1985]. The presence of outwardly rectifying channels was confirmed in these cells (J. A. Tabcharani, T. J. Jensen, J. R. Riordan, J. W. Hanrahan, *J. Memb. Biol.*, in press) but the CF cells were insensitive to activation by cyclic AMP (T. J. Jensen, J. W. Hanrahan, J. A. Tabcharani, M. Buchwald and J. R. Riordan, *Pediatric Pulmonology*, Supplement 2, 100, 1988). RNA was isolated from them by the method of J. J. Chirgwin et al (*Biochemistry* 18, 5294, 1979). Poly A+RNA was selected (H. Aviv and P. Leder, *Proc. Natl. Acad. Sci. USA* 69, 1408, 1972) and used as template for the synthesis of cDNA with oligo (dT) 12–18 as a primer. The second strand was synthesized according to Gubler and Hoffman (*Gene* 25, 263, 1983). This was methylated with Eco RI methylase and ends were made flush with T4 DNA polymerase. Phosphorylated Eco RI linkers were ligated to the cDNA and restricted with Eco RI. Removal of excess linkers and partial size fractionation was achieved by Biogel A-50 chromatography. The cDNAs were then ligated into the Eco RI site of the commercially available lamdba ZAP. Recombinant were packaged and propagated in *E. coli* BB4. Portion of the packaging mixes were amplified and the remainder retained for screening prior to amplification. The same procedures were used to construct a library from RNA isolated from preconfluent cultures of the T-84 colonic carcinoma cell line (Dharmsathaphorn, K. et al. *Am. J. Physiol.* 246, G204, 1984). The numbers of independent recombinant in the three libraries were: $2 \times 10^6$ for the non-CF sweat gland cells, $4.5 \times 10^6$ for the CF sweat gland cells and $3.2 \times 10^6$ from T-84 cells. These phages were plated at 50,000 per 15 cm plate and plaque lifts made using nylon membranes (Biodyne) and probed with DNA fragments labelled with $^{32}P$ using DNA polymerase I and a random mixture of oligonucleotides as primer. Hybridization conditions were according to G. M. Wahl and S. L. Berger (*Meth. Enzymol.* 152, 415, 1987). Bluescript™ plasmids were rescued from plaque purified clones by excision with M13 helper phage. The lung and pancreas libraries were purchased from Clontech Lab Inc. with reported sizes of $1.4 \times 10^6$ and $1.7 \times 10^6$ independent clones.

After screening 7 different libraries each containing $1 \times 10^5 - 5 \times 10^6$ independent clones, 1 single clone (identified as 10-1) was isolated with H1.6 from a cDNA library made from the cultured sweat gland epithelial cells of an unaffected (non-CF) individual.

DNA sequencing analysis showed that probe 10-1 contained an insert of 920 bp in size and one potential, long open reading frame (ORF). Since one end of the sequence shared perfect sequence identity with H1.6, it was concluded that the cDNA clone was probably derived from this region. The DNA sequence in common was, however, only 113 bp long (see FIGS. 1 and 7). As detailed below, this sequence in fact corresponded to the 5'-most exon of the putative CF gene. The short sequence overlap thus explained the weak hybridization signals in library screening and inability to detect transcripts in RNA gel-blot analysis. In addition, the orientation of the transcription unit was tentatively established on the basis of alignment of the genomic DNA sequence with the presumptive ORF of 10-1.

Since the corresponding transcript was estimated to be approximately 6500 nucleotides in length by RNA gel-blot hybridization experiments, further cDNA library screening was required in order to clone the remainder of the coding region. As a result of several successive screenings with cDNA libraries generated from the colonic carcinoma cell line T84, normal and CF sweat gland cells, pancreas and adult lungs, 18 additional clones were isolated (FIG. 7, as subsequently discussed in greater detail). DNA sequence analysis revealed that none of these cDNA clones corresponded to the length of the observed transcript, but it was possible to derive a consensus sequence based on overlapping regions. Additional cDNA clones corresponding to the 5' and 3' ends of the transcript were derived from 5' and 3' primer-extension experiments. Together, these clones span a total of about 6.1 kb and contain an ORF capable of encoding a polypeptide of 1480 amino acid residues (FIG. 1).

Figure 7A:
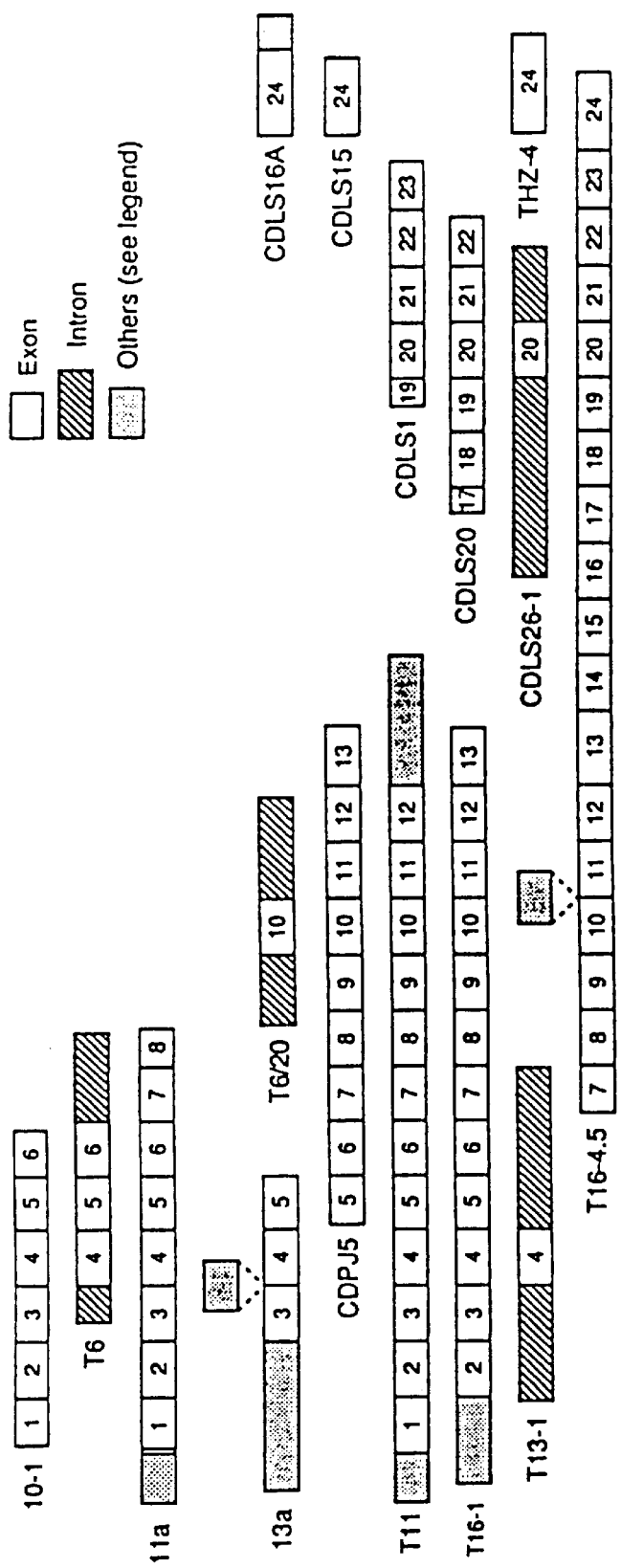
FIG. 7 is a restriction map of the CFTR cDNA showing alignment of the cDNA to the genomic DNA fragments.
Figure 7B:
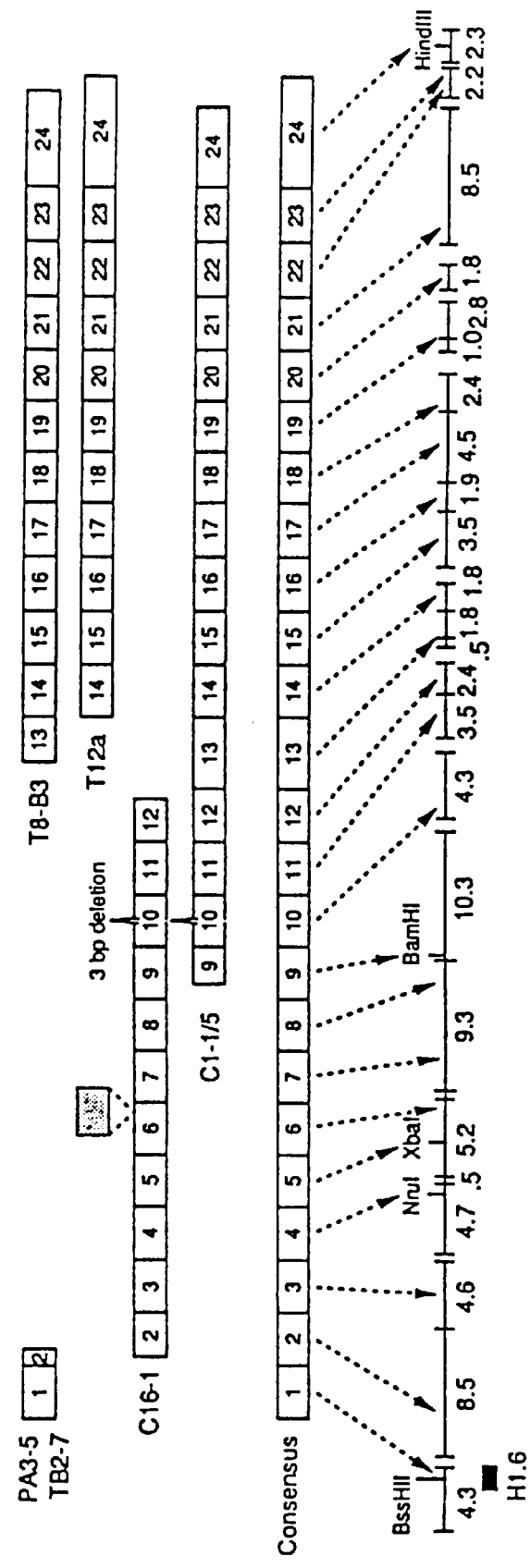

It was unusual to observe that most of the cDNA clones isolated here contained sequence insertions at various locations of the restriction map of FIG. 7. The map details the genomic structure of the CF gene. Exon/intron boundaries are given where all cDNA clones isolated are schematically represented on the upper half of the figure. Many of these extra sequences clearly corresponded to intron regions reversely transcribed during the construction of the cDNA, as revealed upon alignment with genomic DNA sequences.

Since the number of recombinant cDNA clones for the CF gene detected in the library screening was much less than would have been expected from the abundance of transcript estimated from RNA hybridization experiments, it seemed probable that the clones that contained aberrant structures were preferentially retained while the proper clones were lost during propagation. Consistent with this interpretation, poor growth was observed for the majority of the recombinant clones isolated in this study, regardless of the vector used.

The procedures used to obtain the 5' and 3' ends of the cDNA were similar to those described (M. Frohman et al, *Proc. Nat. Acad. Sci*, USA, 85, 8998–9002, 1988). For the 5' end clones, total pancreas and T84 poly A+RNA samples were reverse transcribed using a primer, (10b), which is specific to exon 2 similarly as has been described for the primer extension reaction except that radioactive tracer was included in the reaction. The fractions collected from an agarose bead column of the first strand synthesis were assayed by polymerase chain reaction (PCR) of eluted fractions. The oligonucleotides used were within the 10-1 sequence (145 nucleotides apart) just 5' of the extension primer. The earliest fractions yielding PCR product were pooled and concentrated by evaporation and subsequently tailed with terminal deoxynucleotidyl transferase (BRL Labs.) and dATP as recommended by the supplier (BRL Labs). A second strand synthesis was then carried out with Taq Polymerase (Cetus, AmpliTaq™) using an oligonucleotide containing a tailed linker sequence 5'CGGAATTCTCGAGATC(T)$_{12}$3' (SEQ ID NO: 5).

Amplification by an anchored (PCR) experiment using the linker sequence and a primer just internal to the extension primer which possessed the Eco RI restriction site at its 5' end was then carried out. Following restriction with the enzymes Eco RI and Bgl II and agarose gel purification size selected products were cloned into the plasmid Bluescript KS available from Stratagene by standard procedures (Maniatis et al, supra). Essentially all of the recovered clones contained inserts of less than 350 nucleotides. To obtain the 3' end clones, first strand cDNA was prepared with reverse transcription of 2 λg T84 poly A RNA using the tailed linker oligonucleotide previously described with conditions similar to those of the primer extension. Amplification by PCR was then carried out with the linker oligonucleotide and three different oligonucleotides corresponding to known sequences of clone T16-4.5. A preparative scale reaction (2×100 ul) was carried out with one of these oligonucleotides with the sequence 5'ATGAAGTCCAAG-GATTTAG3' (SEQ ID NO: 6).

This oligonucleotide is approximately 70 nucleotides upstream of a Hind III site within the known sequence of T16-4.5. Restriction of the PCR product with Hind III and Xho 1 was followed by agarose gel purification to size select a band at 1.0–1.4 kb. This product was then cloned into the plasmid Bluescript KS available from Stratagene. Approximately 20% of the obtained clones hybridized to the 3' end portion of T16-4.5. 10/10 of plasmids isolated from these clones had identical restriction maps with insert sizes of approx. 1.2 kb. All of the PCR reactions were carried out for 30 cycles in buffer suggested by an enzyme supplier.

An extension primer positioned 157 nt from the 5' end of 10-1 clone was used to identify the start point of the putative CF transcript. The primer was end labelled with γ[$^{32}$P]ATP at 5000 Curies/mole and T4 polynucleotide kinase and purified by spun column gel filtration. The radiolabeled primer was then annealed with 4–5 ug poly A+RNA prepared from T-84 colonic carcinoma cells in 2X reverse transcriptase buffer for 2 hrs. at 60° C. Following dilution and addition of AMV reverse transcriptase (Life Sciences, Inc.) incubation at 41° C. proceeded for 1 hour. The sample was then adjusted to 0.4M NaOH and 20 mM EDTA, and finally neutralized, with NH$_4$OAc, pH 4.6, phenol extracted, ethanol precipitated, redissolved in buffer with formamide, and analyzed on a polyacrylamide sequencing gel. Details of these methods have been described (*Meth. Enzymol.* 152, 1987, Ed. S. L. Berger, A. R. Kimmel, Academic Press, N.Y.).

Results of the primer extension experiment using an extension oligonucleotide primer starting 157 nucleotides from the 5' end of 10-1 is shown in Panel A of FIG. 10. End labelled øX174 bacteriophage digested with Hae III (BRL Labs) is used as size marker. Two major products are observed at 216 and 100 nucleotides. The sequence corresponding to 100 nucleotides in 10-1 corresponds to a very GC rich sequence (11/12) suggesting that this could be a reverse transcriptase pause site. The 5' anchored PCR results are shown in panel B of FIG. 10. The 1.4% agarose gel shown on the left was blotted and transferred to Zetaprobe™ membrane (Bio-Rad Lab). DNA gel blot hybridization with radiolabeled 10-1 is shown on the right. The 5' extension products are seen to vary in size from 170–280 nt with the major product at about 200 nucleotides. The PCR control lane shows a fragment of 145 nucleotides. It was obtained by using the test oligomers within the 10-1 sequence. The size markers shown correspond to sizes of 154, 220/210, 298, 344, 394 nucleotides (1kb ladder purchased from BRL Lab).

The schematic shown below Panel B of FIG. 10 outlines the procedure to obtain double stranded cDNA used for the amplification and cloning to generate the clones PA3-5 and TB2-7 shown in FIG. 7. The anchored PCR experiments to characterize the 3' end are shown in panel C. As depicted in the schematic below FIG. 10C, three primers whose relative position to each other were known were used to amplification with reversed transcribed T84 RNA as described. These products were separated on a 1% agarose gel and blotted onto nylon membrane as described above. DNA-blot hybridization with the 3' portion of the T16-4.5 clone yielded bands of sizes that corresponded to the distance between the specific oligomer used and the 3' end of the transcript. These bands in lanes 1, 2a and 3 are shown schematically below Panel C in FIG. 10. The band in lane 3 is weak as only 60 nucleotides of this segment overlaps with the probe used. Also indicated in the schematic and as shown in the lane 2b is the product generated by restriction of the anchored PCR product to facilitate cloning to generate the THZ-4 clone shown in FIG. 7.

DNA-blot hybridization analysis of genomic DNA digested with EcoRI and HindIII enzymes probed with portions of cDNAs spanning the entire transcript suggest that the gene contains at least 26 exons numbered as Roman numerals I through XXVI (see FIG. 9). These correspond to the number 1 through 26 shown in FIG. 7. The size of each band is given in kb.

In FIG. 7, open boxes indicate approximate positions of the 24 exons which have been identified by the isolation of >22 clones from the screening of cDNA libraries and from anchored PCR experiments designed to clone the 5' and 3' ends. The lengths in kb of the Eco RI genomic fragments detected by each exon is also indicated. The hatched boxes in FIG. 7 indicate the presence of intron sequences and the stippled boxes indicate other sequences. Depicted in the lower left by the closed box is the relative position of the clone H1.6 used to detect the first cDNA clone 10-1 from among 10$^6$ phage of the normal sweat gland library. As shown in FIGS. 4(D) and 7, the genomic clone H1.6 partially overlaps with an EcoRI fragment of 4.3 kb. All of the cDNA clones shown were hybridized to genomic DNA and/or were fine restriction mapped. Examples of the restriction sites occurring within the cDNAs and in the corresponding genomic fragments are indicated.

With reference to FIG. 9, the hybridization analysis includes probes; i.e., cDNA clones 10-1 for panel A, T16-1 (3' portion) for panel B, T16-4.5 (central portion) for panel C and T16-4.5 (3' end portion) for panel D. In panel A of FIG. 9, the cDNA probe 10-1 detects the genomic bands for exons I through VI. The 3' portion of T16-1 generated by NruI restriction detects exons IV through XIII as shown in Panel B. This probe partially overlaps with 10-1. Panels C and D, respectively, show genomic bands detected by the central and 3' end EcoRI fragments of the clone T16-4.5. Two EcoRI sites occur within the cDNA sequence and split exons XIII and XIX. As indicated by the exons in parentheses, two genomic EcoRI bands correspond to each of these exons. Cross hybridization to other genomic fragments was observed. These bands, indicated by N, are not of chromosome 7 origin as they did not appear in human-hamster hybrids containing human chromosome 7. The faint band in panel D indicated by XI in brackets is believed to be caused by the cross-hybridization of sequences due to internal homology with the cDNA.

Since 10-1 detected a strong band on gel blot hybridization of RNA from the T-84 colonic carcinoma cell line, this cDNA was used to screen the library constructed from that source. Fifteen positives were obtained from which clones T6, T6/20, T11, T16-1 and T13-1 were purified and sequenced. Rescreening of the same library with a 0.75 kb Bam Hi-Eco RI fragment from the 3' end of T16-1 yielded T16-4.5. A 1.8 kb EcoRI fragment from the 3' end f T16-4.5 yielded T8-B3 and T12a, the latter of which contained a polyadenylation signal and tail. Simultaneously a human lung cDNA library was screened; many clones were isolated including those shown here with the prefix 'CDL'. A pancreas library was also screened, yielding clone CDPJ5.

To obtain copies of this transcript from a CF patient, a cDNA library from RNA of sweat gland epithelial cells from a patient was screened with the 0.75 kb Bam HI-Eco RI fragment from the 3' end of T16-1 and clones C16-1 and C1-1/5, which covered all but exon 1, were isolated. These two clones both exhibit a 3 bp deletion in exon 10 which is not present in any other clone containing that exon. Several clones, including CDL26-1 from the lung library and T6/20 and T13-1 isolated from T84 were derived from partially processed transcripts. This was confirmed by genomic hybridization and by sequencing across the exon-intron boundaries for each clone. T11 also contained additional sequence at each end. T16-4.5 contained a small insertion near the boundary between exons 10 and 11 that did not correspond to intron sequence. Clones CDLS16A, 11a and 13a from the lung library also contained extraneous sequences of unknown origin. The clone C16-1 also contained a short insertion corresponding to a portion of the γ-trnasposon of *E. coli*; this element was not detected in the other cones. The 5' clones PA3–5, generated from pancreas RNA and TB2–7 generated from T84 RNA using the anchored PCR technique have identical sequences except for a single nucleotide difference in length at the 5' end as shown in FIG. 1. The 3' clone, THZ-4 obtained from T84 RNA contains the 3' sequence of the transcript in concordance with the genomic sequence of this region.

A combined sequence representing the presumptive coding region of the CF gene was generated from overlapping cDNA clones. Since most of the cDNA clones were apparently derived from unprocessed transcripts, further studies were performed to ensure the authenticity of the combined sequence. Each cDNA clone was first tested for localization to chromosome 7 by hybridization analysis with a human-hamster somatic cell hybrid containing a single human chromosome 7 and by pulsed field gel electrophoresis. Fine restriction enzyme mapping was also performed for each clone. While overlapping regions were clearly identifiable for most of the clones, many contained regions of unique restriction patterns.

To further characterize these cDNA clones, they were used as probes in gel hybridization experiments with EcoRI- or HindIII-digested human genomic DNA. As shown in FIG. 9, five to six different restriction fragments could be detected with the 10-1 cDNA and a similar number of fragments with other cDNA clones, suggesting the presence of multiple exons for the putative CF gene. The hybridization studies also identified those cDNA clones with unprocessed intron sequences as they showed preferential hybridization to a subset of genomic DNA fragments. For the confirmed cDNA clones, their corresponding genomic DNA segments were isolated and the exons and exon/intron boundaries sequenced. As indicated in FIG. 7, at least 27 exons have been identified which includes split exons 6a, 6b, 14a, 14b and 17a, 17g. Based on this information and the results of physical mapping experiments, the gene locus was estimated to span 250 kb on chromosome 7.

2.6 The Sequence

Figure 11:
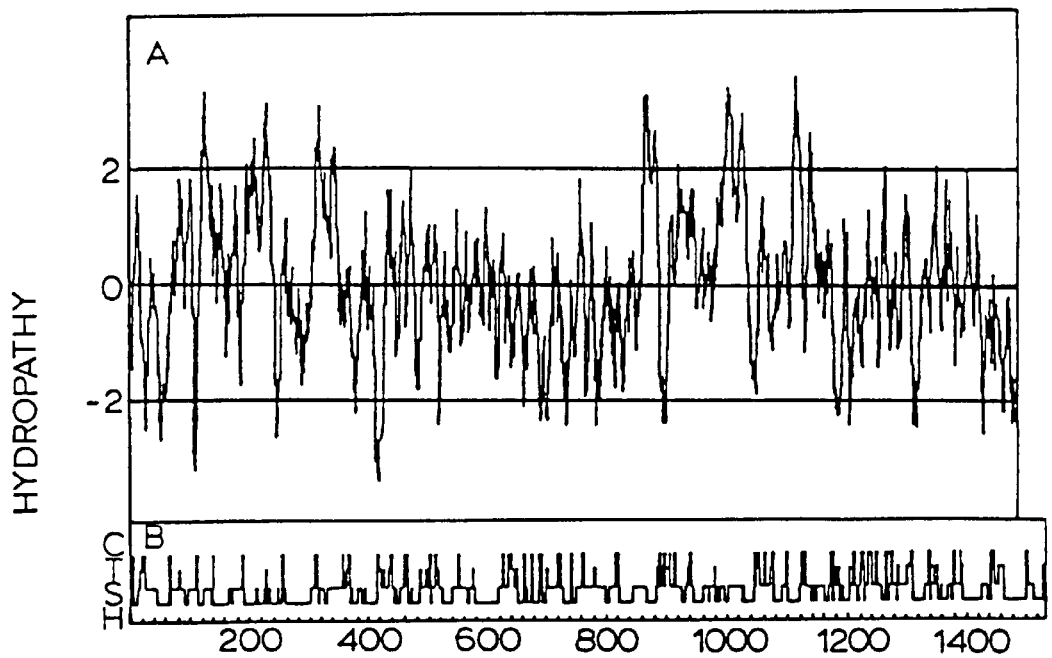
FIG. 11 is a hydropathy profile and shows predicted secondary structures of CFTR.

FIG. 1 shows the nucleotide sequence (SEQ ID NO: 1) of the cloned cDNA encoding CFTR together with the deduced amino acid sequence (SEQ ID NO: 2). The first base position corresponds to the first nucleotide in the 5' extension clone PA3-5 which is one nucleotide longer than TB2-7. Arrows indicate position of transcription initiation site by primer extension analysis. Nucleotide 6129 is followed by a poly (dA) tract. Positions of exon junctions are indicated by vertical lines. Potential membrane-spanning segments were ascertained using the algorithm of Eisenberg et al *J. Mol. Biol.* 179:125 (1984). Potential membrane-spanning segments as analyzed and shown in FIG. 11 are enclosed in boxes of FIG. 1. In FIG. 11, the mean hydropathy index [Kyte and Doolittle, *J. Molec. Biol.* 157: 105, (1982)] of 9 residue peptides is plotted against the amino acid number. The corresponding positions of features of secondary structure predicted according to Garnier et al, [*J. Molec. Biol.* 157, 165 (1982)] are indicated in the lower panel. Amino acids comprising putative ATP-binding bolds are underlined in FIG. 1. Possible sites of phosphorylation by protein kinases A (PKA) or C (PKC) are indicated by open and closed circles, respectively. The open triangle is over the 3 bp (CTT) which are deleted in CF (see discussion below). The cDNA clones in FIG. 1 were sequenced by the dideoxy chain termination method employing $^{35}$S labelled nucleotides by the Dupont Genesis 2000™ automatic DNA sequencer.

The combined cDNA sequence spans 6129 base pairs excluding the poly(A) tail at the end of the 3' untranslated region and it contains an ORF capable of encoding a polypeptide of 1480 amino acids (FIG. 1). An ATG (AUG) triplet is present at the beginning of this ORF (base position 133–135). Since the nucleotide sequence surrounding this codon (5'-AGACCAUGCA-3') (SEQ ID NO: 7) has the proposed features of the consensus sequence (CC) A/GCC AUGG(G) of an eukaryotic translation initiation site with a highly conserved A at the −3 position, it is highly probably that this AUG corresponds to the first methionine codon for the putative polypeptide.

To obtain the sequence corresponding to the 5' end of the transcript, a primer-extension experiment was performed, as described earlier. As shown in FIG. 10A, a primer extension product of approximately 216 nucleotides could be observed suggesting that the 5' end of the transcript initiated approximately 60 nucleotides upstream of the end of cDNA clone 10-1. A modified polymerase chain reaction (anchored PCR) was then used to facilitate cloning of the 5'-end sequences (FIG. 10*b*). Two independent 5'-extension clones, one from pancreas and the other from T84 RNA, were characterized by DNA sequencing and were found to differ by only 1 base in length, indicating the most probable initiation site for the transcript as shown in FIG. 1.

Since most of the initial cDNA clones did not contain a polyA tail indicative of the end of a mRNA, anchored PCR was also applied to the 3' end of the transcript (Frohman et al, 1988, supra). Three 3'-extension oligonucleotides were made to the terminal portion of the cDNA clone T16-4.5. As shown in FIG. 10*c*, 3 PCR products of different sizes were obtained. All were consistent with the interpretation that the end of the transcript was approximately 1.2 kb downstream of the HindIII site at nucleotide position 5027 (see FIG. 1). The DNA sequence derived from representative clones was in agreement with that of the T84 cDNA clone T12a (see FIGS. 1 and 7) and the sequence of the corresponding 2.3 kb EcoRI genomic fragment.

3.0 Molecular Genetics of CF 3.1 Sites of Expression

To visualize the transcript for the putative CF gene, RNA gel blot hybridization experiments were performed with the 10-1 cDNA as probe. The RNA hybridization results are shown in FIG. 8.

RNA samples were prepared from tissue samples obtained from surgical pathology or at autopsy according to methods previously described (A. M. Kimmel, S. L. Berger, eds. *Meth. Enzymol.* 152, 1987). Formaldehyde gels were transferred onto nylon membranes (Zetaprobe™; BioRad Lab). The membranes were then hybridized with DNA probes labeled to high specific activity by the random priming method (A. P. Feinberg and B. Vogelstein, *Anal. Biochem.* 132, 6, 1983) according to previously published procedures (J. Rommens et al, *Am. J. Hum. Genet.* 43, 645–663, 1988). FIG. 8 shows hybridization by the cDNA clone 10-1 to a 6.5 kb transcript in the tissues indicated. Total RNA (10 μg) of each tissue, and Poly A+ RNA (1 μg) of the T84 colonic carcinoma cell line were separated on a 1% formaldehyde gel. The positions of the 28S and 18S rRNA bands were indicated. Arrows indicate the position of transcripts. Sizing was established by comparison to standard RNA markers (BRL Labs). HL60 is a human promyelocytic leukemia cell line, and T84 is a human colon cancer cell line.

Analysis reveals a prominent band of approximately 6.5 kb in size in T84 cells. Similar, strong hybridization signals were also detected in pancreas and primary cultures of cells from nasal polyps, suggesting that the mature mRNA of the putative CF gene is approximately 6.5 kb. Minor hybridization signals, probably representing degradation products, were detected at the lower size ranges but they varied between different experiments. Identical results were obtained with other cDNA clones as probes. Based on the hybridization band intensity and comparison with those detected for other transcripts under identical experimental conditions, it was estimated that the putative CF transcripts constituted approximately 0.01% of total mRNA in T84 cells.

A number of other tissues were also surveyed by RNA gel blot hybridization analysis in an attempt to correlate the expression pattern of the 10-1 gene and the pathology of CF. As shown in FIG. 8, transcripts, all of identical size, were found in lung, colon, sweat glands (cultured epithelial cells), placenta, liver, and parotid gland but the signal intensities in these tissues varied among different preparations and were generally weaker than that detected in the pancreas and nasal polyps. Intensity varied among different preparations, for example, hybridization in kidney was not detected in the preparation shown in FIG. 8, but can be discerned in subsequent repeated assays. No hybridization signals could be discerned in the brain or adrenal gland (FIG. 8), nor in skin fibroblast and lymphoblast cell lines.

In summary, expression of the CF gene appeared to occur in many of the tissues examined, with higher levels in those tissues severely affected in CF. While this epithelial tissue-specific expression pattern is in good agreement with the disease pathology, no significant difference has been detected in the amount or size of transcripts from CF and control tissues, consistent with the assumption that CF mutations are subtle changes at the nucleotide level.

3.2 The Major CF Mutation

Figure 16A:
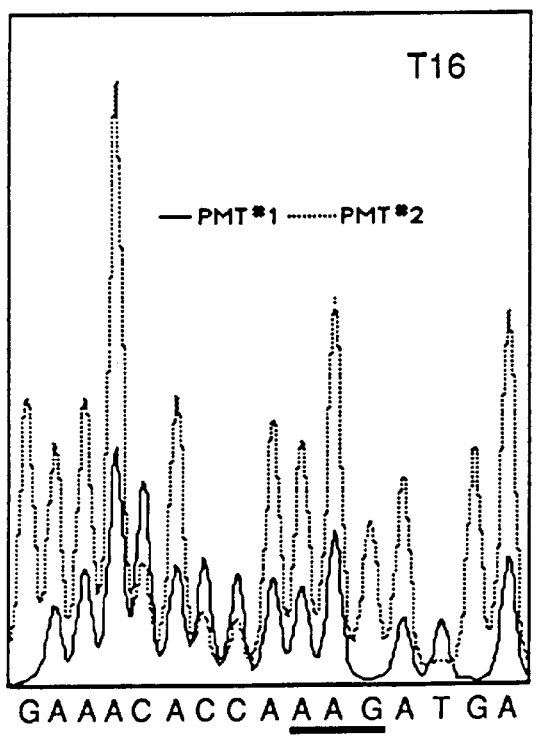
FIGS. 16A and 16B show the DNA sequence around the F508 deletion.
Figure 16B:
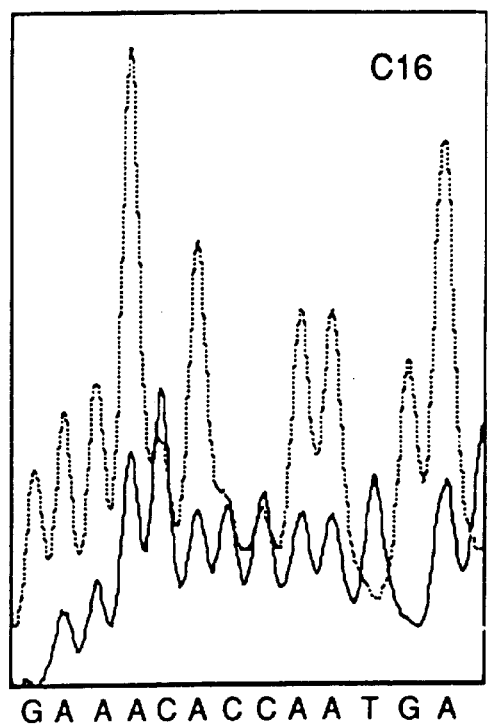

FIG. 16 shows the DNA sequence at the F508 deletion. On the left, the reverse complement of the sequence from base position 1649–1664 of the normal sequence (as derived from the cDNA clone T16). The nucleotide sequence is displayed as the output (in arbitrary fluorescence intensity units, y-axis) plotted against time (x-axis) for each of the 2 photomultiplier tubes (PMT#1 and #2) of a Dupont Genesis 2000™ DNA analysis system. The corresponding nucleotide sequence is shown underneath. On the right is the same region from a mutant sequence (as derived from the cDNA clone C16). Double-stranded plasmid DNA templates were prepared by the alkaline lysis procedure. Five µg of plasmid DNA and 75 ng of oligonucleotide primer were used in each sequencing reaction according to the protocol recommended by Dupont except that the annealing was done at 45° C. for 30 min and that the elongation/termination step was for 10 min at 42° C. The unincorporated fluorescent nucleotides were removed by precipitation of the DNA sequencing reaction product with ethanol in the presence of 2.5 M ammonium acetate at pH 7.0 and rinsed one time with 70% ethanol. The primer used for the T16-1 sequencing was a specific oligonucleotide 5'GTTGGCATGCTTTGAT-GACGCTTC3' (SEQ ID NO: 8) spanning base position 1708–1731 and that the C16-1 was the universal primer SK for the Bluescript vector (Stratagene).

Figure 17A:
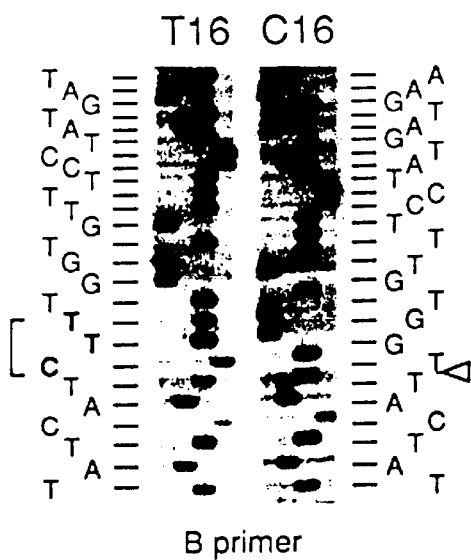
FIGS. 17A and 17B are representations of the nucleotide sequencing gels showing the DNA sequence at the F508 deletion.
Figure 17B:
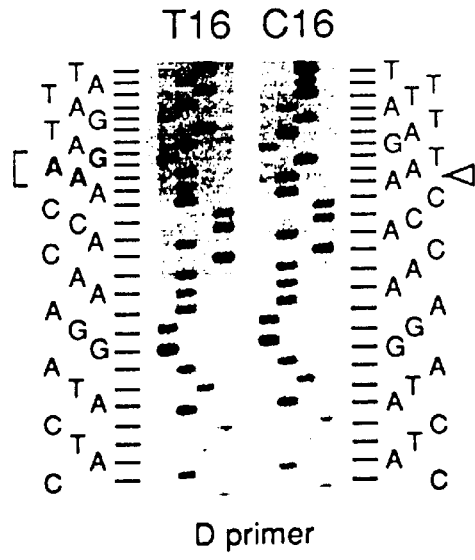

FIG. 17 also shows the DNA sequence around the F508 deletion, as determined by manual sequencing. The normal sequence from base position 1726–1651 (from cDNA T16-1) is shown beside the CF sequence (from cDNA C16-1). The left panel shows the sequences from the coding strands obtained with the B primer (5'GTTTTCCTGGATTATGCCTGGCAC3') (SEQ ID NO: 9) and the right panel those from the opposite strand with the D primer (5'GTTGGCATGCTTTGATGACGCTTC3') (SEQ ID NO: 8). The brackets indicate the three nucleotides in the normal that are absent in CF (arrowheads). Sequencing was performed as described in F. Sanger, S. Nicklen, A. R. Coulsen, *Proc. Nat. Acad. Sci. U.S.A.* 74: 5463 (1977).

The extensive genetic and physical mapping data have directed molecular cloning studies to focus on a small segment of DNA on chromosome 7. Because of the lack of chromosome deletions and rearrangements in CF and the lack of a well-developed functional assay for the CF gene product, the identification of the CF gene required a detailed characterization of the locus itself and comparison between the CF and normal (N) alleles. Random, phenotypically normal, individuals could not be included as controls in the comparison due to the high frequency of symptomless carriers in the population. As a result, only parents of CF patients, each of whom by definition carries an N and a CF chromosome, were suitable for the analysis. Moreover, because of the strong allelic association observed between CF and some of the closely linked DNA markers, it was necessary to exclude the possibility that sequence differences detected between N and CF were polymorphisms associated with the disease locus.

3.3 Identification of RFLPs and Family Studies

Figure 14:
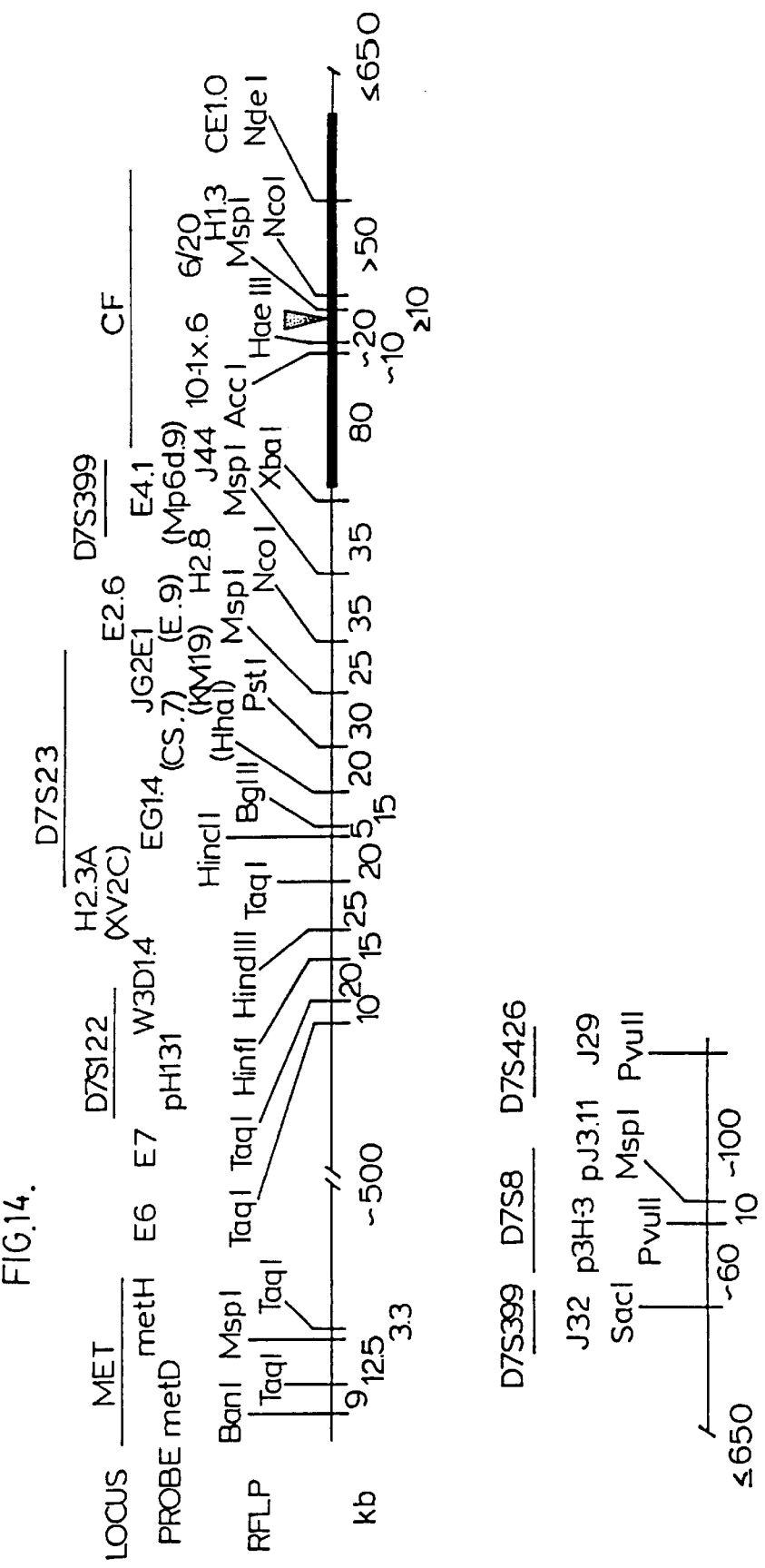
FIG. 14 is a schematic diagram of the restriction fragment length polymorphisms (RFLP's) closely linked to the CF gene where the inverted triangle indicates the location of the F508 3 base pair deletion.

To determine the relationship of each of the DNA segments isolated from the chromosome walking and jumping experiments to CF, restriction fragment length polymorphisms (RFLPs) were identified and used to study families where crossover events had previously been detected between CF and other flanking DNA markers. As shown in FIG. 14, a total of 18 RFLPs were detected in the 500 kb region; 17 of them (from E6 to CE1.0) listed in Table 2; some of them correspond to markers previously reported.

Five of the RFLPs, namely 10-1X.6, T6/20, H1.3 and CE1.0, were identified with cDNA and genomic DNA probes derived from the putative CF gene. The RFLP data are presented in Table 2, with markers in the MET and D7S8 regions included for comparison. The physical distances between these markers as well as their relationship to the MET and D7S8 regions are shown in FIG. 14.

TABLE 2

RFLPs ASSOCIATED WITH THE CF GENE

| Probe name | Enzyme | Frag-length | N[a] | CF-PI[a] | A[b] | *[c] | Reference |
|---|---|---|---|---|---|---|---|
| metD | BanI | 7.6(kb) | 28 | 48 | 0.60 | 0.10 | J. E. Spence et al, Am. J. Hum. Genet 39:729 (1986) |
| | | 6.8 | 59 | 25 | | | |
| metD | TaqI | 6.2 | 74 | 75 | 0.66 | 0.06 | R. White et al, Nature |

TABLE 2-continued

RFLPs ASSOCIATED WITH THE CF GENE

| Probe name | Enzyme | Frag-length | N[a] | CF-PI[a] | A[b] | *[c] | Reference |
|---|---|---|---|---|---|---|---|
| | | | | | | | 318:382 (1985) |
| | | 4.8 | 19 | 4 | | | |
| metH | TaqI | 7.5 | 45 | 49 | 0.35 | 0.05 | White et al, supra |
| | | 4.0 | 38 | 20 | | | |
| E6 | TaqI | 4.4 | 58 | 62 | 0.45 | 0.06 | B. Keren et al, Am. J. Hum. Genet. 44:827 (1989) |
| | | 3.6 | 42 | 17 | | | |
| E7 | TaqI | 3.9 | 40 | 16 | 0.47 | 0.07 | |
| pH131 | HinfI | 3 + 0.9 | 51 | 57 | | | |
| | | 0.4 | 81 | 33 | 0.73 | 0.15 | J. M. Rommens et al, Am. J. Hum. Genet. 43:645 (1988) |
| | | 0.3 | 18 | 47 | | | |
| W3D1.4 | HindIII | 20 | 82 | 33 | 0.68 | 0.13 | B. Kerem et al, supra |
| | | 10 | 22 | 47 | | | |
| H2.3A | TaqI | 2.1 | 39 | 53 | 0.64 | 0.09 | X. Estivill et al, Nature 326:840 (1987); X. Estivill et al, Genomics 1:257 (1987) |
| (XV2C) | | 1.4 | 37 | 11 | | | |
| EG1.4 | HincIII | 3.8 | 31 | 69 | 0.89 | 0.17 | |
| | | 2.8 | 56 | 7 | | | |
| EG1.4 | BgII | 20 | 27 | 69 | 0.89 | 0.18 | |
| | | 15 | 62 | 9 | | | |
| JG2E1 | PstI | 7.8 | 69 | 10 | 0.88 | 0.18 | X. Estivill et al supra and B. Kerem et al supra(KM19)6 63070 |
| E2.6/E.9 | MspI | 13 | 34 | 6 | 0.85 | 0.14 | |
| | | 8.5 | 26 | 55 | | | |
| H2.8A | NcoI | 25 | 22 | 55 | 0.87 | 0.18 | |
| | | 8 | 52 | 9 | | | |
| E4.1 | MspI | 12 | 37 | 8 | 0.77 | 0.11 | G. Romeo, personal communication |
| (Mp6d9) | | 8.5 + 3.5 | 38 | 64 | | | |
| J44 | XbaI | 15.3 | 40 | 70 | 0.86 | 0.13 | |
| | | 15 + .3 | 44 | 6 | | | |
| 10-1X.6 | AccI | 6.5 | 67 | 15 | 0.90 | 0.24 | |
| | | 3.5 + 3 | 14 | 60 | | | |
| 10-1X.6 | HaeIII | 1.2 | 14 | 61 | 0.91 | 0.25 | |
| | | .6 | 72 | 15 | | | |
| T6/20 | MspI | 8 | 56 | 66 | 0.51 | 0.54 | |
| | | 4.3 | 21 | 8 | | | |
| H1.3 | NcoI | 2.4 | 53 | 7 | 0.87 | 0.15 | |
| | | 1 + 1.4 | 35 | 69 | | | |
| CE1.0 | NdeI | 5.5 | 81 | 73 | 0.41 | 0.03 | |
| | | 4.7 + 0.8 | 8 | 3 | | | |
| J32 | SacI | 15 | 21 | 24 | 0.17 | 0.02 | M. C. Iannuzi et al Am. J. Genet. 44:695 (1989) |
| | | 6 | 47 | 38 | | | |
| J3.11 | MspI | 4.2 | 36 | 38 | 0.29 | 0.04 | B. J. Wainright et al, Nature 318:384 (1985) |

TABLE 2-continued

RFLPs ASSOCIATED WITH THE CF GENE

| Probe name | Enzyme | Frag- length | N[a] | CF-PI[a] | A[b] | *[c] | Reference |
|---|---|---|---|---|---|---|---|
| J29 | PvuII | 1.8 | 62 | 36 | | | M. C. Iannuzi et al, supra |
| | | 9 | 26 | 36 | 0.36 | 0.06 | |
| | | 6 | 55 | 36 | | | |

NOTES FOR TABLE 2
[a]The number of N and CF-PI (CF with pancreatic insufficiency) chromosomes were derived from the parents in the families used in linkage analysis [Tsui et al. Cold Spring Harbor Symp. Quant. Biol. 51:325 (1986)].
[b]Standardized association (A), which is less influenced by the fluctuation of DNA marker allele distribution among the N chromosomes, is used here for the comparison Yule's association coefficient $A = (ad - bc)/(ad + bc)$, where a, b, c, and d are the number of N chromosomes with DNA marker allele 1, CF with 1, N with 2, and CF with 2 respectively. Relative risk can be calculated using the relationship $RR = (1 + A)/(1 - A)$ or its reverse.
[c]Allelic association (*), calculated according to A. Chadravarti et al, Am. J. Hum. Genet. 36:1239, (1984) assuming the frequency of 0.02 for CF chromosomes in the population is included for comparison.

Because of the small number of recombinant families available for the analysis, as was expected from the close distance between the markers studied and CF, and the possibility of misdiagnosis, alternative approaches were necessary in further fine mapping of the CF gene.

3.4 Allelic Association

Allelic association (linkage disequilibrium) has been detected for many closely linked DNA markers. While the utility of using allelic association for measuring genetic distance is uncertain, an overall correlation has been observed between CF and the flanking DNA markers. A strong association with CF was noted for the closer DNA markers, D7S23 and D7S122, whereas little or no association was detected for the more distant markers MET, D7S8 or D7S424 (see FIG. 1).

As shown in Table 2, the degree of association between DNA markers and CF (as measured by the Yule's association coefficient) increased from 0.35 for metH and 0.17 for J32 to 0.91 for 10-1X.6 (only CF-PI patient families were used in the analysis as they appeared to be genetically more homogeneous than CF-PS). The association coefficients appeared to be rather constant over the 300 kb from EG1.4 to H1.3; the fluctuation detected at several locations, most notably at H2.3A, E4.1 and T6/20, were probably due to the variation in the allelic distribution among the N chromosomes (see Table 2). These data are therefore consistent with the result from the study of recombinant families (see FIG. 14). A similar conclusion could also be made by inspection of the extended DNA marker haplotypes associated with the CF chromosomes (see below). However, the strong allelic association detected over the large physical distance between EG1.4 and H1.3 did not allow further refined mapping of the CF gene. Since J44 was the last genomic DNA clone isolated by chromosome walking and jumping before a cDNA clone was identified, the strong allelic association detected for the JG2E1-J44 interval prompted us to search for candidate gene sequences over this entire interval. It is of interest to note that the highest degree of allelic association was, in fact, detected between CF and the 2 RFLPs detected by 10-1X.6, a region near the major CF mutation.

Table 3 shows pairwise allelic association between DNA markers closely linked to CF. The average number of chromosomes used in these calculations was 75–80 and only chromosomes from CF-PI families were used in scoring CF chromosomes. Similar results were obtained when Yule's standardized association (A) was used.

TABLE 3

| | | | | | N chromosomes | | | | | |
|---|---|---|---|---|---|---|---|---|---|---|
| | metD | metH | E6 | E7 | pH131 | W3D1.4 | H2.3A | EG1.4 | | JG2E1 |
| | BanI | TaqI | TaqI | TaqI | TaqI | HinfI | HdIII | TaqI | HcII | BglII | PstI |
| metD BanI | — | 0.35 | 0.49 | 0.04 | 0.04 | 0.05 | 0.07 | 0.27 | 0.06 | 0.06 | 0.07 |
| metD TaqI | 0.21 | — | 0.41 | 0.13 | 0.15 | 0.02 | 0.01 | 0.02 | 0.09 | 0.15 | 0.11 |
| metH TaqI | 0.81 | 0.14 | — | 0.01 | 0.05 | 0.06 | 0.06 | 0.24 | 0.05 | 0.08 | 0.07 |
| E6 TaqI | 0.11 | 0.30 | 0.00 | — | 0.93 | 0.07 | 0.05 | 0.04 | 0.02 | 0.03 | 0.00 |
| E7 TaqI | 0.16 | 0.31 | 0.02 | 1.00 | — | 0.11 | 0.09 | 0.03 | 0.03 | 0.04 | 0.01 |
| pH131 HinfI | 0.45 | 0.28 | 0.23 | 0.38 | 0.40 | — | 0.91 | 0.12 | 0.04 | 0.09 | 0.05 |
| W3D1.4 HindIII | 0.45 | 0.28 | 0.23 | 0.45 | 0.47 | 0.95 | — | 0.21 | 0.02 | 0.03 | 0.01 |
| H2.3A TaqI | 0.20 | 0.11 | 0.15 | 0.08 | 0.11 | 0.38 | 0.47 | — | 0.05 | 0.11 | 0.07 |
| EG1.4 HindII | 0.11 | 0.08 | 0.07 | 0.06 | 0.07 | 0.20 | 0.20 | 0.24 | — | 0.95 | 0.87 |
| EG1.4 BglII | 0.03 | 0.08 | 0.07 | 0.06 | 0.07 | 0.27 | 0.27 | 0.40 | 1.00 | — | 0.92 |
| JG2E1 PstI | 0.07 | 0.08 | 0.03 | 0.09 | 0.08 | 0.30 | 0.30 | 0.45 | 0.93 | 0.94 | — |
| E2.6/E.9 MspI | 0.22 | 0.06 | 0.07 | 0.02 | 0.03 | 0.20 | 0.20 | 0.34 | 0.81 | 0.82 | 0.92 |
| H2.8 NcoI | 0.05 | 0.07 | 0.01 | 0.08 | 0.06 | 0.31 | 0.31 | 0.45 | 0.92 | 0.93 | 1.00 |
| E4.1 MspI | 0.12 | 0.06 | 0.07 | 0.05 | 0.03 | 0.25 | 0.25 | 0.48 | 0.82 | 0.86 | 0.94 |
| J44 XbaI | 0.18 | 0.05 | 0.06 | 0.01 | 0.01 | 0.26 | 0.26 | 0.45 | 0.71 | 0.69 | 0.80 |

TABLE 3-continued

| | | | | | N chromosomes | | | | | | |
|---|---|---|---|---|---|---|---|---|---|---|---|
| 10-1X.6 AccI | 0.16 | 0.10 | 0.24 | 0.10 | 0.11 | 0.42 | 0.42 | 0.64 | 0.54 | 0.58 | 0.64 |
| 10-1X.6 HaeIII | 0.16 | 0.10 | 0.25 | 0.08 | 0.11 | 0.41 | 0.41 | 0.65 | 0.54 | 0.58 | 0.64 |
| T6/20 MspI | 0.27 | 0.07 | 0.36 | 0.13 | 0.13 | 0.23 | 0.23 | 0.29 | 0.05 | 0.00 | 0.01 |
| H1.3 NcoI | 0.06 | 0.06 | 0.05 | 0.03 | 0.01 | 0.30 | 0.30 | 0.55 | 0.71 | 0.78 | 0.87 |
| CE1.0 NdeI | 0.00 | 0.04 | 0.02 | 0.11 | 0.11 | 0.25 | 0.25 | 0.06 | 0.69 | 0.59 | 0.55 |
| J32 SacI | 0.03 | 0.13 | 0.07 | 0.17 | 0.13 | 0.17 | 0.24 | 0.07 | 0.21 | 0.21 | 0.24 |
| J3.11 MspI | 0.14 | 0.11 | 0.15 | 0.07 | 0.06 | 0.05 | 0.05 | 0.12 | 0.11 | 0.10 | 0.13 |
| J29 PvuII | 0.11 | 0.12 | 0.09 | 0.10 | 0.10 | 0.00 | 0.00 | 0.09 | 0.10 | 0.10 | 0.14 |

| | E2.6 | H2.8 | E4.1 | J44 | 10-1X.6 | | T6/20 | H1.3 | CE1.0 | J32 | J3.11 | J29 |
|---|---|---|---|---|---|---|---|---|---|---|---|---|
| | MspI | NcoI | MspI | XbaI | AccI | HaeIII | MspI | NcoI | NdeI | SacI | MspI | PvuII |
| metD BanI | 0.14 | 0.07 | 0.09 | 0.03 | 0.06 | 0.10 | 0.03 | 0.16 | 0.05 | 0.07 | 0.11 | 0.02 |
| metD TaqI | 0.07 | 0.24 | 0.03 | 0.11 | 0.08 | 0.02 | 0.06 | 0.13 | 0.15 | 0.09 | 0.09 | 0.05 |
| metH TaqI | 0.13 | 0.15 | 0.07 | 0.04 | 0.02 | 0.02 | 0.07 | 0.02 | 0.03 | 0.21 | 0.04 | 0.18 |
| E6 TaqI | 0.19 | 0.02 | 0.09 | 0.19 | 0.09 | 0.11 | 0.09 | 0.15 | 0.07 | 0.11 | 0.20 | 0.00 |
| E7 TaqI | 0.11 | 0.00 | 0.07 | 0.22 | 0.01 | 0.02 | 0.09 | 0.13 | 0.06 | 0.06 | 0.16 | 0.04 |
| pH131 HinfI | 0.06 | 0.03 | 0.03 | 0.08 | 0.16 | 0.15 | 0.20 | 0.04 | 0.03 | 0.06 | 0.08 | 0.06 |
| W3D1.4 HindIII | 0.06 | 0.03 | 0.03 | 0.10 | 0.12 | 0.10 | 0.23 | 0.10 | 0.05 | 0.05 | 0.10 | 0.06 |
| H2.3A TaqI | 0.42 | 0.14 | 0.29 | 0.07 | 0.27 | 0.22 | 0.20 | 0.09 | 0.23 | 0.04 | 0.08 | 0.12 |
| EG1.4 HindII | 0.76 | 0.86 | 0.81 | 0.60 | 0.07 | 0.13 | 0.61 | 0.58 | 0.04 | 0.24 | 0.14 | 0.15 |
| EG1.4 BglII | 0.77 | 0.93 | 0.71 | 0.55 | 0.08 | 0.07 | 0.56 | 0.55 | 0.12 | 0.28 | 0.24 | 0.20 |
| JG2E1 PstI | 0.84 | 1.00 | 0.76 | 0.64 | 0.11 | 0.11 | 0.61 | 0.57 | 0.13 | 0.31 | 0.26 | 0.22 |
| E2.6/E.9 MspI | — | 0.83 | 0.97 | 0.76 | 0.56 | 0.52 | 0.47 | 0.70 | 0.32 | 0.31 | 0.25 | 0.22 |
| H2.8 Ncol | 0.92 | — | 0.74 | 0.65 | 0.13 | 0.18 | 0.60 | 0.59 | 0.10 | 0.28 | 0.28 | 0.18 |
| E4.1 MspI | 1.00 | 0.93 | — | 0.71 | 0.49 | 0.49 | 0.49 | 0.68 | 0.35 | 0.27 | 0.25 | 0.21 |
| J44 XbaI | 0.90 | 0.80 | 0.85 | — | 0.33 | 0.40 | 0.65 | 0.64 | 0.32 | 0.24 | 0.22 | 0.23 |
| 10-1X.6 AccI | 0.70 | 0.89 | 0.69 | 0.59 | — | 0.91 | 0.19 | 0.36 | 0.56 | 0.00 | 0.02 | 0.03 |
| 10-1X.6 HaeIII | 0.70 | 0.69 | 0.69 | 0.59 | 1.00 | — | 0.18 | 0.43 | 0.62 | 0.02 | 0.02 | 0.08 |
| T6/20 MspI | 0.07 | 0.02 | 0.01 | 0.11 | 0.69 | 0.69 | — | 0.56 | 0.03 | 0.21 | 0.18 | 0.25 |
| H1.3 NcoI | 0.90 | 0.87 | 0.93 | 0.92 | 0.64 | 0.64 | 0.12 | — | 0.40 | 0.19 | 0.13 | 0.20 |
| CE1.0 NdeI | 0.43 | 0.55 | 0.37 | 0.44 | 0.24 | 0.24 | 0.07 | 0.40 | — | 0.19 | 0.20 | 0.14 |
| J32 SacI | 0.22 | 0.24 | 0.21 | 0.21 | 0.27 | 0.26 | 0.13 | 0.21 | 0.18 | — | 0.84 | 0.97 |
| J3.11 MspI | 0.18 | 0.19 | 0.15 | 0.20 | 0.28 | 0.29 | 0.24 | 0.14 | 0.07 | 0.81 | — | 0.71 |
| J29 PvuII | 0.17 | 0.20 | 0.16 | 0.16 | 0.29 | 0.29 | 0.23 | 0.16 | 0.06 | 0.85 | 0.97 | — |

Strong allelic association was also detected among subgroups of RFLPs on both the CF and N chromosomes. As shown in Table 3, the DNA markers that are physically close to each other generally appeared to have strong association with each other. For example, strong (in some cases almost complete) allelic association was detected between adjacent markers E6 and E7, between pH131 and W3D1.4 between the AccI and HaeIII polymorphic sites detected by 10-1X.6 and amongst EG1.4, JG2E1, E2.6 (E.9), E2.8 and E4.1. The two groups of distal markers in the MET and D7S8 region also showed some degree of linkage disequilibrium among themselves but they showed little association with markers from E6 to CE1.0, consistent with the distant locations for MET and D7S8. On the other hand, the lack of association between DNA markers that are physically close may indicate the presence of recombination hot spots. Examples of these potential hot spots are the region between E7 and pH131, around H2.3A, between J44 and the regions covered by the probes 10-1X.6 and T6/20 (see FIG. 14). These regions, containing frequent recombination breakpoints, were useful in the subsequent analysis of extended haplotype data for the CF region.

3.5 Haplotype Analysis

Extended haplotypes based on 23 DNA markers were generated for the CF and N chromosomes in the collection of families previously used for linkage analysis. Assuming recombination between chromosomes of different haplotypes, it was possible to construct several lineages of the observed CF chromosomes and, also, to predict the location of the disease locus.

To obtain further information useful for understanding the nature of different CF mutations, the F508 deletion data were correlated with the extended DNA marker haplotypes. As shown in Table 4, five major groups of N and CF haplotypes could be defined by the RFLPs within or immediately adjacent to the putative CF gene (regions 6–8).

TABLE 4

DNA MARKER HAPLOTYPES SPANNING THE CF LOCUS

| | HAPLOTYPES[a] | | | | | | | | | CF[b] | | | | |
|---|---|---|---|---|---|---|---|---|---|---|---|---|---|---|
| | | | | | | | | | | PI | PS | PI | PS | |
| | 1 | 2 | 3 | 4 | 5 | 6 | 7 | 8 | 9 | (F508) | (F508) | others | others | N |
| I.(a) | A | A | A | A | A | A | A | A | A | 10 | 1 | . | . | . |
| | A | A | A | A | A | A | . | A | A | 3 | . | . | . | . |
| | A | A | A | A | . | A | A | . | A | 1 | . | . | . | . |

TABLE 4-continued

DNA MARKER HAPLOTYPES SPANNING THE CF LOCUS

|     |   |     |   |   |   |   |   |     |   |    |   |   |   |    |
|-----|---|-----|---|---|---|---|---|-----|---|----|---|---|---|----|
|     | A | A   | A | A | . | . | A | .   | A | .  | . | . | . | 1  |
|     | A | A   | A | A | A | A | A | A   | B | 10 | . | . | . | 1  |
|     | A | A   | . | A | A | A | A | A   | B | 4  | . | . | . | .  |
|     | A | A   | A | A | . | A | A | A   | B | 1  | . | . | . | .  |
|     | A | A   | . | A | A | A | A | A   | C | 1  | . | . | . | .  |
|     | B | A   | A | A | A | A | A | A   | A | 4  | . | . | . | .  |
|     | B | A   | . | A | A | A | A | A   | A | 1  | . | . | . | .  |
|     | B | A   | A | A | . | A | A | A   | A | .  | 1 | . | . | .  |
|     | B | A   | A | A | A | A | A | A   | . | 1  | . | . | . | .  |
|     | B | A   | A | A | . | . | A | .   | A | 1  | . | . | . | .  |
|     | A | B   | A | A | A | A | A | A   | A | 1  | . | . | . | .  |
|     | A | D   | A | A | A | A | A | A   | A | 1  | . | . | . | .  |
|     | A | G   | A | A | A | A | A | A   | A | 1  | . | . | . | .  |
|     | B | B   | A | A | A | A | A | A   | A | 1  | . | . | . | .  |
|     | B | C   | A | A | A | A | A | A   | A | 2  | . | . | . | .  |
|     | E | B   | A | A | . | . | A | .   | A | 1  | . | . | . | .  |
|     | D | B   | A | A | . | A | . | A   | A | 1  | . | . | . | .  |
|     | D | B   | B | A | A | A | A | A   | A | 1  | . | . | . | .  |
|     | B | A   | . | A | A | A | A | A   | B | 1  | . | . | . | .  |
|     | C | A   | . | A | A | A | A | A   | B | 1  | . | . | . | .  |
|     | A | D   | A | A | A | A | A | A   | B | 1  | . | . | . | .  |
|     | D | C   | A | A | A | A | A | A   | B | .  | 1 | . | . | .  |
|     | A | D   | A | A | . | A | A | A   | B | 1  | . | . | . | .  |
|     | D | D   | . | A | A | A | A | A   | B | .  | . | . | . | 1  |
|     | B | B   | . | A | A | A | . | A   | B | 1  | . | . | . | .  |
|     | A | B   | A | A | A | A | A | A   | E | 2  | . | . | . | .  |
|     | A | B   | . | A | A | A | A | A   | E | 1  | 1 | . | . | .  |
|     | A | E   | B | A | A | A | A | A   | E | 1  | . | . | . | .  |
|     | A | C   | A | A | A | A | A | A   | B | 1  | . | . | . | .  |
|     | A | C   | . | C | . | A | A | A   | B | .  | 1 | . | . | .  |
|     | A | B   | A | B | A | A | . | A   | . | .  | . | . | . | 1  |
|     | B | C   | B | A | . | A | A | A/D | B | 1  | . | . | . | .  |
| (b) | A | C   | . | A | A | A | A | A   | A | .  | . | . | 1 | .  |
|     | A | C   | A | A | A | A | A | A   | . | .  | . | 1 | . | .  |
|     | D | C   | . | A | A | A | A | A   | B | .  | . | 1 | . | .  |
|     | D | C   | A | A | A | A | A | A   | D | .  | . | . | . | 1  |
|     | F | C   | . | A | A | A | A | A   | B | .  | . | 1 | . | .  |
|     | B | C   | A | A | A | A | A | A   | B | .  | . | 3 | . | .  |
| (c) | B | C   | A | B | C | A | A | D   | A | .  | . | . | . | 1  |
|     | B | C   | A | B | C | A | A | D   | B | .  | . | 1 | . | .  |
|     | F | C   | A | B | C | A | A | D   | B | .  | . | . | . | 1  |
|     | F | A   | A | B | C | A | A | D   | B | .  | . | . | . | 1  |
|     | A | B   | A | B | C | A | A | D   | B | .  | . | . | . | 1  |
|     | B | B   | A | B | C | A | A | D   | B | .  | . | . | . | 1  |
|     | B | D   | A | B | C | A | . | D   | C | .  | . | . | . | 1  |
|     | A | B   | A | B | A | A | . | D   | A | .  | . | . | . | 1  |
| (d) | D | B   | A | A | A | A | A | C   | A | .  | . | . | . | 1  |
|     | B | C   | B | C | A | A | A | C   | B | .  | . | . | . | 1  |
|     |   |     |   |   |   |   |   |     |   | 57 | 5 | 7 | 1 | 14 |
| II.(a) | B | A | . | B | B | B | A | C | B | . | . | 1 | . | . |
|     | . | B/C | B | B | B | B | A | C   | B | .  | . | 1 | . | .  |
|     | B | A   | . | B | . | B | A | A/C | B | .  | . | . | 1 | .  |
|     | A | B   | B | B | B | B | A | C   | B | .  | . | 1 | . | .  |
|     | B | B   | B | B | B | B | A | C   | A | .  | . | . | . | 3  |
|     | A | C   | B | B | B | B | A | C   | A | .  | . | . | . | 1  |
|     | A | C   | B | B | B | . | A | C   | A | .  | . | . | . | 1  |
|     | F | C   | B | B | B | B | A | C   | A | .  | . | . | . | 1  |
|     | A | C   | B | B | B | B | A | C   | B | .  | . | . | . | 1  |
|     | A | C   | . | B | B | B | . | C   | C | .  | . | . | . | 1  |
|     | B | C   | B | B | . | B | A | C   | C | .  | . | . | 1 | .  |
|     | B | C   | B | B | B | B | A | C   | B | .  | . | . | . | 1  |
|     | B | C   | B | B | B | B | A | C   | A | .  | . | . | . | 1  |
|     | B | C   | B | B | B | B | A | C   | D | .  | . | . | . | 1  |
|     | B | C   | . | B | B | B | A | C   | B | .  | . | . | . | 1  |
|     | B | C   | B | B | B | B | . | C   | B | .  | . | . | . | 1  |
|     | D | C   | B | B | B | B | A | C   | B | .  | . | . | . | 2  |
|     | D | .   | B | B | . | B | A | C   | B | .  | . | . | . | 1  |
|     | F | C   | B | B | B | B | A | C   | B | .  | . | . | . | 1  |
|     | C | C   | . | B | B | B | A | C   | B | .  | . | . | . | 1  |
|     | A | A   | A | B | B | B | A | C   | B | .  | . | . | . | 1  |
|     | B | G   | A | B | B | B | A | C   | B | .  | . | . | . | 1  |
|     | F | A   | . | B | B | B | A | C   | B | .  | . | . | . | 1  |
|     | B | H   | . | B | B | B | A | C   | B | .  | . | . | . | 1  |
|     | B | B   | . | B | B | B | A | C   | B | .  | . | . | . | 1  |
|     | A | B   | A | B | B | B | A | C   | B | .  | . | . | . | 1  |
|     | F | D   | A | B | B | B | A | C   | B | .  | . | . | . | 1  |

TABLE 4-continued

DNA MARKER HAPLOTYPES SPANNING THE CF LOCUS

|     |   |   |   |   |   |   |   |   |   |   |   |   |   |   |
|-----|---|---|---|---|---|---|---|---|---|---|---|---|---|---|
|     | C | D | A | B | B | B | A | C | A | . | . | . | . | 1 |
|     | B | D | A | B | B | B | A | C | A | . | . | . | . | 1 |
|     | B | C | A | B | B | B | A | C | A | . | . | . | . | 2 |
|     | A | C | A | B | B | B | A | C | B | . | . | . | . | 1 |
|     | A | C | A | B | B | B | . | C | B | . | . | . | . | 1 |
|     | A | C | A | B | B | B | A | C | C | . | . | . | . | 1 |
|     | B | C | A | B | B | B | A | C | B | . | . | . | . | 1 |
|     | D | B/C | . | B | B | B | A | C | A | . | . | . | . | 2 |
|     | C | C | A | B | B | B | A | C | A | . | . | . | 1 | . |
|     | D | B | . | B | B | B | A | A/C | B | . | . | . | . | 1 |
|     | D | B | A | B | . | B | A | C | B | . | . | . | . | 1 |
|     | A | G | A | B | B | B | A | C | A | . | . | . | . | 1 |
|     | B | C | . | B | B | B | A | A/C | A | . | . | . | . | 1 |
|     | A | C | B | D | B | B | A | C | B | . | . | 1 | . | . |
|     | A | C | . | D | . | B | A | C | B | . | . | . | . | 1 |
|     | B | B | B | E | B | B | A | C | C | . | . | . | . | 1 |
|     | F | D | A | B | B | B | A | C | C | . | . | . | 1 | . |
|     | A | A | A | A | B | B | A | C | D | . | . | . | . | 1 |
|     | . | B/C | A | B | C | B | A | C | B | . | . | . | . | 1 |
|     | A | B | A | B | B | B/C | A | C | A | . | . | . | . | 1 |
| (b) | A | C | A | B | B | B | A | B | E | . | . | 1 | . | . |
|     | A | C | . | B | B | B | A | B | B | . | . | 1 | . | . |
| (c) | B | D | . | B | . | B | A | A | A | . | . | . | . | 1 |
|     |   |   |   |   |   |   |   |   |   | 0 | 0 | 6 | 4 | 45 |
| III.(a) | B | C | B | A | A | C | B | A | B | 1 | . | . | . | . |
| (b) | B | A | B | A | A | C | B | A | B | . | . | 1 | . | . |
|     | B | C | B | A | A | C | B | A | A | . | . | 1 | . | . |
|     | B | C | B | A | A | C | B | A | B | . | . | . | . | 1 |
|     | B | C | . | A | A | C | B | A | B | . | . | . | . | 2 |
|     | A | B | . | A | A | C | B | A | B | . | . | . | . | 1 |
|     | A | B | . | A | A | C | B | A | C | . | . | . | . | 1 |
|     | B | B | B | A | A | C | B | A | B | . | . | . | . | 2 |
|     | D | C | B | A | A | C | B | A | A | . | . | . | 1 | . |
|     | A | B | B | C | A | C | B | A | B | . | . | . | . | 1 |
|     | B | B | A | A | A | C | B | A | B | . | . | 2 | . | 1 |
|     | B | B | . | A | A | C | B | A | B | . | . | 1 | . | 1 |
|     | B | B | A | A | A | C | B | A | A | . | . | . | 1 | . |
|     | D | A | A | A | A | C | B | A | B | . | . | . | . | 1 |
|     | D | C | A | A | A | C | B | A | B | . | . | . | . | 2 |
|     | A | C | . | A | A | C | B | A | B | . | . | 1 | . | 1 |
|     | D | B | A | A | A | C | . | A | C | . | . | . | . | 1 |
| (c) | A | A | A | B | B | C | B | A | . | . | . | 1 | . | . |
|     | F | B | B | B | B | C | B | A | B | . | . | . | . | 1 |
|     | D | B | B | B | B | C | B | A | A | . | . | . | . | 1 |
|     |   |   |   |   |   |   |   |   |   | 1 | 0 | 7 | 2 | 17 |
| IV. | F | C | B | A | A | C | B | C | A | . | . | . | 1 | . |
|     | B | C | A | A | A | C | B | C | . | . | . | . | . | 1 |
|     | A | B | A | A | A | C | . | C | B | . | . | . | . | 1 |
|     | A | H | B | A | . | C | . | C | B | . | . | . | . | 1 |
|     | D | B | B | B | B | C | B | C | B | . | . | . | . | 1 |
|     |   |   |   |   |   |   |   |   |   | . | . | . | . | 1 |
|     |   |   |   |   |   |   |   |   |   | 0 | 0 | 0 | 1 | 4 |
| V.(a) | B | C | B | B | B | C | A | C | A | . | . | 1 | . | . |
|     | A | C | B | B | . | . | A | . | a | . | . | 1 | . | . |
|     | B | B | B | B | B | C | A | C | B | . | . | . | . | 1 |
|     | B | C | B | B | B | C | A | C | B | . | . | . | . | 1 |
|     | B | C | . | B | B | C | A | C | B | . | . | . | . | 1 |
|     | D | . | A | B | B | C | . | C | B | . | . | . | . | 1 |
| (b) | B | C | A | B | C | C | A | C | A | . | . | . | 1 | . |
|     | B | C | . | B | C | C | . | C | D | . | . | . | . | 1 |
|     |   |   |   |   |   |   |   |   |   | 0 | 0 | 2 | 1 | 5 |
| Others | B | C | B | A | A | B | B | A | B | . | . | . | . | 1 |
|     | B | C | B | A | A | D | B | A | B | . | . | . | . | 1 |
|     | B | C | B | E | B | A | B | D | A | . | . | . | . | 1 |
|     | B | C | A | B | B | E | . | C | . | . | . | . | . | 1 |
|     | B | D | B | B | B | F | A | C | B | . | . | . | . | 1 |
|     | A | C | . | A | A | C | B | D | A | . | . | . | . | 1 |
|     | G | B | B | A | A | B/C | A | A/D | B | . | . | . | . | 1 |
|     |   |   |   |   |   |   |   |   |   | 0 | 0 | 0 | 0 | 7 |

TABLE 4-continued

DNA MARKER HAPLOTYPES SPANNING THE CF LOCUS

| | | | | | | | |
|---|---|---|---|---|---|---|---|
| Unclassified: | . | . | . | . | . | . | . . | 4 | 10 | 2 | 18 | 6 |
| Total: | | | | | | | 62 | 15 | 24 | 27 | 98 |

[a]The extended haplotype data are derived from the CF families used in previous linkage studies (see footnote (a) of Table 3) with additional CF-PS families collected subsequently (Kerem et al, Am. J. Genet. 44:827 (1989)). The data are shown in groups (regions) to reduce space. The regions are assigned primarily according to pairwise association data shown in Table 4 with regions 6–8 spanning the putative CF locus (the F508) deletion is between regions 6 and 7). A dash (—) is shown at the region where the haplotype has not been determined due to incomplete data or inability to establish phase. Alternative haplotype assignments are also given where date are incomplete. Unclassified includes those chromosomes with more than 3 unknown assignments. The haplotype definitions for each of the 9 regions are:

| Region 1 | metD<br>BanI | metD<br>TaqI | metH<br>TaqI | |
|---|---|---|---|---|
| A = | 1 | 1 | 1 | |
| B = | 2 | 1 | 2 | |
| C = | 1 | 1 | 2 | |
| D = | 2 | 2 | 1 | |
| E = | 1 | 2 | — | |
| F = | 2 | 1 | 1 | |
| G = | 2 | 2 | 2 | |

| Region 2 | E6<br>TaqI | E7<br>TaqI | pH131<br>HinfI | W3D1.4<br>HindIII |
|---|---|---|---|---|
| A = | 1 | 2 | 2 | 2 |
| B = | 2 | 1 | 1 | 1 |
| C = | 1 | 2 | 1 | 1 |
| D = | 2 | 1 | 2 | 2 |
| E = | 2 | 2 | 2 | 1 |
| F = | 2 | 2 | 1 | 1 |
| G = | 1 | 2 | 1 | 2 |
| H = | 1 | 1 | 2 | 2 |

| Region 3 | H2.3A<br>TaqI | | |
|---|---|---|---|
| A = | 1 | | |
| B = | 2 | | |

| Region 4 | EG1.4<br>HincII | EG1.4<br>BglI | JG2E1<br>PstI |
|---|---|---|---|
| A = | 1 | 1 | 2 |
| B = | 2 | 2 | 1 |
| C = | 2 | 2 | 2 |
| D = | 1 | 1 | 1 |
| E = | 1 | 2 | 1 |

| Region 5 | E2.6<br>MspI | E2.8<br>NcoI | E4.1<br>MspI |
|---|---|---|---|
| A = | 2 | 1 | 2 |
| B = | 1 | 2 | 1 |
| C = | 2 | 2 | 2 |

| Region 6 | J44<br>XbaI | 10-1X.6<br>AccI | 10-1X.6<br>HaeIII |
|---|---|---|---|
| A = | 1 | 2 | 1 |
| B = | 2 | 1 | 2 |
| C = | 1 | 1 | 2 |
| D = | 1 | 2 | 2 |
| E = | 2 | 2 | 2 |
| F = | 2 | 2 | 1 |

| Region 7 | T6/20<br>MspI | |
|---|---|---|
| A = | 1 | |
| B = | 2 | |

| Region 8 | H1.3<br>NcoI | CE1.0<br>NdeI |
|---|---|---|
| A = | 2 | 1 |
| B = | 1 | 2 |
| C = | 1 | 1 |
| D = | 2 | 2 |

| Region 9 | J32<br>SacI | J3.11<br>MspI | J29<br>PvuII |
|---|---|---|---|
| A = | 1 | 1 | 1 |

TABLE 4-continued

DNA MARKER HAPLOTYPES SPANNING THE CF LOCUS

| | | | |
|---|---|---|---|
| B = | 2 | 2 | 2 |
| C = | 2 | 1 | 2 |
| D = | 2 | 2 | 1 |
| E = | 2 | 1 | 1 |

[b]Number of chromosomes scored in each class:
CF-PI(F) = CF chromosomes from CF-PI patients with the F508 deletion;
CF-PS(F) = CF chromosomes from CF-PS patients with the F508 deletion;
CF-PI = Other CF chromosomes from CF-PI patients;
CF-PS = Other CF chromosomes from CF-PS patients;
N = Normal chromosomes derived from carrier parents It was apparent that most recombinations between haplotypes occurred between regions 1 and 2 and between regions 8 and 9, again in good agreement with the relatively long physical distance between these regions. Other, less frequent, breakpoints were noted between short distance intervals and they generally corresponded to the hot spots identified by pairwise allelic association studies as shown above. It is of interest to note that the F508 deletion associated almost exclusively with Group I, the most frequent CF haplotype, supporting the position that this deletion constitutes the major mutation in CF. More important, while the F508 deletion was detected in 89% (62/70) of the CF chromosomes with the AA haplotype (corresponding to the two regions, 6 and 7) flanking the deletion, it was not was found in the 14 N chromosomes within the same group ($x^2$=47.3, $p<10^{-4}$). The F508 deletion was therefore not a sequence polymorphism associated with the core of the Group I haplotype (see Table 5).

Together, the results of the oligonucleotide hybridization study and the haplotype analysis support the fact that the gene locus described here is the CF gene and that the 3 bp (F508) deletion is the most common mutation in CF.

3.6 Intron/Exon Boundaries

The entire genomic CF gene includes all of the regulatory genetic information as well as intron genetic information which is spliced out in the expression of the CF gene. Portions of the introns at the intron/exon boundaries for the exons of the CF gene are very helpful in locating mutations in the CF gene, as they permit PCR analysis from genomic DNA. Genomic DNA can be obtained from any tissue including leukocytes from blood. Such intron information can be employed in PCR analysis for purposes of CF screening which will be discussed in more detail in a later section. As set out in FIG. 18 with the headings "Exon 1 through Exon 24", there are portions of the bounding introns in particular those that flank the exons which are essential for PCR exon amplification.

Figure 21A:
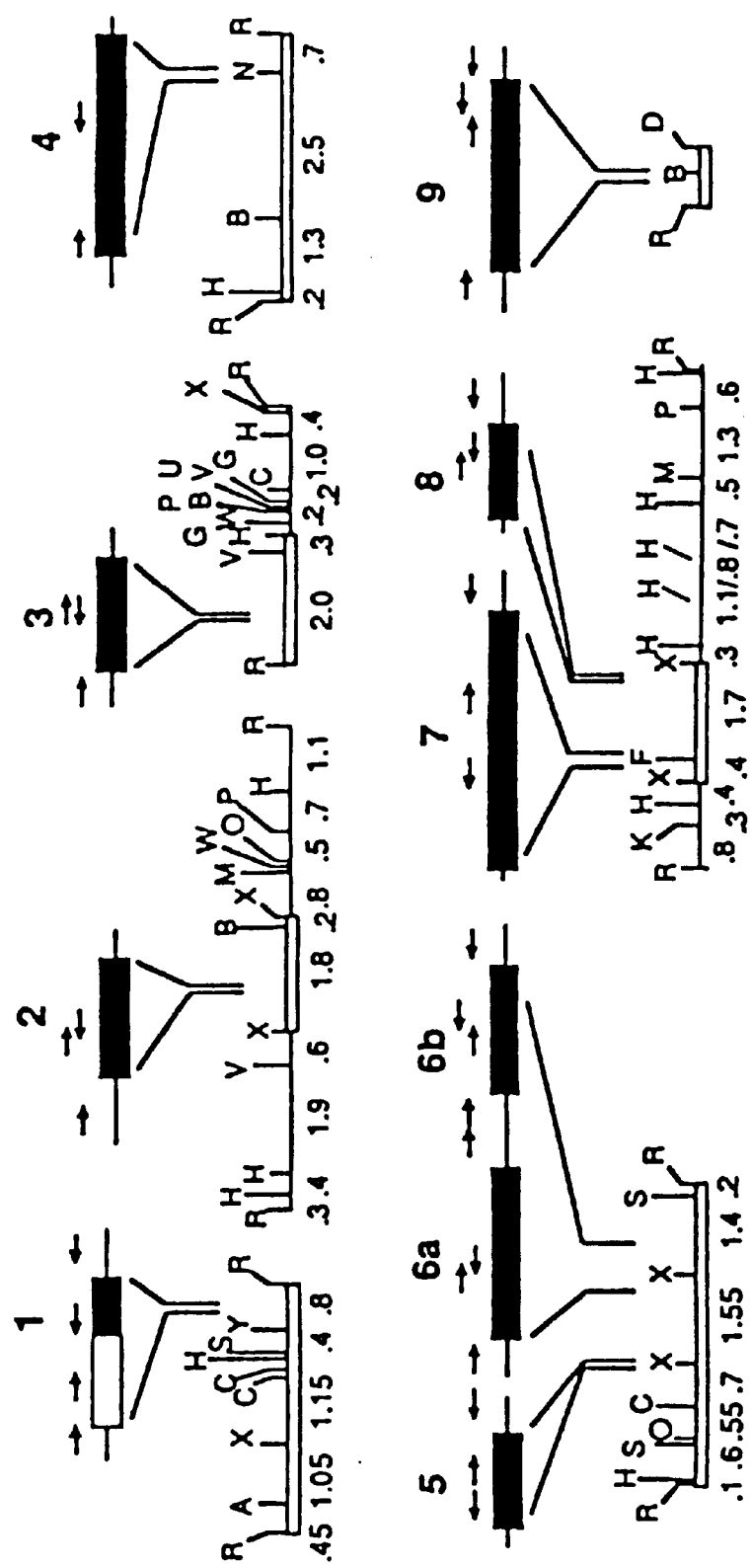
FIG. 21 is a restriction mapping of cloned intron and exon portions of genomic DNA which introns and exons are identified in FIG. 18.
Figure 21B:
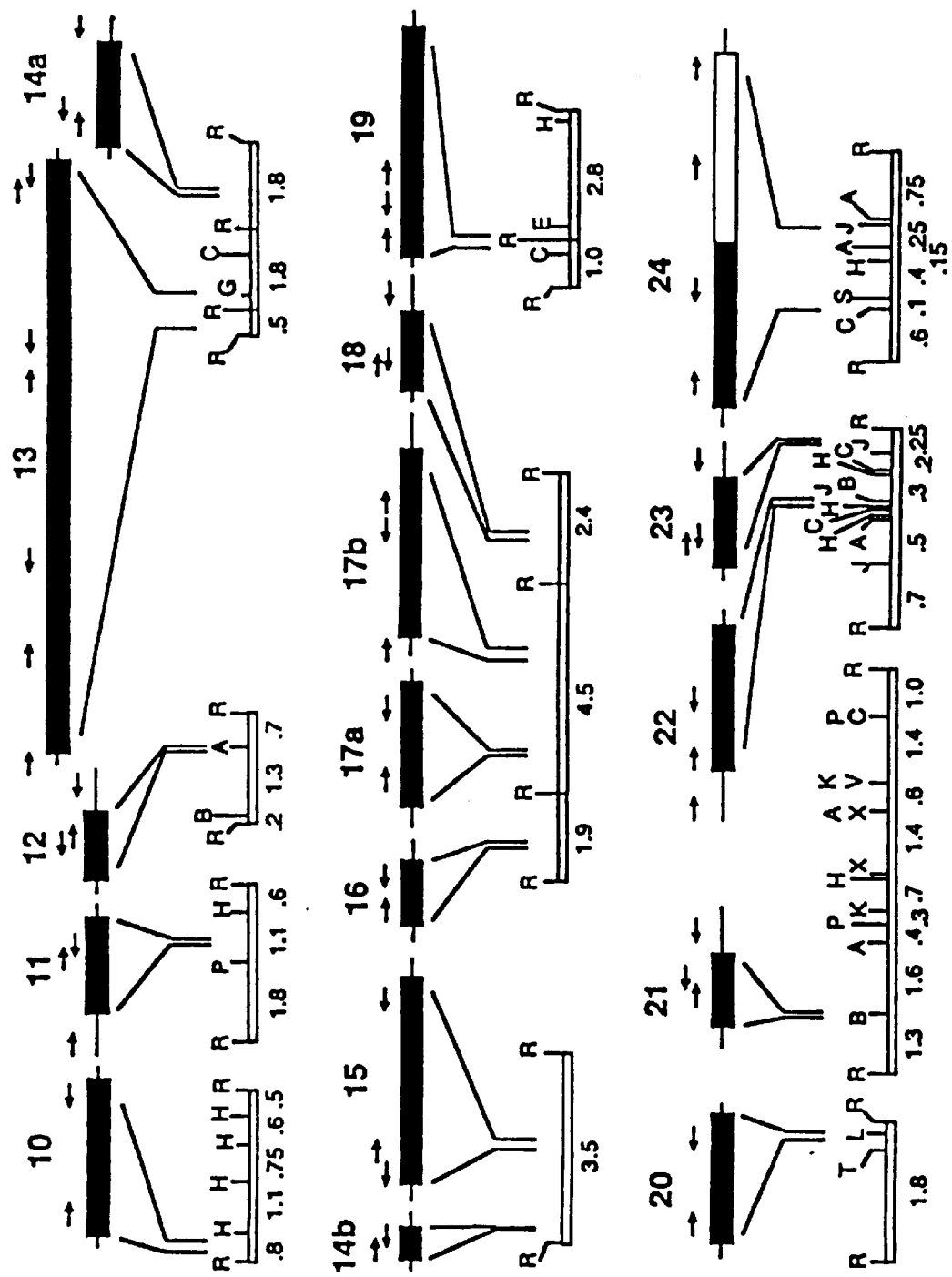

Further assistance in interpreting the information of FIG. 18 is provided in FIG. 21. Genomic DNA clones containing the coding region of the CFTR gene are provided. As is apparent from FIG. 21, there are considerable gaps between the clones of the exons which indicates the gaps in the intron portions between the exons of FIG. 18. These gaps in the intron portions are indicated by " . . . ". In FIG. 21, the clones were mapped using different restriction endonucleases (AccI,A; AvaI,W; BamHI,B; BglII,G; BssHI,Y; EcoRV,V; FspI,F; HincII,C; HindIII,H; KpnI,K; NcoI,J; PstI,P; PvuII,U; SmaI,M; SacI,S; SspI,E; StyI,T; XbaI,X; XhoI,O). In FIG. 21, the exons are represented by boxed regions. The open boxes indicate non-coding portions of the exons, whereas closed boxes indicate coding portions. The probable positions of the exons within the genomic DNA are also indicated by their relevative positions. The arrows above the boxes mark the location of the oligonucleotides used as sequencing primers in the PCR amplification of the genomic DNA. The numbers provided beneath the restriction map represent the size of the restriction fragments in kb.

In sequencing the intron portions, it has been determined that there are at least 27 exons instead off the previously reported 24 exons in applicants' aforementioned co-pending applications. Exons 6, 14 and 17, as previously reported, are found to be in segments and are now named exons 6a, 6b, exons 14a, 14b and exons 17a, 17b.

The intron portions, which have been used in PCR amplification, are identified in the following Table 5 and underlined in FIG. 18. The portions identified by the arrows are selected, but it is understood that other portions of the intron sequences are also useful in the PCR amplification technique. For example, for exon 10 the relevant genetic information which is preferred in PCR is noted by reference to the 5' and 3' ends of the sequence. The intron section is identified with an "i". Hence in Table 5 for exon 2, the preferred portions are identified by 2i-5 and 2i-3 and similarly for exons 3 through 24. For exon 1, the selected portions include the sequence GGA . . . AAA for B115-B and ACA . . . GTG for 10D. For exon 13, portions are identified by two sets: 13i-5 and C1-1m and X13B-5 and 13i-3A. (This exon (13) is large and most practical to be completed in two sections). C1-1M and X13B-5 are from exon sequences. The specific conditions for PCR amplification of indivisual exons are summarized in the following Table 6 and are discussed in more detail hereinafter with respect to the procedure explained in R. K. Saiki et al, *Science* 230:1350 (1985).

These oligonucleotides, as derived from the intron sequence, assist in amplifying by PCR the respective exon, thereby providing for analysis for DNA sequence alterations corresponding to mutations of the CF gene. The mutations can be revealed by either direct sequence determination of the PCR products or sequencing the products cloned in plasmid vectors. The amplified exon can also be analyzed by use of gel electrophoresis in the manner to be further described. It has been found that the sections of the intron for each respective exon are of sufficient length to work particularly well with PCR technique to provide for amplification of the relevant exon.

TABLE 5

Oligonucleotides used for amplification of CF gene exons by PCR

| Exon | PCR primers: 5' -> 3' | Amplified product (bp) |
|---|---|---|
| 1 | GGAGTTCACTCACCTAAA (B115-B) ACACGCCCTCCTCTTTCGTG (10D) | 933 |
| 2 | CCAAATCTGTATGGAGACCA (2i-5) TATGTTGCCCAGGCTGGTAT (2i-3) | 378 |
| 3 | CTTGGGTTAATCTCCTTGGA (3i-5) ATTCACCAGATTTCGTAGTC (3i-3) | 309 |
| 4 | TCACATATGGTATGACCCTC (4i-5) TTGTACCAGCTCACTACCTA (4i-3) | 438 |
| 5 | ATTTCTGCCTAGATGCTGGG (5i-5) AACTCCGCCTTTCCAGTTGT (5i-3) | 395 |
| 6a | TTAGTGTGCTCAGAACCACG (6Al-5) CTATGCATAGAGCAGTCCTG (6Al-3) | 385 |
| 6b | TGGAATGAGTCTGTACAGCG (6Ci-5) GAGGTGGAAGTCTACCATGA (6Ci-3) | 417 |
| 7 | AGACCATGCTCAGATCTTCCAT (7i-5) GCAAAGTTCATTAGAACTGATC (7i-3) | 410 |
| 8 | TGAATCCTAGTGCTTGGCAA (8i-5) TCGCCATTAGGATGAAATCC (8i-3) | 359 |
| 9 | TAATGGATCATGGGCCATGT (9i-5) ACAGTGTTGAATGTGGTGCA (9i-3) | 560 |
| 10 | GCAGAGTACCTGAAACAGGA (10i-5) CATTCACAGTAGCTTACCCA (10i-3) | 491 |
| 11 | CAACTGTGGTTAAAGCAATAGTGT (11l-5) GCACAGATTCTGAGTAACCATAAT (11l-3) | 425 |
| 12 | GTGAATCGATGTGGTGACCA (12i-5) CTGGTTTAGCATGAGGCGGT (12i-3) | 426 |
| 13 (a) | TGCTAAAATACGAGACATATTGCA (13i-5) ATCTGGTACTAAGGACAG (C1-1M) | 528 |
| (b) | TCAATCCAATCAACTCTATACGAA (X13B-5) TACACCTTATCCTAATCCTATGAT (13l-3A) | 497 |
| 14a | AAAAGGTATGCCACTGTTAAG (14Al-5) GTATACATCCCCAAACTATCT (14Al-3) | 511 |
| 14b | GAACACCTAGTACAGCTGCT (14Bl-5) AACTCCTGGGCTCAAGTGAT (14Bl-3) | 449 |
| 15 | GTGCATGCTCTTCTAATGCA (15i-5) AAGGCACATGCCTCTGTGCA (15i-3) | 485 |
| 16 | CAGAGAAATTGGTCGTTACT (16i-5) ATCTAAATGTGGGATTGCCT (16i-3) | 570 |
| 17a | CAATGTGCACATGTACCCTA (17Ai-5) TGTACACCAACTGTGGTAAG (17Ai-3) | 579 |
| 17b | TTCAAAGAATGGCACCAGTGT (17Bl-5) ATAACCTATAGAATGCAGCA (17Bl-3) | 463 |
| 18 | GTAGATGCTGTGATGAACTG (18l-5) AGTGGCTATCTATGAGAAGG (18l-3) | 451 |
| 19 | GCCCGACAAATAACCAAGTGA (19i-5) GCTAACACATTGCTTCAGGCT (19i-3) | 454 |
| 20 | GGTCAGGATTGAAAGTGTGCA (20i-5) CTATGAGAAAACTGCACTGGA (20i-3) | 473 |
| 21 | AATGTTCACAAGGGACTCCA (21i-5) CAAAAGTACCTGTTGCTCCA (21i-3) | 477 |
| 22 | AAACGCTGAGCCTCACAAGA (22i-5) TGTCACCATGAAGCAGGCAT (22i-3) | 562 |
| 23 | AGCTGATTGTGCGTAACGCT (23i-5) TAAAGCTGGATGGCTGTATG (23i-3) | 400 |
| 24 | GGACACAGCAGTTAAATGTG (24i-5) ACTATTGCCAGGAAGCCATT (24i-3) | 569 |

TABLE 6

| | | Thermal cycle | | | |
|---|---|---|---|---|---|
| Exon | Buffer* | Initial denaturation time/temp | Denaturation time/temp | Annealing time/temp | Extension time/temp | Final extension time/temp |
| 3–5, 6a, 6b, 7–10, 12, 14a, 16, 17b, 18–24 | A(1.5) | 6 min/94 C. | 30 sec/94 C. | 30 sec/55 C. | 1 min/72 C. | 7 min/72 C. |
| 1 | B | 6 min/94 C. | 30 sec/94 C. | 30 sec/55 C. | 2.5 min/72 C. | 7 min/72 C. |
| 2, 11 | B | 6 min/94 C. | 30 sec/94 C. | 30 sec/52 C. | 1 min/72 C. | 7 min/72 C. |
| 13a | A(1.75) | 6 min/94 C. | 30 sec/94 C. | 30 sec/54 C. | 2.5 min/72 C. | 7 min/72 C. |
| 13b | A(1.75) | 6 min/94 C. | 30 sec/94 C. | 30 sec/52 C. | 2.5 min/72 C. | 7 min/72 C. |
| 14b | B | 6 min/94 C. | 30 sec/94 C. | 30 sec/56 C. | 1 min/72 C. | 7 min/72 C. |
| 17a | A(1.5) | 6 min/94 C. | 30 sec/94 C. | 30 sec/56 C. | 1 min/72 C. | 7 min/72 C. |

(a)Buffer A(1.5): *buffer with 1.5 mM $MgCl_2$
Buffer A(1.75): *buffer with 1.75 mM $MgCl_2$
Buffer B: 67 mM Tris-HCl pH 8.8, 6.7 mM $MgCl_2$, 16.6 mM $(NH_4)_2SO_4$, 0.67 uM $EDT^A$, 10 mM B-mercaptoethanol, 170 ug/ml BSA, 10% DMSO, 1.5 mM of each dNTP's
*Buffer A contains: 10 mM Tris pH 8.3 (@ 25° C.)
50 mM KCl
0.001% (w/w) gelatin
0.2 mM dNTPs.
dNTPs = deoxynucleotide triphosphates

3.7 CF Mutations—ΔI506 or ΔI507

The association of the F508 deletion with 1 common and 1 rare CF haplotype provided further insight into the number of mutational events that could contribute to the present patient population. Based on the extensive haplotype data, the original chromosome in which the F508 deletion occurred is likely to carry the haplotype —AAAAAAA— (Group Ia), as defined in Table 4. The other Group I CF chromosomes carrying the deletion are probably recombination products derived from the original chromosome. If the CF chromosomes in each haplotype group are considered to be derived from the same origin, only 3–4 additional mutational events would be predicted (see Table 4). However, since many of the CF chromosomes in the same group are markedly different from each other, further subdivision within each group is possible. As a result, a higher number of independent mutational events could be considered and the data suggest that at least 7 additional, putative mutations also contribute to the CF-PI phenotype (see Table 3). The mutations leading to the CF-PS subgroup are probably more heterogeneous.

The 7 additional CF-PI mutations are represented by the haplotypes: —CAAAAAA— (Group Ib), —CABCAAD— (Group Ic), —BBBAC— (Group IIa), —CABBBAB— (Group Va). Although the molecular defect in each of these mutations has yet to be defined, it is clear that none of these mutations severely affect the region corresponding to the oligonucleotide binding sites used in the PCR/hybridization experiment.

One CF chromosome hydridizing to the ΔF508-ASO probe, however, has been found to associate with a different haplotype (group IIIa). It appeared that the ΔF508 should have occurred in both haplotypes, but with the discovery of ΔI507, it is discovered that it is not. Instead, the ΔF508 is in group Ia, whereas the ΔI507 is in group IIIa. None of the other CF nor the normal chromosomes of this haplotype group (IIIa) have shown hybridization to the mutant (ΔF508) ASO [B. Kerem et al, *Science* 245:1073 (1989)]. In view of the group Ia and IIIa haplotypes being distinctly different from each other, the mutations harbored by these two groups of CF chromosomes must have originated independently. To investigate the molecular nature of the mutation in this group IIIa CF chromosome, we further characterized the region of interest through amplification of the genomic DNA from an individual carrying the chromosome IIIa by the polymerase chain reaction (PCR).

These polymerase chains reactions (PCR) were performed according to the procedure of R. K. Saiki et al *Science* 230::1350 (1985). A specific DNA segment of 491 bp including exon 10 of the CF gene was amplified with the use of the oligonucleotide primers 10i-5 (5'-GCAGAGTACCTGAAACAGGA-3') (SEQ ID NO:10) and 10i-3 (5'CATTCACAGTAGCTTACCCA-3') (SEQ ID NO:11) located in the 5' and 3' flanking regions, respectively, as shown in FIG. 18 and itemzied in Table 5. Both oligonucleotides were purchased from the HSC DNA Biotechnology Service Center (Toronto). Approximately 500 ng of genomic DNA from cultured lymphoblastoid cell lines of the parents and the CF child of Family 5 were used in each reaction. The DNA samples were denatured at 94° C. for 30 sec., primers annealed at 55° C. for 30 sec., and extended at 72° C. for 50 sec. (with 0.5 unit of Taq polymerase, Perkin-Elmer/Cetus, Norwalk, Conn.) for 30 cycles and a final extension period of 7 min. in a Perkin-Elmer/Cetus DNA Thermal Cycler. Reaction conditions for PCR amplification of other exons are set out in Table 6.

Hydridization analysis of the PCR products from three individuals of Family 5 of group IIIa was performed. The carrier mother and father are represented by a half-filled circle and square, respectively, and the affected son is a filled square in FIG. 19*a*. The conditions for hybridizaton and washing have been previously described (Kerem et al, supra). There is a relatively weak signal in the father's PCR product with the mutant (oligo ΔF508) probe. In FIG. 19*b*, DNA sequence analysis of the clone 5-3-15 and the PCR products from the affected son and the carrier father are shown. The arrow in the center panel indicates the presence of both A and T nucleotide residue in the same position; the arrow in the right panel indicates the points of divergence between the normal and the ΔI507 sequence. The sequence ladders shown are derived from the reverse-complements as will be described later. FIG. 19*c* shows the DNA sequences and their corresponding amino acid sequences of the normal ΔI507, and ΔF508 alleles spanning the mutation sites are shown. With reference to FIG. 19*a*, the PCR-amplified DNA from the carrier father, who contributed the group IIIa CF chromosome to the affected son, hybridized less efficiently with the ΔF508 ASO than that from the mother who carried the group Ia CF chromosome. The difference became apparent when the hybridization signals were compared to that with the normal ASO probe. This result therefore indicated that the mutation carried by the group IIIa CF chromosome might not be identical to ΔF508.

To define the nucleotide sequence corresponding to the mutant allele on this chromosome, the PCR-amplified product of the father's DNA was excised from a polyacrylamide-electrophoretic gel and cloned into a sequencing vector.

The general procedures for DNA isolation and purification for purposes of cloning into a sequencing vector are described in J. Sambrook, E. F. Fritsch, T. Maniatis, *Molecular Cloning: A Laboratory Manual,* 2nd ed. (Cold Spring Harbor Press, N.Y. 1989). The two homoduplexes generated by PCR amplification of the paternal DNA were purified from a 5% non-denaturing polyacrylamide gel (30:1 acrylamide:bis-acrylamide). The appropriate bands were visualized by staining with ethidium bromide, excised and eluted in TE (10 mM Tris-HCl; 1 mM EDTA; pH 7.5) for 2 to 12 hours at room temperature. The DNA solution was sequentially treated with Tris-equilibrated phenol, phenol/CHCl$_3$ and CHCl$_3$. The DNA samples were concentrated by precipitation in ethanol and resuspension in TE, incubated with T4 polynucleotide kinase in the presence of ATP, and ligated into diphosphorylated, blunt-ended Bluescript KS™ vector (Stratagene, San Diego, Calif.). Clones containing amplified product generated from the normal parental chromosome were identified by hybridization with the oligonucleotide N as described in Kerem et al supra.

Clones containing the mutant sequence were identified by their failure to hybridize to the normal ASO (Kerem et al, supra). One clone, 5-3-15 was isolated and its DNA sequence determined. The general protocol for sequencing cloned DNA is essentially as described [J. R. Riordan et al, *Science* 245:1066 (1989)] with the use of an U.S. Biochemicals Sequenase™ kit. To verify the sequence and to exclude any errors introduced by DNA polymerase during PCR, the DNA sequences for the PCR products from the father and one of the affected children were also determined directly without cloning.

This procedure was accomplished by denaturing 2 pmoles of gel-purified double-stranded PCR product in 0.2 M NaOH/0.2 mM EDTA (5 min. at room temperature), neutralized by adding 0.1 volume of 2 M ammonium acetate (pH 5.4) and precipitated with 2.5 volumes of ethanol at −70° C. for 10 min. After washing with 70% ethanol, the DNA pellet was dried and redissolved in a sequencing reaction buffer containing 4 pmoles of the oligonucleotide primer 10i-3 of FIG. 18, dithiothreitol (8.3 mM) and [α-35S]-dATP (0.8 μM, 1000 Ci/mmole). The mixture was incubated at 37° C. for 20 min., following which 2 μl of labelling mix, as included in the "Sequenase" Kit and then 2 units of Sequenase enzyme were added. Aliquotes of the reaction mixture (3.5 μl) were transferred, without delay, to tubes each containing 2.5 μl of ddGTP, ddATP, ddTTP and ddCTP solutions (U.S. Biochemicals Sequenase kit) and the reactions were stopped by addition of the stop solution.

The DNA sequence for this mutant allele is shown in FIG. 19b. The data derived from the cloned DNA and direct sequencing of the PCR products of the affected child and the father are all consistent with a 3 bp deletion when compared to the normal sequence (FIG. 19c). The deletion of this 3 bp (ATC) at the I506 or I507 position results in the loss of an isoleucine residue from the putative CFTR, within the same ATP-binding domain where ΔF508 resides, but it is not evident whether this deleted amino acid corresponds to the position 506 or 507. Since the 506 and 507 positions are repeats, it is at present impossible to determine in which position the 3 bp deletion occurs. For convenience in later discussions, however, we refer to this deletion as ΔI507.

The fact that the ΔI507 and ΔF508 mutations occur in the same region of the presumptive ATP-binding domain off CFTR is surprising. Although the entire sequence of ΔI507 allele has not been examined, as has been done for ΔF508, the strategic location of the deletion argues that it is the responsible mutation for this allele. This argument is further supported by the observation that this alteration was not detected in any of the normal chromosomes studied to data (Kerem et al, supra). The identification of a second single amino acid deletion in the ATP-binding domain of CFTR also provides information about the structure and function of this protein. Since deletion of either the phenylalanine residue at position 508 or isoleucine at position ΔI507 is sufficient to affect the function of CFTR such that it causes CF disease, it is suggested that these residues are involved in the folding of the protein but not directly in the binding of ATP. That is, the length of the peptide is probably more important than the actual amino acid residues in this region. In support of this hypothesis, it has been found that the phenylalanine residue can be replaced by a serine and that isoleucine at position 506 with valine, without apparent loss of function of CFTR.

When the nucleotide sequence of ΔI507 is compared to that of ΔF508 at the ASO-hybridizing region, it was noted that the difference between the two alleles was only an A→T change (FIG. 19c). This subtle difference thus explained the cross-hybridization of the ΔF508-ASO to ΔI507. These results therefore exemplified the importance of careful examination of both parental chromosomes in performing ASO-based genetic diagnosis. It has been determined that the ΔF508 and ΔI507 mutations can be distinguished by increasing the stringency of oligonucleotide hybridization condition or by detecting the unique mobility of the heteroduplexes formed between each of these sequences and the normal DNA on a polyacrylaminde gel. The stringency of hybridization can be increased by using a washing temperature at 45° C. instead of the prior 39° C. in the presence of 2XSSC (1XSSC=150 mM NaCL and 15 mM Na citrate).

Identification of the ΔI507 and ΔF508 alleles by polyacrylamide gel electrophoresis is shown in FIG. 20. The PCR products were prepared from the three family members and separated on a 5% polyacrylamide gel as described above. A DNA sample from a known heterozygous ΔF508 carrier is included for comparison. With reference to FIG. 20, the banding pattern of the PCR-amplified genomic DNA from the father, who is the carrier of ΔI507, is clearly distinguishable from that of the mother, who is of the type of carriers with the ΔF508 mutation. In this gel electrophoresis test, there were actually three individuals (the carrier father and the two affected sons in Family 5) who carried the ΔI507 deletion. Since they all belong to the same family, they only represent one single CF chromosome in our population analysis [Kerem et al, supra] The two patients who also inherited the ΔF508 mutation from their mother showed typical symptoms of CF with pancreatic insufficiency. The father of this family was the only parent who carries this ΔI507 mutation; no other CF parents showed reduced hybridization intensity signal with the ΔF508 mutant oligonucleotide probe or a peculiar heteroduplex pattern for the PCR product (as defined above) in the retrospective study. In addition, two representatives of the group IIIb and one of the group IIIc CF chromosomes from our collection [Kerem et al, supra] were sequenced, but none were found to contain ΔI507. Since the electrophoresis technique eliminates the need for probe-labelling and hybridization, it may prove to be the method of choice for detecting carriers in a large population scale [J. M. Rommens et al, *Am. J. Hum. Genet.* 46:395–396 (1990)].

The present data also indicate that there is a strict correlation between DNA marker haplotype and mutation in CF. The ΔF508 deletion is the most common CF mutation that occurred on a group Ia chromosome background [Kerem et al, supra]. The ΔI507 mutation is, however, rare in the CF population; the one group IIIa CF chromosome carrying this deletion is the only example in our studied population (1/219). Since the group III haplotype is relatively common among the normal chromosomes (17/198), the ΔI507 deletion probably occurred recently. Additional studies with larger populations of different geographic and ethnic backgrounds should provide further insight in understanding the origins of these mutations.

3.8 Additional CF Mutations

Following the above procedures, other mutations in the CF gene have been identified. The following brief description of each identified mutation is based on the previously described procedures for locating the mutation involving use of PCR procedures. The mutations are given short form names. The numbering used in these abbreviations refers to either the DNA sequence or the amino acid sequence position of the mutation depending on the type of mutation. For example, splice mutations and frameshift mutations are defined using the DNA sequence position. Most other mutations derive their nomenclature from the amino acid residue position. The description of each mutation clarifies the nomenclature in any event.

For example, mutations G542X, Q493X, 3659 del C, 556 del A result in shortened polypeptides significantly different from the single amino acid deletions or alteration. G542X and Q493X involve a polypeptide including on the first 541 and 493 amino acid residues, respectively, of the normal 1480 amino acid polypeptide. 3659 del C and 556 del A also involve shortened versions and will include additional amino acid residues. Mutation 711+1G→T and 1717–1G→A are predicted to lead to polypeptides which cannot be as of yet exactly defined. They probably do lead to shortened polypeptides but could contain additional amino acids. DNA sequences encoding these mutant polypeptides will now contain intron sequence from the normal gene or possibly deleted exons.

3.8.0 Mutations in Exon 1

In the 129G→C mutation, there is a single basepair change of G to C at nucleotide 129 of the cDNA sequence of FIG. 1. The PCR product for amplifying genomic DNA containing this mutation is derived from the B115-B and 10D primers as set out in Table 5. The genomic DNA is amplified as per the conditions of Table 6.

3.8.1 Mutations in Exon 3

The G85E mutation in exon 3 involves a G to A transition at nucleotide position 386. It is detected in family #26, a French Canadian family classified as PI. This predicted Gly to Glu amino acid change is associated with a group IIb haplotype. The mutation destroys a Hinfl site. The PCR product derived from the 3i-5 and 3i-3 primers, as per conditions of Table 6, is cleaved by this enzyme into 3 fragment, 172, 105 and 32 bp, respectively, for the normal sequence; a fragment of 277 bp would be present for the mutant sequence. We analyzed 54 CF chromosomes, 8 from group II, and 50 normal chromosomes, 44 from group II, and did not find another example of G85E.

3.8.2 Mutations in Exon 4

556 del A is a frameshift mutation in exon 4 in a single CF chromosome (Toronto family #17, GM1076). There is a deletion of A at nucleotide position 556. This mutation is associated with Group IIIb haplotype and is not found in 31 other CF chromosomes (9 from IIIb) and 30 N chromosomes (16 from IIIb). The mutation creates a BglI 1 enzyme cleavage site. The PCR primers are 4i-5 and 4i-3 (see Table 5) where the enzyme cuts the mutant PCR product (437 bp) into 2 fragments of 287 and 150 bp in size.

The I148T mutation in exon 4 involves a T to C basepair transition at nucleotide position 575. This results in an Ile to Thr change at amino acid position 148 of FIG. 1. The PCR product used in amplifying genomic DNA containing this mutation uses primers 4i-5 and 4i-3 as set out in Table 5. The reaction conditions for amplyfing the genomic DNA are set out in Table 6.

3.8.3 Mutations in Exon 5

In mutation G178R the Gly to Arg missense mutation in exon 5 is due to a G to A change at nucleotide position 664. The mutation is found on the mother's CF chromosome in family #50; the other mutation in this family is ΔF508. Primers 5i-5 and 5i-3 were used for amplifying genomic DNA as outlined in Tables 5 and 6.

3.8.4 Mutations in Exon 9

A mutation in exon 9 is a change of alanine (GCG) to glutamic acid (GAG) at amino acid position 455 (A455→E). Two of the 38 non-ΔF508 CF chromosomes examined carries this mutation; both of them are from patients of a French-Canadian origin, which we have identified in our work as families #27 and #53, and they belong to haplotype group Ib. The mutation is detectable by allele-specific oligonucleotide (ASO) hybridization with PCR-amplified genomic DNA sequence. The PCR primers are 9i-5 (5'-TAATGGATCATGGGCCATGT-3') (SEQ ID NO:12) and 9i-3 (5'-ACAGTGTTGAATGTGGTGCA-3') (SEQ ID NO:13) for amplifying genomic DNA under the conditions of Table 6. The ASOs are 5'-GTTGTTGGCGGTTGCT-3' (SEQ ID NO:14) for the normal allele and 5'-GTTGTTGGAGGTTGCT-3' (SEQ ID NO:15) for the mutant. The oligonucleotide hybridization is as described in Kerem et al (1989) supra at 37° C. and the washings are done twice with 5XSSC for 10 min each at room temperature followed by twice with 2×SSC for 30 min each at 52° C. Although the alanine at position 455 (Ala455) is not present in all ATP-binding folds across species, it is present in all known members of the P-glycoprotein family, the protein most similar to CFTR. Further, A455→E is believed to be a mutation rather than a sequence polymorphism because the change is not found in 16 non-ΔF508 CF chromosomes and three normal chromosomes carrying the same group I haplotype.

3.8.5 Mutations in Exon 10

In the Q493X mutation Gln493 (CAG) is changed into a stop codon (TAG) in Toronto family #9 (nucleotide position 1609 C→T). The muation occurs on a CF chromosome with haplotype IIIb; it is not found in 28 normal chromosomes (15 of which belong to 11b) nor in 33 other CF chromosomes (5 of which IIIb). The mutation can be detected by allele-specific PCR, with 10i-5 as the common PCR primer, 5'-GGCATAATCCAGGAAAACTG-3' (SEQ ID NO:16) for the normal sequence and 5'-GGCATAATCCAGGAAAACTA-3' (SEQ ID NO:17) for the mutant allele. The PCR condition is 6 min at 94° followed by cycles of 30 sec at 94°, 30 sec at 57° and 90 sec at 72°, with 100 ng of each primer and ~400 ng genomic DNA. The primers 9i-3 and 9i-5 may be used for internal PCR control as they share the same reaction condition.

3.8.6 Mutations in Exon 11

In mutation G542X the glycine codon (GGA) at amino acid position 542 is changed to a stop codon (TGA) (G542→Stop). The single chromosome carrying this mutation is of Ashkenazic Jewish origin (family A) and has the B haplotype (XV2C allele 1; KM.19 allele 2). The mutant sequence can be detected by hybridization analysis with allele-specific oligonucleotides (ASOs) on genomic DNA amplified under conditions of Table 6 by PCR with the 11i-5 and 11i-3 oligonucleotide primers. The normal ASO is 5'-ACCTTCTCCAAGAACT-3' (SEQ ID NO:18) and the mutant ASO, 5'-ACCTTCTCAAAGAACT-3' (SEQ ID NO:19). The oligonucleotide hybridization condition is as described in Kerem et al (1989) supra and the washing conditions are twice in 5×SSC for 10 min. each at room temperature followed by twice in 2×SSC for 30 min. each at 45° C. The mutation is not detected in 52 other non-ΔF508 CF chromosomes, 11 of which are of Jewish origin (three have a B haplotype), nor in 13 normal chromosomes.

In mutation S549R, the highly conserved serine residue of the nucleotide binding domain at position 549 is changed to arginine (S549→R); the codon change is AGT→AGG. The CF chromosome with this mutation is carried by a non-Ashkenazic Jewish pateitn from Morocco (family B). The chromosome also has the B haplotype. Detection of this mutation may be achieved by ASO hybridization or allele-specific PCR. In the ASO hybridization procedure, the genomic DNA sequence is first amplified under conditions of Table 6 by PCR with the 11i-5 and 11i-3 oligonucleotides; the ASO for the normal sequence is 5'-ACACTGAGTGGAGGTC-3' (SEQ ID NO:20) and that for the mutant is 5'-ACACTGAGGGGAGGTC (SEQ ID NO:21). The oligonucleotide hybridization condition is as described by Kerem et al (1989) supra and the washings are done twice in 5×SSC for 10 min. each at room temperature followed by twice in 2×SSC for 30 min. each at 56° C. In the allele-specific PCR amplification, the oligonucleotide primer for the normal sequence is 5'TGCTCGTTGACCTCCA-3' (SEQ ID NO:22), that for the mutant is 5'TGCTCGTTGACCTCCC-3' (SEQ ID NO:23) and that for the common, outside sequence is 11i-5. The reaction is performed with 500 ng of genomic DNA, 100 ng of each of the oligonucleotides and 0.5 unit of Taq polymerase. The DNA template is first denatured by heating at 94° C. for 6 min., followed by 30 cycles of 94° for 30 sec, 55° for 30 sec and 72° for 60 sec. The reaction is completed by a 6 min heating at 72° for 7 min. This S549→R mutation is not present in 52 other non-ΔF508 CF chromosomes, 11 of which are of Jewish origin (three have a B haplotype), nor in 13 normal chromosomes.

In the S549I mutation there is an AGT→ATT change (nucleotide position 1778 G→T) which represent the third mutation involving this amino acid codon resulting in a loss of the DdeI site. We have only one example who is of Arabic origin and is sequenced; no other Ddel-resistant chromosome is found in 5 other Arabic CF, 21 Jewish CF, 41 Canadian CF, and 13 Canadian normal chromosomes.

In mutation R560T the arginine (AAG) at amino acid position 560 is changed to threonine (AAC). The individual carrying this mutation (R560→T) is from a family we have identified in our work as family #32 and the chromosome is marked by haplotype IIIb. The mutation creates a MaeII site which cleaves the PCR product of exon 11 (generated with primers 11i-5 and 11i-3 under conditions of Table 6) into two fragments of 214 and 204 bp in size. None of the 36 non-ΔF508 CF chromosomes (seven of which have haplotype IIIb) or 23 normal chromosomes (16 have haplotype IIIb) carried this sequence alteration. The R560→T mutation is also not present on eight CF chromosomes with the ΔF508 mutation.

In mutation G551D glycine (G) at amino acid position 551 is changed to aspartic acid (D). G551 is a highly conserved residue within the ATP-binding fold. The corresponding codon change is from GGT to GAT. The G551→D change is found in 2 of our families (#1, #38) with pancreatic insufficient (PI) CF patients and 1 family (#54) with a pancreatic sufficient (PS) patient. The other CF chromosomes in family #1 and #38 carry the ΔF508 mutation and that in family #54 is unknown. Based on our "severe and mild mutation" hypothesis (Kerem et al. 1989), this mutation is expected to be a "severe" one. All 3 chromosomes carrying this mutation belong to Group IIIb. This G551→D substitution does not represent a sequence polymorphism because the change is not detected in 35 other CF chromosomes without the ΔF508 deletion (5 of them from group IIIb) and 19 normal chromosomes (including 5 from group IIIb). To detect this mutation, the genomic DNA region may be amplified under conditions of Table 6 by PCR with primers 11i-5 (5'-CAACTGTGGTTAAAGCAATAGTGT-3') (SEQ ID NO:24) and 11i-3 (5'-GCACAGATTCTGAGTAACCATAAT-3') (SEQ ID NO:25) and examined for the presence of a MboI (Sau3A) site created by nucleotide change; the uncut (normal) form is 419 bp in length and the digestion products (from the mutant form) are 241 and 178 bp.

3.8.7 Mutations in Exon 12

In the Y563N mutation a T to A change is detected at nucleotide position 1820 in exon 12. This switch would result in a change from Tyr to Asn at amino acid position 563. It is found in a single family with 2 PS patients but the mutation in the other chromosome is unknown. We think Y563N is probably a missense mutation because (1) the T to A change is not found in 59 other CF chromosomes, with 8 having the same haplotype (IIa) and 30 having ΔF508; and (2) this alteration is not found in 54 normal chromosomes, with 39 having the 11a haplotype. Unfortunately, the amino acid change is not drastic enough to permit a strong argument. This putative mutation can be detected by ASO hybridization with a normal (5'-AGCAGTATACAAAGATGC-3') and a mutant (5'-AGCAGTAAACAAAGATGC-3') oligonucleotide probe. The washing condition is 54° C. with 2×SSC.

In the P574H mutation the C at nucleotide position 1853 is changed to A. Although the amino acid Pro at this position is not highly conserved across different ATP-binding folds, c change to His could be a drastic substitution. This change is not detected in 52 other CF chromosomes nor 15 normal chromosomes, 4 of which have the same group IV haplotype. Based on these arguments, we believe P574H is a mutation. To detect this putative mutation, one may use the following ASOs: 5'-GACTCTCCTTTTGGA-3' (SEQ ID NO:26) for the normal and 5'-GACTCTCATTTTGGA-3' (SEQ ID NO:27) for the mutant. Washing should be done at 47° in 2×SSC.

In the L1077P mutation, the T at nucleotide position 3362 is changed to C. This results in a change of the amino acid Leu to Pro at amino position 1077 in FIG. 1. As with the other mutations in this exon, the genomic DNA is amplified by use of the primers of Table 5; namely 17bi-5 and 17bi-3. The reaction conditions in amplifying the genomic DNA are set out in Table 6.

The Y1092X mutation involves a change of C at nucleotide position 3408 to A. This would result in protein synthesis termination at amino position 1092. Hence the amino acid Tyr is not present in the truncated polypeptide. As with the above procedures, the primers used in amplifying this mutation are 17bi-3 and 17bi-3.

3.8.8 Mutations in Exon 19

3659 del C is a frameshift mutation in exon 19 in a single CF chromosome (Toronto family #2); deletion of C at nucleotide position 3659 or 3960; haplotype IIa; not present in 57 non-ΔF508 CF chromosomes (7 from IIa) and 50 N chromosomes (43 from IIa); the deletion may be detected by PCR with a common oligonucleotide primer 19i-5 (see Table 5) and 2 ASO primers HSC8 (5'-GTATGGTTTGGTTGACTT GG-3') (SEQ ID NO:28) for the normal and HSC9 (5'-GTATGGTTTGGTTGACTTGT-3') (SEQ ID NO:29) for the mutant allele; the PCR condition is as usual except the annealing temperature is at 60° C. to improve specificity.

3.8.9 Mutations in Intron 4

In the 621+1G→T mutation there is a single bp change affecting the splice site (GT→TT) at the 3' end of exon 4; this mutation is detected in 5 French-Canadian CF chromosomes (one each in Toronto families #22, 23, 26, 36 and 53) but not in 33 other CF chromosomes (18 from the same group, group I) and 29 N chromosomes (13 from group I); the mutation creates a MseI site; genomic DNA may be amplified by the 2 intron primers, 4i-5 and 4i-3, and cut with Mse1 to distinguish the normal and mutant alleles; the normal would give 4 fragments of 33, 35, 71 and 298 bp in size; the 298 bp fragment in the mutant is cleaved by the enzyme to give a 54 and 244 bp fragments.

3.8.10 Mutations in Intron 5

In the 711+1G→T mutation this G to T switch occurs at the splice junction after exon 5. The mutation is found on the mother's CF chromosome in family #22, a French Canadian family from Chicoutimi. The other mutation in this family is 621+1G→T.

3.8.11 Mutations in Intron 10

In the 1717–1G→A mutation a putative splice mutation is found in front of exon 11. This mutation is located at the last nucleotide of the intron before exon 11. The mutation may be detected with the following ASO's: normal=5'-TTTGGTAATAGGACATCTCC-3' (SEQ ID NO:30); mutant ASO=5'-TTTGGTAATAAGACATCTCC-3' (SEQ ID NO:31). The washing conditions afer hybridization are 5×SSC twice for 10 min at room temp, 2×SSC twice for 30 min at 47° for the mutant and 2×SSC twice to 30 min at 48° for the normal ASO. We have only 1 single example from an Arabic patient and there is no haploytpe data. The mutation is not found in 5 other Arabic, 21 Jewish, and 41 Canadian CF chromosomes, nor in 13 normal chromosomes.

3.9 DNA Sequence Polymorphisms

| Nucleotide position | Amino acid change |
|---|---|
| 1540 (A or G) | Met or Val |
| 1716 (G or A) | no change (Glu) |
| 2694 (T or G) | no change (Thr) |
| 356 (G or A) | Arg or Gln |

A polymorphism is detected at nucleotide position 1540– the A residue can be substituted by G, changing the corresponding amino acid from Met to Val. At postion 2694– the T residue can be a G; although it does not change the encoded amino acid. The polymorphism may be detected by restriction enzymes AvaII or Sau9GI. These changes are present in the normal population and show good correlation with haploytpes but not in CF disease.

There can be a G to A change for the last nucleotide of exon 10 (nucleotide position 1716). We think that this nucleotide substitution is a sequence polymorphism because (a) it does not alter the amino acid, (b) it is unlikely to cause a splicing defect and (c) it occurs on some normal chromosomes. In two Canadian families, this rare allele is found associated with haplotype IIIb.

The more common nucleotide at 356 (G) is found to be changed to A in the father's normal chromosome in family #54. The amino acid changes from Arg to Gln.

4.0 CFTR Protein

As discussed with respect to the DNA sequence of FIG. 1, analysis of the sequence of the overlapping cDNA clones predicted an unprocessed polypeptide of 1480 amino acids with a molecular mass of 168,138 daltons. As later described, due to polymorphisms in the protein, the molecular weight of the protein can vary due to possible substitutions or deletion of certain amino acids. The molecular weight will also change due to the addition of carbohydrate units to form a glycoprotein. It is also understood that the functional protein in the cell will be similar to the unprocessed polypeptide, but may be modified due to cell metabolism.

Accordingly, purified normal CFTR polypeptide is characterized by a molecular weight of about 170,000 daltons and having epithelial cell transmembrane ion conductance activity. The normal CFTR polypeptide, which is substantially free of other human proteins, is encoded by the aforementioned DNA sequences and according to one embodiment, that of FIG. 1. Such polypeptide displays the immunological or biological activity of normal CFTR polypeptide. As will be later discussed, the CFTR polypeptide and fragments thereof may be made by chemical or enzymatic peptide synthesis or expressed in an appropriate cultured cell system. The invention provides purified 507 mutant CFTR polypeptide which is characterized by cystic fibrosis-associated activity in human epithelial cells. Such 507 mutant CFTR polypeptide, as substantially free of other human proteins, can be encoded by the 507 mutant DNA sequence.

4.1 Structure of CFTR

Figure 12:
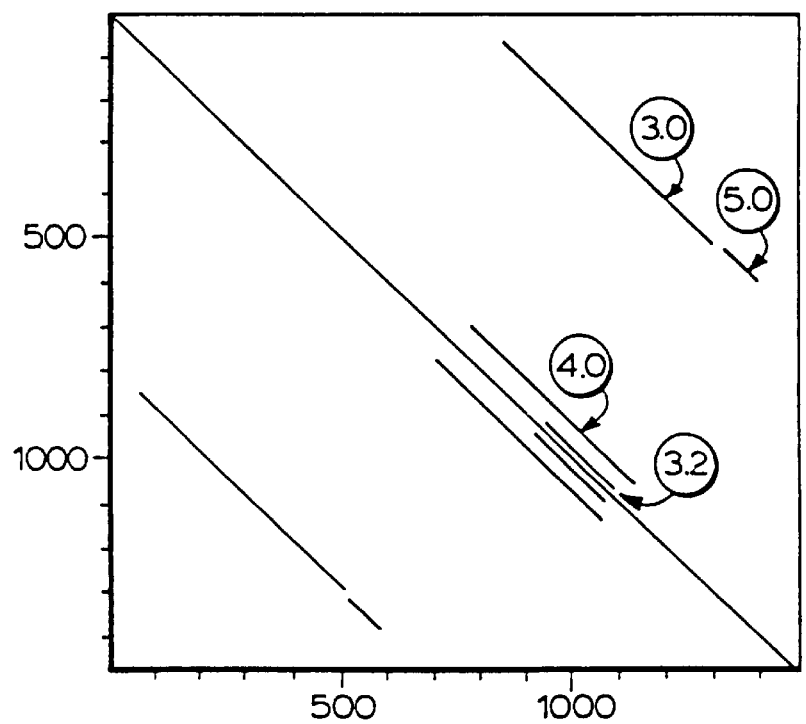
FIG. 12 is a dot matrix analysis of internal homologies in the predicted CFTR polypeptide.

The most characteristic feature of the predicted protein is the presence of two repeated motifs, each of which consists of a set of amino acid residues capable of spanning the membrane several times followed by sequence resembling consensus nucleotide (ATP)-binding folds (NBFs) (FIGS. 11, 12 and 15). These characteristics are remarkably similar to those of the mammalian multidrug resistant P-glycoprotein and a number of other membrane-associated proteins, thus implying that the predicted CF gene product is likely to be involved in the transport of substances (ions) across the membrane and is probably a member of a membrane protein super family.

FIG. 13 is a schematic model of the predicted CFTR protein. In FIG. 13, cylinders indicate membrane spanning helices, hatched spheres indicate NBFs. The strippled sphere is the polar R-domain. The 6 membrane spanning helices in each half of the molecule are depicted as cylinders. The inner cytoplasmically oriented NBFs are shown as hatched spheres with slots to indicate the means of entry by the nucleotide. The large polar R-domain which links the two halves is represented by an stippled sphere. Charged individual amino acids within the transmembrane segments and on the R-domain surface are depicted as small circles containing the charge sign. Net charges on the internal and external loops joining the membrane cylinders and on regions of the NBFs are contained in open squares. Sites for phosphorylation by protein kinases A or C are shown by closed and open triangles respectively. K, R, H, D, and E are standard nomenclature for the amino acids, lysine, arginine, histidine, aspartic acid and glutamic acid respectively.

Each of the predicted membrane-associated regions of the CFTR protein consists of 6 highly hydrophobic segments capable of spanning a lipid bilayer according to the algorithms of Kyte and Doolittle and of Garnier et al (*J. Mol. Biol.* 120, 97 (1978) (FIG. 13). The membrane-associated regions are each followed by a large hydrophilic region containing the NBFs. Based on sequence alignment with other known nucleotide binding proteins, each of the putative NBFs in CFTR comprises at least 150 residues (FIG. 13). The 3 bp deletion at position 507 as detected in CF patients is located between the 2 most highly conserved segments of the first NBF in CFTR. The amino acid sequence identity between the region surrounding the isoleucine deletion and the corresponding regions of a number of other proteins suggests that this region is of functional importance (FIG. 15). A hydrophobic amino acid, usually one with an aromatic side chain, is present in most of these proteins at the position corresponding to I507 of the CFTR protein. It is understood that amino acid polymorphisms may exist as a result of DNA polymorphisms. Similarly, mutations at the other positions in the protein suggested that corresponding regions of the protein are also of functional importance. Such additional mutations include substitutions of:

i) Glu for Gly at amino acid position 85;
ii) Thr for Ile at amino acid position 148;
iii) Arg for Gly at amino acid position 178;
iv) Glu for ALA at amino position 455;
v) stop codon for Gln at amino acid position 493;
vi) stop codon for Gly at amino acid position 542;
vii) Arg for Ser or Ile for Ser at amino acid position 549;
viii) Asp for Gly at amino acid position 551;
ix) Thr for Arg at amino acid position 560;
x) Asn for Tyr at amino acid position 563;
xi) His for Pro at amino acid position 574;
xii) Pro for Leu at amino acid position 1077;
xiii) Stop codon for Tyr at amino acid position 1092.

FIG. 15 shows alignment of the 3 most conserved segments of the extended NBF's of CFTR with comparable regions of other proteins. These 3 segments consist of residues 433–473, 488–513, and 542–584 of the N-terminal half and 1219–1259, 1277–1302, and 1340–1382 of the C-terminal half of CFTR. The heavy overlining points out the regions of greatest similarity. Additional general homology can be seen even without the introduction of gaps.

Despite the overall symmetry in the structure of the protein and the sequence conservation of the NBFs, sequence homology between the two halves of the predicted CFTR protein is modest. This is demonstrated in FIG. 12, where amino acids 1–1480 are represented on each axis. Lines on either side of the identity diagonal indicate the positions of internal similarities. Therefore, while four sets of internal sequence identity can be detected as shown in FIG. 12, using the Dayhoff scoring matrix as applied by Lawrence et al. [C. B. Lawrence, D. A. Goldman, and R. T. Hood, *Bull Math Biol.* 48, 569 (1986)], three of these are only apparent at low threshold settings for standard deviation. The strongest identity's between sequences at the carboxyl ends of the NBFs. Of the 66 residues aligned 27% are identical and another 11% are functionally similar. The overall weak internal homology is in contrast to the much higher degree (>70%) in P-glycoprotein for which a gene duplication hypothesis has been proposed (Gros et al, *Cell* 47, 371, 1986, C. Chen et al, *Cell* 47, 381, 1986, Gerlach et al, *Nature,* 324, 485, 1986, Gros et al, *Mol. Cell. Biol.* 8, 2770, 1988). The lack of conservation in the relative positions of the exon-intron boundaries may argue against such a model for CFTR (FIG. 2).

Since there is apparently no signal-peptide sequence at the amino-terminus of CFTR, the highly charged hydrophilic segment preceding the first transmembrane sequence is probably oriented in the cytoplasm. Each of the 2 sets of hydrophobic helices are expected to form 3 transversing loops across the membrane and little sequence of the entire protein is expected to be exposed to the exterior surface, except the region between transmembrane segment 7 and 8. It is of interest to note that the latter region contains two potential sites for N-linked glycosylation.

Each of the membrane-associated regions is followed by a NBF as indicated above. In addition, a highly charged cytoplasmic domain can be identified in the middle of the predicted CFTR polypeptide, linking the 2 halves of the protein. This domain, named the R-domain, is operationally defined by a single large exon in which 69 of the 241 amino acids are polar residues arranged in alternating clusters of positive and negative charges. Moreover, 9 of the 10 consensus sequences required for phosphosphorylation by protein kinase A (PKA), and, 7 of the potential substrate sites for protein kinase C (PKC) found in CFTR are located in this exon.

4.2 Function of CFTR

Properties of CFTR can be derived from comparison to other membrane-associated proteins (FIG. 15). In addition to the overall structural similarity with the mammalian P-glycoprotein, each of the two predicted domains in CFTR also shows remarkable resemblance to the single domain structure of hemolysin B of *E. coli* and the product of the White gene of Drosophila. These latter proteins are involved in the transport of the lytic peptide of the hemolysin system and of eye pigment molecules, respectively. The vitamin B12 transport system of *E. coli,* BtuD and MbpX which is a liverwort chloroplast gene whose function is unknown also have a similar structural motif. Furthermore, the CFTR protein shares structural similarity with several of the periplasmic solute transport systems of gram negative bacteria where the transmembrane region and the ATP-binding folds are contained in separate proteins which function in concert with a third substrate-binding polypeptide.

The overall structural arrangement of the transmembrane domains in CFTR is similar to several cation channel proteins and some cation-translocating ATPases as well as the recently described adenylate cyclase of bovine brain. The functional significance of this topological classification, consisting of 6 transmembrane domains, remains speculative.

Short regions of sequence identity have also been detected between the putative transmembrane regions of CFTR and other membrane-spanning proteins. Interestingly, there are also sequences, 18 amino acids in length situated approximately 50 residues from the carboxyl terminus of CFTR and the raf serine/threonine kinase protooncogene of *Xenopus laevis* which are identical at 12 of these positions.

Finally, an amino acid sequence identity (10/13 conserved residues) has been noted between a hydrophilic segment (position 701–713) within the highly charged R-domain of CFTR and a region immediately preceding the first transmembrane loop of the sodium channels in both rat brain and eel. The charged R-domain of CFTR is not shared with the topologically closely related P-glycoprotein; the 241 amino acid linking-peptide is apparently the major difference between the two proteins.

In summary, features of the primary structure of the CFTR protein indicate its possession of properties suitable to participation in the regulation and control of ion transport in the epithelial cells of tissues affected in CF. Secure attachment to the membrane in two regions serve to position its three major intracellular domains (nucleotide-binding folds 1 and 2 and the R-domain) near the cytoplasmic surface of the cell membrane where they can modulate ion movement through channels formed either by CVTR transmembrane segments themselves or by other membrane proteins.

In view of the genetic data, the tissue-specificity, and the predicted properties of the CFTR protein, it is reasonable to conclude that CFTR is directly responsible for CF. It, however, remains unclear how CFTR is involved in the regulation of ion conductance across the apical membrane of epithelial cells.

It is possible that CFTR serves as an ion channel itself. As depicted in FIG. 13, 10 of the 12 transmembrane regions contain one or more amino acids with charged side chains, a property similar to the brain sodium channel and the GABA receptor chloride channel subunits, where charged residues are present in 4 of the 6, and 3 of the 4, respective membrane-associated domains per subunit or repeat unit. The amphipathic nature of these transmembrane segments is believed to contribute to the channel-forming capacity of these molecules. Alternatively, CFTR may not be an ion channel but instead serve to regulate ion channel activities. In support of the latter assumption, none of the purified polypeptides from trachea and kidney that are capable of reconstituting chloride channels in lipid membranes [Landry et al, *Science* 224:1469 (1989)] appear to be CFTR if judged on the basis of the molecular mass.

In either case, the presence of ATP-binding domains in CFTR suggests that ATP hydrolysis is directly involved and required for the transport function. The high density of phosphorylation sites for PKA and PKC and the clusters of charged residues in the R-domain may both serve to regulate this activity. The deletion of a phenylalanine residue in the NBF may prevent proper binding of ATP or the conformational change which this normally elicits and consequently result in the observed insensitivity to activation by PKA- or PKC-mediated phosphorylation of the CF apical chloride conductance pathway. Since the predicted protein contains several domains and belongs to a family of proteins which frequently function as parts of multi-component molecular systems, CFTR may also participate in epithelial tissue functions of activity or regulation not related to ion transport.

With the isolated CF gene (cDNA) now in hand it is possible to define the basic biochemical defect in CF and to further elucidate the control of ion transport pathways in epithelial cells in general. Most important, knowledge gained thus far from the predicted structure of CFTR together with the additional information from studies of the protein itself provide a basis for the development of improved means of treatment of the disease. In such studies, antibodies have been raised to the CFTR protein as later described.

5.0 CF Screening 5.1 DNA Based Diagnosis

Given the knowledge of the 85, 148, 178, 455, 493, 507, 542, 549, 551, 560, 563, 574, 1077 and 1092 amino acid position mutations and the nucleotide sequence varients at DNA sequence positions 129, 556, 621+1, 711+1, 1717-1 and 3659 as disclosed herein, carrier screening and prenatal diagnosis can be carried out as follows.

The high risk population for cystic fibrosis is Caucasians. For example, each Caucasian woman and/or man of child-bearing age would be screened to determine if she or he was a carrier (approximately a 5% probability for each individual). If both are carriers, they are a couple at risk for a cystic fibrosis child. Each child of the at risk couple has a 25% chance of being affected with cystic fibrosis. The procedure for determining carrier status using the probes disclosed herein is as follows.

For purposes of brevity, the discussion on screening by use of one of the selected mutations is directed to the I507 mutation. It is understood that screening can also be accomplished using one of the other mutations or using several of the mutations in a screening process or mutation detection process of this section on CF screening involving DNA diagnosis and mutation detection.

One major application of the DNA sequence information of the normal and 507 mutant CF gene is in the area of genetic testing, carrier detection and prenatal diagnosis. Individuals carrying mutations in the CF gene (disease carrier or patients) may be detected at the DNA level with the use of a variety of techniques. The genomic DNA used for the diagnosis may be obtained from body cells, such as those present in peripheral blood, urine, saliva, tissue biopsy, surgical specimen and autopsy material. The DNA may be used directly for detection of specific sequence or may be amplified enzymatically in vitro by using PCR [Saiki et al. *Science* 230: 1350–1353, (1985), Saiki et al. *Nature* 324: 163–166 (1986)] prior to analysis. RNA or its cDNA form may also be used for the same purpose. Recent reviews of this subject have been presented by Caskey, [*Science* 236: 1223-8 (1989) and by Landegren et al (*Science* 242: 229–237 (1989)].

The detection of specific DNA sequence may be achieved by methods such as hybridization using specific oligonucleotides [Wallace et al. *Cold Spring Harbour Symp. Quant. Biol.* 51: 257–261 (1986)], direct DNA sequencing [Church and Gilbert, *Proc. Nat. Acad. Sci. U. S. A.* 81: 1991–1995 (1988)], the use of restriction enzymes [Flavell et al. *Cell* 15: 25 (1978), Geever et al *Proc. Nat. Acad. Sci. U. S. A.* 78: 5081 (1981)], discrimination on the basis of electrophoretic mobility in gels with denaturing reagent (Myers and Maniatis, *Cold Spring Harbour Sym. Quant. Biol.* 51: 275–284 (1986)), RNase protection (Myers, R. M., Larin, J., and T. Maniatis *Science* 230: 1242 (1985)), chemical cleavage (Cotton et al *Proc. Nat. Acad. Sci. U. S. A.* 85: 4397–4401, (1985)) and the ligase-mediated detection procedure [Landegren et al *Science* 241:1077 (1988)].

Oligonucleotides specific to normal or mutant sequences are chemically synthesized using commercially available machines, labelled radioactively with isotopes (such as $^{32}P$) or non-radioactively (with tags such as biotin (Ward and Langer et al. *Proc. Nat. Acad. Sci. U. S. A.* 78: 6633–6657 (1981)), and hybridized to individual DNA samples immobilized on membranes or other solid supports by dot-blot or transfer from gels after electrophoresis. The presence or absence of these specific sequences are visualized by methods such as autoradiography or fluorometric (Landegren et al, 1989, supra) or colorimetric reactions (Gebeyshu et a. *Nucleic Acids Research* 15: 4513–4534 (1987)). An embodiment of this oligonucleotide screening method has been applied in the detection of the I507 deletion as described herein.

Sequence differences between normal and mutants may be revealed by the direct DNA sequencing method of Church and Gilbert (supra). Cloned DNA segments may be used as probes to detect specific DNA segments. The sensitivity of this method is greatly enhanced when combined with PCR [Wrichnik et al, *Nucleic Acids Res.* 15:529–542 (1987); Wong et al, *Nature* 330:384–386 (1987); Stoflet et al, *Science* 239:491–494 (1988)]. In the latter procedure, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent-tags.

Sequence alterations may occasionally generate fortuitous restriction enzyme recognition sites which are revealed by the use of appropriate enzyme digestion followed by conventional gel-blot hybridization (Southern, *J. Mol. Biol* 98: 503 (1975)). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

Genetic testing based on DNA sequence differences may be achieved by detection of alteration in electrophoretic mobility of DNA fragments in gels with or without denaturing reagent. Small sequence deletions and insertions can be visualized by high resolution gel electrophoresis. For example, the PCR product with the 3 bp deletion is clearly distinguishable from the normal sequence on an 8% non-denaturing polyacrylamide gel. DNA fragments of different sequence compositions may be distinguished on denaturing formamide gradient gel in which the mobilities of different DNA fragments are retarded in the gel at different positions according to their specific "partial-melting" temperature (Myers, supra). In addition, sequence alterations, in particular small deletions, may be detected as changes in the migration pattern of DNA heteroduplexes in non-denaturing gel electrophoresis, as have been detected for the 3 dp (I507) mutation and in other experimental systems [Nagamine et al, *Am. J. Hum. Genet,* 45:337–339 (1989)]. Alternatively, a method of detecting a mutation comprising a single base substitution or other small change could be based on differential primer length in a PCR. For example, one invariant primer could be used in addition to a primer specific for a mutation. The PCR products of the normal and mutant genes can then be differentially detected in acrylamide gels.

Sequence changes at specific locations may also be revealed by nuclease protection assays, such as RNase (Myers, supra) and S1 protection (Berk, A. J., and P. A. Sharpe *Proc. Nat. Acad. Sci. U. S. A.* 75: 1274 (1978)), the chemical cleavage method (Cotton, supra) or the ligase-mediated detection procedure (Landegren supra).

In addition to conventional gel-electrophoresis and blot-hybridization methods, DNA fragments may also be visualized by methods where the individual DNA samples are not immobilized on membranes. The probe and target sequences may be both in solution or the probe sequence may be immobilized [Saiki et al, *Proc. Natl. Acad. Sci USA*, 86:6230–6234 (1989)]. A variety of detection methods, such as autoradiography involving radioisotopes, direct detection of radioactive decay (in the presence or absence of scintillant), spectrophotometry involving colorigenic reactions and fluorometry involving fluorogenic reactions, may be used to identify specific individual genotypes.

Since more than one mutation is anticipated in the CF gene such as I507 and F508, a multiples system is an ideal protocol for screening CF carriers and detection of specific mutations. For example, a PCR with multiple, specific oligonucleotide primers and hybridization probes, may be used to identify all possible mutations at the same time (Chamberlain et al. *Nucleic Acids Research* 16: 1141–1155 (1988)). The procedure may involve immobilized sequence-specific oligonucleotides probes (Saiki et al, supra).

5.2 Detecting the CF 507 Mutation

These detection methods may be applied to prenatal diagnosis using amniotic fluid cells, chorionic villi biopsy or sorting fetal cells from maternal circulation. The test for CF carriers in the population may be incorporated as an essential component in a broad-scale genetic testing program for common diseases.

According to an embodiment of the invention, the portion of the DNA segment that is informative for a mutation, such as the mutation according to this embodiment, that is, the portion that immediately surrounds the I507 deletion, can then be amplified by using standard PCR techniques [as reviewed in Landegren, Ulf, Robert Kaiser, C. Thomas Caskey and Leroy Hood, DNA Diagnostics—Molecular Techniques and Automation, in *Science* 242: 229–237 (1988)]. It is contemplated that the portion of the DNA segment which is used may be a single DNA segment or a mixture of different DNA segments. A detailed description of this technique now follows.

A specific region of genomic DNA from the person or fetus is to be screened. Such specific region is defined by the oligonucleotide primers C16B (5'GTTTTCCTGGATTATGCCTGGCAC3') (SEQ ID NO:9) (5'GTTGGCATGCTTTGATGACGCTTC3') (SEQ ID NO:10) or as shown in FIG. 18 by primers 10i-5 and 10i-3. The specific regions using 10i-5 and 10i-3 were amplified by the polymerase chain reaction (PCR). 200–400 ng of genomic DNA, from either culture lymphoblasts or peripheral blood samples of CF individuals and their parents, were used in each PCR with the oligonucleotides primers indicated above. The oligonucleotides were purified with Oligonucleotide Purification Cartridges™ (Applied Biosystems) or NENSORB™ PREP columns (Dupont) with procedures recommended by the suppliers. The primers were annealed at 55° C. for 30 sec, extended at 72° C. for 60 sec (with 2 units of Taq DNA polymerase) and denatured at 94° C. for 60 sec, for 30 cycles with a final cycle of 7 min for extension in a Perkin-Elmer/Cetus automatic thermocycler with a Step-Cycle program (transition setting at 1.5 min). Portions of the PCR products were separated by electrophoresis on 1.4% agarose gels, transferred to Zetabind™; (Biorad) membrane according to standard procedures.

The normal and ΔI507 oligonucleotide probes of FIG. 19 (10 ng each) are labeled separately with 10 units of T4 polynucleotide kinase (Pharmacia) in a 10 μl reaction containing 50 mM Tris-HCl (pH7.6), 10 mM $MgCl_2$, 0.5 mM dithiothreitol, 10 mM spermidine, 1 mM EDTA and 30–30 μCi of γ[$^{32}$P]—ATP for 20–30 min at 37° C. The unincorporated radionucleotides were removed with a Sephadex G25 column before use. The hybridization conditions were as described previously (J. M. Rommens et al *Am. J. Hum. Genet.* 43,645 (1988)) except that the temperature can be 37° C. The membranes are washed twice at room temperature with 5×SSC and twice at 39° C. with 2×SSC (1×SSC= 150 mM NaCl and 15 mM Na citrate). Autoradiography is performed at room temperature overnight. Autoradiographs are developed to show the hybridization results of genomic DNA with the 2 specific oligonucleotide probes. Probe C normal detects the normal DNA sequence and Probe C ΔI507 detects the mutant sequence.

Genomic DNA sample from each family member can, as explained, be amplified by the polymerase chain reaction using the intron sequences of FIG. 18 and the products separated by electrophoresis on a 1.4% agarose gel and then transferred to Zetabind (Biorad) membrane according to standard procedures. The 3 bp deletion of ΔI507 can be revealed by a very convenient polyacrylamide gel electrophoresis procedure. When the PCR products generated by the above-mentioned 10i-5 and 10i-3 primers are applied to an 5% polyacrylamide gel, electrophoresed for 3 hrs at 20V/cm in a 90 mM Tris-borate buffer (pH 8.3), DNA fragments of a different mobility are clearly detectable for individuals without the 3 bp deletion, heterozygous or homozygous for the deletion.

As already explained with respect to FIG. 20, the PCR amplified genomic DNA can be subjected to gel electrophoresis to identify the 3 bp deletion. As shown in FIG. 20, in the four lanes the first lane is a control with a normal/ ΔF508 deletion. The next lane is the father with a normal/ ΔI507 deletion. The third lane is the mother with a normal/ ΔF508 deletion and the fourth lane is the child with a ΔF508/ΔI507 deletion. The homoduplexes show up as solid bands across the base of each lane. In lanes 1 and 3, the two heteroduplexes show up very clearly as two spaced apart bands. In lane 2, the father's ΔI507 mutation shows up very clearly, whereas in the fourth lane, the child with the adjacent 507, 508 mutations, there is no distinguishable heteroduplexes. Hence the showing is at the homoduplex line. Since the father in lane 2 and the mother in lane 3 show heteroduplex banding and the child does not, indicates either the child is normal or is a patient. This can be further checked if needed, such as in embryoic analysis by mixing the 507 and 508 probes to determine the presence of the ΔI507 and ΔF508 mutations.

Similar alteration in gel mobility for heteroduplexes formed during PCR has also been reported for experimental systems where small deletions are involved (Nagamine et al supra). These mobility shifts may be used in general as the basis for the non-radioactive genetic screening tests.

5.3 CF Screening Programs

It is appreciated that approximately 1% of the carriers can be detected using the specific ΔI507 probes of this particular embodiment of the invention. Thus, if an individual tested is not a carrier using the ΔI507 probes, their carrier status can not be excluded, they may carry some other mutation, such as the ΔF508 as previously noted. However, if both the individual and the spouse of the individual tested are a carrier for the ΔI507 mutation, it can be stated with certainty that they are an at risk couple. The sequence of the gene as disclosed herein is an essential prerequisite for the determination of the other mutations.

Prenatal diagnosis is a logical extension of carrier screening. A couple can be identified as at risk for having a cystic fibrosis child in one of two ways: if they already have a cystic fibrosis child, they are both, by definition, obligate carriers of the defective CFTR gene, and each subsequence child has a 25% chance of being affected with cystic fibrosis. A major advantage of the present invention eliminates the need for family pedigree analysis, whereas, according to this invention, a gene mutation screening program as outlined above or other similar method can be used to identify a genetic mutation that leads to a protein with altered function. This is not dependent on prior ascertainment of the family through an affected child. Fetal DNA samples, for example, can be obtained, as previously mentioned, from amniotic fluid cells and chorionic villi specimens. Amplification by standard PCR techniques can then be performed on this template DNA.

If both parents are shown to be carriers with the ΔI507 deletion, the interpretation of the results would be the following. If there is hybridization of the fetal DNA to the normal probe, the fetus will not be affected with cystic fibrosis, although it may be a CF carrier (50% probability for each fetus of an at risk couple). If the fetal DNA hybridizes only to the ΔI507 deletion probe and not to the normal probe, the fetus will be affected with cystic fibrosis.

It is appreciated that for this and other mutations in the CF gene, a range of different specific procedures can be used to provide a complete diagnosis for all potential CF carriers or patients. A complete description of these procedures is later described.

The invention therefore provides a method and kit for determining if a subject is a CF carrier or CF patient. In summary, the screening method comprises the steps of:

providing a biological sample of the subject to be screened; and providing an assay for detecting in the biological sample, the presence of at least a member from the group consisting of a 507 mutant CF gene, 507 mutant CF gene products and mixtures thereof.

The method may be further characterized by including at least one more nucleotide probe which is a different DNA sequence fragment of, for example, the DNA of FIG. 1, or a different DNA sequence fragment of human chromosome 7 and located to either side of the DNA sequence of FIG. 1. In this respect, the DNA fragments of the intron portions of FIG. 2 are useful in further confirming the presence of the mutation. Unique aspects of the introns at the exon boundaries may be relied upon in screening procedures to further confirm the presence of the mutation at the I507 position or othe mutant positions.

A kit, according to an embodiment of the invention, suitable for use in the screening technique and for assaying for the presence of the mutant CF gene by an immunoassay comprises:

(a) an antibody which specifically binds to a gene product of the mutant CF gene having a mutation at one of the amino acid positions of 85, 148, 178, 455, 493, 507, 542, 549, 551, 560, 563, 574, 1077 and 1092 SEQ ID NO:2;

(b) reagent means for detecting the binding of the antibody to the gene product; and (c) the antibody and reagent means each being present in amounts effective to perform the immunoassay.

The kit for assaying for the presence for the mutant CF gene may also be provided by hybridization techniques. The kit comprises:

(a) an oligonucleotide probe which specifically binds to the mutant CF gene encoding a peptide having a mutation at one of the amino acid positions 85, 148, 178, 455, 493, 507, 542, 549, 551, 560, 563, 574, 1077 and 1092 SEQ ID NO:2;

(b) reagent means for detecting the hybridization of the oligonucleotide probe to the mutant CF gene; and (c) the probe and reagent means each being present in amounts effective to perform the hybridization assay.

5.4 Antibodies to Detect Mutant CFTR

As mentioned, antibodies to epitopes within the mutant CFTR protein at positions 85, 148, 178, 455, 493, 507, 542, 549, 551, 560, 563, 574, 1077 and 1092 are SEQ ID NO:2 raised to provide extensive information on the characteristics of the mutant protein and other valuable information which includes:

1. The antibodies can be used to provide another technique in detecting any of the other CF mutations which result in the synthesis of a protein with an altered size.

2. Antibodies to distinct domains of the mutant protein can be used to determine the topological arrangement of the protein in the cell membrane. This provides information on segments of the protein which are accessible to externally added modulating agents for purposes of drug therapy.

3. The structure-function relationships of portions of the protein can be examined using specific antibodies. For example, it is possible to introduce into cells antibodies recognizing each of the charged cytoplasmic loops which join the transmembrane sequences as well as portions of the nucleotide binding folds and the R-domain. The influence of these antibodies on functional parameters of the protein provide insight into cell regulatory mechanisms and potentially suggest means of modulating the activity of the defective protein in a CF patient.

4. Antibodies with the appropriate avidity also enable immunoprecipitation and immuno-affinity purification of the protein. Immunoprecipitation will facilitate characterization of synthesis and post translational modification including ATP binding and phosphorylation. Purification will be required for studies of protein structure and for reconstitution of its function, as well as protein based therapy.

In order to prepare the antibodies, fusion proteins containing defined portions of anyone of the mutant CFTR polypeptides can be synthesized in bacteria by expression of corresponding mutant DNA sequence in a suitable cloning vehicle. Smaller peptide may be synthesized chemically. The fusion proteins can be purified, for example, by affinity chromatography on glutathione-agarose and the peptides coupled to a carrier protein (hemocyanin), mixed with Freund's adjuvant and injected into rabbits. Following booster injections at bi-weekly intervals, the rabbits are bled and sera isolated. The developed polyclonal antibodies in the sera may then be combined with the fusion proteins. Immunoblots are then formed by staining with, for example, alkaline-phosphatase conjugated second antibody in accordance with the procedure of Blake et al., *Anal. Biochem.* 136:175 (1984).

Thus, it is possible to raise polyclonal antibodies specific for both fusion proteins containing portions of the mutant CFTR protein and peptides corresponding to short segments of its sequence. Similarly, mice can be injected with KLH conjugates of peptides to initiate the production of monoclonal antibodies to corresponding segments of mutant CFTR protein.

As for the generation of monoclonal antibodies, immunogens for the raising of monoclonal antibodies (mAbs) to the mutant CFTR protein are bacterial fusion proteins [Smith et al, *Gene* 67:31 (1988)] containing portions of the CFTR polypeptide or synthetic peptides corresponding to short (12 to 25 amino acids in length) segments of the mutant sequence. The essential methodology is that of Kohler and Milstein [*Nature* 256:495 (1975)].

Balb/c mice are immunized by intraperitoneal injection with 500 µg of pure fusion protein or synthetic peptide in incomplete Freund's adjuvant. A second injection is given after 14 days, a third after 21 days and a fourth after 28 days. Individual animals so immunized are sacrificed one, two and four weeks following the final injection. Spleens are removed, their cells dissociated, collected and fused with Sp2/O-Ag14 myeloma cells according to Gefter et al, *Somatic Cell Genetics* 3:231 (1977). The fusion mixture is distributed in culture medium selective for the propagation of fused cells which are grown until they are about 25% confluent. At this time, culture supernatants are tested for the presence of antibodies reacting with a particular CFTR antigen. An alkaline phosphatase labelled anti-mouse second antibody is then used for detection of positives. Cells from positive culture wells are then expanded in culture, their supernatants collected for further testing and the cells stored deep frozen in cryoprotectant-containing medium. To obtain large quantities of a mAb, producer cells are injected into the peritoneum at $5 \times 10^6$ cells per animal, and ascites fluid is obtained. Purification is by chromatography on Protein G- or Protein A-agarose according to Ey et al, *Immunochemistry* 15:429 (1977).

Reactivity of these mAbs with the mutant CFTR protein can be confirmed by polyacrylamide gel electrophoresis of membranes isolated from epithelial cells in which it is expressed and immunoblotted [Towbin et al, *Proc. Natl. Acad. Sci. USA* 76:4350 (1979)].

In addition to the use of monoclonal antibodies specific for the particular mutant domain of the CFTR protein to probe their individual functions, other mAbs, which can distinguish between the normal and mutant forms of CFTR protein are used to detect the mutant protein in epithelial cell samples obtained from patients, such as nasal mucosa biopsy "brushings" [R. De-Lough and J. Rutland, *J. Clin. Pathol.* 42, 613 (1989)] or skin biopsy specimens containing sweat glands.

Antibodies capable of this distinction are obtained by differentially screening hybridomas from paired sets of mice immunized with a peptide containing, for example, the isoleucine at amino acid position 507 (e.g. GTIKENIIFGVSY) (SEQ ID NO:32) or a peptide which is identical except for the absence of I507 (GTIKENIFGVSY) (SEQ ID NO:33). mAbs capable of recognizing the other mutant forms of CFTR protein present in patients in addition or instead of I507 deletion are obtained using similar monoclonal antibody production strategies.

Antibodies to normal and CF versions of CFTR protein and of segments thereof are used in diagnostically immunocytochemical and immunofluorescence light microscopy and immunoelectron microscopy to demonstrate the tissue, cellular and subcellular distribution of CFTR within the organs of CF patients, carriers and non-CF individuals.

Antibodies are used to therapeutically modulate by promoting the activity of the CFTR protein in CF patients and in cells of CF patients. Possible modes of such modulation might involve stimulation due to cross-linking of CFTR protein molecules with multivalent antibodies in analogy with stimulation of some cell surface membrane receptors, such as the insulin receptor [O'Brien et al, *Euro. Mol. Biol. Organ, J.* 6:64003 (1987)], epidermal growth factor receptor [Schreiber et al, *J. Biol. Chem.* 258:846 (1983)] and T-cell receptor-associated molecules such as CD4 [Veillette et al *Nature,* 338:257 (1989)].

Antibodies are used to direct the delivery of therapeutic agents to the cells which express defective CFTR protein in CF. For this purpose, the antibodies are incorporated into a vehicle such as a liposome [Matthay et al, *Cancer Res.* 46:4904 (1986)] which carries the therapeutic agent such as a drug or the normal gene.

5.5 RFLP Analysis

DNA diagnosis is currently being used to assess whether a fetus will be born with cystic fibrosis, but historically this has only been done after a particular set of parents has already had one cystic fibrosis child which identifies them as obligate carriers. However, in combination with carrier detection as outlined above, DNA diagnosis for all pregnancies of carrier couples will be possible. If the parents have already had a cystic fibrosis child, an extended haplotype analysis can be done on the fetus and thus the percentage of false positive or false negative will be greatly reduced. If the parents have not already had an affected child and the DNA diagnosis on the fetus is being performed on the basis of carrier detection, haplotype analysis can still be performed.

Although it has been thought for many years that there is a great deal of clinical heterogeneity in the cystic fibrosis disease, it is now emerging that there are two general categories, called pancreatic sufficiency (CF-PS) and pancreatic insufficiency (CF-PI). If the mutations related to these disease categories are well characterized, one can associate a particular mutation with a clincal phenotype of the disease. This allows changes in the treatment of each patient. Thus the nature of the mutation will to a certain extent predict the prognosis of the patient and indicate a specific treatment.

6.0 Molecular Biology of Cystic Fibrosis

The postulate that CFTR may regulate the activity of ion channels, particularly the outwardly rectifying Cl channel implicated as the functional defect in CF, can be tested by the injection and translation of full length in vitro transcribed CFTR mRNA in Xenopus oocytes. The ensuing changes in ion currents across the oocyte membrane can be measured as the potential is clamped at a fixed value. CFTR may regulate endogenous oocyte channels or it may be necessary to also introduce epithelial cell RNA to direct the translation of channel proteins. Use of mRNA coding for normal and for mutant CFTR, as provided by this invention, makes these experiments possible.

Other modes of expression in heterologous cell system also facilitate dissection of structure-function relationships. The complete CFTR DNA sequence ligated into a plasmid expression vector is used to transfect cells so that its influence on ion transport can be assessed. Plasmid expression vectors containing part of the normal CFTR sequence along with portions of modified sequence at selected sites can be used in vitro mutagenesis experiments performed in order to identify those portions of the CFTR protein which are crucial for regulatory function.

6.1 Expression of the Mutant DNA Sequence

The mutant DNA sequence can be manipulated in studies to understand the expression of the gene and its product, and, to achieve production of large quantities of the protein for functional analysis, antibody production, and patient therapy. The changes in the sequence may or may not alter the expression pattern in terms of relative quantities, tissue-specificity and functional properties. The partial or full-length cDNA sequences, which encode for the subject protein, unmodified or modified, may be ligated to bacterial expression vectors such as the pRIT (Nilsson et al. *EMBO J.* 4: 1075–1080 (1985)), pGEX (Smith and Johnson, *Gene* 67: 31–40 (1988)) or pATH (Spindler et al. *J. Virol.* 49: 132–141

(1984)) plasmids which can be introduced into *E. coli* cells for production of the corresponding proteins which may be isolated in accordance with the previously discussed protein purification procedures. The DNA sequence can also be transferred from its existing context to other cloning vehicles, such as other plasmids, bacteriophages, cosmids, animal virus, yeast artificial chromosomes (YAC) (Burke et al. *Science* 236: 806–812, (1987)), somatic cells, and other simple or complex organisms, such as bacteria, fungi (Timberlake and Marshall, *Science* 244: 1313–1317 (1989), invertebrates, plants (Gasser and Fraley, *Science* 244: 1293 (1989), and pigs (Pursel et al. *Science* 244: 1281–1288 (1989)).

For expression in mammalian cells, the cDNA sequence may be ligated to heterologous promoters, such as the simian virus (SV) 40, promoter in the pSV2 vector [Mulligan and Berg, *Proc. Natl. Acad. Sci USA,* 78:2072–2076 (1981)] and introduced into cells, such as monkey COS-1 cells [Gluzman, *Cell,* 23:175–182 (1981)], to achieve transient or long-term expression. The stable integration of the chimeric gene construct may be maintained in mammalian cells by biochemical selection, such as neomycin [Southern and Berg, *J. Mol. Appln. Genet.* 1:327–341 (1982)] and mycophoenolic acid [Mulligan and Berg, supra].

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use or specific oligonucleotides in combination with PCR.

The cDNA sequence (or portions derived from it), or a mini gene (a cDNA with an intron and its own promoter) is introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the simian virus (SV)40 or long terminal repeat (LTR) of the Rous Sarcoma virus and polyadenylation and splicing signal from SV 40 are readily available [Mulligan et al *Proc. Natl. Acad. Sci, USA* 78:1078–2076, (1981); Gorman et al *Proc Natl. Acad. Sci USA* 79: 6777–6781 (1982)]. Alternatively, the CFTR endogenous promoter may be used. The level of expression of the cDNA can be manipulated with this type of vector, either by using promoters that have different activities (for example, the baculovirus pAC373 can express cDNAs at high levels in *S. frungiperda* cells [M. D. Summers and G. E. Smith in, Genetically Altered Viruses and the Environment (B. Fields, et al, eds.) vol. 22 no 319–328, Cold Spring Harbour Laboratory Press, Cold Spring Harbour, N.Y., 1985] or by using vectors that contain promoters amenable to modulation, for example the glucocorticoid-responsive promoter from the mouse mammary tumor virus [Lee et al, *Nature* 294:228 (1982)]. The expression of the cDNA can be monitored in the recipient cells 24 to 72 hours after introduction (transient expression).

In addition, some vectors contain selectable markers [such as the gpt (Mulligan et Berg supra] or neo [Southern and Berg *J. Mol. Appln. Genet* 1:327–341 (1982)] bacterial genes that permit isolation of cells, by chemical selection, that have stable, long term expression of the vectors (and therefore the cDNA) in the recipient cell. The vectors can be maintained in the cells as episomal, freely replicating entities by using regulator elements of viruses such as papilloma [Sarver et al *Mol. Cell Biol.* 1:486 (1981)] or Epstein-Barr [Sugden et al *Mol. Cell Biol.* 5:410 (1985)]. Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product [Alt et al. *J. Biol. Chem.* 253: 1357 (1978)].

The transfer of DNA into eukaryotic, in particular human or other mammalian cells is now a conventional technique. The vectors are introduced into the recipient cells as pure DNA (transfection) by, for example, precipitation with calcium phosphate [Graham and vancer Eb, *Virology* 52:466 (1973) or strontium phosphate [Brash et al *Mol. Cell Biol.* 7:2013 (1987)], electroporation [Neumann et al *EMBO J* 1:841 (1982)], lipofection [Felgner et al *Proc Natl. Acad. Sci USA* 84:7413 (1987)], DEAE dextran [McCuthan et al *J. Natl Cancer Inst.* 41:351 1968)], microinjection [Mueller et al *Cell* 15:579 1978)], protoplast fusion [Schafner, *Proc Natl. Aca. Sci USA* 72:2163] or pellet guns [Klein et al, *Nature* 327: 70 (1987)]. Alternatively, the cDNA can be introduced by infection with virus vectors. Systems are developed that use, for example, retroviruses [Bernstein et al. *Genetic Engineering* 7: 235, (1985)], adenoviruses [Ahmad et al *J. Virol* 57:267 (1986)] or Herpes virus [Spaete et al *Cell* 30:295 (1982)].

These eukaryotic expression systems can be used for many studies of the mutant CF gene and the mutant CFTR product, such as at protein positions 85, 148, 178, 455, 493, 507, 542, 549, 551, 560, 563, 574, 1077 and 1092. These include, for example: (1) determination that the gene is properly expressed and that all post-translational modifications necessary for full biological activity have been properly completed (2) identify regulatory elements located in the 5' region of the CF gene and their role in the tissue- or temporal-regulation of the expression of the CF gene (3) production of large amounts of the normal protein for isolation and purification(4) to use cells expressing the CFTR protein as an assay system for antibodies generated against the CFTR protein or an assay system to test the effectiveness of drugs, (5) study the function of the normal complete protein, specific portions of the protein, or of naturally occurring or artificially produced mutant proteins. Naturally occurring mutant proteins exist in patients with CF while artificially produced mutant protein can be designed by site directed sequence alterations. These latter studies can probe the function of any desired amino acid residue in the protein by mutating the nucleotides coding for that amino acid.

Using the above techniques, the expression vectors containing the mutant CF gene sequence or fragments thereof can be introduced into human cells, mammalian cells from other species or non-mammalian cells as desired. The choice of cell is determined by the purpose of the treatment. For example, one can use monkey COS cells [Gluzman, *Cell* 23:175 (1981)], that produce high levels of the SV40 T antigen and permit the replication of vectors containing the SV40 origin of replication, can be used to show that the vector can express the protein product, since function is not required. Similar treatment could be performed with Chinese hamster ovary (CHO) or mouse NIH 3T3 fibroblasts or with human fibroblasts or lymphoblasts.

The recombinant cloning vector, according to this invention, then comprises the selected DNA of the DNA sequences of this invention for expression in a suitable host. The DNA is operatively linked in the vector to an expression control sequence in the recombinant DNA molecule so that normal CFTR polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, and combinations thereof.

The host cell, which may be transfected with the vector of this invention, may be selected from the group consisting of *E. coli, Pseudomonas, Bacillus subtilis, Bacillus stearothermophilus* or other bacili; other bacteria; yeast; fungi; insect; mouse or other animal; or plant hosts; or human tissue cells.

It is appreciated that for the mutant DNA sequence similar systems are employed to express and produce the mutant product.

6.2 Protein Function Considerations

To study the function of the mutant CFTR protein, it is preferable to use epithelial cells as recipients, since proper functional expression may require the presence of other pathways or gene products that are only expressed in such cells. Cells that can be used include, for example, human epithelial cell lines such as T84 (ATCC #CRL 248) or PANC-1 (ATCC #CLL 1469), or the T43 immortalized CF nasal epithelium cell line [Jettan et al, *Science* (1989)] and primary [Yanhoskes et al. *Ann. Rev. Resp. Dis.* 132: 1281 (1985)] or transformed [Scholte et al. *Exp. Cell. Res.* 182: 559(1989)] human nasal polyp or airways cells, pancreatic cells [Harris and Coleman *J. Cell. Sci.* 87: 695 (1987)], or sweat gland cells [Collie et al. *In Vitro* 21: 597 (1985)] derived from normal or CF subjects. The CF cells can be used to test for the functional activity of mutant CF genes. Current functional assays available include the study of the movement of anions (Cl or I) across cell membranes as a function of stimulation of cells by agents that raise intracellular AMP levels and activate chloride channels [Strutto et al. *Proc. Nat. Acad. Sci. U. S. A.* 82: 6677 (1985)]. Other assays include the measurement of changes in cellular potentials by patch clamping of whole cells or of isolated membranes [Frizzell et al. *Science* 233: 558 (1986), Welsch and Liedtke *Nature* 322: 467 (1986)]or the study of ion fluxes in epithelial sheets of confluent cells [Widdicombe et al. *Proc. Nat. Acad. Sci.* 82: 6167 (1985)]. Alternatively, RNA made from the CF gene could be injected into Xenopus oocytes. The oocyte will translate RNA into protein and allow its study. As other more specific assays are developed these can also be used in the study of transfected mutant CFTR protein function.

"Domain-switching" experiments between mutant CFTR and the human multidrug resistance P-glycoprotein can also be performed to further the study of the mutant CFTR protein. In these experiments, plasmid expression vectors are constructed by routine techniques from fragments of the mutant CFTR sequence and fragments of the sequence of P-glycoprotein ligated together by DNA ligase so that a protein containing the respective portions of these two proteins will be synthesized by a host cell transfected with the plasmid. The latter approach has the advantage that many experimental parameters associated with multidrug resistance can be measured. Hence, it is now possible to assess the ability of segments of mutant CFTR to influence these parameters.

These studies of the influence of mutant CFTR on ion transport will serve to bring the field of epithelial transport into the molecular arena.

6.3 Therapies

It is understood that the major aim of the various biochemical studies using the compositions of this invention is the development of therapies to circumvent or overcome the CF defect, using both the pharmacological and the "gene-therapy" approaches.

In the pharmacological approach, drugs which circumvent or overcome the CF defect are sought. Initially, compounds may be tested essentially at random, and screening systems are required to discriminate among many candidate compounds. This invention provides host cell systems, expressing various of the mutant CF genes, which are particularly well suited for use as first level screening systems. Preferably, a cell culture system using mammalian cells (most preferably human cells) transfected with an expression vector comprising a DNA sequence coding for CFTR protein containing a CF-generating mutation, for example the I507 deletion, is used in the screening process. Candidate drugs are tested by incubating the cells in the presence of the candidate drug and measuring those cellular functions dependent on CFTR, especially by measuring ion currents where the transmembrane potential is clamped at a fixed value. To accommodate the large number of assays, however, more convenient assays are based, for example, on the use of ion-sensitive fluorescent dyes. To detect changes in $Cl^{-1}$ on concentration SPQ or its analogues are useful.

Alternatively, a cell-free system could be used. Purified CFTR could be reconstituted into artificial membranes and drugs could be screened in a cell-free assay [Al-Aqwatt, *Science,* (1989)].

At the second level, animal testing is required. It is possible to develop a model of CF by interfering with the normal expression of the counterpart of the CF gene in an animal such as the mouse. The "knock-out" of this gene by introducing a mutant form of it into the germ line of animals will provide a strain of animals with CF-like syndromes. This enables testing of drugs which showed a promise in the first level cell-based screen.

As further knowledge is gained about the nature of the protein and its function, it will be possible to predict structures of proteins or other compounds that interact with the CFTR protein. That in turn will allow for certain predictions to be made about potential drugs that will interact with this protein and have some effect on the treatment of the patients. Ultimately such drugs may be designed and synthesized chemically on the basis of structures predicted to be required to interact with domains of CFTR. This approach is reviewed in Capsey and Delvatte, *Genetically Engineered Human Therapeutic Drugs* Stockton Press, New York, 1988. These potential drugs must also be tested in the screening system.

6.3.1 Protein Replacement Therapy

Treatment of CF can be performed by replacing the defective protein with normal protein, by modulating the function of the defective protein or by modifying another step in the pathway in which CFTR participates in order to correct the physiological abnormality.

To be able to replace the defective protein with the normal version, one must have reasonably large amounts of pure CFTR protein. Pure protein can be obtained as described earlier from cultured cell systems. Delivery of the protein to the affected airways tissue will require its packaging in lip-containing vesicles that facilitate the incorporation of the protein into the cell membrane. It may also be feasible to use vehicles that incorporate proteins such as surfactant protein, such as SAP(Val) or SAP(Phe) that performs this function naturally, at least for lung alveolar cells. (PCT Patent Application WO/8803170, Whitsett et al, May 7, 1988 and PCT Patent Application WO89/04327, Benson et al, May 18, 1989). The CFTR-containing vesicles are introduced into the airways by inhalation or irrigation, techniques that are currently used in CF treatment (Boat et al, supra).

6.3.2 Drug Therapy

Modulation of CFTR function can be accomplished by the use of therapeutic agents (drugs). These can be identified by random approaches using a screening program in which their effectiveness in modulating the defective CFTR protein is monitored in vitro. Screening programs can use cultured cell systems in which the defective CFTR protein is expressed. Alternatively, drugs can be designed to modulate CFTR activity from knowledge of the structure and function correlations of CFTR protein and from knowledge of the specific defect in the CFTR mutant protein (Capsey and Delvatte, supra). It is possible that the mutant CFTR protein will require a different drug for specific modulation. It will then be necessary to identify the specific mutation(s) in each CF patient before initiating drug therapy.

Drugs can be designed to interact with different aspects of CFTR protein structure or function. For example, a drug (or antibody) can bind to a structural fold of the protein to correct a defective structure. Alternatively, a drug might bind to a specific functional residue and increase its affinity for a substrate or cofactor. Since it is known that members of the class of proteins to which CFTR has structural homology can interact, bind and transport a variety of drugs, it is reasonable to expect that drug-related therapies may be effective in treatment of CF.

A third mechanism for enhancing the activity of an effective drug would be to modulate the production or the stability of CFTR inside the cell. This increase in the amount of CFTR could compensate for its defective function.

Drug therapy can also be used to compensate for the defective CFTR function by interactions with other components of the physiological or biochemical pathway necessary for the expression of the CFTR function. These interactions can lead to increases or decreases in the activity of these ancillary proteins. The methods for the identification of these drugs would be similar to those described above for CFTR-related drugs.

In other genetic disorders, it has been possible to correct for the consequences of altered or missing normal functions by use of dietary modifications. This has taken the form of removal of metabolites, as in the case of phenylketonuria, where phenylalanine is removed from the diet in the first five years of life to prevent mental retardation, or by the addition of large amounts of metabolites to the diet, as in the case of adenosime deaminase deficiency where the functional correction of the activity of the enzyme can be produced by the addition of the enzyme to the diet. Thus, once the details of the CFTR function have been elucidated and the basic defect in CF has been defined, therapy may be achieved by dietary manipulations.

The second potential therapeutic approach is so-called "gene-therapy" in which normal copies of the CF gene are introduced in to patients so as to successfully code for normal protein in the key epithelial cells of affected tissues. It is most crucial to attempt to achieve this with the airway epithelial cells of the respiratory tract. The CF gene is delivered to these cells in form in which it can be taken up and code for sufficient protein to provide regulatory function. As a result, the patient's quality and length of life will be greatly extended. Ultimately, of course, the aim is to deliver the gene to all affected tissues.

6.3.3 Gene Therapy

One approach to therapy of CF is to insert a normal version of the CF gene into the airway epithelium of affected patients. It is important to note that the respiratory system is the primary cause of morbidity and mortality in CF; while pancreatic disease is a major feature, it is relatively well treated today with enzyme supplementation. Thus, somatic cell gene therapy [for a review, see T. Friedmann, *Science* 244:1275 (1989)] targeting the airway would alleviate the most severe problems associated with CF.

A. Retroviral Vectors

Retroviruses have been considered the preferred vector for experiments in somatic gene therapy, with a high efficiency of infection and stable integration and expression [Orkin et al *Prog. Med. Genet* 7:130, (1988)]. A possible drawback is that cell division is necessary for retroviral integration, so that the targeted cells in the airway may have to be nudged into the cell cycle prior to retroviral infection, perhaps by chemical means. The full length CF gene cDNA can be cloned into a retroviral vector and driven from either its endogenous promoter or from the retroviral LRT (long terminal repeat). Expression of levels of the normal protein as low as 10% of the endogenous mutant protein in CF patients would be expected to be beneficial, since this is a recessive disease. Delivery of the virus could be accomplished by aerosol or instillation into the trachea.

B. Other Viral Vectors

Other delivery systems which can be utilized include adeno-associated virus [AAV, McLaughlin et al, *J. Virol* 62:1963 (1988)], vaccinia virus [Moss et al *Annu. Rev. Immunol,* 5:305, 1987)], bovine papilloma virus [Rasmussen et al, *Methods Enzymol* 139:642 (1987)] or member of the herpesvirus group such as Epstein-Barr virus (Margolskee et al *Mol. Cell. Biol* 8:2937 (1988)]. Though much would need to be learned about their basic biology, the idea of using a viral vector with natural tropism for the respiratory track (e.g. respiratory syncytial virus, echovirus, Coxsackie virus, etc.) is possible.

C. Non-viral Gene Transfer

Other methods of inserting the CF gene into respiratory epithelium may also be productive; many of these are lower efficiency and would potentially require infection in vitro, selection of transfectants, and reimplantation. This would include calcium phosphate, DEAE dextran, electroporation, and protoplast fusion. A particularly attractive idea is the use of liposome, which might be possible to carry out in vivo [Ostro, Liposomes, Marcel-Dekker, 1987]. Synthetic cationic lipids such as DOTMA [Felger et al *Proc. Natl. Acad. Sci USA* 84:7413 (1987)] may increase the efficiency and ease of carrying out this approach.

6.4 CF Animal Models

The creation of a mouse or other animal model for CF will be crucial to understanding the disease and for testing of possible therapies [(for general review of creating animal models, see Erickson, *Am. J. Hum. Genet* 43:582 (1988)]. Currently no animal model of the CF exists. The evolutionary conservation of the CF gene (as demonstrated by the cross-species hybridization blots for E4.3 and H1.6), as is shown in FIG. 4, indicate that an orthologous gene exists in the mouse (hereafter to be denoted mCF, and its corresponding protein as mCFTR), and this will be possible to clone in mouse genomic and cDNA libraries using the human CF gene probes. It is expected that the generation of a specific mutation in the mouse gene analogous to the I507 mutation will be most optimum to reproduce the phenotype, though complete inactivation of the mCFTR gene will also be a useful mutant to generate.

A. Mutagensis

Inactivation of the mCF gene can be achieved by chemical [e.g. Johnson et al *Proc. Natl. Acad. Sci. USA* 78:3138 (1981)] or X-ray mutagenesis [Popp et al *J. Mol. Biol.* 127:141 (1979)] of mouse gametes, followed by fertilization. Offspring heterozygous for inactivation of mCFTR can then be identified by Southern blotting to demonstrate loss of one allele by dosage, or failure to inherit one parental allele if an RFLP marker is being assessed. This approach has previously been successfully used to identify mouse mutants for α-globin [Whitney et al *Proc. Natl. Acad. Sci. USA* 77:1087 (1980)], phenylalanine hydroxylase [McDonald et al *Pediatr. Res* 23:63 (1988)], and carbonic anhydrase II [Lewis et al *Proc. Natl. Acad. Sci. USA* 85:1962, (1988)].

B. Transgenics

A mutant version of CFTR or mouse CFTR can be inserted into the mouse germ line using now standard techniques of oocyte injection [Camper, *Trends in Genetics* (1988)]; alternatively, if it is desirable to inactivate or replace the endogenous mCF gene, the homologous recombination system using embryonic stem (ES) cells [Capecchi, *Science* 244:1288 (1989)] may be applied.

1. Oocyte Injection

Placing one or more copies of the normal or mutant mCF gene at a random location in the mouse germline can be accomplished by microinjection of the pronucleus of a just-fertilized mouse oocyte, followed by reimplantation into a pseudo-pregnant foster mother. The liveborn mice can then be screened for integrants using analysis of tail DNA for the presence of human CF gene sequences. The same protocol can be used to insert a mutant mCF gene. To generate a mouse model, one would want to place this transgene in a mouse background where the endogenous mCF gene has been inactivated, either by mutagenesis (see above) or by homologous recombination (see below). The transgene can be either: a) a complete genomic sequence, though the size of this (about 250 kb) would require that it be injected as a yeast artificial chromosome or a chromosome fragment; b) a cDNA with either the natural promoter or a heterologous promoter; c) a "minigene" containing all of the coding region and various other elements such as introns, promoter, and 3' flanking elements found to be necessary for optimum expression.

2. Retroviral Infection of Early Embryos

This alternative involves inserting the CFTR or mCF gene into a retroviral vector and directly infecting mouse embroyos at early stages of development generating a chimera [Soriano et al *Cell* 46:19 (1986)]. At least some of these will lead to germline transmission.

3. ES Cells and Homologous Recombination

The embryonic stem cell approach (Capecchi, supra and [Capecchi, *Trends Genet* 5:70 (1989)] allows the possibility of performing gene transfer and then screening the resulting totipotent cells to identify the rare homologous recombination events. Once identified, these can be used to generate chimeras by injection of mouse blastocysts, and a proportion of the resulting mice will show germline transmission from the recombinant line. There are several ways this could be useful in the generation of a mouse model for CF:

a) Inactivation of the mCF gene can be conveniently accomplished by designing a DNA fragment which contains sequences from a mCFTR exon flanking a selectable marker such as neo. Homologous recombination will lead to insertion of the neo sequences in the middle of an exon, inactivating mCFTR. The homologous recombination events (usually about 1 in 1000) can be recognized from the heterologous ones by DNA analysis of individual clones [usually using PCR, Kim et al *Nucleic Acids Res.* 16:8887 (1988), Joyner et al *Nature* 338:153 (1989); Zimmer et al supra, p. 150] or by using a negative selection against the heterologous events [such as the use of an HSV TK gene at the end of the construct, followed by the gancyclovir selection, Mansour et al, *Nature* 336:348 (1988)]. This inactivated mCFTR mouse can then be used to introduce a mutant CF gene or mCF gene containing, for example, the I507 abnormality or any other desired mutation.

b) It is possible that specific mutants of mCFTR cDNA be created in one step. For example, one can make a construct containing mCF intron 9 sequences at the 5' end, a selectable neo gene in the middle, and intro 9+exon 10 (containing the mouse version of the I507 mutation) at the 3' end. A homologous recombination event would lead to the insertion of the neo gene in intron 9 and the replacement of exon 10 with the mutant version.

c) If the presence of the selectable neo marker in the intron altered expression of the mCF gene, it would be possible to excise it in a second homologous recombination step.

d) It is also possible to create mutations in the mouse germline by injecting oligonucleotides containing the mutation of interest and screening the resulting cells by PCR.

This embodiment of the invention has considered primarily a mouse model for cystic fibrosis. FIG. 4 shows cross-species hybridization not only to mouse DNA, but also to bovine, hamster and chicken DNA. Thus, it is contemplated that an orthologous gene will exist in many other species also. It is thus contemplated that it will be possible to generate other animal models using similar technology.

Although preferred embodiments of the invention have been described herein in detail, it will be understood by those skilled in the art that variations may be made thereto without departing from the spirit of the invention or the scope of the appended claims.

We claim:

1. A method of screening in vitro a subject to determine if said subject is a CF carrier or a CF patient comprising the steps of:

providing a biological sample from the subject to be screened; and performing an in vitro nucleic acid assay for detecting in the biological sample the presence of a mutant CF gene, wherein said mutant gene encodes a mutant CFTR polypeptide product being defined by mutations selected from the group consisting of protein positions 85, 148, 178, 455, 493, 507, 542, 549, 551, 560, 563, 574, 1077, and 1092 of SEQ ID NO:2, and wherein an alteration at position 549 is either S549R or S549I.

2. A method for screening in vitro a subject to determine if said subject is a CF carrier or a CF patient comprising the steps of:

providing a biological sample from the subject to be screened; and performing an in vitro nucleic acid assay for detecting in the biological sample the presence of a mutant CF gene having mutations at DNA sequence positions selected from the group consisting of 129, 556, 621+1, 711+1, 1717-1, and 3659 of SEQ ID NO:1.

3. The method of claim 1 or 2 wherein the biological sample includes at least part of the genome of the subject and the assay comprises a hybridization assay.

4. The method of claim 3 wherein the assay further comprises a labelled nucleotide probe comprising a DNA or RNA nucleotide sequence selected from the group consisting of:

(a) DNA sequences comprising DNA sequences which encompass any one of said mutations of claims 1 or 2, said DNA sequence including at least 16 nucleotides;

(b) DNA sequences comprising at least 16 nucleotides and encode a fragment of the selected amino acid sequence of claim 1 or 2; and (c) DNA sequences encoding an epitope characteristic of the mutant CFTR protein encoded by at least 18 sequential nucleotides in the selected sequence of claims 1 or 2.

5. The method of claim 4 wherein said DNA or RNA nucleotide sequence comprises AAA GAA AAT ATC TTT GGT GTT of SEQ ID NO:1, and its complement.

6. The method of claim 4, wherein the assay further includes at least one additional nucleotide probe comprising a DNA or RNA nucleotide sequence selected from the group consisting of:

(a) DNA sequences comprising DNA sequences which encompass any one of said mutations of claims 1 or 2, said DNA sequence including at least 16 nucleotides;

(b) DNA sequences comprising at least 16 nucleotides and encode a fragment of the selected amino acid sequence of claim 1 or 2; and (c) DNA sequence encoding an epitope characteristic of the mutant CFTR protein encoded by at least 18 sequential nucleotides in the selected sequence of claims 1 or 2.

7. The method of claim 6, wherein the assay further includes at least one additional nucleotide probe comprising a different DNA sequence fragment of the DNA sequence of SEQ ID NO:1 or its RNA homologue or a different DNA sequence fragment of human chromosome 7 and located to either side of the DNA sequence of SEQ ID NO:1.

8. The method of claim 1 or 2 wherein the subject is a human fetus in utero.

9. In a process for screening a potential CF carrier or patient to indicate the presence of an identified cystic fibrosis mutation in the CF gene, said process including the steps of:

(a) isolating genomic DNA from said potential CF carrier or said potential patient;

(b) hybridizing a DNA probe onto said isolated genomic DNA, said DNA probe spanning a mutation in said CF gene wherein said DNA probe is capable of detecting said mutation, said mutation being selected from the group of mutations at protein positions 85, 148, 178, 455, 493, 507, 542, 549, 551, 560, 563, 574, 1077 and 1092 of SEQ ID NO:2, and wherein an alteration at position 549 is either S549R or S549I.

10. The method of claim 9, wherein said method further includes after step (a) the step of amplifying a selected exon within said genomic DNA, said exon having a cDNA sequence of SEQ ID NO:1, using oligonucleotide primers in a polymerase chain reaction, the use of oligonucleotide primers being from intron portions of said genomic sequence near the 5' and 3' boundaries of a selected exon of SEQ ID NO:3.

11. In a process for screening a potential CF carrier or patient to indicate the presence of an identified cystic fibrosis mutation in the CF gene, said process including the steps of:

(a) isolating genomic DNA from said potential CF carrier or said potential patient;

(b) hybridizing a DNA probe onto said isolated genomic DNA, said DNA probe spanning a mutation in said CF gene where said DNA probe is capable of detecting said mutation, said mutation being selected from the group of mutations at DNA sequence positions 129, 556, 621+1, 711+1, 1717-1 and 3659 of SEQ ID NO:1.

12. A process for detecting cystic fibrosis carriers of a mutant CF gene wherein said process consists of determining differential mobility of heteroduplex PCR products in polyacrylamide gels as a result of deletions or alterations in the mutant CF gene at one or more of the protein positions 85, 148, 178, 455, 493, 507, 542, 549, 551, 560, 563, 574, 1077 and 1092 of SEQ ID NO:2.

13. A process for detecting cystic fibrosis carriers of a mutant CF gene wherein said process consists of determining differential mobility of heteroduplex PCR products in polyacrylamid gels as a result of deletions or alterations in the mutant CF gene at one or more of the DNA sequence positions 129, 556, 621+1, 711+1, 1717-1 and 3659 of SEQ ID NO:1.

14. A kit for assaying for the presence of a CF gene by hybridization comprising:

(a) an oligonucleotide probe which specifically binds to a mutant CF gene;

(b) reagent means for detecting the hybridization of the oligonucleotide probe to a mutant CF gene having a mutation at a protein position selected from the group consisting of protein positions 85, 148, 178, 455, 493, 507, 542, 549, 551, 560, 563, 574, 1077 and 1092 of SEQ ID NO:2, and wherein an alteration at position 549 is either S549R or S549I; and (c) the probe and reagent means each being present in amounts effective to perform the hybridization assay.

15. A kit for assaying for the presence of a CF gene by hybridization comprising:

(a) an oligonucleotide probe which specifically binds to a mutant CF gene;

(b) reagent means for detecting the hybridization of the oligonucleotide probe to a mutant CF gene having a mutation at a DNA sequence position selected from the group consisting of DNA sequence positions 129, 556, 621+1, 711+1, 1717-1 and 3659 of SEQ ID NO:1; and (c) the probe and reagent means each being present in amounts effective to perform the hybridization assay.

* * * * *

UNITED STATES PATENT AND TRADEMARK OFFICE
CERTIFICATE OF CORRECTION

PATENT NO. : 5,981,178

DATED : November 9, 1999

INVENTOR(S) : Tsui et al.

It is certified that error appears in the above-identified patent and that said Letters Patent is hereby corrected as shown below:

Title page, item [56],
In the References Cited, OTHER PUBLICATIONS,

Column 2, line 2, "Rgulator" should read --Regulator--; line 6, "1227-1223" should read --1227-1233--; line 7, "Electrolyye" should read --Electrolyte--.

Signed and Sealed this

Fifth Day of September, 2000

Attest:

Attesting Officer

Q. TODD DICKINSON

Director of Patents and Trademarks

UNITED STATES PATENT AND TRADEMARK OFFICE
CERTIFICATE OF CORRECTION

PATENT NO.    : 5,981,178
DATED         : November 9, 1999
INVENTOR(S)   : Tsui et al.

It is certified that error appears in the above-identified patent and that said Letters Patent is hereby corrected as shown below:

Column 122,
Line 27, after "SEQ ID NO:2," delete the ".", and insert -- , and wherein an alteration at position 549 is either S549R or S549I. --

Signed and Sealed this

Fourteenth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 5,981,178
DATED : November 9, 1999
INVENTOR(S) : Tsui et al.

It is certified that error appears in the above-identified patent and that said Letters Patent is hereby corrected as shown below:

Column 119,
Line 67, delete "551,".

Column 121,
Line 58, delete "551,".

Column 122,
Lines 26 and 43, delete "551,".

Signed and Sealed this

Third Day of August, 2004

JON W. DUDAS
*Acting Director of the United States Patent and Trademark Office*